(12) United States Patent
Rhodes et al.

(10) Patent No.: US 7,115,381 B1
(45) Date of Patent: Oct. 3, 2006

(54) METHODS FOR TREATING CARDIOVASCULAR DISORDERS

(76) Inventors: Kenneth Rhodes, 808 Atkinson Cir., Neshanic Station, NJ (US) 08853; Wenqian An, 1500 Worcester Rd. Apt. #212, Framingham, MA (US) 01702

( * ) Notice: Subject to any disclaimer, the term of this patent is extended or adjusted under 35 U.S.C. 154(b) by 0 days.

(21) Appl. No.: 09/400,492

(22) Filed: Sep. 21, 1999

Related U.S. Application Data

(63) Continuation-in-part of application No. 09/350,874, filed on Jul. 9, 1999, now abandoned, which is a continuation-in-part of application No. 09/350,614, filed on Jul. 9, 1999, now Pat. No. 6,689,581, which is a continuation-in-part of application No. 09/298,731, filed on Apr. 23, 1999, now Pat. No. 6,369,197.

(60) Provisional application No. 60/110,277, filed on Nov. 30, 1998, provisional application No. 60/110,033, filed on Nov. 25, 1998, provisional application No. 60/109,333, filed on Nov. 20, 1998.

(51) Int. Cl.
*C12N 15/12* (2006.01)
*C12N 15/63* (2006.01)
*C12N 15/00* (2006.01)
*G01N 33/566* (2006.01)
*G01N 33/53* (2006.01)

(52) U.S. Cl. .................. 435/7.2; 435/69.1; 435/320.1; 435/325; 435/7.8; 530/350

(58) Field of Classification Search .................. 435/7.2, 435/69.1, 325, 320.1, 7.8; 530/350
See application file for complete search history.

(56) References Cited

FOREIGN PATENT DOCUMENTS

| WO | WO 97/31112 |   | 8/1997 |
|----|-------------|---|--------|
| WO | WO 9731112  | * | 8/1997 |
| WO | WO 98/16185 |   | 4/1998 |
| WO | WO 99/49038 |   | 9/1999 |

OTHER PUBLICATIONS

Oberste-Berghaus et al. Thyroid Hormone-independent Interaction between the Thyroid Hormone Receptor b2 Amino Terminus and Coactivators. Journal of Biological Chemistry. vol. 275, No. 3, Issue of Jan. 21, pp. 1787-1792, 2000.*

Beers and Berkow, eds. The Merck Manual of Diagnosis and Therapy. Merck Research Laboratories, Whitehouse Station, N.J. Seventeenth Edition 1999, pp. 1599-1601, 1629-1632, 1682-1685, 1710-1712.*

Bonaldo et al., GenBank Accession No. AA859724 [online], "Calcium-binding protein NCS-1" (Mar. 14, 1998).

Castagna, Michela et al. "Molecular Characteristics of Mammalian and Insect Amino Acid Transporters: Implications for Amino Acid Homeostatis" *The Journal of Experimental Biology* 200:269-286 (1997).

Lombardi, Stephen J. et al. "Structure-Activity Relationships of the $K_v$ $\beta 1$ Inactivation Domain and Its Putative Receptor Probed Using Peptide Analogs of Voltage-gated Potassium Channel $\alpha$- and $\beta$-Supunits" *The Journal of Biological Chemistry* 273(46):30092-30096 (Nov. 13, 1998).

National Cancer Intsitute-Cancer Genome Aanatomy Project, GenBank Accession No. A1038858 [online], ". . . *Homo sapiens*cDNA clone IMAGE:1659605 3' similar to SW:VIS3_Rat P35333 Visinin-like Protein" (Jul. 1, 1998).

Sasaki, Z. et al., GenBank Accession No. AU035979 [online], "Sugano Mouse Brain mncb Mus musculus cDNA clone MNCb-7005" (Oct. 8, 1998).

Van Hille, Benoit et al. "Identification of Two Subunit A Isoforms of the Vacuolar $H^+$-ATPase in Human Ostroclastoma" *The Journal of Biological Chemistry* 268(10):7075-7080 (Apr. 5, 1993).

Kim, E. et al. "Clustering of Shaker-type $K^+$channels by interaction with a family of membrane-associated guanylate kinases" *Nature* 378:85-88 (Nov. 2, 1995).

Scannevin, R.H. and Trimmer, J.S. "Cytoplasmic Domains of Voltage-Sensitive $K^+$Channels Involved in Mediating Protein-Protein Interactions" *Biochemical and Biophysical Research Communications* 232:585-589 (1997).

Sheng, M. and Kim, E. "Ion channel associated proteins" *Current Opinion in Neurobiology* 6:602-608 (1996).

Genbank Accession No. AU035979, Sugano mouse brain mncb Mus musculus cDNA clone MNCb-7005, mRNA sequence [Jul. 12, 2000].

* cited by examiner

Primary Examiner—Marianne P. Allen
(74) Attorney, Agent, or Firm—Woodcock Washburn LLP

(57) ABSTRACT

The invention provides methods for identifying compounds suitable for treating a cardiovascular disorder, as well as methods for treating a cardiovascular disorder. The invention also provides methods for determining if a subject is at risk for a cardiovascular disorder.

12 Claims, 44 Drawing Sheets

HUMAN 1V DNA (CD:225-875)

GAATAGCCCCCTTTCACTTCTGAGTCCCTGCATGTGCGGGGCTGAAGAAGGAAGCCAGAAGCCTCCTAGCCTCGCCTCCA
CGTTTGCTGAATACCAAGCTGCAGGCGAGCTGCCGGGCGCTTTTCTCTCCTCCAATTCAGAGTAGACAAACCACGGGGAT
TTCTTTCCAGGGTAGGGGAGGGGCCGGGCCCGGGGTCCCAACTCGCACTCAAGTCTTCGCTGCCATGGGGGCCGTCATGG
GCACCTTCTCATCTCTGCAAACCAAACAAAGGCGACCCTCGAAAGATAAGATTGAAGATGAGCTGGAGATGACCATGGTT
TGCCATCGGCCCGAGGGACTGGAGCAGCTCGAGGCCCAGACCAACTTCACCAAGAGGGAGCTGCAGGTCCTTTATCGAGG
CTTCAAAAATGAGTGCCCCAGTGGTGTGGTCAACGAAGACACATTCAAGCAGATCTATGCTCAGTTTTTCCCTCATGGAG
ATGCCAGCACGTATGCCCATTACCTCTTCAATGCCTTCGACACCACTCAGACAGGCTCCGTGAAGTTCGAGGACTTTGTA
ACCGCTCTGTCGATTTTATTGAGAGGAACTGTCCACGAGAAACTAAGGTGGACATTTAATTTGTATGACATCAACAAGGA
CGGATACATAAACAAAGAGGAGATGATGGACATTGTCAAAGCCATCTATGACATGATGGGGAAATACACATATCCTGTGC
TCAAAGAGGACACTCCAAGGCAGCATGTGGACGTCTTCTTCCAGAAAATGGACAAAAATAAAGATGGCATCGTAACTTTA
GATGAATTTCTTGAATCATGTCAGGAGGACGACAACATCATGAGGTCTCTCCAGCTGTTTCAAAATGTCATGTAACTGGT
GACACTCAGCCATTCAGCTCTCAGAGACATTGTACTAAACAACCACCTTAACACCCTGATCTGCCCTTGTTCTGATTTTA
CACACCAACTCTTGGGACAGAAACACCTTTTACACTTTGGAAGAATTCTCTGCTGAAGACTTTCTTATGGAACCCAGCAT
CATGTGGCTCAGTCTCTGATTGCCAACTCTTCCTCTTTCTTCTTCTTGAGAGAGACAAGATGAAATTTGAGTTTGTTTTG
GAAGCATGCTCATCTCCTCACACTGCTGCCCTATGGAAGGTCCCTCTGCTTAAGCTTAAACAGTAGTGCACAAAATATGC
TGCTTACGTGCCCCCAGCCCACTGCCTCCAAGTCAGGCAGACCTTGGTGAATCTGGAAGCAAGAGGACCTGAGCCAGATG
CACACCATCTCTGATGGCCTCCCAAACCAATGTGCCTGTTTCTCTTCCTTTGGTGGGAAGAATGAGAGTTATCCAGAACA
ATTAGGATCTGTCATGACCAGATTGGGAGAGCCAGCACCTAACATATGTGGGATAGGACTGAATTATTAAGCATGACATT
GTCTGATGACCCAAACTGCCCCG

HUMAN 1V PROTEIN

MGAVMGTFSSLQTKQRRPSKDKIEDELEMTMVCHRPEGLEQLEAQTNFTKRELQVLYRGFKNECPSGVVNEDTFKQIYAQ

FFPHGDASTYAHYLFNAFDTTQTGSVKFEDFVTALSILLRGTVHEKLRWTFNLYDINKDGYINKEEMMDIVKAIYDMMGK

YTYPVLKEDTPRQHVDVFFQKMDKNKDGIVTLDEFLESCQEDDNIMRSLQLFQNVM

Fig. 1

RAT 1vN (r1vN) DNA (CD: 339-1037)
GGCACACAACCCCTGGATTCTTCGGAGAATATGCCGTGAGGTGTTGCCAATTATTAGTTCTCTTGGCTAGCAGATGTTTA
GGGACTGGTtaaGCCTTTGGAGAAATTACCTTAGGAAAACGGGGAAATAAAAGCAAAGATTACCATGAATTGCAAGATTA
CCTAGCAATTGCAAGGtagGAGGAGAGAGGTGGAGGGCGGAGTAGACAGGAGGGAGGGAGAAAGtgaGAGGAAGCTAGGC
TGGTGGAAATAACCCTGCACTTGGAACAGCGGCAAAGAAGCGCGATTTTCCAGCTTtaaATGCCTGCCCGCGTTCTGCTT
GCCTACCCGGGAACGGAGATGTTGACCCAGGGCGAGTCTGAAGGGCTCCAGACCTTGGGGATAGTAGTGGTCCTGTGTTC
CTCTCTGAAACTACTGCACTACCTCGGGCTGATTGACTTGTCGGATGACAAGATCGAGGATGATCTGGAGATGACCATGG
TTTGCCATCGGCCTGAGGGACTGGAGCAGCTTGAGGCACAGACGAACTTCACCAAGAGAGAACTGCAAGTCCTTTACCGG
GGATTCAAAAACGAGTGCCCCAGTGGTGTGGTTAACGAAGAGACATTCAAGCAGATCTACGCTCAGTTTTTCCCTCATGG
AGATGCCAGCACATACGCACATTACCTCTTCAATGCCTTCGACACCACCCAGACAGGCTCTGTAAAGTTCGAGGACTTTG
TGACTGCTCTGTCGATTTTACTGAGAGGAACGGTCCATGAAAAACTGAGGTGGACGTTTAATTTGTACGACATCAATAAA
GACGGCTACATAAACAAAGAGGAGATGATGGACATAGTGAAAGCCATCTATGACATGATGGGGAAATACACCTATCCTGT
GCTCAAAGAGGACACTCCCAGGCAGCACGTGGACGTCTTCTTCCAGAAAATGGATAAAAATAAAGATGGCATTGTAACGT
TAGACGAATTTCTCGAGTCCTGTCAGGAGGATGACAACATCATGAGGTCTCTACAGCTGTTCCAAAATGTCATGTAACTG
AGGACACTGGCCATCCTGCTCTCAGAGACACTGACAAACACCTCAATGCCCTGATCTGCCCTTGTTCCAGTTTTACACAT
CAACTCTCGGGACAGAAATACCTTTTACACTTTGGAAGAATTCTCTGCTGAAGACTTTCTACAAAACCTGGCACCGAGTG
GCTCAGTCTCTGATTGCCAACTCTTCCTCCCTCCTCCTCTTGAGAGGGACGAGCTGAAATCCGAAGTTTGTTTTGGAAGC
ATGCCCATCTCTCCATGCTGCTGCTGCCCTGTGGAAGGCCCCTCTGCTTGAGCTTAAACAGTAGTGCACAGTTTTCTGCG
TATACAGATCCCCAACTCACTGCCTCTAAGTCAGGCAGACCCTGATCAATCTGAACCAAATGTGCACCATCCTCCGATGG
CCTCCCAAGCCAATGTGCCTGCTTCTCTTCCTCTGGTGGGAAGAAAGAACGCTCTACAGAGCACTTAGAGCTTACCATGA
AAATACTGGGAGAGGCAGCACCTAACACATGTAGAATAGGACTGAATTATTAAGCATGGTGGTATCAGATGATGCAAACA
GCCCATGTCATTTTTTTTTCCAGAGGTAGGGACTAATAATTCTCCCACACTAGCACCTACGATCATAGAACAAGTCTTTT
AACACATCCAGGAGGGAAACCGCTGCCCAGTGGTCTATCCCTTCTCTCCAT RAT 1vN (r1vN) PROTEIN MLTQGESEGLQTLGIVVVLCSSLKLLHYLGLIDLSDDKIEDDLEMTMVCHRPEGLEQLEAQTNFTKRELQVLYRGFKNEC
PSGVVNEETFKQIYAQFFPHGDASTYAHYLFNAFDTTQTGSVKFEDFVTALSILLRGTVHEKLRWTFNLYDINKDGYINK
EEMMDIVKAIYDMMGKYTYPVLKEDTPRQHVDVFFQKMDKNKDGIVTLDEFLESCQEDDNIMRSLQLFQNVM.

Fig. 2B

MOUSE 1V (CD:477-1127)
CGGCCCCCTGAGATCCAGCCCGAGCGCGGGGCGGAGCGGCCGGGTGGCAGCAGGGGCGGGCGGGCGGAGCGCAGCTCCCG
CACCGCACGCGGCGCGGGCTCGGCAGCCTCGGCCGTGCGGGCACGCCGGCCCCGTGTCCAACATCAGGCAGGCTTTGGGG
CTCGGGGCTCGGCCTCGGAGAAGCCAGTGGCCCGGCTGGGTGCCCGCACCGGGGGGCGCCTGTCAAGGCTCCCGCGAGC
CTCTGGCCCTGGGAGTCAGTGCATGTGCCTGGCTGAAGAAGGCAGCAGCCACGAGCTCCAGGCGCCCCGGCCCCACGTTT
TCTGAATACCAAGCTGCAGGCGAGCTGCTCGGGGCTTTTTTGCTTTCTCGCTTTTCCTCTCCTCCAATTCAAAGTGGGCA
ATCCACACCGATTTCTTTTCAGGGGAGGGAAGAGACAGGGCCTGGGGTCCCAAGACGCACACAAGTCTTCGCTGCCATGG
GGGCCGTCATGGGCACTTTCTCCTCCCTGCAGACCAAACAAAGGCGACCCTCTAAAGACAAGATTGAGGATGAGCTAGAG
ATGACCATGGTTTGCCACCGGCCTGAGGGACTGGAGCAGCTTGAGGCACAGACGAACTTCACCAAGAGAGAACTGCAAGT
CTTGTACCGGGGATTCAAAAACGAGTGCCCTAGCGGTGTGGTCAATGAAGAAACATTCAAGCAGATCTACGCTCAGTTTT
TCCCTCACGGAGATGCCAGCACATATGCACATTACCTCTTCAATGCCTTCGACACCACCCAGACAGGCTCTGTAAAGTTC
GAGGACTTTGTGACTGCTCTGTCGATTTTACTGAGAGGGACAGTCCATGAAAAACTAAGGTGGACGTTTAATTTGTATGA
CATCAATAAAGACGGCTACATAAACAAAGAGGAGATGATGGACATAGTCAAAGCCATCTATGACATGATGGGGAAATACA
CCTATCCTGTGCTCAAAGAGGACACTCCCAGGCAGCATGTGGATGTCTTCTTCCAGAAAATGGATAAAAATAAAGATGGC
ATTGTAACGTTAGATGAATTTCTTGAATCATGTCAGGAGGATGACAACATCATGAGATCTCTACAGCTGTTCCAAAATGT
CATGTAACTGAGGACACTGGCCATTCTGCTCTCAGAGACACTGACAAACACCTTAATGCCCTGATCTGCCCTTGTTCCAA
TTTTACACACCAACTCTTGGGACAGAAATACCTTTTACACTTTGGAAGAATTCTCTGCTGAAGACTTTCTACAAAACCTG
GCACCACGTGGCTCTGTCTCTGAGGGACGAGCGGAGATCCGACTTTGTTTTGGAAGCATGCCCATCTCTTCATGCTGCTG
CCCTGTGGAAGGCCCCTCTGCTTGAGCTTAATCAATAGTGCACAGTTTTATGCTTACACATATCCCCAACTCACTGCCTC
CAAGTCAGGCAGACTCTGATGAATCTGAGCCAAATGTGCACCATCCTCCGATGGCCTCCCAAGCCAATGTGCCTGCTTCT
CTTCCTCTGGTGGGAAGAAAGAGTGTTCTACGGAACAATTAGAGCTTACCATGAAAATATTGGGAGAGGCAGCACCTAAC
ACATGTAGAATAGGACTGAATTATTAAGCATGGTGATATCAGATGATGCAAATTGCCCATGTCATTTTTTTCAAAGGTAG
GGACAAATGATTCTCCCACACTAGCACCTGTGGTCATAGAGCAAGTCTCTTAACATGCCCAGAAGGGGAACCACTGTCCA
GTGGTCTATCCCTCCTCTCCATCCCCTGCTCAAACCCAGCACTGCATGTCCCTCCAAGAAGGTCCAGAATGCCTGCGAAA
CGCTGTACTTTTATACCCTGTTCTAATCAATAAACAGAACTATTTCGTAAAAAAAAAAAAAAAAAAAA

MOUSE 1V PROTEIN
MGAVMGTFSSLQTKQRRPSKDKIEDELEMTMVCHRPEGLEQLEAQTNFTKRELQVLYRGFKNECPSGVVNEETFKQIYAQ
FFPHGDASTYAHYLFNAFDTTQTGSVKFEDFVTALSILLRGTVHEKLRWTFNLYDINKDGYINKEEMMDIVKAIYDMMGK
YTYPVLKEDTPRQHVDVFFQKMDKNKDGIVTLDEFLESCQEDDNIMRSLQLFQNVM.

Fig. 3

RAT 1VL DNA (CD: 31-714)
GTCCCAAGTCGCACACAAGTCTTCGCTGCCATGGGGGCCGTCATGGGTACCTTCTCGTCCCTGCAGACCAAACAAAGGCG
ACCCTCTAAAGACATCGCCTGGTGGTATTACCAGTATCAGAGAGACAAGATCGAGGATGATCTGGAGATGACCATGGTTT
GCCATCGGCCTGAGGGACTGGAGCAGCTTGAGGCACAGACGAACTTCACCAAGAGAGAACTGCAAGTCCTTTACCGGGGA
TTCAAAAACGAGTGCCCCAGTGGTGTGGTTAACGAAGAGACATTCAAGCAGATCTACGCTCAGTTTTTCCCTCATGGAGA
TGCCAGCACATACGCACATTACCTCTTCAATGCCTTCGACACCACCCAGACAGGCTCTGTAAAGTTCGAGGACTTTGTGA
CTGCTCTGTCGATTTTACTGAGAGGAACGGTCCATGAAAAACTGAGGTGGACGTTTAATTTGTACGACATCAATAAAGAC
GGCTACATAAACAAAGAGGAGATGATGGACATAGTGAAAGCCATCTATGACATGATGGGGAAATACACCTATCCTGTGCT
CAAAGAGGACACTCCCAGGCAGCACGTGGACGTCTTCTTCCAGAAAATGGATAAAAATAAAGATGGCATTGTAACGTTAG
ACGAATTTCTCGAGTCCTGTCAGGAGGATGACAACATCATGAGGTCTCTACAGCTGTTCCAAAATGTCATGTAACTGAGG
ACACTGGCCATCCTGCTCTCAGAGACACTGACAAACACCTCAATGCCCTGATCTGCCCTTGTTCCAGTTTTACACATCAA
CTCTCGGGACAGAAATACCTTTTACACTTTGGAAGAATTCTCTGCTGAAGACTTTCTACAAAACCTGGCACCGCGTGGCT
CAGTCTCTGATTGCCAACTCTTCCTCCCTCCTCCTCTTGAGAGGGACGAGCTGAAATCCGAAGTTTGTTTTGGAAGCATG
CCCATCTCTCCATGCTGCTGCTGCCCTGTGGAAGGCCCCTCTGCTTGAGCTTAAACAGTAGTGCACAGTTTTCTGCGTAT
ACAGATCCCCAACTCACTGCCTCTAAGTCAGGCAGACCCTGATCAATCTGAACCAAATGTGCACCATCCTCCGATGGCCT
CCCAAGCCAATGTGCCTGCTTCTCTTCCTCTGGTGGGAAGAAAGAACGCTCTACAGAGCACTTAGAGCTTACCATGAAAA
TACTGGGAGAGGCAGCACCTAACACATGTAGAATAGGACTGAATTATTAAGCATGGTGGTATCAGATGATGCAAACAGCC
CATGTCATTTTTTTTCCAGAGGTAGGGACTAATAATTCTCCCACACTAGCACCTACGATCATAGAACAAGTCTTTTAACA
CATCCAGGAGGGAAACCGCTGCCCAGTGGTCTATCCCTTCTCTCCATCCCCTGCTCAAGCCCAGCACTGCATGTCTCTCC
CGGAAGGTCCAGAATGCCTGTGAAATGCTGTAACTTTTATACCCTGTTATAATCAATAAACAGAACTATTTCGTACAAAA
AAAAAAAAAAAAAA
RAT 1VL PROTEIN
MGAVMGTFSSLQTKQRRPSKDIAWWYYQYQRDKIEDDLEMTMVCHRPEGLEQLEAQTNFTKRELQVLYRGFKNECPSGVV
NEETFKQIYAQFFPHGDASTYAHYLFNAFDTTQTGSVKFEDFVTALSILLRGTVHEKLRWTFNLYDINKDGYINKEEMMD
IVKAIYDMMGKYTYPVLKEDTPRQHVDVFFQKMDKNKDGIVTLDEFLESCQEDDNIMRSLQLFQNVM.

Fig. 4

MOUSE 1VL DNA (CD: 77-760)
ATCCACACCGATTTCTTTTCAGGGGAGGGAAGAGACAGGGCCTGGGGTCCCAAGACGCACACAAGTCTTCGCTGCCATGG

GGGCCGTCATGGGCACTTTCTCCTCCCTGCAGACCAAACAAAGGCGACCCTCTAAAGACATCGCCTGGTGGTATTACCAG

TATCAGAGAGACAAGATTGAGGATGAGCTAGAGATGACCATGGTTTGCCACCGGCCTGAGGGACTGGAGCAGCTTGAGGC

ACAGACGAACTTCACCAAGAGAGAACTGCAAGTCTTGTACCGGGGATTCAAAAACGAGTGCCCTAGCGGTGTGGTCAATG

AAGAAACATTCAAGCAGATCTACGCTCAGTTTTTCCCTCACGGAGATGCCAGCACATATGCACATTACCTCTTCAATGCC

TTCGACACCACCCAGACAGGCTCTGTAAAGTTCGAGGACTTTGTGACTGCTCTGTCGATTTTACTGAGAGGGACAGTCCA

TGAAAAACTAAGGTGGACGTTTAATTTGTATGACATCAATAAAGACGGCTACATAAACAAAGAGGAGATGATGGACATAG

TCAAAGCCATCTATGACATGATGGGGAAATACACCTATCCTGTGCTCAAAGAGGACACTCCCAGGCAGCATGTGGATGTC

TTCTTCCAGAAAATGGATAAAAATAAAGATGGCATTGTAACGTTAGATGAATTTCTTGAATCATGTCAGGAGGATGACAA

CATCATGAGATCTCTACAGCTGTTCCAAAATGTCATGTAACTGAGGACACTGGCCATTCTGCTCTCAGAGACACTGACAA

ACACCTTAATGCCCTGATCTGCCCTTGTTCCAATTTTACACACCAACTCTTGGGACAGAAATACCTTTTACACTTTGGAA

GAATTCTCTGCTGAAGACTTTCTACAAAACCTGGCACCACGTGGCTCTGTCTCTGAGGGACGAGCGGAGATCCGACTTTG

TTTTGGAAGCATGCCCATCTCTTCATGCTGCTGCCCTGTGGAAGGCCCCTCTGCTTGAGCTTAATCAATAGTGCACAGTT

TTATGCTTACACATATCCCCAACTCACTGCCTCCAAGTCAGGCAGACTCTGATGAATCTGAGCCAAATGTGCACCATCCT

CCGATGGCCTCCCAAGCCAATGTGCCTGCTTCTCTTCCTCTGGTGGGAAGAAAGAGTGTTCTACGGAACAATTAGAGCTT

ACCATGAAAATATTGGGAGAGGCAGCACCTAACACATGTAGAATAGGACTGAATTATTAAGCATGGTGATATCAGATGAT

GCAAATTGCCCATGTCATTTTTTTCAAAGGTAGGGACAAATGATTCTCCCACACTAGCACCTGTGGTCATAGAGCAAGTC

TCTTAACATGCCCAGAAGGGGAACCACTGTCCAGTGGTCTATCCCTCCTCTCCATCCCCTGCTCAAACCCAGCACTGCAT

GTCCCTCCAAGAAGGTCCAGAATGCCTGCGAAACGCTGTACTTTTATACCCTGTTCTAATCAATAAACAGAACTATTTCG

TACAAAAAAAAAAAAAAAAA

MOUSE 1VL PROTEIN

MGAVMGTFSSLQTKQRRPSKDIAWWYYQYQRDKIEDELEMTMVCHRPEGLEQLEAQTNFTKRELQVLYRGFKNECPSGVV
NEETFKQIYAQFFPHGDASTYAHYLFNAFDTTQTGSVKFEDFVTALSILLRGTVHEKLRWTFNLYDINKDGYINKEEMMD
IVKAIYDMMGKYTYPVLKEDTPRQHVDVFFQKMDKNKDGIVTLDEFLESCQEDDNIMRSLQLFQNVM.

Fig. 5

RAT 1VN DNA (FIRST-PASS, PARTIAL; CD: 345-955)
GTCCGGGCACACAACCCCTGGATTCTTCGGAGAATATGCCGTGACGGTGTTGCCAATTATTAGTTCTCTTGGCTAGCAGA
TGTTTAGGGACTGGTTAAGCCTTTGGAGAAATTACCTTAGGAAAACGGGGAAATAAAAGCAAAGATTACCATGAATTGCA
AGATTACCTAGCAATTGCAAGGTAGGAGGAGAGAGGTGGAGGGCGGAGTAGACAGGAGGGAGGGAGAAAGTGAGAGGAAG
CTAGGCTGGTGGAAATAACCCTGCACTTGGAACAGCGGCAAAGAAGCGCGATTTTCCAGCTTTAAATGCCTGCCCGCGTT
CTGCTTGCCTACCCGGGAACGGAGATGTTGACCCAGGGCGAGTCTGAAGGGCTCCAGACCTTGGGGATAGTAGTGGTCCT
GTGTTCCTCTCTGAAACTACTGCACTACCTCGGGCTGATTGACTTGTCGGATGACAAGATCGAGGATGATCTGGAGATGA
CCATGGTTTGCCATCGGCCTGAGGGACTGGAGCAGCTTGAGGCACAGACGAACTTCACCAAGAGAGAACTGCAAGTCCTT
TACCGGGGATTCAAAAACGAGTGCCCCAGTGGTGTGGTTAACGAAGAGACATTCAAGCNGATCTACGCTCAGTTTTTCCC
TCATGGAGATGCCAGCACATACGCACATTACCTCTTCAATGCCTTCGACACCACCCAGACAGGCTCTGTAAAGTTCGAGG
ACTTTGTGACTGCTCTGTCGATTTTACTGAGAGGAACGGTCCATGAAAAACTGAAGTGGACGTTTAATTTGTACGACATC
AATAAAGACGGCTACATAAACAAAGAGGAGATGATGGACATAGTGAAAGCCATCTATGACATGATGGGGAAATACACCTA
TCTTGTGCTCAAAGAGGACACTTCCAGGCAGCACGTGGACGTCTTCTTCCAGAAAATGGATAAAAATAAAGATGG

RAT 1VN PROTEIN (PARTIAL)
MLTQGESEGLQTLGIVVVLCSSLKLLHYLGLIDLSDDKIEDDLEMTMVCHRPEGLEQLEAQTNFTKRELQVLYRGFKNEC
PSGVVNEETFKXIYAQFFPHGDASTYAHYLFNAFDTTQTGSVKFEDFVTALSILLRGTVHEKLKWTFNLYDINKDGYINK
EEMMDIVKAIYDMMGKYTYLVLKEDTSRQHVDVFFQKMDKNKD

Fig. 6

HUMAN 9QL DNA (CD:207-1019)

CTCACCTGCTGCCTAGTGTTCCCTCTCCTGCTCCAGGACCTCCGGGTAGACCTCAGACCCCGGGCCCATTCCCAGACTCA
GCCTCAGCCCGGACTTCCCCAGCCCCGACAGCACAGTAGGCCGCCAGGGGGCGCCGTGTGAGCGCCCTATCCCGGCCACC
CGGCGCCCCCTCCCACGGCCCGGGCGGGAGCGGGGCGCCGGGGGCCATGCGGGGCCAGGGCCGCAAGGAGAGTTTGTCCG
ATTCCCGAGACCTGGACGGCTCCTACGACCAGCTCACGGGCCACCCTCCAGGGCCCACTAAAAAAGCGCTGAAGCAGCGA
TTCCTCAAGCTGCTGCCGTGCTGCGGGCCCCAAGCCCTGCCCTCAGTCAGTGAAACATTAGCCGCCCCAGCCTCCCTCCG
CCCCCACAGACCCCGCCTGCTGGACCCAGACAGCGTGGACGATGAATTTGAATTGTCCACCGTGTGTCACCGGCCTGAGG
GTCTGGAGCAGCTGCAGGAGCAAACCAAATTCACGCGCAAGGAGTTGCAGGTCCTGTACCGGGGCTTCAAGAACGAATGT
CCCAGCGGAATTGTCAATGAGGAGAACTTCAAGCAGATTTACTCCCAGTTCTTTCCTCAAGGAGACTCCAGCACCTATGC
CACTTTTCTCTTCAATGCCTTTGACACCAACCATGATGGCTCGGTCAGTTTTGAGGACTTTGTGGCTGGTTTGTCCGTGA
TTCTTCGGGGAACTGTAGATGACAGGCTTAATTGGGCCTTCAACCTGTATGACCTTAACAAGGACGGCTGCATCACCAAG
GAGGAAATGCTTGACATCATGAAGTCCATCTATGACATGATGGGCAAGTACACGTACCCTGCACTCCGGGAGGAGGCCCC
AAGGGAACACGTGGAGAGCTTCTTCCAGAAGATGGACAGAAACAAGGATGGTGTGGTGACCATTGAGGAATTCATTGAGT
CTTGTCAAAAGGATGAGAACATCATGAGGTCCATGCAGCTCTTTGACAATGTCATCTAGCCCCCAGGAGAGGGGGTCAGT
GTTTCCTGGGGGGACCATGCTCTAACCCTAGTCCAGGCGGACCTCACCCTTCTCTTCCCAGGTCTATCCTCATCCTACGC
CTCCCTGGGGGCTGGAGGGATCCAAGAGCTTGGGGATTCAGTAGTCCAGATCTCTGGAGCTGAAGGGGCCAGAGAGTGGG
CAGAGTGCATCTCGGGGGGTGTTCCCAACTCCCACCAGCTCTCACCCCCTTCCTGCCTGACACCCAGTGTTGAGAGTGCC
CCTCCTGTAGGAATTGAGCGGTTCCCCAC CTCCTACCCTACTCTAGAAACACACTAGAGCGATGTCTCCTGCTATGGTGC
TTCCCCCATCCCTGACCTCATAAACATTTCCCCTAAGACTCCCCTCTCAGAGAGAATGCTCCATTCTTGGCACTGGCTGG
CTTCTCAGACCAGCCATTGAGAGCCCTGTGGGAGGGGGACAAGAATGTATAGGGAGAAATCTTGGGCCTGAGTCAATGGA
TAGGTCCTAGGAGGTGGGTGGGGTTGAGAATAGAAGGGCCTGGACAGATTATGATTGCTCAGGCATACCAGGTTATAGCT
CCAAGTTCCACAGGTCTGCTACCACAGGCCATCAAAATATAAGTTTCCAGGCTTTGCAGAAGACCTTGTCTCCTTAGAAA
TGCCCCAGAAATTTTCCACACCCTCCTCGGTATCCATGGAGAGCCTGGGGCCAGATATCTGGCTCATCTCTGGCATTGCT
TCCTCTCCTTCCTTCCTGCATGTGTTGGTGGTGGTTGTGGTGGGGGAATGTGGATGGGGATGTCCTGGCTGATGCCTGC
CAAAATTTCATCCCACCCTCCTTGCTTATCGTCCCTGTTTTGAGGGCTATGACTTGAGTTTTTGTTTCCCATGTTCTCTA
TAGACTTGGGACCTTCCTGAACTTGGGGCCTATCACTCCCCACAGTGGATGCCTTAGAAGGGAGAGGGAAGGAGGGAGGC
AGGCATAGC

Fig. 7A

HUMAN 9QL PROTEIN

MRGQGRKESLSDSRDLDGSYDQLTGHPPGPTKKALKQRFLKLLPCCGPQALPSVSETLAAPASLRPHRPRLLDPDSVDDE
FELSTVCHRPEGLEQLQEQTKFTRKELQVLYRGFKNECPSGIVNEENFKQIYSQFFPQGDSSTYATFLFNAFDTNHDGSV
SFEDFVAGLSVILRGTVDDRLNWAFNLYDLNKDGCITKEEMLDIMKSIYDMMGKYTYPALREEAPREHVESFFQKMDRNK
DGVVTIEEFIESCQKDENIMRSMQLFDNVI.

Fig. 7B

RAT 9QL DNA (PARTIAL; CD: 2-775)

CCGAGATCTGGACGGCTCCTATGACCAGCTTACGGGCCACCCTCCAGGGCCCAGTAAAAAAGCCCTGAAGCAGCGTTTCC
TCAAGCTGCTGCCGTGCTGCGGGCCCCAAGCCCTGCCCTCAGTCAGTGAAACATTAGCTGCCCCAGCCTCCCTCCGCCCC
CACAGACCCCGCCCGCTGGACCCAGACAGCGTAGAGGATGAGTTTGAATTATCCACGGTGTGTCACCGACCTGAGGGCCT
GGAACAACTCCAGGAACAGACCAAGTTCACACGCAGAGAGCTGCAGGTCCTGTACCGAGGCTTCAAGAACGAATGCCCCA
GTGGGATTGTCAACGAGGAGAACTTCAAGCAGATTTATTCTCAGTTCTTTCCCCAAGGAGACTCCAGCAACTATGCTACT
TTTCTCTTCAATGCCTTTGACACCAACCACGATGGCTCTGTCAGTTTTGAGGACTTTGTGGCTGGTTTGTCGGTGATTCT
TCGGGGGACCATAGATGATAGACTGAGCTGGGCTTTCAACTTATATGACCCTCAACAAGGACGGCTGTATCACAAAGGAGG
AAATGCTTGACATTATGAAGTCCATCTATGACATGATGGGCAAGTACACATACCCTGCCCTCCGGGAGGAGGCCCCAAGA
GAACACGTGGAGAGCTTCTTCCAGAAGATGGACAGGAACAAGGACGGCGTGGTGACCATCGAGGAATTCATCGAGTCTTG
TCAACAGGACGAGAACATCATGAGGTCCATGCAGCTCTTTGATAATGTCATCTAGCTCCCCAGGGAGAGGGGTTAGTGTG
TCCTAGGGTGACCAGGCTGTAGTCCTAGTCCAGACGAACCTAACCCTCTCTCTCCAGGCCTGTCCTCATCTTACCTGTAC
CCTGGGGGCTGTAGGGATTCAATATCCTGGGGCTTCAGTAGTCCAGATCCCTGAGCTAAGTCACAAAAGTAGGCAAGAGT
AGGCAAGCTAAATCTGGGGGCTTCCCAACCCCCGACAGCTCTCACCCCTTCTCAACTGATACCTAGTGCTGAGGACACCC
CTGGTGTAGGGACCAAGTGGTTCTCCACCTTCTAGTCCCACTCTAGAAACCACATTAGACAGAAGGTCTGGTGCTATGGT
GCTTTCCCCATCCCTAATCTCTTAGATTTTCCTCAAGACTCCCTTCTCAGAGAACACGCTCTGTCCATGTCCCCAGCTGG
GGACATGGACAGAGCGTGTTCTCTAGTTCTAGATCGCGAGCGGCCGC

RAT 9QL PROTEIN (PARTIAL)

RDLDGSYDQLTGHPPGPSKKALKQRFLKLLPCCGPQALPSVSETLAAPASLRPHRPRPLDPDSVEDEFELSTVCHRPEGL
EQLQEQTKFTRRELQVLYRGFKNECPSGIVNEENFKQIYSQFFPQGDSSNYATFLFNAFDTNHDGSVSFEDFVAGLSVIL
RGTIDDRLSWAFNLYDLNKDGCITKEEMLDIMKSIYDMMGKYTYPALREEAPREHVESFFQKMDRNKDGVVTIEEFIESC
QQDENIMRSMQLFDNVI.

Fig. 8

MOUSE 9QL DNA (CD: 181-993)
CGGGACTCTGAGGTGGGCCCTAAAATCCAGCGCTCCCCAGAGAAAAGCCTTGCCAGCCCCTACTCCCGGCCCCCAGCCCC
AGCAGGTCGCTGCGCCGCCAGGGGGCACTGTGTGAGCGCCCTATCCTGGCCACCCGGCGCCCCCTCCCACCGCCCAGGCG
GGAGCGGGGCGCCGGGGGCCATGCGGGGCCAAGGCCGAAAGGAGAGTTTGTCCGAATCCCGAGATTTGGACGGCTCCTAT
GACCAGCTTACGGGCCACCCTCCAGGGCCCAGTAAAAAAGCCCTGAAGCAGCGTTTCCTCAAGCTGCTGCCGTGCTGCGG
GCCCCAAGCCCTGCCCTCAGTCAGTGAAACATTAGCTGCCCCAGCCTCCCTCCGCCCCAGAGACCCCGCCCGCTGGACC
CAGACAGCGTGGAGGATGAGTTTGAACTATCCACGGTGTGCCACCGGCCTGAGGGTCTGGAACAACTCCAGGAACAAACC
AAGTTCACACGCAGAGAGTTGCAGGTCCTGTACAGAGGCTTCAAGAACGAATGTCCCAGCGGAATTGTCAACGAGGAGAA
CTTCAAGCAAATTTATTCTCAGTTCTTTCCCCAAGGAGACTCCAGCAACTACGCTACTTTTCTCTTCAATGCCTTTGACA
CCAACCATGATGGCTCTGTCAGTTTTGAGGACTTTGTGGCTGGTTTGTCAGTGATTCTTCGGGGAACCATAGATGATAGA
CTGAACTGGGCTTTCAACTTATATGACCTCAACAAGGATGGCTGTATCACGAAGGAGGAAATGCTCGACATCATGAAGTC
CATCTATGACATGATGGGCAAGTACACCTACCCTGCCCTCCGGGAGGAGGCCCCGAGGGAACACGTGGAGAGCTTCTTCC
AGAAGATGGACAGAAACAAGGACGGCGTGGTGACCATTGAGGAATTCATTGAGTCTTGTCAACAGGACGAGAACATCATG
AGGTCCATGCAACTCTTTGATAATGTCATCTAGCTCCCCAGGGAGAGGGGTTAGTGTGTCCCAGGGTAACCATGCTGTAG
CCCTAGTCCAGGCAAACCTAACCCTCCTCTCCCCGGGTCTGTCCTCATCCTACCTGTACCCTGGGGGCTGTAGGGATTCA
ACATCCTGGCGCTTCAGTAGTCCAGATCCCTGAGCTAAGTGGCGAGAGTAGGCAAGCTAAGTCTTTGGAGGGTGGGTGGG
GGCGCGCAGATTCCCAACCCCCGACGACTCTCACCCCTTTCTCGACTGATACCCAGTGCTGAGGCTACCCCTGGTGTCGG
GAACGACCAAAGTGGTTCTCTGCCTCCCCAGCCCACTCTAGAGACCCACACTAGACGGGAATATCTCCTGCTATGGTGCT
TTCCCCATCCCTGACCGCAGATTTTCCTCCTAAGACTCCCTTCTCAGAGAATATGCTTTTGTCCCTTGTCCCTGGCTGGC
TTTTCAGCCTAGCCTTTGAGGACCCTGTGGGAGGGGAGAATAAGAAAGCAGACAAAATCTTGGCCCTGAGCCAGTGGTTA
GGTCCTAGGAATCAGGCTGGAGTGGAGACCAGAAAGCCTGGGCAGGCTATGAGAGCCCCAGGTTGGCTTGTCACCGCCAG
GTTCCACAGGGCTGCTGCTCTGGGTCAGCAGAGTATGAGTTTCCAGACTTTCCAGAAGGCCTTATGTCCTTAGCAATGTC
CCAGAAATTCACCATACACTTCTCAGTGTCTTAGGATCCAGATGTCCGGTCCATCCCTGAAACCTCTCCCTCCTCCTTGC
TCCTATGGTGGGAGTGGTGGCCAGGGGACGATGAGTGAGCCGGTGTCCTGGATGATGCCTGTCAAGGTCCCACCTACCCT
CCGGCTGTCAAGCCGTTCTGGTGACCCTGTTTGATTCTCCATGACCCCTGTCTAGATGTAGAGGTGTGGAGTGAGTCTAG
TGGCAGCCTTAGGGGAATGGGAAGAACGAGAGGGGCACTCCATCTGAACCCAGTGTGGGGGCATCCATTCGAATCTTTGC
CTGGCTCCCCACAATGCCCTAGGATCCTCTAGGGTCCCCACCCCCACTCTTTAGTCTACCCAGAGATGCTCCAGAGCTCA
CCTAGAGGGCAGGGACCATAGGATCCAGGTCCAACCTGTCATCAGCATCCGGCCATGCTGCTGCTGCTTATTAATAAACC
TGCTTGTCGTTCAGCGCCCCTTCCCAGTCAGCCAGGGTCTGAGGGGAAGGCCCCCACTTTCCCGCCTCCTGTCAGACATT
GTTGACTGCTTTGCATTTTGGGCTCTTCTACCTATATTTTGTATAATAAGAAAGACACCAGATCCAATAAAACACATGGC
TATGCACAAAAAAAAAAAAAAAAA

MOUSE 9QL PROTEIN
MRGQGRKESLSESRDLDGSYDQLTGHPPGPSKKALKQRFLKLLPCCGPQALPSVSETLAAPASLRPHRPRPLDPDSVEDE
FELSTVCHRPEGLEQLQEQTKFTRRELQVLYRGFKNECPSGIVNEENFKQIYSQFFPQGDSSNYATFLFNAFDTNHDGSV
SFEDFVAGLSVILRGTIDDRLNWAFNLYDLNKDGCITKEEMLDIMKSITDMMGKYTYPALREEAPREHVESFFQKMDRNK
DGVVTIEEFIESCQQDENIMRSMQLFDNVI

Fig. 9

HUMAN 9QM DNA (CD: 207-965)

CTCACCTGCTGCCTAGTGTTCCCTCTCCTGCTCCAGGACCTCCGGGTAGACCTCAGACCCCGGGCCCATTCCCAGACTCA
GCCTCAGCCCGGACTTCCCCAGCCCCGACAGCACAGTAGGCCGCCAGGGGGCGCCGTGTGAGCGCCCTATCCCGGCCACC
CGGCGCCCCCTCCCACGGCCCGGGCGGGAGCGGGGCGCCGGGGGCCATGCGGGGCCAGGGCCGCAAGGAGAGTTTGTCCG
ATTCCCGAGACCTGGACGGCTCCTACGACCAGCTCACGGGCCACCCTCCAGGGCCCACTAAAAAAGCGCTGAAGCAGCGA
TTCCTCAAGCTGCTGCCGTGCTGCGGGCCCCAAGCCCTGCCCTCAGTCAGTGAAAACAGCGTGGACGATGAATTTGAATT
GTCCACCGTGTGTCACCGGCCTGAGGGTCTGGAGCAGCTGCAGGAGCAAACCAAATTCACGCGCAAGGAGTTGCAGGTCC
TGTACCGGGGCTTCAAGAACGAATGTCCCAGCGGAATTGTCAATGAGGAGAACTTCAAGCAGATTTACTCCCAGTTCTTT
CCTCAAGGAGACTCCAGCACCTATGCCACTTTTCTCTTCAATGCCTTTGACACCAACCATGATGGCTCGGTCAGTTTTGA
GGACTTTGTGGCTGGTTTGTCCGTGATTCTTCGGGGAACTGTAGATGACAGGCTTAATTGGGCCTTCAACCTGTATGACC
TTAACAAGGACGGCTGCATCACCAAGGAGGAAATGCTTGACATCATGAAGTCCATCTATGACATGATGGGCAAGTACACG
TACCCTGCACTCCGGGAGGAGGCCCCAAGGGAACACGTGGAGAGCTTCTTCCAGAAGATGGACAGAAACAAGGATGGTGT
GGTGACCATTGAGGAATTCATTGAGTCTTGTCAAAAGGATGAGAACATCATGAGGTCCATGCAGCTCTTTGACAATGTCA
TCTAGCCCCCAGGAGAGGGGGTCAGTGTTTCCTGGGGGGACCATGCTCTAACCCTAGTCCAGGCGGACCTCACCCTTCTC
TTCCCAGGTCTATCCTCATCCTACGCCTCCCTGGGGGCTGGAGGGATCCAAGAGCTTGGGGATTCAGTAGTCCAGATCTC
TGGAGCTGAAGGGGCCAGAGAGTGGGCAGAGTGCATCTCGGGGGGTGTTCCCAACTCCCACCAGCTCTCACCCCCTTCCT
GCCTGACACCCAGTGTTGAGAGTGCCCCTCCTGTAGGAATTGAGCGGTTCCCCACCTCCTACCCTACTCTAGAAACACAC
TAGAGCGATGTCTCCTGCTATGGTGCTTCCCCCATCCCTGACCTCATAAACATTTCCCCTAAGACTCCCCTCTCAGAGAG
AATGCTCCATTCTTGGCACTGGCTGGCTTCTCAGACCAGCCATTGAGAGCCCTGTGGGAGGGGGACAAGAATGTATAGGG
AGAAATCTTGGGCCTGAGTCAATGGATAGGTCCTAGGAGGTGGGTGGGGTTGAGAATAGAAGGGCCTGGACAGATTATGA
TTGCTCAGGCATACCAGGTTATAGCTCCAAGTTCCACAGGTCTGCTACCACAGGCCATCAAAATATAAGTTTCCAGGCTT
TGCAGAAGACCTTGTCTCCTTAGAAATGCCCCAGAAATTTTCCACACCCTCCTCGGTATCCATGGAGAGCCTGGGGCCAG
ATATCTGGCTCATCTCTGGCATTGCTTCCTCTCCTTCCTTCCTGCATGTGTTGGTGGTGGTTGTGGTGGGGGAATGTGGA
TGGGGGATGTCCTGGCTGATGCCTGCCAAAATTTCATCCCACCCTCCTTGCTTATCGTCCCTGTTTTGAGGGCTATGACT
TGAGTTTTTGTTTCCCATGTTCTCTATAGACTTGGGACCTTCCTGAACTTGGGGCCTATCACTCCCCACAGTGGATGCCT
TAGAAGGGAGAGGGAAGGAGGGAGGCAGGCATAGC

Fig. 10A

HUMAN 9QM PROTEIN

MRGQGRKESLSDSRDLDGSYDQLTGHPPGPTKKALKQRFLKLLPCCGPQALPSVSENSVDDEFELSTVCHRPEGLEQLQE

QTKFTRKELQVLYRGFKNECPSGIVNEENFKQIYSQFFPQGDSSTYATFLFNAFDTNHDGSVSFEDFVAGLSVILRGTVD

DRLNWAFNLYDLNKDGCITKEEMLDIMKSIYDMMGKYTYPALREEAPREHVESFFQKMDRNKDGVVTIEEFIESCQKDEN

IMRSMQLFDNVI.

Fig. 10B

RAT 9QM DNA (CD: 214-972)
CTCACTTGCTGCCCAAGGCTCCTGCTCCTGCCCCAGGACTCTGAGGTGGGCCCTAAAACCCAGCGCTGTCTAAAGAAAAG
CCTTGCCAGCCCCTACTCCCGGCCCCCAACCCCAGCAGGTCGCTGCGCCGCCAGGGGGCGCTGTGTGAGCGCCCTATTCT
GGCCACCCGGCGCCCCCTCCCACGGCCCAGGCGGGAGCGGGGCGCCGGGGGCCATGCGGGGCCAAGGCAGAAAGGAGAGT
TTGTCCGAATCCCGAGATCTGGACGGCTCCTATGACCAGCTTACGGGCCACCCTCCAGGGCCCAGTAAAAAAGCCCTGAA
GCAGCGTTTCCTCAAGCTGCTGCCGTGCTGCGGGCCCCAAGCCCTGCCCTCAGTCAGTGAAAACAGCGTAGAGGATGAGT
TTGAATTATCCACGGTGTGTCACCGACCTGAGGGCCTGGAACAACTCCAGGAACAGACCAAGTTCACACGCAGAGAGCTG
CAGGTCCTGTACCGAGGCTTCAAGAACGAATGCCCCAGTGGGATTGTCAACGAGGAGAACTTCAAGCAGATTTATTCTCA
GTTCTTTCCCCAAGGAGACTCCAGCAACTATGCTACTTTTCTCTTCAATGCCTTTGACACCAACCACGATGGCTCTGTCA
GTTTTGAGGACTTTGTGGCTGGTTTGTCGGTGATTCTTCGGGGACCATAGATGATAGACTGAGCTGGGCTTTCAACTTA
TATGACCTCAACAAGGACGGCTGTATCACAAAGGAGGAAATGCTTGACATTATGAAGTCCATCTATGACATGATGGGCAA
GTACACATACCCTGCCCTCCGGGAGGAGGCCCCAAGAGAACACGTGGAGAGCTTCTTCCAGAAGATGGACAGGAACAAGG
ACGGCGTGGTGACCATCGAGGAATTCATCGAGTCTTGTCAACAGGACGAGAACATCATGAGGTCCATGCAGCTCTTTGAT
AATGTCATCTAGCTCCCCAGGGAGAGGGGTTAGTGTGTCCTAGGGTGACCAGGCTGTAGTCCTAGTCCAGACGAACCTAA
CCCTCTCTCTCCAGGCCTGTCCTCATCTTACCTGTACCCTGGGGGCTGTAGGGATTCAATATCCTGGGGCTTCAGTAGTC
CAGATCCCTGAGCTAAGTCACAAAAGTAGGCAAGAGTAGGCAAGCTAAATCTGGGGGCTTCCCAACCCCCGACAGCTCTC
ACCCCTTCTCAACTGATACCTAGTGCTGAGGACACCCCTGGTGTAGGGACCAAGTGGTTCTCCACCTTCTAGTCCCACTC
TAGAAACCACATTAGACAGAAGGTCTCCTGCTATGGTGCTTTCCCCATCCCTAATCTCTTAGATTTTCCTCAAGACTCCC
TTCTCAGAGAACACGCTCTGTCCATGTCCCCAGCTGGCTTCTCAGCCTAGCCTTTGAGGGCCCTGTGGGGAGGCGGGGAC
AAGAAAGCAGAAAAGTCTTGGCCCCGAGCCAGTGGTTAGGTCCTAGGAATTGGCTGGAGTGGAGGCCAGAAAGCCTGGGC
AGATGATGAGAGCCCAGCTGGGCTGTCACTGCAGGTTCCGGGGCCTACAGCCCTGGGTCAGCAGAGTATGAGTTCCCAGA
CTTTCCAGAAGGTCCTTAGCAATGTCCCAGAAATTCACCGTACACTTCTCAGTGTCTTAGGAGGGCCCGGGATCCAGATG
TCTGGTTCATCCCTGAATCCTCTCCCTCCTTCTTGCTCGTATGGTGGGAGTGGTGGCCAGGGGAAGATGAGTGGTGTCCC
GGATGATGCCTGTCAAGGTCCCACCTCCCCTCCGGCTGTTCTCATGACAGCTGTTTGGTTCTCCATGACCCCTATCTAGA
TGTAGAGGCATGGAGTGAGTCAGGGATTTCCCGAACTTGAGTTTTACCACTCCTCCTAGTGGCTGCCTTAGGGGAATGGG
AAGAACCCAGTGTGGGGGCACCCATTAGAATCTTTGCCCGGCTCCTCACAATGCCCTAGGGTCCCCTAGGGTACCCGCTC
CCTCTGTTTAGTCTACCCAGAGATGCTCCTGAGCTCACCTAGAGGGTAGGGACGGTAGGCTCCAGGTCCAACCTCTCCAG
GTCAGCACCCTGCCATGCTGCTGCTCCTCATTAACAAACCTGCTTGTCTCCTCCTGCGCCCCTTCTCAGTCAGCCAGGGT
CTGAGGGGAAGGGCCTCCCGTTTCCCCATCCGTCAGACATGGTTGACTGCTTTGCATTTTGGGCTCTTCTATCTATTTTG
TAAAATAAGACATCAGATCCAATAAAACACACGGCTATGCACAAAAAAAAAAAAAAAAAAA

RAT 9QM PROTEIN
MRGQGRKESLSESRDLDGSYDQLTGHPPGPSKKALKQRFLKLLPCCGPQALPSVSENSVEDEFELSTVCHRPEGLEQLQE
QTKFTRRELQVLYRGFKNECPSGIVNEENFKQIYSQFFPQGDSSNYATFLFNAFDTNHDGSVSFEDFVAGLSVILRGTID
DRLSWAFNLYDLNKDGCITKEEMLDIMKSIYDMMGKYTYPALREEAPREHVESFFQKMDRNKDGVVTIEEFIESCQQDEN
IMRSMQLFDNVI.

Fig. 11

HUMAN 9QS DNA (CD: 207-869)

CTCACCTGCTGCCTAGTGTTCCCTCTCCTGCTCCAGGACCTCCGGGTAGACCTCAGACCCCGGGCCCATTCCCAGACTCA
GCCTCAGCCCGGACTTCCCCAGCCCCGACAGCACAGTAGGCCGCCAGGGGGCGCCGTGTGAGCGCCCTATCCCGGCCACC
CGGCGCCCCCTCCCACGGCCCGGGCGGGAGCGGGGCGCCGGGGGCCATGCGGGGCCAGGGCCGCAAGGAGAGTTTGTCCG
ATTCCCGAGACCTGGACGGCTCCTACGACCAGCTCACGGACAGCGTGGACGATGAATTTGAATTGTCCACCGTGTGTCAC
CGGCCTGAGGGTCTGGAGCAGCTGCAGGAGCAAACCAAATTCACGCGCAAGGAGTTGCAGGTCCTGTACCGGGGCTTCAA
GAACGAATGTCCCAGCGGAATTGTCAATGAGGAGAACTTCAAGCAGATTTACTCCCAGTTCTTTCCTCAAGGAGACTCCA
GCACCTATGCCACTTTTCTCTTCAATGCCTTTGACACCAACCATGATGGCTCGGTCAGTTTTGAGGACTTTGTGGCTGGT
TTGTCCGTGATTCTTCGGGGAACTGTAGATGACAGGCTTAATTGGGCCTTCAACCTGTATGACCTTAACAAGGACGGCTG
CATCACCAAGGAGGAAATGCTTGACATCATGAAGTCCATCTATGACATGATGGGCAAGTACACGTACCCTGCACTCCGGG
AGGAGGCCCCAAGGGAACACGTGGAGAGCTTCTTCCAGAAGATGGACAGAAACAAGGATGGTGTGGTGACCATTGAGGAA
TTCATTGAGTCTTGTCAAAAGGATGAGAACATCATGAGGTCCATGCAGCTCTTTGACAATGTCATCTAGCCCCCAGGAGA
GGGGGTCAGTGTTTCCTGGGGGGACCATGCTCTAACCCTAGTCCAGGCGGACCTCACCCTTCTCTTCCCAGGTCTATCCT
CATCCTACGCCTCCCTGGGGGCTGGAGGGATCCAAGAGCTTGGGGATTCAGTAGTCCAGATCTCTGGAGCTGAAGGGGCC
AGAGAGTGGGCAGAGTGCATCTCGGGGGGTGTTCCCAACTCCCACCAGCTCTCACCCCCTTCCTGCCTGACACCCAGTGT
TGAGAGTGCCCCTCCTGTAGGAATTGAGCGGTTCCCCACCTCCTACCCTACTCTAGAAACACACTAGAGCGATGTCTCCT
GCTATGGTGCTTCCCCCATCCCTGACCTCATAAACATTTCCCCTAAGACTCCCCTCTCAGAGAGAATGCTCCATTCTTGG
CACTGGCTGGCTTCTCAGACCAGCCATTGAGAGCCCTGTGGGAGGGGGACAAGAATGTATAGGGAGAAATCTTGGGCCTG
AGTCAATGGATAGGTCCTAGGAGGTGGGTGGGGTTGAGAATAGAAGGGCCTGGACAGATTATGATTGCTCAGGCATACCA
GGTTATAGCTCCAAGTTCCACAGGTCTGCTACCACAGGCCATCAAAATATAAGTTTCCAGGCTTTGCAGAAGACCTTGTC
TCCTTAGAAATGCCCCAGAAATTTTCCACACCCTCCTCGGTATCCATGGAGAGCCTGGGGCCAGATATCTGGCTCATCTC
TGGCATTGCTTCCTCTCCTTCCTTCCTGCATGTGTTGGTGGTGGTTGTGGTGGGGAATGTGGATGGGGGATGTCCTGGC
TGATGCCTGCCAAAATTTCATCCCACCCTCCTTGCTTATCGTCCCTGTTTTGAGGGCTATGACTTGAGTTTTTGTTTCCC
ATGTTCTCTATAGACTTGGGACCTTCCTGAACTTGGGGCCTATCACTCCCCACAGTGGATGCCTTAGAAGGGAGAGGGAA
GGAGGGAGGCAGGCATAGC

Fig. 12

MONKEY 9QS DNA (CD: 133-795)
CCCACGCGTCCGCCCACGCGTCCGCGGACGCGTGGGGTGCACTAGGCCGCCAGGGGGCGCCGTGTGAGCGCCCTATCCCG
GCCACCCGGCGCCCCCTCCCACGGACCGGGCGGGAGCGGGGCGCCGGGGGCCATGCGGGGCCAGGGCCGCAAGGAGAGTT
TGTCCGATTCCCGAGACCTGGACGGATCCTACGACCAGCTCACGGACAGCGTGGAGGATGAATTTGAATTGTCCACCGTG
TGTCACCGGCCTGAGGGTCTGGAGCAGCTGCAGGAGCAAACCAAATTCACGCGCAAGGAGTTGCAGGTCCTGTACCGGGG
CTTCAAGAACGAATGTCCGAGCGGAATTGTCAATGAGGAGAACTTCAAGCAAATTTACTCCCAGTTCTTTCCTCAAGGAG
ACTCCAGCACCTATGCCACTTTTCTCTTCAATGCCTTTGACACCAACCATGATGGCTCGGTCAGTTTTGAGGACTTTGTG
GCTGGTTTGTCCGTGATTCTTCGGGGAACTGTAGATGACAGGCTTAATTGGGCCTTCAACTTGTATGACCTCAACAAGGA
CGGCTGCATCACCAAGGAGGAAATGCTTGACATCATGAAGTCCATCTATGACATGATGGGCAAGTACACATACCCTGCAC
TCCGGGAGGAGGCCCCAAGGGAACATGTGGAGAACTTCTTCCAGAAGATGGACAGAAACAAGGATGGCGTGGTGACCATT
GAGGAATTCATTGAGTCTTGTCAAAAGGATGAGAACATCATGAGGTCCATGCAGCTCTTTGACAATGTCATCTAGCCCCC
AGGAGAGGGGGTCAGTGTTTCCTGGGGGGACCATGCTCTAACCCTAGTCCAGGTGGACCTCACCCTTCTCTTCCCAGGTC
TATCCTTGTCCTAGGCCTCCCTGGGGGCTGGAGGGATCCAAGAGCTTGGGGATTCAGTAGTCCAGATCTCTGGAGCTGAA
GGGGCCAGAGAGTGGGCAGAGTGCATCTTGGGGGGTGTTCCCAACTCCCACCAGCTTTCACCCGCTTCCTGCCTGACACC
CAGTGTTGAGAGTGCCCCTCCTGTAGGAACTGAGTGGTTCCCCACCTCCTACCCCCACTCTAGAAACACACTAGACAGAT
GTCTCCTGCTATGGTGCTTCCCCCATCCCTGACTTCATAAACATTTCCCCTAAAACTCCCTTCTCAGAGAGAATGCTCCA
TTCTTGGCACTGGCTGGCTTCTCAGACCAGCCTTTGAGAGCCCTGTGGGAGGGGGACAAGAATGTATAGGGGAGAAATCT
TGGGCCTGAGTCAATGGATAGGTCCTAGGAGGTGGCTGGGGTTGAGAATAGAAAGGCCTGGACACAATGTGATTGCTCAG
GCATACCAAGTTATAGCTCCAAGTTCCACAGGTCTGCTACCACAGGCCATCAAAATATAAGTTTCCAGGCTTTGCAGAAG
ACCTTGTCTCCTTGGAAATGCCCCAGATATTTTCCATACCCTCCTCGATATCCATGGAGAGCCTGGGGCTAGATATCTGG
CATATCCCTGGCATTGCTTCCTCTCCTTCCTTCCTGCATGTGTTGGTGGTGGTTGTGGCAGGGGAATGTGGATAGGAGAT
GTCCTGGCAGATGCCTGCCAAAGTTTCATCCCACCCTCCCTGCTCATCGCCCCTGTTTTGAGGGCTGTGACTTGAGTTTT
TGTTTCCCATGTTCTCTATAGACTTGGGACCTTCCTGAACTTGGGGCCTATCACTCCCCACAGTGGATGCCTTAGAAGGG
AGAGGGAAGGAGGGAGGCAGGCATAGCATCTGAACCCAGTGTGGGGCATTCACTAGGATCTTCAATCAACCCGGGCTCT
CCCCAACCCCCCAGATAACCTCCTCAGTTCCCTAGAGTCTCCTCTTGCTCTACTCAATCTACCCAGAGATGCCCCTTAGC
ACACTCAGAGGGCAGGGACCATAGGACCCAGGTTCCAACCCCATTGTCAGCACCCCAGCCATGCTGCCATCCCTTAGCAC
ACCTGCTCGTCCCATTCAGCTTACCCTCCCAGTCAGCCAGAATCTGAGGGGAGGGCCCCAGAGAGCCCCCTTCCCCATC
AGAAGACTGTTGACTGCTTTGCATTTTGGGCTCTTCTATATATTTTGTAAAATAAGAACTATACCAGATCTAATAAAACA
CAATGGCTATGCAAAAAAAAAAAAAAAAAAAA

MONKEY 9QS PROTEIN
MRGQGRKESLSDSRDLDGSYDQLTDSVEDEFELSTVCHRPEGLEQLQEQTKFTRKELQVLYRGFKNECPSGIVNEENFKQ
IYSQFFPQGDSSTYATFLFNAFDTNHDGSVSFEDFVAGLSVILRGTVDDRLNWAFNLYDLNKDGCITKEEMLDIMKSIYD
MMGKYTYPALREEAPREHVENFFQKMDRNKDGVVTIEEFIESCQKDENIMRSMQLFDNVI

Fig. 13

RAT 9QC DNA (CD: 208-966)

TGCTGCCCAAGGCTCCTGCTCCTGCCCCAGGACTCTGAGGTGGGCCCTAAAACCCAGCGCTCTCTAAAGAAAAGCCTTGC
CAGCCCCTACTCCCGGCCCCCAACCCCAGCAGGTCGCTGCGCCGCCAGGGGGCGCTGTGTGAGCGCCCTATTCTGGCCAC
CCGGCGCCCCCTCCCACGGCCCAGGCGGGAGCGGGGCGCCGGGGGCCATGCGGGGCCAAGGCAGAAAGGAGAGTTTGTCC
GAATCCCGAGATCTGGACGGCTCCTATGACCAGCTTACGGGCCACCCTCCAGGGCCCAGTAAAAAAGCCCTGAAGCAGCG
TTTCCTCAAGCTGCTGCCGTGCTGCGGGCCCCAAGCCCTGCCCTCAGTCAGTGAAAACAGCGTAGAGGATGAGTTTGAAT
TATCCACGGTGTGTCACCGACCTGAGGGCCTGGAACAACTCCAGGAACAGACCAAGTTCACACGCAGAGAGCTGCAGGTC
CTGTACCGAGGCTTCAAGAACGAATGCCCCAGTGGGATTGTCAACGAGGAGAACTTCAAGCAGATTTATTCTCAGTTCTT
TCCCCAAGGAGACTCCAGCAACTATGCTACTTTTCTCTTCAATGCCTTTGACACCAACCACGATGGCTCTGTCAGTTTTG
AGGACTTTGTGGCTGGTTTGTCGGTGATTCTTCGGGGGACCATAGATGATAGACTGAGCTGGGCTTTCAACTTATATGAC
CTCAACAAGGACGGCTGTATCACAAAGGAGGAAATGCTTGACATTATGAAGTCCATCTATGACATGATGGGCAAGTACAC
ATACCCTGCCCTCCGGGAGGAGGCCCCAAGAGAACACGTGGAGAGCTTCTTCCAGAAGATGGACAGGAACAAGGACGGCG
TGGTGACCATCGAGGAATTCATCGAGTCTTGTCAACAGGACGAGAACATCATGAGGTCCATGCAGCTCTCACCCCTTCTC
AACTGATACCTAGTGCTGAGGACACCCCTGGTGTAGGGACCAAGTGGTTCTCCACCTTCTAGTCCCACTCTAGAAACCAC
ATTAGACAGAAGGTCTCCTGCTATGGTGCTTTCCCCATCCCTAATCTCTTAGATTTTCCTCAAGACTCCCTTCTCAGAGA
ACACGCTCTGTCCATGTCCCCAGCTGGCTTCTCAGCCTAGCCTTTGAGGGCCCTGTGGGGAGGCGGGGACAAGAAAGCAG
AAAAGTCTTGGCCCCGAGCCAGTGGTTAGGTCCTAGGAATTGGCTGGAGTGGAGGCCAGAAAGCCTGGGCAGATGATGAG
AGCCCAGCTGGGCTGTCACTGCAGGTTCCGGGGCCTACAGCCCTGGGTCAGCAGAGTATGAGTTCCCAGACTTTCCAGAA
GGTCCTTAGCAATGTCCCAGAAATTCACCGTACACTTCTCAGTGTCTTAGGAGGGCCCGGGATCCAGATGTCTGGTTCAT
CCCTGAATCCTCTCCCTCCTTCTTGCTCGTATGGTGGGAGTGGTGGCCAGGGGAAGATGAGTGGTGTCCCGGATGATGCC
TGTCAAGGTCCCACCTCCCCTCCGGCTGTTCTCATGACAGCTGTTTGGTTCTCCATGACCCCTATCTAGATGTAGAGGCA
TGGAGTGAGTCAGGGATTTCCCGAACTTGAGTTTTACCACTCCTCCTAGTGGCTGCCTTAGGGGAATGGGAAGAACCCAG
TGTGGGGGCACCCATTAGAATCTTTGCCCGGCTCCTCACAATGCCCTAGGGTCCCCTAGGGTACCCGCTCCCTCTGTTTA
GTCTACCCAGAGATGCTCCTGAGCTCACCTAGAGGGTAGGGACGGTAGGCTCCAGGTCCAACCTCTCCAGGTCAGCACCC
TGCCATGCTGCTGCTCCTCATTAACAAACCTGCTTGTCTCCTCCTGCGCCCCTTCTCAGTCAGCCAGGGTCTGAGGGGAA
GGGCCTCCCGTTTCCCCATCCGTCAGACATGGTTGACTGCTTTGCATTTTGGGCTCTTCTATCTATTTTGTAAAATAAGA
CATCAGATCCAATAAAACACACGGCTATGCACAAAAAAAAAAAAAAAAAAAAAAAAAA

RAT 9QC PROTEIN

MRGQGRKESLSESRDLDGSTDQLTGHPPGPSKKALKQRFLKLLPCCGPQALPSVSENSVEDEFELSTVCHRPEGLEQLQE
QTKFTRRELQVLYRGFKNECPSGIVNEENFKQIYSQFFPQGDSSNYATFLFNAFDTNHDGSVSFEDFVAGLSVILRGTID
DRLSWAFNLYDLNKDGCITKEEMLDIMKSIYDMMGKYTYPALREEAPREHVESFFQKMDRNKDGVVTIEEFIESCQQDEN
IMRSMQLSPLLN.

Fig. 14

RAT 8T (9Q SPLICE VARAIANT) DNA (MAY NOT BE FULL LENGTH, CD: 1-678)
ATGAACCACTGCCCTCGCAGGTGCCGGAGCCCGTTGGGGCAGGCAGCTCGATCTCTCTACCAGTTGGTAACTGGGTCGCT
GTCGCCAGACAGCGTAGAGGATGAGTTTGAATTATCCACGGTGTGTCACCGACCTGAGGGCCTGGAACAACTCCAGGAAC
AGACCAAGTTCACACGCAGAGAGCTGCAGGTCCTGTACCGAGGCTTCAAGAACGAATGCCCCAGTGGGATTGTCAACGAG
GAGAACTTCAAGCAGATTTATTCTCAGTTCTTTCCCCAAGGAGACTCCAGCAACTATGCTACTTTTCTCTTCAATGCCTT
TGACACCAACCACGATGGCTCTGTCAGTTTTGAGGACTTTGTGGCTGGTTTGTCGGTGATTCTTCGGGGGACCATAGATG
ATAGACTGAGCTGGGCTTTCAACTTATATGACCTCAACAAGGACGGCTGTATCACAAAGGAGGAAATGCTTGACATTATG
AAGTCCATCTATGACATGATGGGCAAGTACACATACCCTGCCCTCCGGGAGGAGGCCCCAAGAGAACACGTGGAGAGCTT
CTTCCAGAAGATGGACAGGAACAAGGACGGCGTGGTGACCATCGAGGAATTCATCGAGTCTTGTCAACAGGACGAGAACA
TCATGAGGTCCATGCAGCTCTTTGATAATGTCATCTAGCTCCCCAGGGAGAGGGGTTAGTGTGTCCTAGGGTGACCAGGC
TGTAGTCCTAGTCCAGACGAACCTAACCCTCTCTCTCCAGGCCTGTCCTCATCTTACCTGTACCCTGGGGGCTGTAGGGA
TTCAATATCCTGGGGCTTCAGTAGTCCAGATCCCTGAGCTAAGTCACAAAAGTAGGCAAGAGTAGGCAAGCTAAATCTGG
GGGCTTCCCAACCCCCGACAGCTCTCACCCCTTCTCAACTGATACCTAGTGCTGAGGACACCCCTGGTGTAGGGACCAAG
TGGTTCTCCACCTTCTAGTCCCACTCTAGAAACCACATTAGACAGAAGGTCTCCTGCTATGGTGCTTTCCCCATCCCTAA
TCTCTTAGATTTTCCTCAAGACTCCCTTCTCAGAGAACACGCTCTGTCCATGCCCCAGCTGGCTTCTCAGCCTAGCCTT
TGAGGGCCCTGTGGGGAGGCGGGGACAAGAAAGCAGAAAAGTCTTGGCCCCGAGCTAGTGGTTAGGTCCTAGGAATTGGC
TGGAGTGGAGGCCAGAAAGCCTGGGCAGATGATGAGAGCCCAGCTGGGCTGTCACTGCAGGTTCCAGGGCCTACAGCCCT
GGGTCAGCAGAGTATGAGTTCCCAGACTTTCCAGAAGGTCCTTAGCAATGTCCCAGAAATTCACCATACACTTCTCAGTG
TCCCGGATGATGCCTGTCAAGGTCCCACCTCCCCTCCGGCTGTTCTCATGACAGCTGTTTGGTTCTCCATGACCCCTATC
TAGATGTAGAGGCATGGAGTGAGTCAGGGATTTCCCGAACTTGAGTTTTACCACTCCTCCTAGTGGCTGCCTTAGGGGAA
TGGGAAGAACCCAGTGTGGGGGCACCCATTAGAATCTTTGCCCGGTTCCTCACAATGCCCTAGGGTCCCCTAGGGTACCC
GCTCCCTCTGTTTAGTCTACCCAGAGATGCTCCTGAGCTCACCTAGAGGGTAGGGACGGTAGGCTCCAGGTCCAACCTCT
CCAGGTCAGCACCCTGCCATGCTGCTGCTCCTCATTAACAAACCTGCTTGTCTCCTCCTGCGCCCCTTCTCAGTCAGCCA
GGGTCTGAGGGGAAGGGCCTCCCGTTTCCCCATCCGTCAGACATGGTTGACTGCTTTGCATTTTGGGCTCTTCTATCTAT
TTTGTAAAATAAGACATCAGATCCAATAAAACACACGGCTATGCACAAAAAAAAAAAAAAAAAA

RAT 8T (9Q SPLICE VARAIANT) PROTEIN (MAY NOT BE FULL LENGTH)
MNHCPRRCRSPLGQAARSLYQLVTGSLSPDSVEDEFELSTVCHRPEGLEQLQEQTKFTRRELQVLYRGFKNECPSGIVNE
ENFKQIYSQFFPQGDSSNYATFLFNAFDTNHDGSVSFEDFVAGLSVILRGTIDDRLSWAFNLYDLNKDGCITKEEMLDIM
KSIYDMMGKYTYPALREEAPREHVESFFQKMDRNKDGVVTIEEFIESCQQDENIMRSMQLFDNVI

Fig. 15

>human KChIP3 cds = 1-7
ATGCAGCCGGCTAAGGAAGTGACAAAGGCGTCGGACGGCAGCCTCCTGGGGGACCTCGGGC
ACACACCACTTAGCAAGAA
GGAGGGTATCAAGTGGCAGAGGCCGAGGCTCAGCCGCCAGGCTTTGATGAGATGCTGCCTG
GTCAAGTGGATCCTGTCCA
GCACAGCCCCACAGGGCTCAGATAGCAGCGACAGTGAGCTGGAGCTGTCCACGGTGCGCCA
CCAGCCAGAGGGGCTGGAC
CAGCTGCAGGCCCAGACCAAGTTCACCAAGAAGGAGCTGCAGTCTCTCTACAGGGGCTTTA
AGAATGAGTGTCCCACGGG
CCTGGTGGACGAAGACACCTTCAAACTCATTTACGCGCAGTTCTTCCCTCAGGGAGATGCCA
CCACCTATGCACACTTCC
TCTTCAACGCCTTTGATGCGGACGGGAACGGGGCCATCCACTTTGAGGACTTTGTGGTTGGC
CTCTCCATCCTGCTGCGG
GGCACAGTCCACGAGAAGCTCAAGTGGGCCTTTAATCTCTACGACATTAACAAGGATGGCT
ACATCACCAAAGAGGAGAT
GCTGGCCATCATGAAGTCCATCTATGACATGATGGGCCGCCACACCTACCCCATCCTGCGGG
AGGACGCGCCGGCGGAGC
ACGTGGAGAGGTTCTTCGAGAAAATGGACCGGAACCAGGATGGGGTAGTGACCATTGAAGA
GTTCCTGGAGGCCTGTCAG
AAGGATGAGAACATCATGAGCTCCATGCAGCTGTTTGAGAATGTCATCTAGgacacgtccaaaggagt
gcatggccacag
ccacctccaccccaagaaacctccatcctgccaggagcagcctccaagaaacttttaaaaaatagatttgcaaaaagtg
aacagattgctacacacacacacacacacacacacacacacacacacacacagccattcatctgggctggcagaggggac
agagttcagggaggggctgagtctggctaggggccgagtccaggagccccagccagcccttcccaggccagcgaggcgag
gctgcctctgggtgagtggctgacagagcaggtctgcaggccaccagctgctggatgtcaccaagaaggggctcgagtgc
ccctgcaggggagggtccaatctccggtgtgagcccacctcgtcccgttctccattctgctttcttgccacacagtgggc
cggccccaggctcccctggtctcctccccgtagccactctctgcccactacctatgcttctagaaagcccctcacctcag
gaccccagagggaccagctggggggcaggggggagaggggggtaatggaggccaagcctgcagctttctggaaattcttcc
ctgggggtcccaggatcccctgctactccactgacctggaagagctgggtaccaggccacccactgtggggcaagcctga
gtggtgaggggccactgggcccattctccctccatggcaggaaggcgggggatttcaagtttagggattgggtcgtggt
ggagaatctgagggcactctctgccagctccacagggtgggatgagcctctccttgccccagtcctggttcagtgggaat
gcagtgggtggggctgtacacaccctccagcacagactgttccctccaaggtcctcttaggtcccgggaggaacgtggtt
cagagactggcagccagggagcccggggcagagctcagaggagtctgggaaggggcgtgtccctcctcttcctgtagtgc
ccctcccatggcccagcagcttggctgagccccctctcctgaagcagtgtcgccgtccctctgccttgcacaaaaagcac
aagcattccttagcagctcaggcgcagccctagtgggagcccagcacactgcttctcggaggccaggccctcctgctggc
tgaggcttgggcccagtagccccaatatggtggccctggggaagaggccttgggggtctgctctgtgcctgggatcagtg
gggcccccaaagcccagcccggctgaccaacattcaaaagcacaaaccctggggactctgcttggctgtcccctccatctg
gggatggagaatgccagcccaaagctggagccaatggtgagggctgagaggggctgtggctgggtggtcagcagaaacccc
caggaggagagagatgctgctcccgcctgattgggggcctcacccagaaggaacccggtcccaggccgcatggcccctcca
ggaacattcccacataatacattccatcacagccagcccagctccactcagggctggcccgggggagtccccgtgtgcccc
aagaggctagccccagggtgagcagggccctcagaggaaaggcagtatggcggaggccatgggggcccctcggcattcac
acacagcctggcctcccctgcggagctgcatggacgcctggctccaggatccaggctgactgggggcctctgcctccagg
agggcatcagctttccctggctcagggatcttctcctccctcacccgctgcccagccctcccagctggtgtcactctg
cctctaaggccaaggcctcaggagagcatcaccaccacacccctgccggccttggccttggggccagactggctgcacag
cccaaccaggaggggtctgcctcccacgctgggacacagaccggaagcatgtctgcatggcagaagcgtctcccttggcc
acggcctgggagggtggttcctgttctcagcatccactaatattcagtcctgtatatttttaataaaataaacttgacaaa
ggaaaaaaaaaaaaaaaaaattcctgcggccgcgttctcca >human KChIP3
MQPAKEVTKASDGSLLGDLGHTPLSKKEGIKWQRPRLSRQALMRCCLVKWILSSTAPQGSDSSD
SELELSTVRHQPEGLD
QLQAQTKFTKKELQSLYRGFKNECPTGLVDEDTFKLIYAQFFPQGDATTYAHFLFNAFDADGNG
AIHFEDFVVGLSILLR
GTVHEKLKWAFNLYDINKDGYITKEEMLAIMKSIYDMMGRHTYPILREDAPAEHVERFFEKMD
RNQDGVVTIEEFLEACQ
KDENIMSSMQLFENVI

Fig. 16

RAT P19 DNA (FIRST-PASS, PARTIAL; CD: 1-330)
TTTGAGGACTTTGTGGTTGGGCTCTCCATCCTGCTTCGAGGGACCGTCCATGAGAAGCTCAAGTGGGCCTTCAATCTCTA
CGACATCAACAAGGACGGTTACATCACCAAAGAGGAGATGCTGGCCATCATGAAGTCCATCTACGACATGATGGGCCGCC
ACACCTACCCTATCCTGCGGGAGGACGCACCTCTGGAGCATGTGGAGAGGTTCTTCCAGAAAATGGACAGGAACCAGGAT
GGAGTAGTGACTATTGATGAATTTCTGGAGACTTGTCAGAAGGACGAGAACATCATGAGCTCCATGCAGCTGTTTGAGAA
CGTCATCTAGGACATGTAGGAGGGGACCCTGGGTGGCCATGGGTTCTCAACCCAGAGAAGCCTCAATCCTGACAGGAGAA
GCCTCTATGAGAAACATTTTTCTAATATATTTGCAAAAAGTG

RAT P19 PROTEIN (PARTIAL)
FEDFVVGLSILLRGTVHEKLKWAFNLYDINKDGYITKEEMLAIMKSIYDMMGRHTYPILREDAPLEHVERFFQKMDRNQD
GVVTIDEFLETCQKDENIMSSMQLFENVI

Fig. 17

MOUSE P19 DNA (CD: 49-819)
CGGGCTGCAAAGCGGGAAGATTAGTGACGGTCCCTTTCAGCAGCAGAGATGCAGAGGACCAAGGAAGCCGTGAAGGCATC
AGATGGCAACCTCCTGGGAGATCCTGGGCGCATACCACTGAGCAAGAGGGAAAGCATCAAGTGGCAAAGGCCACGGTTCA
CCCGCCAGGCCCTGATGCGTTGCTGCTTAATCAAGTGGATCCTGTCCAGTGCTGCCCCACAAGGCTCAGACAGCAGTGAC
AGTGAACTGGAGTTATCCACGGTGCGCCATCAGCCAGAGGGCTTGGACCAGCTACAAGCTCAGACCAAGTTCACCAAGAA
GGAGCTGCAGTCCCTTTACCGAGGCTTCAAGAATGAGTGTCCCACAGGCCTGGTGGATGAAGACACCTTCAAACTCATTT
ATTCCCAGTTCTTCCCTCAGGGAGATGCCACCACCTATGCACACTTCCTCTTCAATGCCTTTGATGCTGATGGGAACGGG
GCCATCCACTTTGAGGACTTTGTGGTTGGGCTCTCCATCCTGCTTCGAGGGACGGTCCATGAGAAGCTCAAGTGGGCCTT
CAATCTCTATGACATTAACAAGGATGGTTGCATCACCAAGGAGGAGATGCTGGCCATCATGAAGTCCATCTACGACATGA
TGGGCCGCCACACCTACCCCATCCTGCGGGAGGATGCACCCCTGGAGCATGTGGAGAGGTTCTTTCAGAAAATGGACAGG
AACCAGGATGGAGTGGTGACCATTGATGAATTTCTGGAGACTTGTCAGAAGGATGAGAACATCATGAACTCCATGCAGCT
GTTTGAGAACGTCATCTAGGACATGTGGGAGGGGACCCCAGTGGTCATTGCTTCTCAACCCAGAGAAGCCTCAATCCTGA
CAGGAGAAGCCTCTATGAGAAACATTTTTCTAATATATTTGCAAAAAGTGAGCAGTTTACTTCCAAGACACAGCCACCGT
CACACACAGACACAGACATACAGACACACACACACACACACACATGGTTCCTCTGGCTTGGCCAAGGAAGTGGCAGCC
AGAAGGCACCCCGCCTATTCCTAGGTCAATAAAAAAGGCTGCCTCTGGGATGGCCAGCCCTGGCTAGATGTTACCCACA
AGGAACTCAGAGATCGAGAGGACCAGGTCTACAAAGCTAAGGTCCCTGTGTCTTTTCTACCACTCGGGAGATCAAACTAC
TCCCTGCCTATGGACCCATGCTCTTAGGAAGCTCCCAGAAACTCCAAGGGGACAAAGAGGGGAGAGGTCTATAGGAAGAA
ATGGTTTTGGAAGCTGGGCTTGCAGCCTTATGCTAATGATCACCTGGGGTCCTGGAACCCGAGTGCCAGGCTACCTACTA
TGCCGTGAGCTTAGATAGTGAGGGGCCATTGGACTAAGACCTCCTGTAAGAGTGGGGCAGGATTGAGGTTTTTGGAGAAA
CTGAGGAAACAATTTGTCCATACCACTGGGTGAAGACTGCTGGCCAGTGGGAATGTGGCTGGTGGAGATTTCCCAACTTC
CAGCACCAGGATGGCCTCTCCAAGGTCCTCTTTGATTCCCTGGGGAGATCACCTGGCTCATAGACTGACAACCAGGGAAC
TGGGCTGAAATGGGAGGTCTGGTAGGGGGCATCCCCCTCCTTTTCCCTGGCCACTTGCCACCCAGTTCCTTAACACAGTG
GATCGGCCACACCTCTGTGGCTGCCCTTGAACAGACTCATCCCGACCAAGACAAAAAAGCACAAACTCCTAGCAGCTCAG
GCCAAGCCCACAAGGGAAGGCCTGGGTCCCTGCAGCCCTGATTCAGTGGCCGAGGAAGACGCTCAGACATCCATCCTGTA
CCTCGGAGCCTTGGGGGTCTCACAGCCCTTTCCAGCCCAGCTCGCCAACATTCTAAAGCACAAACCTGCGGATTCTGCT
TGCTTGGGCTGCGCCCTGGGGATTGAAGGCCACTGTTAACCCTAAGCTGGAGCTAGCCCTGAGGGCTGGGGACCTGTGAC
CAGGCAACAGGTCAGCAGACCCTCAGGAGGAGAGAGAGCTGTTCCTGCCTCCCCAGGCCTCGCCCAGAAGGAACAGTGTC
CCAAGAAGCATGTTTCCTGGAGGAACATCCCCACAAAAGTACATTCCATCATCTGAAGCCCGGTCTCTGCTCAGGCCTGC
CTCTGAAAGTCCACGTGTGTTCCCCAGAAGGCCAGCCCCAAGATAAGGGAGGTCCTTAGAGGAAGGACAGGGTGACAACA
CCCCTATACACAGGTGGACCCCCCCTCTGAGGACTGTACTGACCCCATCTCCATCCTGACCGGGGCCTTCCTTTACCCGA
TCTACAGACCACCAGTTCTCCCTGGCTCAGGGACCCCCTGTCCCCAGTCTGACTCTTCCCATCGAGGTCCCTGTCTTGT
GAAAAGCCAAGGCCACGGGAAAAGGCCACCACTCTAACCTGCTGCATCCCTTAGCCTCTGGCTGCACGCCCAACCTGGAG
GGGTCTGTCCCCTTTGCAGGGACACAGACTGGCCGCATGTCCGCATGGCAGAAGCGTCTCCCTTGGGTGCAGCCTGGAAG
GGTGGTTTCTGTCTCAGCGCCCACCAATATTCAGTCCTATATATTTTAATAAAAGAAACTTGACAAAGGAAAAAAAAAAA
AAAA

Fig. 18

>AI 352454 (partial) cds = 1-339
CACGAGGTGGAAAGCATTTCGGCTCAGCTGGAGGAGGCCAGCTCTACAGGCGGTTTCCTGT
ACGCTCAGAACAGCACCAA
GCGCAGCATTAAAGAGCGGCTCATGAAGCTCTTGCCCTGCTCAGCTGCCAAAACGTCGTCTC
CTGCTATTCAAAACAGCG
TGGAAGATGAACTGGAGATGGCCACCGTCAGGCATCGGCCCGAAGCCCTTGAGCTTCTGGA
AGCCCAGAGCAAATTTACC
AAGAAAGAGCTTCAGATCCTTTACAGAGGATTTAAGAACGTAAGAACTTTCTTTTTGACTTT
ACCTTCACACAATTCCCA
GAGGAGCATTGAGAAATGAgaggaaaaggggggaaaatatcccattctatgagaagccccatcatatgtatatttcatact
gatccttcccagataggaatataatcagtatctgtggactttgaatctctgtggcacacccatgctggcatactgtaatt
gcccattaaacaaanagtttttgagaaaaaaaaaaaaaaaaaaaaaaaaaa >AI 352454
HEVESISAQLEEASSTGGFLYAQNSTKRSIKERLMKLLPCSAAKTSSPAIQNSVEDELEMATVRHR
PEALELLEAQSKFT
KKELQILYRGFKNVRTFFLTLPSHNSQRSIEK

Fig. 19

P193 (AA349365) DNA (CD: 2-127, partial)
TGAAAGGTTCTTCGAGAAAATGGACCGGAACCAGGATGGGGTAGTGACCATTGAAGAGTTCCTGGAGGC
CTGTCAGAAGGATGAGAACATCATGAGCTCCATGCAGCTGTTTGAGAATGTCATCTAGGACACGTCCAAA
GGAGTGCATGGCCACAGCCACCTCCACCCCCAAGAAACCTCCATCCTGCCAGGAGCAGCCTCCAAGAAA
CTTTTAAAAAATAGATTTGCAAAAAGTGAACAGATTGCTACACACACACACACACACACACACACACAC
ACACACACACAGCCATTCATCTGGGCTGGCAGAGGGGACAGAGTTCAGGGAGGGGCTGAGTCTGGCTAG
GGGCCGAGTCCAGGAGCCCCAGCCAGCCCTTCCCAGGCCAGCGAGGCGAGGCTGCCTCTGGGTGAGTGG
CTGACAGAGCAGGTCTGCAGGCCACCAGCTGCTGGATGTCACCAAGAAGGGGCTCGAGTGCCCCTGCAG
GGGAGGGTCCAATCTCCGGTGTGAGCCCACCTCGTCCCGTTCTCCATTCTGCTTTCTTGCCACACAGTGGG
CCGGCCCCAGGCTCCCCTGGTCTCCTCCCCGTAGCCACTCTCTGCCCACTACCTATGCTTCTAGAAAGCCC
CTCACCTCAGGACCCCAGAGGGACCAGCTGGGGGGCAGGGGGGAGAGGGGGTAATGGAGGCCAAGCCT
GCAGCTTTCTGGAAATTCTTCCCTGGGGGTCCCAGGATCCCCTGCTACTCCACTGACCTGGAAGAGCTGG
GTACCAGGCCACCCACTGTGGGGCAAGCCTGAGTGGTGAGGGGCCACTGGGCCCCATTCTCCCTCCATGG
CAGGAAGGCGGGGGATTTCAAGTTTAGGGATTGGGTCGTGGTGGAGAATCTGAGGGCACTCTCTGCCAG
CTCCACAGGGTGGGATGAGCCTCTCCTTGCCCCAGTCCTGGTTCAGTGGGAATGCAGTGGGTGGGCTGT
ACACACCCTCCAGCACAGACTGTTCCCTCCAAGGTCCTCTTAGGTCCCGGGAGGAACGTGGTTCAGAGAC
TGGCAGCCAGGGAGCCCGGGGCAGAGCTCAGAGGAGTCTGGGAAGGGGCGTGTCCCTCCTCTTCCTGTA
GTGCCCCTCCCATGGCCCAGCAGCTTGGCTGAGCCCCCTCTCCTGAAGCAGTGTCGCCGTCCCTCTGCCTT
GCACAAAAAGCACAAGCATTCCTTAGCAGCTCAGGCGCAGCCCTAGTGGGAGCCCAGCACACTGCTTCT
CGGAGGCCAGGCCCTCCTGCTGGCTGAGGCTTGGGCCCAGTAGCCCCAATATGGTGGCCCTGGGGAAGA
GGCCTTGGGGGTCTGCTCTGTGCCTGGGATCAGTGGGGCCCCAAAGCCCAGCCCGGCTGACCAACATTCA
AAAGCACAAACCCTGGGGACTCTGCTTGGCTGTCCCCTCCATCTGGGGATGGAGAATGCCAGCCCAAAG
CTGGAGCCAATGGTGAGGGCTGAGAGGGCTGTGGCTGGGTGGTCAGCAGAAACCCCCAGGAGGAGAGA
GATGCTGCTCCCGCCTGATTGGGGCCTCACCCAGAAGGAACCCGGTCCCAGGCCGCATGGCCCCTCCAGG
AACATTCCCACATAATACATTCCATCACAGCCAGCCCAGCTCCACTCAGGGCTGGCCCGGGGAGTCCCCG
TGTGCCCCAAGAGGCTAGCCCCAGGGTGAGCAGGGCCCTCAGAGGAAAGGCAGTATGGCGGAGGCCATG
GGGGCCCCTCGGCATTCACACACAGCCTGGCCTCCCCTGCGGAGCTGCATGGACGCCTGGCTCCAGGCTC
CAGGCTGACTGGGGGCCTCTGCCTCCAGGAGGGCATCAGCTTTCCCTGGCTCAGGGATCTTCTCCCTCCC
CTCACCCGCTGCCCAGCCCTCCCAGCTGGTGTCACTCTGCCTCTAAGGCCAAGGCCTCAGGAGAGCATCA
CCACCACACCCCTGCCGGCCTTGGCCTTGGGGCCAGACTGGCTGCACAGCCCAACCAGGAGGGGTCTGC
CTCCCACGCTGGGACACAGACCGGCCGCATGTCTGCATGGCAGAAGCGTCTCCCTTGGCCACGGCCTGGG
AGGGTGGTTCCTGTTCTCAGCATCCACTAATATTCAGTCCTGTATATTTTAATAAAATAAACTTGACAAAG
GAAAAAAAAAAAAAAAAA

P193 PROTEIN (PARTIAL)
ERFFEKMDRNQDGVVTIEEFLEACQKDENIMSSMQLFENVI

Fig. 20 exon1 SEQUENCE (WITH INTRONS INCLUDED):
CGGGAGGAGAGAGGCAGCTCGGCTCGGCTCCGCGCTCAGCTCCGCTCTGCCTCCGGCTCTGCGCTCACCTGCTGCCT
AGTGTTCCCTCTCCTGCTCCAGGACCTCCGGGTAGACCTCAGACCCCGGGCCCATTCCCAGACTCAGCCTCAGCCCG
GACTTCCCCAGCCCCGACAGCACAGTAGGCCGCCAGGGGGCGCCGTGTGAGCGCCCTATCCCGGCCACCCGGCGCCC
CCTCCCACGGCCCGGGCGGGAGCGGGGCGCCGGGGGCCATGCGGGGCCAGGGCCGCAAGGAGAGTTTGTCCGATTCC
CGAGACCTGGACGGCTCCTACGACCAGCTCACGGGTGAGTCAGTGACGTGGGGGTCGCGGGAGGGAGGGTGGATTCC
ATTCCTCCAGACCCTTCCGCCTCTCCGACCCCGGCCTGGCCCGCACCAACACTCTGCCCCATTCCCAGGCACTCTTA
TGGCCGGTCTGGGCGGCAGGACACTGGGGGTTCAAAGCCTTGGGTCCCGCAGGGGTTGGGGAGGAACAGAAGAGGCA
GGTGTGGAGAGGCAGCAGGTGTGGGCGTATGTGACACAGGGCTGAGAGGGTGTCTGGAGTGGGAGGTGTTACCGTGC
GTGAGCACCTGTCATTCTGTGTGTGTGTGTGTGTGCGCGCGCACCTCCCACAGCTGGTTGCCATGTGCCCTGGGC
TTGGTGACAGCTAGGGTGAGTGTGATTGTATGTGGCAGTGCAATTGTATGGTCTCGTCAGATGTTTGAGTTTGCGTA
GGACCCTGGTTGTACTGATGAAGTTGTTTTGACCATGTGTCTYTATGTGCAACGATGTGTTGTGAGTGTGTAATTCT
GTATGAAAGTGGTGTGTAACTACCAGAATGTGTCAGGGCTCTACTTTAGGGTGGCTTGTCTCTTTG

Fig. 22A exon 2-11 SEQUENCE (WITH INTRONS INCLUDED):
AGCCNANTGGGTCNCCATGTGTATGCATCCTGTTTACTTAGGTCACATTTGTATATGTTGTGTAAGGAGTACCAGGT
CAATGTGTGTGTGTGTGTGAGCATGNATAAACGCCANCAGGTGTGAGTTANTGAATATCAAGCTGTCACTGGCACCC
ATCACTGTGATGTATTGTTCATACATGTCACNAACACGGCCTGTCACTGTAGGTGTGTGTATRAGAGAGGTGTTCTT
ACCCAGGCAATCCTTGGGTTGGACATCATCNTGAGAGGTCCAGCCATGGCACTTGAGCCAAGGGTACTAGGTCAGCA
AAGACATTGAGGCCACTGCCACCTCATCCTTGCCGCCTCGCTGTCACCGGCCACGTCCCATTAAACCAAGTGCNTGA
GCCTCACCTCTATGGACTCACTGGGCTCCCCTAACCCGATTCCAACCACCCTTGCCATTCCTTTCCTCCCCTTAATT
CCTCCCCCAGCCCGGTCCCCAGATGGGGTTGATTTGTGACTGGCGGGGAGGGGACAGGGAACAGAGGGACCCCGGGA
GTTAATGTGCCTTCCTGGGGTCTTTCTCTCTTCNCAGGCCACCCTCCAGGGCCCACTAAAAAAGCGCTGAAGCAGCGA
TTCCTCAAGCTGCTGCCGAGCTGCGGGCCCCAAGCCCTGCCCTCAGTCAGTGAAAGCAAGTGCCTCTCATGTGCTTC
CCGGGGCGGGGCTCGATGTGTGCGTGCGTGTCTGTGCATGANTGTGTGCGCGTGTGCCCCAGGCCTGCRAGTGTKCS
CATGYTCCAGGCTTGCATGTGTGGGGGGGCGTGCCCCAAGCCTKSGTGTTTGGGGGTGGGGCCTGCCCCAVGCCTGT
GCGTGTGTATGTGTGTGCATGTGCGCRCGAGCGTRCCCCAGACCGGCGTGTGTGTGTGGGGGCGTGCCCTACCCC
TGCATGTGTGTGGAGGGCGTGCCCCAKGCCCKCGGCGNGTTGTTTGTTGTGTATGGGAAGGCGTACCGCACGCCTGC
GTGTGGGGGAGGGCGTGCCCCAGAGCCTGCGTGCGTGTGTGTGTGTGTGTGTGTGTGTGGGCGTGACCAGCG
TGGCGAGGGCGGGTGCTGGCAAGGCTGGAGCATAAGNGGGCGNGGCTACATGTGTGNGTGTACGNCTGAAGCCAGCG
TGTGTGGGCGTGGTCAGTTGGNAGCGGGTGTGTGTCACCGCTCCCGCAAAACTGTGGGACCCGAGAGTGTGGGTGTG
ACCATTGTGACCAGGNTGAGGCCTGAGCCTGTGTAGCTGTGGCGGCCTGTGTAGACCAGGCGGCCGTGAGGGTCTGT
ATGTGGCTTAGCTGGGTTAGTGTCTTCAACTCCGTGCGGCCGCCCCCTTCCCCACCGTGTTTTGGACCCCTGATGTG
TGTTGCCTATGCCCCGACAGGATGGTGACAGGTGTAGAGGATGGCGCCTGCCCTCCTCCAGACGCCAGGGTATTTGG
GTTTTCTGTGCCAGCCTGGTCCCCTGCTGAAGTGATCTCCAGTTGAGTGACCTCGCTTTGTCTCTAGGTCTCCATTT
CCTCAGTTGGGCCTTGCCCACCTCATAGGATCATACTGCATTTTGCAAACCATAAAGGCCCGCTTTGTAGTTATTTG
AGCATGCTGTTGTGTTGGACTTAGATGGGTCCCACACGGGGGTGGATTCGGARAAGGACAGGCGTGAGTCCCGCAAG
CTTGTGTGCATGGGGTCCGTTTCGTGTGTGTCTGTGCTGGTTGGGTGTGCCTTTGCACGGGCTGGGTTGTCAGGTTT
GCTCTGAGTGTGAGGGGCCAGGTGTGTGTATGCAGTTGGCCGGGTCTTCCGCTTTCTCGGTGWCAGTTCGCTCCCTT
CAGCATTAGCCGCCCCAGCCTCCCTTCCGCCCCACAGACCCCGCCTGCTGGACCCAGGTGACTTACGCTCCTGGTGG
GGGCGGGGCGGGGCAGGGCGGCTTTGCCATCTTGGGGTGGGGGCACTTGCCTGGGGGCTGGACGTTGGGGCGGGG
CAGGATTGAGATGGGGCCGGGGGTGGGGTCTGGATGGAGGTTGGCTGAGCTGGGCGGGGCATGGCTCAGGCATGGCT
GGGATAGATGGGCCTGGGCGGGGCGAGGGGAGGGGCTGGGTGGGACGAGGGGAGGGTTTGGGCGGGGCAAGGCTGGG
GCTGGGCGGATCTGAGTTGGTCCCCGAAGGCCCGGAGCTCTGACCCTCAGACGCCCCCTCTTGAACTGGCTTTTCCC
ACTCCTCCCTTTCTAAAACGAAGATGCGGCTGGGGGCCTTCCCCTCCAACGAGGGATCGAGGGCCGCGGGGCGAGCA
CTGAGTCGGATCCCTGGCTCTGGGGCCAGGCCAGGCCTTGGCCCGCTGATAGACCTCGAAGATGGCCATCATCTTTT
CTCCTTACCTCAGTGTCCTTGGCTCGGGGCCCAGGGAACTGGCAGCCTGGTCTCCGGCATCGGATGGGACCGGGGGG
CGGGGAGGGGGTGAATGGGGCAGTGATTTGAAGAGGGGTCGCGGAGGCTGGGCATGAGGCGCGGCTGTCCTCACCGC
TCCCGCAGACAGCGTGGACGATGAATTTGAATTGTCCACCGTGTGTCACCGGCCTGAGGGTCTGGAGCAGCTGCAGG
AGCAAACCAAATTCACGCGCAAGGAGTTGCAGGTCCTGTACCGGGGCTTCAAGAACGTGAGTGCNGGGCGAGGCCAA

Fig. 22B

```
ACTCAGCGNGGGTGGGACAGGAGGACCCAANCCGGTCCANATTTTTCCCANAAAGCATGGCTTNGATGCTTGAGGNG
CGGGCGGAAGGGAGGCAAGGCCCTGAGACTGAACTTCTAGCTGGAGGTTCTGGGGCGGGGCCAGAACGRAAGTGGCG
CCTGTAGACTGTCAGTTTCGTTCCATGTTTTTTATTTGTGCACTGGGAAAGAAGTCTTCCCTCCCATCACATGAGCC
ACGTGGTGAGTCCTCTGGAGGCTTGAAGATTATCCCCCTCCCTGGGAGTCTTGGGCCATGGAGGGTGGGGGCGGTGA
ACGGAAGGGGATTTTGTCTCTGCCCTCAGCCTGGTGCCCTCTCCTTCCAGGAATGTCCCAGCGGAATTGTCAATGAG
GAGAACTTCAAGCAGATTTACTCCCAGTTCTTTCCTCAAGGAGGTGAGGGGACAAGGCCCAAGGGGAAGCAGTTGTC
CTTCTCTAGGCTGAGGGAGGGAGGGATTCTGGAGGAGCTGGGAATGCCAAGGTGATGGGGGGTATGGGGAGCTCCTT
AGAGGGAGGAAGTCCTCTCCTGTGTGGAAGCCAACTTCTCCACACTCACCCTGCAGACTCCAGCACCTATGCCACTT
TTCTCTTCAATGCCTTTGACACCAACCATGATGGCTCGGTCAGTTTTGAGGTGAGCTGGGCGAGGTGGGCCAGGGAA
GCCTGTTTCCTGGAGTTCAGGGCCAGGATCTCCAGGCCAAACCCAGAGAAGGAGTTGGGTGAAGAGKACCCGAGGAC
ACAGCTCCCTNCTGCCTTCTTCCCAGGACTTTGTGGCTGGTTTGYCCGTGATTCTTCGGGGAACTGTAGATGACAGG
CTTAATTGGGCCTTCAACCTGTATGACCTTAACAAGGACGGCTGCATCACCAAGGAGGTGCAGGGCAACTGAAGGGC
TGGGGGTCTGTGGCGGTGATGGGGGTGGCGTGCAKAGGGTGATGGGAGGGAAATATGACCCACATATGCCCACAAGC
AATGGGATCAAGGGAGGCTGGAGGCTCTGAGGAAGGATCCTCTTCTCTCTTGGCCTAACAGGAAATGCTTGACATCA
TGAAGTCCATCTATGACATGATGGGCAAGTACACGTACCCTGCACTCCGGGAGGAGGCCCCAAGGGAACACGTGGAG
AGCTTCTTCCAGGTACTTGGGAGTGGGTATGGCTGGAGGGCCCTGGAGTGAAGGGAAGAAGGCCAAGAACCAGCAGG
GAACTCACCTGACTTCTGTCTGCCTCTCTCTTGCCATCCCTCCTGTTCTCCCTGCCTGACCACCTTCTTGCAGAAGA
TGGACAGAAACAAGGATGGTGTGGTGACCATTGAGGAATTCATTGAGTCTTGTCAAAAGGTACAGCTCCCTGCCCTC
TACATTACCCTGACCTGGACTCAGGCCTGATTTAGTAATGCAGGGAAAAGCTTCTTTGGGAAGAATACCACCTTCCC
ACCTCACCCCCATATTTCAATCCTATTCCTTTGTGGGAGGCTTACCCCTTCCCTACCTCAGGTCTCTCTGGGCATCT
CCTTCCTCTGTGCTTTTGAATGTCCCCGTCTGTGACTCAAGTGTCCCTCTCACTGTCTCTGATAAAGCTCCTTCTCT
TTCTCTCTCTTCAATCTGCCTCGCTCACATCATGGCCACAGGATGAGAACATCATGAGGTCCATGCAGCTCTTTGAC
AATGTCATCTAGCCCCCAGGAGAGGGGGTCAGTGTTTCCTGGGGGGACCATGCTCTAACCCTAGTCCAGGCGGACCT
CACCCTTCTCTTCCCAGGTCTATCCTCATCCTACGCCTCCCTGGGGGCTGGAGGGATCCAAGAGCTTGGGGATTCAG
TAGTCCAGATCTCTGGAGCTGAAGGGGCCAGAGAGTGGGCAGAGTGCATCTCGGGGGGTGTTCCCAACTCCCACCAG
CTCTCACCCCCTTCCTGCCTGACACCCAGTGTTGAGAGTGCCCCTCCTGTAGGAATTGAGCGGTTCCCCACCTCCTA
CCCCTACTCTAGAAACACACTAGACAGATGTCTCCTGCTATGGTGCTTCCCCCATCCCTGACCTCATAAACATTTCC
CCTAAGACTCCCCTCTCAGAGAGAATGCTCCATTCTTGGCACTGGCTGGCTTCTCAGACCAGCCATTGAGAGCCCTG
TGGGAGGGGGACAAGAATGTATAGGGAGAAATCTTGGGCCTGAGTCAATGGATAGGTCCTAGRAGGTGGCTGGGGTT
GAGAATAGAAGGGCGTGGACAGATTATGATTGCTCAGGCATACCAGGTTATAGCTCCAAGTTCCACAGGTCTGCTAC
CACAGGCCATCAAAATATAAGTTTCCAGGCTTTGCAGAAGACCTTGTCTCCTTAGAAATGCCCCAGAAATTTTCCAC
ACCCTCCTCGGTATCCATGGAGAGCCTGGGGCCAGATATCTGGCTCATCTCTGGCATTGCTTCCTCTCCTTCTTTCC
TGCATGTGTTGGTGGTGGTTGTGGTGGGGGAATGTGGATGGGGGATGTCCTGGCTGATGCCTGCCAAAATTTCATCC
CACCCTCCTTGCTTATCGTCCCTGTTTTGAGGGCTATGACTTGAGTTTTTGTTTCCATGTTCTCTATAGACTTGGG
ACCTTCCTGAACTTGGGGCCTATCACTCCCACAGTGGATGCCTTAGAAGGGAGAGGGAAGGAGGGAGGCAGGCATA
GCATCTGAACCCAGTGTGGGGGCATTCACTAGAATCTTCAATCAACCTGGGCTCTCCCCACCCCACCCCAGATAACC
TCCTCAGKTCCCTAGGGTCTCTTCTYGCTTGACTCAATCTACCCAGAGATGCCCCTTAGCACACCTAGAGGGCAGGG
ACCATAGGACCCAGGTTCCAACCCCATTGTCAGCACCCCAGCCATGCGGCCACCCCTTAGCACACCTGCTCGTCCCA
TTTAGCTTACCCTCCCAGTTGGCCAGAATCTGAGGGGAGAGCCCCCAGAGAGCCCCCTTCCCCATCAGAAGACTGTT
GACTGCTTTGCATTTTGGGCTCTTCTATATATTTTGTAAAGTAAGAAATATACCAGATC:TAATAAAACACAATGGC
TATGCACAGGCTGCCGTCTCTGCCTTTTGTCCCTCCCACCTACAAATACTACACAACCCCTAACGAATGCACCTGCA
GCCTTTTAGATCCCCAAGAAAGTGGCTTTCTTTTCCATAGTTGGCCATACCTTGGCATGAGACTGAGACACAGGCTC
TGGAATGGTTGGAAACCCACCCAACCTCAGGCCCCCACATGAATCTCCCTCCCACACAGCCTGAGAGGAGACAAGGA
AGGAAGGACAGGACACTGATGTCCCGAAGACTGTGCCAAGCAAGCTGTTTTTTAGCTGACATTCTTACAAGTTGAAT
CACAGATTTCTAATTTACAGACTTTTTAGTTAATCTCAAAGTGCTTTCTTTTGAGGGGCCTCCTTTAAGTTCYTTCT
TTTTTTTTTTTTTTT
```

Fig. 22C

>monkey KChIP4 cds = 265 gtcgacccacgcgtccggtgcgctgtggttgcggggggagccccgccagccaaatgccaggatcagcatgagaggctgg
actttagtccaggtctgtcctcaccccgggggaccgccggctttgcagggtgcagctgcgaggaactgctcactttttc
cccttgcaagtctttgttccaagcctgacgttgctacgattctgtaattaactccctccactccaaagggtctggaggc
tgggatgctctgccagctcagaggATGTTGACTCTGGAGTGGGAGTCCGAAGGACTGCAAACAGTGGGTA
TTGTTGTGAT
TATATGTGCATCTCTGAAGCTGCTTCATTTGCTGGGACTGATTGATTTTTCGGAAGACAGCGT
GGAAGATGAACTGGAGA
TGGCCACTGTCAGGCATCGGCCTGAGGCCCTTGAGCTTCTGGAAGCCCAGAGCAAATTTACC
AAGAAAGAGCTTCAGATC
CTTTACAGAGGATTTAAGAACGAATGCCCCAGTGGTGTTGTTAATGAAGAAACCTTCAAAGA
GATTTACTCGCAGTTCTT
TCCACAGGGAGACTCTACAACATATGCACATTTTCTGTTCAATGCGTTTGATACGGACCACA
ATGGAGCTGTGAGTTTCG
AGGATTTCATCAAAGGTCTTTCCATTTTGCTCCGGGGGACAGTACAAGAAAAACTCAATTGG
GCATTTAATCTGTATGAT
ATAAATAAAGATGGCTACATCACTAAAGAGGAAATGCTTGATATAATGAAAGCAATATACG
ACATGATGGGTAAAATGTAC
ATATCCTGTCCTCAAAGAAGATGCACCCAGACAACACGTCGAAACATTTTTTCAGAAAATGG
ACAAAAATAAAGATGGGG
TTGTTACCATAGATGAGTTCATTGAAAGCTGCCAAAAAGATGAAAACATAATGCGCTCCATG
CAGCTCTTTGAAAATGTG
ATTTAActtgtcaactagatcctgaatccaacagacaaatgtgaactattctaccacccttaaagtcggagctaccactt
ttagcatagattgctcagcttgacactgaagcatattatgcaaacaagctttgttttaatataaagcaatccccaaaaga
tttgagtttctcagttataaatttgcatcctttccataatgccactgagttcatgggatgttctaactcatttcatactc
tgtgaatattcaaaagtaatagaatctggcatatagttttattgattccttagccatgggattattgaggctttcacata
tcagtgattttaaaataccagtgttttttgctctcatttgtatgtattcagtcctaggattttgaatggttttctaatat
actgacatctgcatttaatttccagaaattaaattaattttcatgtctgaatgctgtaattccatttatatactttaagt
aaacaaataagattactacaattaaacacatagttccagtttctatggccttcccttcccaccttctattataaattaat
tttatctggtatttttaaacatttaaaaatttatcatcagatatcagcatatgcctaattatgcctaatgaaacttaata
agcatttaattttccatcatacattatagccaaggcctatatactatatataattttggatttgtttaatcttacaggct
gttttccattgtatcatcaagtggaagttcaagacggcatcaaacaaaacaaggatgtttacagacatatgcaaagggtc
aggatatctatcctccagtatatgttaatgcttaataacaagtaatcctaacagcattaaaggccaaatctgtcctcttt
ccctgacttccttacagcatgtttatattacaagccattcagggacaaagaaaccttgactacccactgtctactagg
aacaaacaaacagcaagcaaaattcactttgaaagcaccagtggttccattacattgacaactactaccaagattcagta
gaaaataagtgctcaacaactaatccagattacaatatgatttagtgcatcataaaattccaacaattcagattattttt
aatcatctcagccacaactgtaaagttgccacattactaaagacacacacatcgtcctgttttgtagaaatatcacaaa
gaccaagaggctacagaaggaggaaatttgcaactgtctttgcaacaataaatcaggtatctattctggtgtagagatag
gatgttgaaagctgccctgctatcaccagtgtagaaattaagagtagtacaatacatgtacactgaaatttgccatcgcg
tgtttgtgtaaactcaatgtgcacattttgtatttcaaaaagaaaaaataaaagcaaaataaaatgttwawaamwmwaaa
aaaaaaaaaaaa >monkey KChIP4

MLTLEWESEGLQTVGIVVIICASLKLLHLLGLIDFSEDSVEDELEMATVRHRPEALELLEAQSKFT
KKELQILYRGFKNE
CPSGVVNEETFKEIYSQFFPQGDSTTYAHFLFNAFDTDHNGAVSFEDFIKGLSILLRGTVQEKLNW
AFNLYDINKDGYIT
KEEMLDIMKAIYDMMGKCTYPVLKEDAPRQHVETFFQKMDKNKDGVVTIDEFIESCQKDENIM
RSMQLFENVI

Fig. 23

>monkey KChIP4 C terminal splice variant cds = 265-966 gtcgacccacgcgtccggtgcgctgtggttgcggggggggagccccgccagccaaatgccaggatcagcatgagaggctgg
actttagtccaggtctgtcctcaccccgggggaccgccggctttgcagggtgcagctgcgaggaactgctcacttttttc
cccttgcaagtctttgttccaagcctgacgttgctacgattctgtaattaactccctccactccaaagggggtctggaggc
tgggatgctctgccagctcagaggATGTTGACTCTGGAGTGGGAGTCCGAAGGACTGCAAACAGTGGGTA
TTGTTGTGAT
TATATGTGCATCTCTGAAGCTGCTTCATTTGCTGGGACTGATTGATTTTTCGGAAGACAGCGT
GGAAGATGAACTGGAGA
TGGCCACTGTCAGGCATCGGCCTGAGGCCCTTGAGCTTCTGGAAGCCCAGAGCAAATTTACC
AAGAAAGAGCTTCAGATC
CTTTACAGAGGATTTAAGAACGAATGCCCCAGTGGTGTTGTTAATGAAGAAACCTTCAAAGA
GATTTACTCGCAGTTCTT
TCCACAGGGAGACTCTACAACATATGCACATTTTCTGTTCAATGCGTTTGATACGGACCACA
ATGGAGCTGTGAGTTTCG
AGGATTTCATCAAAGGTCTTTCCATTTTGCTCCGGGGGACAGTACAAGAAAAACTCAATTGG
GCATTTAATCTGTATGAT
ATAAATAAAGATGGCTACATCACTAAAGAGGAAATGCTTGATATAATGAAAGCAATATACG
ACATGATGGGTAAATGTAC
ATATCCTGTCCTCAAAGAAGATGCACCCAGACAACACGTCGAAACATTTTTTCAGGCTGTTT
TCCATTGTATCATCAAGT
GGAAGTTCAAGACGGCATCAAACAAAACAAGGATGTTTACAGACATATGCAAAGGGTCAGG
ATATCTATCCTCCAGTATA
TGTTAAtgcttaataacaagtaatcctaacagcattaaaggccaaatctgtcctctttcccctgacttccttacagcatg
tttatattacaagccattcagggacaaagaaaccttgactacccactgtctactaggaacaaacaaacagcaagcaaaa
ttcactttgaaagcaccagtggttccattacattgacaactactaccaagattcagtagaaaataagtgctcaacaacta
atccagattacaatatgatttagtgcatcataaaattccaacaattcagattattttttaatcatctcagccacaactgta
aagttgccacattactaaagacacacacatcgtccctgttttgtagaaatatcacaaagaccaagaggctacagaaggag
gaaatttgcaactgtctttgcaacaataaatcaggtatctattctggtgtagagataggatgttgaaagctgccctgcta
tcaccagtgtagaaattaagagtagtacaatacatgtacactgaaatttgccatcgcgtgtttgtgtaaactcaatgtgc
acatttgtatttcaaaaagaaaaaataaaagcaaaataaaatgttwawaamwmwaaaaaaaaaaaaaaaa >monkey KChIP4 C terminal splice variant
MLTLEWESEGLQTVGIVVIICASLKLLHLLGLIDFSEDSVEDELEMATVRHRPEALELLEAQSKFT
KKELQILYRGFKNE
CPSGVVNEETFKEIYSQFFPQGDSTTYAHFLFNAFDTDHNGAVSFEDFIKGLSILLRGTVQEKLNW
AFNLYDINKDGYIT
KEEMLDIMKAIYDMMGKCTYPVLKEDAPRQHVETFFQAVFHCIIKWKFKTASNKTRMFTDICK
GSGYLSSSIC

Fig. 24

```
KChIP1_1v     ---------------MGAVMGTF------SSLQTKQ----RRP---------------
KChIP2_9ql    MRGQGRKESLSDSRDLDGSYDQLTGHPPGPTKKALKQRFLKLLPCCGPQALPSVSETLAA
KChIP3_p19    --MQPAKEVTKAS----DGSLLGDLGH----TPLSKKEGIKWQRPRLSRQALMRCCLVKWI
KChIP4_352    ---MLTLEWESEGLQTVGIVVIICAS----LKLLHLLGLIDFSE----------------
KChIP4_231    ---MLTLEWESEGLQTVGIVVIICAS----LKLLHLLGLIDFSE----------------
hsncspara     ----HEVESISAQLEEASSTGGFLYAQN-STKRSIKERLMKLLPCS--------------

KChIP1_1v     -------------SKDKIEDELEMTMVCHRPEGLEQLEAQTNFTKRELQVLYRGFKNECPS
KChIP2_9ql    PASLRPHRPRLLDPDSVDDEFELSTVCHRPEGLEQLQEQTKFTRKELQVLYRGFKNECPS
KChIP3_p19    LSSTAPQ-----GSDSSDSELELSTVRHQPEGLDQLQAQTKFTKKELQSLYRGFKNECPT
KChIP4_352    --------------DSVEDELEMATVRHRPEALELLEAQSKFTKKELQILYRGFKNECPS
KChIP4_231    --------------DSVEDELEMATVRHRPEALELLEAQSKFTKKELQILYRGFKNECPS
hsncspara     -AAKTSSP---AIQNSVEDELEMATVRHRPEALELLEAQSKFTKKELQILYRGFKNVRTF KChIP1_1v     GVVNEDTFKQIYAQFFPHGDASTYAHYLFNAFDTTQTGSVKFEDFVTALSILLRGTVHEK
KChIP2_9ql    GIVNEENFKQIYSQFFPQGDSSTYATFLFNAFDTNHDGSVSFEDFVAGLSVILRGTVDDR
KChIP3_p19    GLVDEDTFKLIYAQFFPQGDATTYAHFLFNAFDAGNGAIRFEDFVVGLSILLRGTVHEK
KChIP4_352    GVVNEETFKEIYSQFFPQGDSTTYAHFLFNAFDTDHNGAVSFEDFIKGLSILLRGTVQEK
KChIP4_231    GVVNEETFKEIYSQFFPQGDSTTYAHFLFNAFDTDHNGAVSFEDFIKGLSILLRGTVQEK
hsncspara     FLTLPSHNSQRSIEK---------------------------------------------

KChIP1_1v     LRWTFNLYDINKDGYINKEEMMDIVKAIYDMMGKYTYPVLKEDAPRQHVDMFFQKMD---
KChIP2_9ql    LNWAFNLYDLNKDGCITKEEMLDIMKSIYDMMGKYTYPALREEAPREHVESFFQKMD---
KChIP3_p19    LKWAFNLYDINKDGYITKEEMLAIMKSIYDMMGRHTYPILREDAPAEHVERFFEKMD---
KChIP4_352    LNWAFNLYDINKDGYITKEEMLDIMKAIYDMMGKCTYPVLKEDAPRQHVETFFQKMD---
KChIP4_231    LNWAFNLYDINKDGYITKEEMLDIMKAIYDMMGKCTYPVLKEDAPRQHVETFFQAVFHCI
hsncspara     ------------------------------------------------------------

KChIP1_1v     ---KNKDGIVTLDEFLESCQEDDNIMRSLQLFQNVM
KChIP2_9ql    ---RNKDGVVTIEEFIESCQKDENIMRSMQLFDNVI
KChIP3_p19    ---RNQDGVVTIEEFLEACQKDENIMSSMQLFENVI
KChIP4_352    ---KNKDGVVTIDEFIESCQKDENIMRSMQLFENVI
KChIP4_231    IKWKFKTASNKTRMFTDICKGSGYLSSSIC------
hsncspara     ------------------------------------
```

Fig. 25

Rat 33b07 protein
MNGVEGNNELPLANTSTSALVPEDLDLKQDQPLSEETDTVREMEAAGEAGAEGGASPDSEHCDPQLCLRVAENGCAAAAG
EGLEDGLSSSKCGDAPLASVAANDANKNGCQLAGPLSPAKPKTLEASGAVGLGSQMMPGPKKTKVMTTKGAISATTGKEG
EAGAAMQEKKGVQKEKKAAGGGKDETRPRAPKINNCMDSLEAIDQELSNVNAQADRAFLQLERKFGRMRRLHMQRRSFII
QNIPGFWVTAFRNHPQLSPMISGQDEDMMRYMINLEVEELKHPRAGCKFKFIFQSNPYFRNEGLVKEYERRSSGRVVSLS
TPIRWHRGQEPQAHIHRNREGNTIPSFFNWFSDHSLLEFDRIAEIIKGELWSNPLQYYLMGDGPRRGVRVPPRQPVESPR
SFRFQSG.

Rat 33b07 DNA (coding: 85-1308)
GGTGGAGCTAAGCACTCACTGCGGTGCTGCCCTGCGTCTGCAGAGAACAAGGAAAGCTTCTCTGCAGGGCTGTCAGCTGC
CAAAATGAACGGCGTGGAAGGGAACAACGAGCTCCCTCTCGCTAACACCTCGACCTCCGCCCTTGTCCCGGAAGATCTGG
ATCTGAAGCAAGACCAGCCGCTCAGCGAGGAAACTGACACGGTGCGGGAGATGGAGGCTGCAGGTGAGGCCGGTGCGGAG
GGAGGCGCGTCCCCCGATTCGGAGCACTGCGACCCCCAGCTCTGCCTCCGAGTGGCTGAGAATGGCTGTGCTGCCGCAGC
GGGAGAGGGCTGGAGGATGGTCTGTCTTCATCAAAGTGTGGGGACGCACCCTTGGCGTCTGTGGCAGCCAACGACAGCA
ATAAAAATGGCTGTCAGCTTGCAGGGCCGCTCAGCCCTGCTAAGCCAAAAACTCTGGAAGCCAGTGGTGCAGTGGGCCTG
GGGTCGCAGATGATGCCAGGGAAGAAGAAGACCAAGGTAATGACTACCAAGGGCGCCATCTCTGCGACTACAGGCAAGGA
AGGAGAAGCAGGGGCGGCAATGCAGGAAAAGAAGGGGGTGCAGAAAGAAAAAAAGGCAGCTGGAGGAGGGAAAGACGAGA
CTCGTCCTAGAGCCCCTAAGATCAATAACTGCATGGACTCCCTGGAAGCCATCGATCAAGAGCTGTCAAATGTAAATGCG
CAAGCTGACAGGGCCTTCCTCCAGCTGGAACGCAAATTTGGGCGGATGAGAAGGCTCCACATGCAGCGCCGAAGTTTCAT
CATCCAAAACATCCCAGGTTTCTGGGTCACAGCGTTTCGGAACCACCCGCAACTGTCACCGATGATCAGTGGCCAAGATG
AAGACATGATGAGGTACATGATCAATTTAGAGGTGGAGGAGCTTAAGCACCCAAGAGCAGGGTGCAAATTTAAGTTCATC
TTCCAAAGCAACCCCTACTTCCGAAATGAGGGGCTGGTCAAAGAGTACGAGCGCAGATCCTCAGGTCGAGTGGTGTCGCT
CTCTACGCCAATCCGCTGGCACCGGGGTCAAGAACCCCAGGCCCATATCCACAGGAATAGAGAGGGGAACACGATTCCCA
GTTTCTTCAATTGGTTGTCAGACCACAGCCTCCTAGAATTCGACAGAATAGCTGAAATTATCAAAGGGGAGCTTTGGTCC
AATCCCCTACAATACTACCTGATGGGCGATGGGCCACGCAGAGGAGTTCGAGTCCCACCAAGGCAGCCAGTGGAGAGTCC
CAGGTCCTTCAGGTTCCAGTCTGGCTAAGCTCTGCCCTCGTGAGAAGCTCTTACAGAAGAGTCCTTACCACCTTCTCAGC
TTGGCTAGCAGCATGCAGCCTTCTGTCTGCTTTCTCTTCCTTGGATTGTGTCCTTTGGTTCTTCTAAGTCTCCGGTAGTT
TCAAGGTTGTGGCTTCCAAGTCTTTGCTCTTCTTTCTCTTGGCCATCACGATGTCCTGCATAGTGTTAATGGTGTTCCAA
GTGCATGGCCTCCAAACTGCTTCTATGCCAAGCTCACGTGCTGTAGTTTGTACTGCTTTTCTTTGCATGGCTTGGTTCCT
GTCTGTGATCTTCTAGGTTTTTTGTTTTCTTTTTTAAAAGTGGTTCTCTATCAAAAGAAAGCTTGACATATCCTTACCAA
GAACTAGCCAGATTTCATACTGTGTTCCCGATATCTATGTACTGTGAAGAACTGTGAGTTTCGCCACTGCAAGATGGGAC
TGTATCCCAATCCAGCCATCAGCCCAACAGGACATTCCAAGCTGTCACCAACTGATCCTAGCTGTCTTCCTGGGCCTTTG
CCATTTACCCTGCTTTTTATCTATAGAATGAGCAGGTGGCTGGTAGGTGACTACTAGGTAAGAGTGAAGTATTAGGTGAG
GAGTGTTTTCTGTCACCACATTGTTCTTGTACCAATGCATCATGATCAGCTTGGATCAGCTACTGACTGTCTGATATTTC
TAACCCCCAACACAAAAAAAAAAAAAAAAAAAAAAAAAAAAAAAAAAAAAAAA

Fig. 26

Human 33b7 (106d5) DNA (coding: 88-1332)
```
GGGGTGGTGCTAGACGTTTCGGGCAGAGCTCGGCCGCTGCGGAGGACAAGGAACTCTCCCTCTCCCACTAGTCTGACTTC
TTCCAAAATGAGCGGCCTGGATGGGGGCAACAAGCTCCCTCTCGCCCAAACCGGCGGCCTGGCTGCTCCCGACCATGCCT
CAGGAGATCCGGACCTAGACCAGTGCCAAGGGCTCCGTGAAGAAACCGAGGCGACACAGGTGATGGCGAACACAGGTGGG
GGCAGCCTGGAGACCGTTGCGGAGGGGGGTGCATCCCAGGATCCTGTCGACTGTGGCCCCGCGCTCCGCGTCCCAGTTGC
CGGGAGTCGCGGCGGTGCAGCGACCAAAGCCGGGCAGGAGGATGCTCCACCTTCTACGAAAGGTCTGGAAGCAGCCTCTG
CCGCCGAGGCTGCTGACAGCAGCCAGAAAAATGGCTGTCAGCTTGGAGAGCCCCGTGGCCCTGCTGGGCAGAAGGCTCTA
GAAGCCTGTGGCGCAGGGGGCTTGGGGTCTCAGATGATACCGGGGAAGAAGGCCAAGGAAGTGACGACTAAAAAACGCGC
CATCTCGGCAGCAGTGGAAAAGGAGGGAGAAGCAGGGGCGGCGATGGAGGAAAAGAAGGTAGTGCAGAAGGAAAAAAAGG
TGGCAGGAGGGGTGAAAGAGGAGACACGGCCCAGGGCCCCGAAGATCAATAACTGCATGGACTCACTGGAGGCCATCGAT
CAAGAGTTGTCAAACGTAAATGCCCAGGCTGACAGGGCCTTCCTTCAGCTTGAGCGCAAGTTTGGCCGCATGCGAAGGCT
CCACATGCAGCGCAGAAGTTTCATTATCCAGAATATCCCAGGTTTCTGGGTTACTGCCTTTCGAAACCACCCCCAGCTGT
CACCTATGATCAGTGGCCAAGATGAAGACATGCTGAGGTACATGATCAATTTGGAGGTGGAGGAGCTTAAACACCCCAGA
GCAGGCTGCAAATTCAAGTTCATCTTTCAGGGCAACCCCTACTTCCGAAATGAGGGGCTTGTCAAGGAATATGAACGCAG
ATCCTCTGGCCGGGTGGTGTCTCTTTCCACTCCAATCCGCTGGCACCGAGGCCAAGACCCCCAGGCTCATATCCACAGAA
ACCGGGAAGGGAACACTATCCCTAGTTTCTTCAACTGGTTTTCAGACCACAGCCTTCTAGAATTCGACAGAATTGCAGAG
ATTATCAAAGGAGAACTGTGGCCCAATCCCCTACAATACTACCTGATGGGTGAAGGGCCCCGTAGAGGAATTCGAGGCCC
ACCAAGGCAGCCAGTGGAGAGCGCCAGATCCTTCAGGTTCCAGTCTGGCTAATCTCTGTCCTGTGAGAAGCTTCTGCACA
AGTTTCCTTACCACCTCCTCTTGGACCTATGCTTGGCCAACAGCATGCAGTCTTCCATCTGCTTTCTCTTCATACTGTGG
ATTATCTTTTCCTTTGGTTCTAAATCTTCAGTAATCGGTTGCAAGATTGTTGGCTTACCTGCCTGTGCCATTCTTCCTCT
GGGCCTTCATGCTTTTCTGCATTGTGTTAACATGTTTCAAGTGCATGGCCTTCTACGGCTTCTATGCCAAGCGTATGATA
CTATAGATATAGTGTACCATACTGCCTTTCTTTGCATGGCTTGGACCCTATCTGTGACCATGCTCTTCTCCCAATTTAAG
TGGTTCTGTACCACAAAGAATCTTGATACATTTTCACAAATAACTGATTGGGCTTCATACTTTATGCTGGCTGTGTCCTG
ATACCCATGTACTTATGGTAAGCTATTTGGGTATTACCACTGCAAGACAAAACTGATATCTTAACCCGGCCATCAACCCA
AATTGGACATTCCAGACTACCACCAACTGGATCCCAGCTGCCTTCCTGGGCTTGTGCCATCCACCCTACTGGTTATCTGA
TAGAACAAGCTGGTGGCTGATGGGTGACTGCTAGGCGTGACTGAGGTAATAGATGAAAAGTGTTCTATGTTATCACATTG
GTTTTCCTGTACCTTTGGTTACTCTACGTCATGACCAGCTGCTGGTGAGTATGAAGCCTGTGCTATAGCCCACCCCTACT
CACTCTCACCTTCTGGTTGAACTTTGCTTAGGCCACCATTGTCTGCCTCATCAGGAACTATCTGTAGACGTAGCTCCCAG
GGAGCTCACAGCAACACCCCCTACCACCAGGATGGGCAGTAATATGTGACAGAGCCCAAAGCAAGGCTGGAACGCAGTCC
CTTCCAGCTTAGTCTTTCTGACTCCTAGCCAACAAACCATCCTTAATGTGAGCAACTTCTTTAGGCATTTCCTCTTTTCC
CCGCCTGCACCCACTCTGAACATGACAAAAGTTGCCAGAGTTGGGGCATTGAGGAAGAGATATTTCTGGAATGTGAGACT
TGTTATGCCTCTGTCTCTTTCTCTCCCTCCCCCTCCCCTCTCCCTCCCCCTCTCCCTCCCATCCCTTTTCTTCCCTTTCA
CTCTGAAGCAGTTTTAGCTTATTAACAGAAAACAAAACTGGCAAAGCAGGCTTTTTGTTTAATTTGCTCTTTCCCTGATT
GTGTTCAGAGAGAAAGGTTATGATTAAATGGGCTCCAGATCTCTTATTGCCCTTATTCCTCCACCCCACTTCTTTTAGCA
AGGTCTGAAAGTTTCAAAGGGAGACCTATAGGTTAATTGTTTAGTTATAGGCAGTGTTAAATTAGGCAGATTTTGACATA
TTTATCTTTTTTACCCCATCCATTCTACCAAAACCTGTGTATTTCTTGAGTTTTTAGTTTGAGAAGCTGGAAAGAGAGAGA
AGGGCCTCACAGTGATGGGTTCAGGACGGGTCAAAGGCAAAGGCCTTTGTGATGTGAGCAAAGGCAACCAAAACTTAGCC
TCACTCCACTTTTCTAAAGATGGAAATTCTTTTTTGGGCCTTGGACTGCTTCTAGGGTAGCATTTTGTAGGTCACTCTTC
TCCTTTGTACTATTTTGTTTCTGCCCTGATGTCCCTTGGGTCTCCATCCTACTGCCTGGCTTTCTTGGCCCTCATTTCTC
AGCTTCTGCATTTCCTTCCCTGCTCCTAACAAATGAAGAAGCAGGCTGCAGCCTGCATTGTGGAAGATCTCCAGCCTCCT
TGTAGGGGATAAGGGGATGTGTAGCATCTGTGTGGATTTTCACGGACAAGTTCCAGTAGGTGGGACAGTGATGCCGTCAA
GGCTTAGTTATGATCATGTGTGGTGATAAAGACCATCCACCATCACCCTTTTCCCCTTTGGTTTTGAAGGCCTTGCCCTA
AGCTACCTGAGGGTTTAGGAGGTCTGAACACACACAGTGGAGAGGTTAATCTAGGTTGGGAAACTGAGTAAAAGTCCAGA
GCAGGAATGAGCCTGCTGTGGCGTGGGTTTGAAAGGCTCACAGGAAAGAACCTGCAGGATCAGGGGTGGGAGGGGAGGC
CCCTGAGGTGCTCTCCAGGGAAGAGGGGCTGGGGTTTAAATAGCATGCTTGGAGGAAGATTTTCCTTCAATTTTTCCTAA
GTCCTTGAATTCACCAGTAGATTTTGTAAACAAAATGTAAGTCGATGTTTTCTCTCAATTATCCTAGGAGTGACCTTTA
TATGTGTGGAAGATTAATGGTATATGCTCCTTATGTCACTGTTTTTGAGTAAAATCCATTTCCTTTCTCTGTTTCAGCCT
ATGACAAAATTGATGTTTACAGGCCTGCTTTTTGCTTATAATTGACAACATGTGCAAAAATACCAAATTTGTGTCCTGTG
CAGTATGAAGAATTCAGTGAATATTCATTAATGTATTAGCTTGTTTTGCTCTCTGTTCATATATGGCTCTATTCTTAGAA
ATATAATTTGAATGTGATCTTTCAATAGTCTGAATATTTTACAAATTATAGCTATGTCTTGTGAAAATAACCTCAAAAAG
AAAAATACGACTCTGTTGTCTTACTTGATATTTCTTGCCCTAGTAATGTACTTGACATTTATGTTCCTAAGCAGTGTAAG
TACCAGTAGAATTTCTCTGTCAAACTCAATGATCATTTAGTACTTTTGTCTTCTCCCATGTGCTTGAAGGAAAATAAAG
TGTCACTACCGTATTTCTTGTTTTCATCAAAAAATAAAAATAATTTAAAAAACAAAAAAAAAAAAA
```

Fig. 27A

Human 33b7 (106d5) protein

```
MSGLDGGNKLPLAQTGGLAAPDHASGDPDLDQCQGLREETEATQVWANTGGGSLETVAEGGASQDPVDCGPALRVPVAGS
RGGAATKAGQEDAPPSTKGLEAASAAEAADSSQKNGCQLGEPRGPAGQKALEACGAGGLGSQMIPGKKAKEVTTKKRAIS
AAVEKEGEAGAAMEEKKVVQKEKKVAGGVKEETRPRAPKINNCMDSLEAIDQELSNVNAQADRAFLQLERKFGRMRRLHM
QRRSFIIQNIPGFWVTAFRNHPQLSPMISGQDEDMLRYMINLEVEELKHPRAGCKFKFIFQGNPYFRNEGLVKEYERRSS
GRVVSLSTPIRWHRGQDPQAHIHRNREGNTIPSFFNWFSDHSLLEFDRIAEIIKGELWPNPLQYYLMGEGPRRGIRGPPR
QPVESARSFRFQSG
```

Fig. 27B

Rat 1p protein (partial)

LKGARPRVVNSTCSDFNHGSALHIAASNLCLGAAKCLLEHGANPALRNRKGQVPAEVVPDPMDMSLDKAEAALVAKELRT
LLEEAVPLSCTLPKVTKPNYDNVPGNLMLSALGLRLGDRVLLDGQKTGTLRFCGTTEFASGQWVGVELDEPEGKNDGSVG
GVRYFICPPKQGLFASVSKVSKAVDAPPSSVTSTPRTPRMDFSRVTGKGRREHKGKKKSPSSPSLGSLQQREGAKAEVGD
QVLVAGQNRDCAFLWEDRLCSRLLVWH

Rat 1p DNA (partial, coding: 1-804)

CTGAAAGGGGCGAGGCCCAGGGTGGTGAACTCCACCTGCAGTGACTTCAACCATGGCTCAGCTCTGCACATCGCTGCCTC
GAATCTGTGCCTGGGCGCCGCCAAATGTTTACTGGAGCATGGTGCCAACCCAGCGCTGAGGAATCGAAAAGGACAGGTAC
CAGCGGAAGTGGTCCCAGACCCCATGGACATGTCCCTTGACAAGGCAGAGGCAGCCCTGGTGGCCAAGGAATTGCGGACG
CTGCTAGAAGAGGCTGTGCCACTGTCCTGCACCCTTCCTAAAGTCACACTACCCAACTATGACAACGTCCCAGGCAATCT
CATGCTCAGCGCGCTGGGCCTGCGTCTAGGAGACCGAGTGCTCCTCGATGGCCAGAAGACGGGCACGCTGAGGTTCTGCG
GGACCACCGAGTTCGCCAGTGGCCAGTGGGTGGGCGTGGAGCTAGATGAACCGGAAGGCAAGAACGACGGCAGCGTTGGG
GGTGTCCGGTACTTCATCTGCCCTCCCAAGCAGGGTCTCTTTGCATCTGTGTCCAAGGTCTCCAAGGCAGTGGATGCACC
CCCCTCATCTGTTACCTCCACGCCCCGCACTCCCCGGATGGACTTCTCCCGTGTAACGGGCAAAGGCCGGAGGGAACACA
AAGGGAAGAAGAAGTCCCCATCTTCCCCATCTCTGGGCAGCCTGCAGCAGCGTGAAGGGGCCAAAGCTGAAGTTGGAGAC
CAAGTCCTTGTGGCAGGCCAGAACAGGGATTGTGCGTTTCTATGGGAAGACAGACTTTGCTCCAGGTTACTGGTATGGCA
TTGAACTGGACCAGCCCACGGGCAAGCATGACGGCTCTGTGTTCGGTGTCCGGTACTTTACCTGTGCCCCGAGGCACGGG
GTCTTTGCACCAGCATCTCGTATCCAGAGGATTGGTGGATCCACTGATCCCCTGGAGACAGTGTTGGAGCAAAAAAAGT
GCATCAAGTGACAATGACACAGCCCAAACGCACCTTCACAACAGTCCGGACCCCAAAGGACATTGCATCAGAGAACTCTA
TCTCCAGGTTACTCTTCTGCTGCTGGTTTCCTTGGATGCTGAGGGCGGAGATGCAGTCTTAGAGACCTGGATACCTGACA
CAGAGACAGAGTCCCCTCTAGCATCTCCTGACACAAGGAGACCCCAGTCACCCTAAGATAGAGATTCCCAGTGACACCTC
CAGAATAGAAACCCCGTTAGCCAGCCCTCGATTACTGAGGTCCCATTATTAACAGATCTCCCATGACGACTCCCCCAAAT
ACAGACCTCATGTTACCCCAAAAGAGATTCCCTGAGTAGCACCTTCAGGCTAGTCCCTGTCCCCTACCCCTCAGAGCAGA
TTTCCCCCAATAAACATTTTCCACATCACCCAAGGGATGCTGACCCTCTCCACGACAGGACGTTCTTGAGTTACCAGTGG
ATTAGAGTCCCATGAATGAAGACCCCCCCCACCCCGGTTCTCCTTAAGCATAGGTCATACCTCCAGAATAGCCAGCCACA
TCACTATCCCCATGTAACATCAGTCTCCTCAAAATGGCGTGAGGTCACTAGAAAGACCTTATACTCTCCTCTCCTTCTCA
GAGATGCCCTCCATTCACTTAAGTCCCTGTTCTCACCCCTGAACAAGACACCTAATTAACCGGCCCACTCACCTCAATTA
CAAACACCAAAATCGTCCTGGAAGCATGAATTACAGGACAGCAAGTCTTCCTGCCCTCTGCACCCTTGAGAAACCCCCAG
TGCCTTGTATGAAGCCCACCCCACATGGCCCACAGTCCCTGTGCTGGCCAAGGCTCCCAGAAAATTCTCTATTTTTTAAA
GTAATAACTTCCCCCCCTTTGGGGGGATCCCCAAATTTGGAGACCCCATTCTAGAACACTGGGGAGTTCAAATTCCAGAG
AGAATATATATTATATATAATCCCCCAATTCCCCATGCTTCCAAGCCCTACAATCTCTAGAAGACCCCAAATTTCTAATTC
CCAGGACTTCCCCTACCCAAGTCACAGAATCTTCAAATCCCCAGGGAATCCCAAACTTAAGATACCAATCCCAAACCCTC
AGGAAATCCCCCAACACAAGGTCCTTAGGACCGGGAGGAAGGAACCTGTTGCCAGGAGAACATCCCAGGCTCTCAGGGCA
TCTCAAACCTGACTCCCAGGCACCAGGAGACCCCAAACAGAAAGTCCCATCTTTGGAACAAGGATAGGACTCTAATACCC
TTAGTCCATGGATCTTTAATTTCCCAACCTCCAAACTCCATGGGCCCCACCCTCAAGGGAACCCCCAAGATCCAAATCTC
TGATAACTAATATGTGCAGGGCCCCAGGGCTCTAACAGGACCCCAAATCATGGAGTCCCTACTTCAATCTACCTTCTGGT
CACAGGTCCAAGACACTAAATCTGAGTCATTGGCCCCAAAGGACTTCACAGCACCTGGGCCAGACTAACAGCCTGAGGGA
GAACCTGAGGGCCCCGTGGGTCCAGAGCAGACCTGGGGCCCTGACCACCAAGGACAGCTCACGACTGCCCCTTCACTGCA
TGTCCCTAAACTCAGCATGACTCCTGTCCTCTTCAATAAAGACGTTTCTATGGCAAAAAAAAAAAAAAAAAAAAAAAAAA
AAA

Fig. 28

Rat 7s protein (partial)
ADSTSRWAEALREISGRLAEMPADSGYPAYLGARLASFYERAGRVKCLGNPEREGSVSIVGAVSPPGGDFSDPVTSATLG
IVQVFWGLDKKLAQRKHFPSVNWLISYSKYMRALDEYYDKHFTEFVPLRTKAKEILQEEEDLAEIVQLVGKASLAETDKI
TLEVAKLIKDDFLQQNGYTPYDRFCPFYKTVGMLSNMISFYDMARRAVETTAQSDNKITWSIIREHMGEILYKLSSMKFK
DPVKDGEAKIKADYAQLLEDMQNAFRSLED Rat 7s DNA (partial, coding: 1-813)
GCTGACTCTACCTCTAGATGGGCTGAGGCCCTCAGAGAAATCTCTGGTCGCTTAGCTGAAATGCCTGCAGATAGTGGATA
CCCTGCATACCTTGGTGCCCGACTGGCTTCTTTCTATGAGCGAGCAGGCAGAGTGAAATGTCTTGGAAACCCTGAGAGAG
AAGGGAGTGTCAGCATTGTAGGAGCAGTTTCTCCACCTGGTGGTGATTTTTCTGATCCAGTCACATCTGCTACTCTGGGT
ATTGTTCAGGTGTTCTGGGGCTTGGATAAGAAGCTAGCTCAGCGCAAGCACTTCCCGTCCGTCAACTGGCTCATTAGCTA
CAGCAAGTACATGCGCGCCCTGGACGAGTACTATGACAAACACTTCACAGAGTTCGTGCCTCTGAGGACCAAAGCTAAGG
AGATTCTGCAGGAAGAGGAGGATCTGGCGGAAATCGTGCAGCTCGTGGGAAAGGCGTCTTTAGCAGAGACAGATAAAATC
ACCCTGGAGGTAGCAAAACTTATCAAAGATGACTTCCTACAACAAAATGGGTACACTCCTTATGACAGGTTCTGTCCATT
CTATAAGACGGTGGGGATGCTGTCCAACATGATTTCATTCTATGATATGGCCCGCCGGGCTGTGGAGACCACCGCCCAGA
GTGACAATAAGATCACATGGTCCATTATCCGTGAGCACATGGGGGAGATTCTCTATAAACTTTCCTCCATGAAATTCAAG
GATCCAGTGAAGGATGGCGAGGCAAAGATCAAGGCCGACTACGCACAGCTTCTTGAAGATATGCAGAACGCATTCCGTAG
CCTGGAAGATTAGAACTGTGACTTCTCTCCTCCTCTTCCGCAGCTCATATGTGTATATTTTCCTGAATTTCTCATCTCCA
ACCCTTTGCTTCCATATTGTGCAGCTTTGAGACTAGTGCCTCGTGCGTTCTCGTTCATTTTGCTGTTTCTTTGGTAGGTC
TTATAAAACACACATTCCTGTGCTCCGCTGTCTGAAGGAGCTCCTGACCTTTGTCTGAAGTGGTGAATGTAGTGCATATG
ATACACAGTGTAACATACACATTGTAACATATACGTTCTGTAAACTTGTATGTAAGGTGACTACCCCTTCCCTCCTCTCC
AGTAAACTGTAAACAGGACTACTGCATGTGCTCTATTGGGGATGGAAGGCCAGATCTCCATACCGTGGACAGGTACATAA
GGAAACTAGACCACTTGCAACTTAGTGTTTGTTGAGTAACCATTTTGCAGGAAGTATTTCCATTTAAAAAACAAAAGATT
AATGTTCCAATTATTTGTAGCTTCCCCAGTATCAATCAGGACTGTTTGTGGCGCACTTGGGAACTATTTTGTTTTCCTAA
CAGACGTTTGCAAGGCTGAACGTAATAGATAAATCAGTTCCCTCTGAAAGTGTGAAAGTAAAAAGAGAGCTAGGTGGTCA
GACTTAAATTGACATCGTCTTGTTTAAGCATATTTTATTTCACTGAGAGATTTAATATCAAGGACTTTTATATACTCAAT
TACTAGGAAATCTTTTTTTTAAGTACAATTTAAAAATCATTGAAAATGTGATCCACATCATAGCCATTTTCCTTATATTTA
GTCAGATGAGCTCAGAGTGGGGAGGGTGTGGGTTAGAATACCACAAGGACACGCAGCAGTGCCTGCAGGCAGTGTGGCCG
GGGGCCAGAGCGGCATTGTTTTCACGAGGTACGTGTGTGGCGTGTGTGTTTGCTTGTTGACACTCTGAAAACAGCAAGCT
TACCAGTTCCAGGAAATATTTTGTTTTCTTTCACTGGCTCAGAAAGCTCCTCAAAGTACCTGGTCCCTGAAGCTTCCTAT
CTGTTAATAGAGACGAGAGAGGTTCTTAAATTTAACTGGTGACAAAACAAAAAGAAAAAAAAGATCGATTTTTGTCTTGC
TGTTTTGGTGTGTTTAAATAATAATTCCATATTTGCATAACGAGGCTCGCTTCTGAGAGCTTGGAGATCGTGCTCCCTCT
TCACTCTCCGGGGTGATAATGCTGGCGCCATGCTACCTCTTCAGGAGGGGAAGGGGATTGAACATGGCTAACACTCTCAA
GTACACAAGCGTAACGACAAAGTATTTATTTTAAGCCTTGGTATGTTGTTTAAATTATTAGGTGGTGCATTTCTTATGGT
CTTTTGGGTAGACATAGTATACACTTCAGATGTAATGTGTAAATCCTTGCTAGTGCATGTCTACACGATAGACTGCTATT
CAAGAAGGATATTCTTCCACATAACAATTTAAAAACTATTAAATCAGATATGGATTATGCAATGACTTGTTGAGAGGTGG
ATTAACGGTGCTGCTTAATCAGTTTGCTTCCAATATGGCTTCGTATCCAGAAGCCCTGACTAGTGGAGATGAGAAAGATT
TCAAAACCTGTCTGCCTACACCTACCAGCAACCTAGGCTTGTGATCAGAATGAATGATCCCAAGAAACTACTTGACCAAG
TGTGTTTTGTTGTCCTGGATTTGAGATGTGCGTTCTTCCTCCCTCTGAGACTGTTGATGTATGAGTGTGAAGAAGTTACA
GAAACAACGCTCAGATTTTCACGGTAACTTTCCCTCTGCCCACACTGTAGAGTTTCAGATTGTTCACTGATAGTGCTTCT
TTCGTAAGGATGTGTTAAAATATAGCAGTCTTTTTAAAAGATTATGCAGTTCTCTATTTATTGTGCTGTGCCTGGTCCTA
AGTGCAGCCGGTTAAACAAGTTTCATATGTATTTTTCCAGTGTTAAATCTCATACCTATGCCCTTTGGAAAGCTCCATCC
TGAACAATGAATAGAAGAGGCTATATAAATTGCCTCCTTATCCTTAAGATTTCACTATCTTTATGTTAAGAGTAATGTAT
AATTATTAAAATCTATGAAAAATAAAAAGTGGATTTAAATTAAGAGATC

Fig. 29

Rat 29x protein
ARLPAPEHARQQPLLSGPEPGSSARVPVPGVASRRQPRGGKPPSGDGLESGPSPRPLLHARGEAGLHRQSGRVPHTGTAY
FADEPTEAQAPGGFCVSPSLLGVRWPACATRTPGSLPLSPPSAQPRTLWPTPPAGPSSRMVARNQVAADNAISPASEPRR
RPEPSSSSSSSSSPAAPARPRPCPVVPAPAPGDTHFRTFRSHSDYRRITRTSALLDACGFYWGPLSVHGAHERLRAEPVGT
FLVRDSRQRNCFFALSVKMASGPTSIRVHFQAGRFHLDGSRETFDCLFELLEHYVAAPRRMLGAPLRQRRVRPLQELCRQ
RIVAAVGRENLARIPLNPVLRDYLSSFPFQI Rat 29x DNA (coding: 433-1071)
GCACGGCTCCCGGCCCCGGAGCATGCGCGACAGCAGCCCCTCCTCtCCGGCCCTGAGCCCGGATCGTCCGCCCGGGTTCC
AGTTCCCGGCGTGGCCAGTAGGCGGCAGCCGCGAGGCGGCAAGCCACCCAGCGGGGACGGCCTGGAGTCGGGCCCCTCTC
CACGCCCCCTTCTCCACGCGCGCGGGGAGGCAGGGCTCCACCGCCAGTCTGGAAGGGTTCCACATACAGGAACGGCCTAC
TTCGCAGATGAGCCCACCGAGGCTCAGGCTCCGGGCGGATTCTGCGTGTCACCCTCGCTCCTTGGGGTCCGCTGGCCGGC
CTGTGCCACCCGGACGCCCGGCTCACTGCCTCTGTCTCCCCCATCAGCGCAGCCCCGGACGCTATGGCCCACCCCTCCAG
CTGGCCCCTCGAGTAGGATGGTAGCACGTAACCAGGTGGCAGCCGACAATGCGATCTCCCCGGCATCAGAGCCCCGACGG
CGGCCAGAGCCATCCTCGTCCTCGTCTTCGTCCTCGCCGGCGGCCCCGGCGCGTCCCCGGCCCTGCCCGGTGGTCCCGGC
CCCGGCTCCGGGCGACACTCACTTCCGCACCTTCCGCTCCCACTCTGATTACCGGCGCATCACGCGGACCAGCGCTCTCC
TGGACGCCTGCGGCTTCTACTGGGGACCCCTGAGCGTGCATGGGCGCACGAACGGCTGCGTGCCGAGCCCGTGGGCACC
TTCTTGGTGCGCGACAGTCGCCAGCGGAACTGCTTCTTCGCGCTCAGCGTGAAGATGGCTTCGGGCCCCACGAGCATTCG
TGTGCACTTCCAGGCCGGCCGCTTCCACCTGGACGGCAGCCGCGAGACCTTCGACTGCCTCTTCGAGCTGCTGGAGCACT
ACGTGGCGGCGCCGCGCCGCATGTTGGGGGCCCCACTGCGCCAGCGCCGCGTGCGGCCGCTGCAGGAGCTGTGTCGCCAG
CGCATCGTGGCCGCCGTGGGTCGCGAGAACCTGGCACGCATCCCTCTTAACCCGGTACTCCGTGACTACCTGAGTTCCTT
CCCCTTCCAGATCTGACCGGCTGCCGCCGTGCCCGCAGCATTAAGTGGGAGCGCCTTATTATTTCTTATTATTAATTATT
ATTATTTTTcTGGAACCACGTGGGAGCCCTCCCCGCCTAGGTCGGAGGGAGTGGGTGTGGAGGGTGAGATGCCTCCCACT
TCTGGCTGGAGACCTTATCCCGCCTCTCGGGGGGCCTCCCCTCCTGGTGCTCCCTCCCGGTCCCCCTGGTTGTAGCAGCT
TGTGTCTGGGGCCAGGACCTGAACTCCACGCCTACCTCTCCATGTTTACATGTTCCCAGTATCTTTGCACAAACCAGGGG
TGGGGGAGGGTCTCTGGCTTCATTTTTCTGCTGTGCAGAATATTCTATTTTATATTTTTACATCCAGTTTAGATAATAAA
CTTTATTATGAAAGTTTTTTTTTTAAAGAAAAAAAAAAAAAAAAAAAAAA

Fig. 30

Rat 25r DNA (coding 130-768)
GGCACGGCTCCCGGCCCCGGAGCATGCGCGACAGCAGCCCCGGAACCCCCAGCCGCGGCGCCCCGCGTCCCGCCGCCAGC
GCAGCCCCGGACGCTATGGCCCACCCCTCCAGCTGGCCCCTCGAGTAGGATGGTAGCACGTAACCAGGTGGCAGCCGACA
ATGCGATCTCCCCGGCATCAGAGCCCCGACGGCGGCCAGAGCCATCCTCGTCCTCGTCTTCGTCCTCGCCGGCGGCCCCG
GCGCGTCCCCGGCCCTGCCCGGTGGTCCCGGCCCCGGCTCCGGGCGACACTCACTTCCGCACCTTCCGCTCCCACTCTGA
TTACCGGCGCATCACGCGGACCAGCGCTCTCCTGGACGCCTGCGGCTTCTACTGGGGACCCCTGAGCGTGCATGGGGCGC
ACGAACGGCTGCGTGCCGAGCCCGTGGGCACCTTCTTGGTGCGCGACAGTCGCCAGCGGAACTGCTTCTTCGCGCTCAGC
GTGAAGATGGCTTCGGGCCCCACGAGCATTCGTGTGCACTTCCAGGCCGGCCGCTTCCACCTGGACGGCAGCCGCGAGAC
CTTCGACTGCCTCTTCGAGCTGCTGGAGCACTACGTGGCGGCGCCGCGCCGCATGTTGGGGGCCCCACTGCGCCAGCGCC
GCGTGCGGCCGCTGCAGGAGCTGTGTCGCCAGCGCATCGTGGCCGCCGTGGGTCGCGAGAACCTGGCACGCATCCCTCTT
AACCCGGTACTCCGTGACTACCTGAGTTCCTTCCCCTTCCAGATCTGACCGGCTGCCGCCGTGCCCGCAGCATTAAGTGG
GAGCGCCTTATTATTTCTTATTATTAATTATTATTATTTTTCTGGAACCACGTGGGAGCCCTCCCCGCCTAGGTCGGAGG
GAGTGGGTGTGGAGGGTGAGATGCCTCCCACTTCTGGCTGGAGACCTTATCCCGCCTCTCGGGGGGCCTCCCCTCCTGGT
GCTCCCTCCCGGTCCCCCTGGTTGTAGCAGCTTGTGTCTGGGGCCAGGACCTGAACTCCACGCCTACCTCTCCATGTTTA
CATGTTCCCAGTATCTTTGCACAAACCAGGGGTGGGGGAGGGTCTCTGGCTTCATTTTTCTGCTGTGCAGAATATTCTAT
TTTATATTTTTACATCCAGTTTAGATAATAAACTTTATTATGAAAGTTTTTTTTTAAAAAAAAAAAAAAAAAAA

Fig. 31

Rat 5p protein
MPSQMEHAMETMMLTFHRFAGEKNYLTKEDLRVLMEREFPGFLENQKDPLAVDKIMKDLDQCRDGKVGFQSFLSLVAGLI
IACNDYFVVHMKQKK Rat 5p DNA (coding: 52-339)
CTTCCAAAGACTGCAGCGCCTCAGGGCCCAGGTTTCAACAGATTCTTCAAAATGCCATCCCAAATGGAGCATGCCATGGA
AACCATGATGCTTACATTTCACAGGTTTGCAGGGGAAAAAAACTACTTGACAAAGGAGGACCTGAGAGTGCTCATGGAAA
GGGAGTTCCCTGGGTTTTTGGAAAATCAAAAGGACCCTCTGGCTGTGGACAAAATAATGAAAGACCTGGACCAGTGCCGA
GATGGAAAAGTGGGCTTCCAGAGCTTTCTATCACTAGTGGCGGGGCTCATCATTGCATGCAATGACTATTTTGTAGTACA
CATGAAGCAGAAGAAGTAGGCCAACTGGAGCCCTGGTACCCACACCTTGATGCGTCCTCTCCCATGGGGTCAACTGAGGA
ATCTGCCCCACTGCTTCCTGTGAGCAGATCAGGACCCTTAGGAAATGTGCAAATAACATCCAACTCCAATTCGACAAGCA
GAGAAAGAAAAGTTAATCCAATGACAGAGGAGCTTTCGAGTTTTATATTGTTTGCATCCGGTTGCCCTCAATAAAGAAAG
TCTTTTTTTTTAAGTTCCGAAAAAAAAAAAAAAAAAAAAA

Fig. 32

Rat 7q protein
MAYAYLFKYIIIGDTGVGKSCLLLQFTDKRFQPVHDLTIGVEFGARMITIDGKQIKLQIWDTAGQESFRSITRSYYRGAA
GALLVYDITRRDTFNHLTTWLEDARQHSNSNMVIMLIGNKSDLESRREVKKEEGEAFAREHGLIFMETSAKTASNVEEAF
INTAKEIYEKIQEGVFDINNEANGIKIGPQHAATNASHGGNQGGQQAGGGCC Rat 7q DNA (coding: 1-639)
ATGGCGTACGCCTATCTCTTCAAGTACATCATCATCGGCGACACAGGTGTTGGTAAATCGTGCTTATTGCTACAGTTTAC
AGACAAGAGGTTTCAGCCGGTGCATGACCTCACAATTGGTGTAGAGTTTGGTGCTCGAATGATAACCATTGATGGGAAAC
AGATAAAACTCCAGATCTGGGATACAGCAGGGCAGGAGTCCTTTCGTTCTATCACAAGGTCATATTACAGAGGTGCAGCG
GGGGCTTTACTAGTGTATGATATTACAAGGAGAGACACGTTCAACCACTTGACAACCTGGTTAGAAGACGCCCGTCAGCA
TTCCAATTCCAACATGGTCATCATGCTTATTGGAAATAAAAGTGACTTAGAATCTAGGAGAGAAGTGAAAAAGGAAGAAG
GTGAAGCTTTTGCACGAGAGCATGGACTTATCTTCATGGAAACTTCTGCCAAGACTGCTTCTAATGTAGAGGAGGCATTT
ATTAACACAGCAAAAGAAATTTATGAAAAAATCCAAGAAGGGGTCTTTGACATTAATAATGAGGCAAACGGCATCAAAAT
TGGCCCTCAGCATGCTGCTACCAATGCATCTCACGGAGGCAACCAAGGAGGGCAGCAGGCAGGGGGAGGCTGCTGCTGA

Fig. 33

Rat 19r protein
MVLLKEYRVILPVSVDEYQVGQLYSVAEASKNETGGGEGVEVLVNEPYEKDDGEKGQYTHKIYHLQSKVPTFVRMLAPEG
ALNIHEKAWNAYPYCRTVITNEYMKEDFLIKIETWHKPDLGTQENVHKLEPEAWKHVEAIYIDIADRSQVLSKDYKAEED
PAKFKSIKTGRGPLGPNWKQELVNQKDCPYMCAYKLVTVKFKWWGLQNKVENFIHKQEKRLFTNFHRQLFCWLDKWVDLT
MDDIRRMEEETKRQKDEMRQKDPVKGMTADD Rat 19r DNA (coding: 1-816)
ATGGTGCTGCTCAAGGAATATCGGGTCATCCTGCCTGTGTCTGTAGATGAGTATCAAGTGGGGCAGCTGTACTCTGTGGC
TGAAGCCAGTAAAAATGAAACTGGTGGTGGGGAAGGTGTGGAGGTCCTGGTGAACGAGCCCTACGAGAAGGATGATGGCG
AGAAAGGCCAGTACACACACAAGATCTACCACTTACAGAGCAAAGTTCCCACGTTTGTTCGAATGCTGGCCCCAGAAGGC
GCCCTGAATATACATGAGAAAGCCTGGAATGCCTACCCTTACTGCAGAACCGTTATTACAAATGAGTACATGAAGGAAGA
CTTTCTCATTAAAATTGAAACCTGGCACAAGCCAGACCTTGGCACCCAGGAGAATGTGCATAAACTGGAGCCTGAGGCAT
GGAAACATGTGGAAGCTATATATATAGACATCGCTGATCGAAGCCAAGTACTTAGCAAGGATTACAAGGCAGAGGAAGAC
CCAGCAAAATTTAAATCTATCAAAACAGGACGAGGACCATTGGGCCCGAATTGGAAGCAAGAACTTGTCAATCAGAAGGA
CTGCCCATATATGTGTGCATACAAACTGGTTACTGTCAAGTTCAAGTGGTGGGGCTTGCAGAACAAAGTGGAAAACTTTA
TACATAAGCAAGAGAAGCGTCTGTTTACAAACTTTCACAGGCAGCTGTTCTGTTGGCTTGATAAATGGGTTGATCTGACT
ATGGATGACATTCGGAGGATGGAAGAAGAGACGAAGAGACAGCTGGATGAGATGAGACAAAAGGACCCCGTGAAAGGAAT
GACAGCAGATGACTAG

Fig. 34

Monkey KChIP4c (jlkxa053c02) DNA sequence (CD: 122-811)
CGCTCTCCTCCTCCCCTTTCTCTAGCAGTAGCCTTCTTAATGTAGTTTAATGGCTTTACAAAGAAAGCCAGGCAGAGGAG
CACTTCTCAGTGGCTGTGGTCGGACCATGACCTAGCTGACCATGAACTTGGAAGGGCTTGAAATGATAGCAGTTCTGATC
GTCATTGTGCTTTTTGTTAAATTATTGGAACAGTTTGGGCTGATTGAAGCAGGTTTAGAAGACAGCGTGGAAGATGAACT
GGAGATGGCCACTGTCAGGCATCGGCCTGAGGCCCTTGAGCTTCTGGAAGCCCAGAGCAAATTTACCAAGAAAGAGCTTC
AGATCCTTTACAGAGGATTTAAGAACGAATGCCCCAGTGGTGTTGTTAATGAAGAAACCTTCAAAGAGATTTACTCGCAG
TTCTTTCCACAGGGAGACTCTACAACATATGCACATTTTCTGTTCAATGCGTTTGATACGGACCACAATGGAGCTGTGAG
TTTCGAGGATTTCATCAAAGGTCTTTCCATTTTGCTCCGGGGACAGTACAAGAAAAACTCAATTGGGCATTTAATCTGT
ATGATATAAATAAAGATGGCTACATCACTAAAGAGGAAATGCTTGATATAATGAAAGCAATATACGACATGATGGGTAAA
TGTACATATCCTGTCCTCAAAGAAGATGCACCCAGACAACACGTCGAAACATTTTTTCAGAAAATGGACAAAAATAAAGA
TGGGGTTGTTACCATAGATGAGTTCATTGAAAGCTGCCAAAAAGATGAAAACATAATGCGCTCCATGCAGCTCTTTGAAA
ATGTGATTTAACTTGTCAACTAGATCCTGAATCCAACAGACAAATGTGAACTATTCTACCACCCCTTAAAGTCGGAGCTAC
CACTTTTAGCATAGATTGCTCAGCTTGACACTGAAGCATATTATGCAAACAAGCTTTGTTTTAATATAAAGCAATCCCCA
AAAGATTTGAGTTTCTCAGTTATAAATTTGCATCCTTTCCATAATGCCACTGAGTTCATGGGATGTTCTAACTCATTTCA
TACTCTGTGAATATTCAAAAGTAATAGAATCTGGCATATAGTTTTATTGATTCCTTAGCCATGGGATTATTGAGGCTTTC
ACATATCAGTGATTTTAAAATACCAGTGTTTTTTGCTACTCATTTGTATGTATTCAGTCCTAGGATTTTGAATGGTTTTC
TAATATACTGACATCTGCATTTAATTTCCAGAAATTAAATTAATTTTCATGTCTGAATGCTGTAATTCCATTTATATACT
TTAAGTAAACAAATAAGATTACTACAATTAAACACATAGTTCCAGTTTCTATGGCCTTCACTTCCCACCTTCTATTAGAA
ATTAATTTTATCTGGTATTTTTAAACATTTAAAAATTTATCATCAGATATCAGCATATGCCTAATTATGCCTAATGAAAC
TTAATAAGCATTTAATTTTCCATCATACATTATAGTCAAGGCCTATATACTATATATAATTTTGGATTTGTTTAATCTTA
CAGGCTGTTTTCCATTGTATCATCAAGTGGAAGTTCAAGACGGCATCAAACAAAACAAGGATGTTTACAGACATATGCAA
AGGGTCAGGATATCTATCCTCCAGTATATGTTAATGCTTAATAACAAGTAATCCTAACAGCATTAAAGGCCAAATCTGTC
CTCTTTCCCCTGACTTCCTTACAGCATGTTTATATTACAAGCCATTCAGGGACAAAGAAACCTTGACTACCCCACTGTCT
ACTAGGAACAAACAAACAGCAAGCAAAATTCACTTTGAAAGCACCAGTGGTTCCATTACATTGACAACTACTACCAAGAT
TCAGTAGAAAATAAGTGCTCAACAACTAATCCAGATTACAATATGATTTAGTGCATCATAAAATTCCAACAATTCAGATT
ATTTTTAATCACCTCAGCCACAACTGTAAAGTTGCCACATTACTAAAGACACACACATCGTCCCTGTTTTGTAGAAATAT
CACAAAGACCAAGAGGCTACAGAAGGAGGAAATTTGCAACTGTCTTTGCAACAATAAATCAGGTATCTATTCTGGTGTAG
AGATAGGATGTTGAAAGCTGCCCTGCTATCACCAGTGTAGAAATTAAGAGTAGTACAATACATGTACACTGAAATTTGCC
ATCGCGTGTTTGTGTAAACTCAATGTGCACATTTTGTATTTCAAAAAGAAAAAATAAAAGCAAATAAAATGTTTATAAC
TCTAAAAAAAAAAAAAAAAAAAA Monkey KChIP4c protein sequence
MNLEGLEMIAVLIVIVLFVKLLEQFGLIEAGLEDSVEDELEMAYVRHRPEALELLEAQSKFTKKELQILYRGFKNECPSG
VVNEETFKEIYSQFFPQGDSTTYAHFLFNAFDTDHNGAVSFEDFIKGLSILLRGTVQEKLNWAFNLYDINKDGYITKEEM
LDIMKAIYDMMGKCTYPVLKEDAPRQHVETFFQKMDKNKDGVVTIDEFIESCQKDENIMRSMQLFENVI.

Fig. 35

Monkey KChIP4d (jlkx015b10) DNA sequence (CD: 64-816)
GTCGACAGACGCCCCTGGCCGGTGGACTCCTGAGTCTTACTCCTGCACCCTGCGTCCCCAGACATGAATGTGAGGAGAGT
GGAAAGCATTTCGGCTCAGCTGGAGGAGGCCAGCTCCACAGGCGGTTTCCTGTATGCTCAGAACAGCACCAAGCGCAGCA
TTAAAGAGCGGCTCATGAAGCTCTTGCCCTGCTCAGCTGCCAAAACATCGTCTCCTGCTATTCAAAACAGCGTGGAAGAT
GAACTGGAGATGGCCACTGTCAGGCATCGGCCTGAGGCCCTTGAGCTTCTGGAAGCCCAGAGCAAATTTACCAAGAAAGA
GCTTCAGATCCTTTACAGAGGATTTAAGAACGAATGCCCCAGTGGTGTTGTTAATGAAGAAACCTTCAAAGAGATTTACT
CGCAGTTCTTTCCACAGGGAGACTCTACAACATATGCACATTTTCTGTTCAATGCGTTTGATACGGACCACAATGGAGCT
GTGAGTTTCGAGGATTTCATCAAAGGTCTTTCCATTTTGCTCCGGGGGACAGTACAAGAAAAACTCAATTGGGCATTTAA
TCTGTATGATATAAATAAAGATGGCTACATCACTAAAGAGGAAATGCTTGATATAATGAAAGCAATATACGACATGATGG
GTAAATGTACATATCCTGTCCTCAAAGAAGATGCACCCAGACAACACGTCGAAACATTTTTTCAGAAAATGGACAAAAAT
AAAGATGGGGTTGTTACCATAGATGAGTTCATTGAAAGCTGCCAAAAAGATGAAAACATAATGCGCTCCATGCAGCTCTT
TGAAAATGTGATTTAACTTGTCAACTAGATCCTGAATCCAACAGACAAATGTGAACTATTCTACCACCCTTAAAGTCGGA
GCTACCACTTTTAGCATAGATTGCTCAGCTTGACACTGAAGCATATTATGCAAACAAGCTTTGTTTTAATATAAAGCAAT
CCCCAAAAGATTTGAGTTTCTCAGTTATAAATTTGCATCCTTTCCATAATGCCACTGAGTTCATGGGATGTTCTGACTCA
TTTCATACTCTGTGAATATTCAAAAGTAATAGAATCTGGCATATAGTTTTATTGATTCCTTAGCCATGGGATTATTGAGG
CTTTCACATATCAGTGATTTTAAAATACCAGTGTTTTTTGCTACTCATTTGTATGTATTCAGTCCTAGGATTTTGAATGG
TTTTCTAATATACTGACATCTGCATTTAATTTCCAGAAATTAAATTAATTTTCATGTCTGAATGCTGTAATTCCATTTAT
ATACTTTAAGTAAACAAATAAGATTACTACAATTAAACACATAGTTCCAGTTTCTATGGCCTTCACTTCCCACCTTCTAT
TAGAAATTAATTTTATCTGGTATTTTTAAACATTTAAAAATTTATCATCAGATATCAGCATATGCCTAATTATGCCTAAT
GAAACTTAATAAGCATTTAATTTTCCATCATACATTATAGTCAAGGCCTATATACTATATATAATTTTGGATTTGTTTAA
TCTTACAGGCTGTTTTCCATTGTATCATCAAGTGGAAGTTCAAGACGGCATCAAACAAAACAAGGATGTTTACAGACATA
TGCAAAGGGTCAGGATATCTATCCTCCAGTATATGTTAATGCTTAATAACAAGTAATCCTAACAGCATTAAAGGCCAAAT
CTGTCCTCTTTCCCCTGACTTCCTTACAGCATGTTTATATTACAAGCCATTCAGGGACAAAGAAACCTTGACTACCCCAC
TGTCTACTAGGAACAAACAAACAGCAAGCAAAATTCACTTTGAAAGCACCAGTGGTTCCATTACATTGACAACTACTACC
AAGATTCAGTAGAAAATAAGTGCTCAACAACTAATCCAGATTACAATATGATTTAGTGCATCATAAAATTCCAACAATTC
AGATTATTTTTAATCACCTCAGCCACAACTGTAAAGTTGCCACATTACTAAAGACACACACATCGTCCCTGTTTTGTAGA
AATATCACAAAGACCAAGAGGCTACAGAAGGAGGAAATTTGCAACTGTCTTTGCAACAATAAATCAGGTATCTATTCTGG
TGTAGAGATAGGATGTTGAAAGCTGCCCTGCTATCACCAGTGTAGAAATTAAGAGTAGTACAATACATGTACACTGAAAT
TTGCCATCGCGTGTTTGTGTAAACTCAATGTGCACATTTTGTATTTCAAAAAGAAAAAATAAAAGCAAAATAAAATGTTA
AAAAAAAAAAAAAAAAAAA Monkey KChIP4d protein sequence
MNVRRVESISAQLEEASSTGGFLYAQNSTKRSIKERLMKLLPCSAAKTSSPAIQNSVEDELEMATVRHRPEALELLEAQS
KFTKKELQILYRGFKNECPSGVVNEETFKEIYSQFFPQGDSTTYAHFLFNAFDTDHNGAVSFEDFIKGLSILLRGTVQEK
LNWAFNLYDINKDGYITKEEMLDIMKAIYDMMGKCTYPVLKEDAPRQHVETFFQKMDKNKDGVVTIDEFIESCQKDENIM
RSMQLFENVI.

Fig. 36

```
                 X  Y  Z -Y -X -Z
h KChIP1  MGA-----------------------VMGTFSSLQTKQRRPSK-----------
h KChIP2  MRGQGRKESLSDSRDLDGSYDQLTGHPPGPTKKALK-----------
h KChIP3  M--QPAKEV---TKASDGSLLGDLGHTPLSKKEGIKWQRPRLSRQALMRCCLVKWILSST
h HIP     MGKQNSK-------------QRFSK---LLPCCGPQ----AL------
r NCS1    MGKSNSK-----------------------------------------

EF1
                                           X  Y  Z -Y -X -Z
h KChIP1  ----DKIEDELEMTMVCHRPEGLEQLEAQTNFTKRELQVLYRGFKNECPSGVVNEDTFK
h KChIP2  PSVSENSVDDEFELSTVCHRPEGLEQLEQLQEQTKFTRKELQVLYRGFKNECPSGIVNEENFK
h KChIP3  APQGSDSSDSELELSTVRHQPEGLDQLQAQTKFTKKELQSLYRGFKNECPTGLVDEDTFK
h HIP     ----LRPEMLQDLRENTEFSELELQEWYKGFLKDCPTGILNVDEFK
r NCS1    ----LKPEVVEELTRKTYFTEKEVQQWYKGFIKDCPSGQLDAAGFQ

EF2
                              X  Y  Z -Y -X -Z
h KChIP1  QIYAQFFPHGDASTYAHYLFNAFDTTQTGSVKFEDFVTALSILLRGTVHEKLRWTFNLYD
h KChIP2  QIYSQFFPQGDSSNYATFLFNAFDTNHDGSVSFEDFVAGLSVILRGTVDDRLNWAFNLYD
h KChIP3  LIYAQFFPQGDATTYAHFLFNAFDADGNGAIHFEDFVVGLSILLRGTVHEKLKWAFNLYD
h HIP     KIYANFFPYGDASKFAEHVFRTFDTNSDGTIDFREFIIALSVTSPGRLEQKLMWAFSMYD
r NCS1    KIYKQFFPFGDPTKFATFVFNVFDENKDGRIEFSEFIQALSVTSRGTLDEKLRWAFKLYD

EF3
           Y  Z -Y -X -Z
h KChIP1  INKDGYINKEEMMDIVKAIYDMMGKYTYPVLKEDTPRQHVDVFFQKMDKNKDGIVTLDEF
h KChIP2  LNKDGCITKEEMLDIMKSIYDMMGKYTYPYPALREEAPREHVESFFQKMDRNKDGVVTIEEF
h KChIP3  INKDGYITKEEMLAIMKSIYDMMGRHTYPILREDAPAEHVERFFEKMDRNQDGVVTIEEF
h HIP     LDGNGYISREEMLEIVQAIYKMVSSVMKMPEDESTPEKRTEKIFRQMDTNNDGKLSLEEF
r NCS1    LDNDGYITRNEMLDIVDAIYQMVGNTVELPEEENTPEKRVDRIFAMMDKNADGKLTLQEF
                                                  EF4
                                          X  Y  Z -Y -X -Z h KChIP1  LESCQEDDNIMRSLQ---LFQNVM.
h KChIP2  IESCQKDENIMRSMQ---LFDNVI..
h KChIP3  LEACQKDENIMSSMQ---LFENVI..
h HIP     IRGAKSDPSIVRLLQCDPSSRSQF..
r NCS1    QEGSKADPSIVQAL---SLYDGLV.
```

Fig. 41

METHODS FOR TREATING CARDIOVASCULAR DISORDERS

RELATED APPLICATIONS

This application is a continuation in part of U.S. Application No. 09/350,874, filed Jul. 9, 1999 (now abandoned) which is a continuation in part of U.S. Application No. 09/298,731 filed Apr. 23, 1999 (now U.S. Pat. No. 6,369, 197) which claims benefit under 35 U.S.C. Sec. 119(e) to U.S. Application Nos. 60/109,333, filed Nov. 20, 1998, 60/110,033, filed on Nov. 25, 1998 and 60/110,277, filed on Nov. 30, 1998.

This application is also a continuation in part of U.S. Application No. 09/350,614 filed Jul. 9, 1999 (now U.S. Pat. No. 6,689,501) which is a divisional of 09/298,731 filed Apr. 23, 1999 (now U.S. Pat. No. 6,369,197) which claims benefit under 35 U.S.C. Sec. 119(e) U.S. Application Nos. 60/109, 333, filed Nov. 20, 1998, 60/110,033, filed on Nov. 25, 1998 and 60/110,277, filed on Nov. 30, 1998.

BACKGROUND OF THE INVENTION

Mammalian cell membranes are important to the structural integrity and activity of many cells and tissues. Of particular interest in membrane physiology is the study of trans-membrane ion channels which act to directly control a variety of pharmacological. physiological, and cellular processes. Numerous ion channels have been identified including calcium, sodium, and potassium channels, each of which have been investigated to determine their roles in vertebrate and insect cells.

Because of their involvement in maintaining normal cellular homeostasis, much attention has been given to potassium channels. A number of these potassium channels open in response to changes in the cell membrane potential. Many voltage-gated potassium channels have been identified and characterized by their electrophysiological and pharmacological properties. Potassium currents are more diverse than sodium or calcium currents and are further involved in determining the response of a cell to external stimuli.

The diversity of potassium channels and their important physiological role highlights their potential as targets for developing therapeutic agents or various diseases. One of the best characterized classes of potassium channels are the voltage-gated potassium channels. The prototypical member of this class is the protein encoded by the Shaker gene in *Drosophila melanogaster*. Proteins of the Shal or Kv4 family are a type of voltage-gated potassium channels that underlies many of the native A type currents that have been recorded from different primary cells. Kv4 channels have a major role in the repolarization of cardiac action potentials. In neurons. Kv4 channels and the A currents they may comprise play an important role in modulation of firing rate, action potential initiation and in controlling dendritic responses to synaptic inputs.

The Kv family of channels includes, among others: (1) the delayed-rectifier potassium channels, which repolarize the membrane after each action potential to prepare the cell to fire again; and (2) the rapidly inactivating (A-type) potassium channels, which are active predominantly at subthreshold voltages and and act to reduce the rate at which excitable cells reach firing threshold. In addition to being critical for action potential conduction. Kv channels also control the response for depolarizing, e.g., synaptic, inputs and play a role in neurotransmitter release. As a result of these activities, voltage-gated potassium channels are key regulators of neuronal excitability (Hille B., Ionic Channels of Excitable Membranes. Second Edition, Sunderland. MA; Sinauer. (1992)).

There is tremendous structural and functional diversity within the Kv potassium channel superfamily. This diversity is generated both by the existence of multiple genes and by alternative splicing of RNA transcripts produced from the same gene. Nonetheless, the amino acid sequences of the known Kv potassium channels show high similarity. All appear to be comprised of four, pore forming α-subunits and some are known to have four cytoplasmic (β-subunit) polypeptides (Jan L. Y. et al. (1990) *Trends Neurosci* 13:415–419, and Pongs, O. et al. (1995) *Sem Neurosci.* 7:137–146). The known Kv channel α-subunits fall into four sub-families named for their homology to channels first isolated from *Drosophila; the Kv*1, or *Shaker*-related subfamily; the Kv2, or *Shaw*-related subfamily; the Kv3, or *Shaw*-related subfamily; and the Kv4, or *Shal*-related subfamily.

Kv4.2 and Kv4.3 are examples of Kv channel α-subunits of the *Shal*-related subfamily. Kv4.3 has a unique neuroanatomical distribution in that its mRNA is highly expressed in brainstem monoaminergic and forebrain cholinergic neurons, where it is involved in the release of the neurotransmitters dopamine, norepinephrine, serotonin, and acetylcholine. This channel is also highly expressed in cortical pyramidal cells and in interneurons. (Serdio P. et al. (1996)*J. Neurophys* 75:2174–2179). Interestingly, the Kv4.3 polypeptide is highly expressed in neurons which express the corresponding mRNA. The Kv4.3 polypeptide is expressed in the somatodendritic membranes of these cells, where it is thought to contribute to the rapidly inactivating K+ conductance. Kv4.2 mRNA is widely expressed in brain, and the corresponding polypeptide also appears to be concentrated in somatodendritic membranes where it also contributes to the rapidly inactivating K+ conductance (Sheng et al. (1992) Neuron 9:271–84). These somatodendrite A-type Kv channels, like Kv4.2 and Kv4.3 are likely involved in processes which underlie learning and memory, such as integration of sub-threshold synaptic responses and the conductance of hack-propagating action potentials (Hoffman D. A. et al. (1997) *Nature* 387:869–875).

Thus, proteins which interact with and modulate the activity of potassium channel proteins e.g., potassium channels having a Kv4.2 or Kv4.3 subunit, provide novel molecular targets to modulate neuronal excitability, e.g., action potential conduction, somatodendrite excitability and neurotransmitter release, in cells expressing these channels. In addition, detection of genetic lesions in the gene encoding these proteins could be used to diagnose and treat cardiovascular disorders such as heart failure, hypertension, atrial fibrillation, dilated cardiomyopathy, idiopathic cardiomyopathy, or angina.

| | | |
|---|---|---|
| A. | Summary of the Invention | -3- |
| B. | Brief Description of the Drawings | -4- |
| C. | Detailed Description of the Invention | -8- |
| | I. Screening Assays | -17- |
| | II. Predictive Medicine | -24- |
| |    1. Diagnostic Assays | -25- |
| |    2. Prognostic Assays | -26- |
| |    3. Monitoring of Effects During Clinical Trials | -31- |
| | III. Methods of Treatment | -32- |
| |    1. Prophylactic Methods | -33- |
| |    2. Therapeutic Methods | -33- |
| |    3. Pharmacogenomics | -40- |
| D. | Examples | -42- |

SUMMARY OF THE INVENTION

The present invention is based, at least in part, on the discovery of novel nucleic acid molecules which encode gene products that interact with potassium channel proteins or possess substantial homology to the gene products of the invention that interact with potassium channel proteins (paralogs). Potassium channel proteins are, for example, potassium channels having a Kv4.2 or Kv4.3 subunit. The nucleic acid molecules of the invention and their gene products are referred to herein as "Potassium Channel Interacting Proteins", "PCIP", or "KChIP" nucleic acid and protein molecules. The PCIP molecules of the present invention are useful as modulating agents to regulate a variety of cellular processes, in particular, cardiac cell processes.

Accordingly, in one aspect, this invention provides a method for identifying a compound suitable for treating a cardiovascular disorder. e.g., arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrillation or congestive heart failure, by contacting a PCIP polypeptide or a fragment thereof, or a cell expressing a PCIP polypeptide or a fragment thereof with a test compound and determining whether the PCIP polypeptide or fragment thereof binds to the test compound, thereby identifying a compound suitable for treating a cardiovascular disorder. In a preferred embodiment, the binding of the test compound to the PCIP polypeptide or fragment thereof is detected by direct detection of test compound/polypeptide binding. In another embodiment, the binding of the test compound to the PCIP polypeptide or fragment thereof is detected by using a competition binding assay. In yet another embodiment, the binding of the test compound to the PCIP polypeptide or fragment thereof is detected by using an assay for PCIP activity.

In another aspect the invention features a method for identifying a compound suitable for treating a cardiovascular disorder, e.g., arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrillation or congestive heart failure, by incubating a cell expressing a potassium channel comprising a Kv4.3 or Kv4.2 subunit, or a fragment of a potassium channel comprising a Kv4.3 or Kv4.2 subunit, and a PCIP polypeptide or fragment thereof, in the presence and absence of a candidate compound; and determining whether the presence of the candidate compound modulates the interaction of the potassium channel or fragment thereof with the PCIP polypeptide or fragment thereof, thereby identifying a compound suitable for treating a cardiovascular disorder.

In yet another aspect, the invention features a method for treating a cardiovascular disorder by contacting a potassium channel with an effective amount of a compound that modulates the binding of a PCIP protein to the potassium channel.

In a further aspect, the invention features a method for determining if a subject is at risk for a cardiovascular disorder by detecting, in a sample of cells from the subject an alteration in a PCIP gene which causes a mutated PCIP polypeptide to be produced, an alteration in a PCIP gene which causes abnormal expression of a PCIP polypeptide, or an alteration in a PCIP gene which causes abnormal processing of a PCIP polypeptide.

In another aspect, the invention features a method for identifying a subject suffering from a cardiovascular disorder by detecting, in a sample of cells from the subject an alteration in a PCIP gene which causes a mutated PCIP polypeptide to be produced, an alteration in a PCIP gene which causes abnormal expression of a PCIP polypeptide, or an alteration in a PCIP gene which causes abnormal processing of a PCIP polypeptide.

In a preferred embodiment, the cardiovascular disorder is associated with an abnormal $I_{to}$ current.

Other features and advantages of the invention will be apparent from the following detailed description and claims.

BRIEF DESCRIPTION OF THE DRAWINGS

FIG. 1 depicts the cDNA sequence and predicted amino acid sequence of human 1v. The nucleotide sequence corresponds to nucleic acids 1 to 1463 of SEQ ID NO:1. The amino acid sequence corresponds to amino acids 1 to 216 of SEQ ID NO:2.

FIG. 2 depicts the cDNA sequence and predicted amino acid sequence of rat 1v. The nucleotide sequence corresponds to nucleic acids 1 to 1856 of SEQ ID NO:3 (FIG. 2A). The amino acid sequence corresponds to amino acids 1 to 245 of SEQ ID NO:4 (FIG. 2B).

FIG. 3 depicts the cDNA sequence and predicted amino acid sequence of mouse 1v. The nucleotide sequence corresponds to nucleic acids 1 to 1907 of SEQ ID NO:5. The amino acid sequence corresponds to amino acids 1 to 216 of SEQ NO:6.

FIG. 4 depicts the cDNA sequence and predicted amino acid sequence of rat 1vl. The nucleotide sequence corresponds to nucleic acids 1 to 1534 of SEQ ID NO:7. The amino acid sequence corresponds to amino acids 1 to 227 of SEQ ID NO:8.

FIG. 5 depicts the cDNA sequence and predicted amino acid sequence of mouse 1vl. The nucleotide sequence corresponds to nucleic acids 1 to 1540 of SEQ ID NO:9. The amino acid sequence corresponds to amino acids 1 to 227 of SEQ ID NO:10.

FIG. 6 depicts the cDNA sequence and predicted amino acid sequence of rat 1vn. The nucleotide sequence corresponds to nucleic acids 1 to 955 of SEQ ID NO:11. The amino acid sequence corresponds to amino acids 1 to 203 of SEQ ID NO:12.

FIG. 7 depicts the cDNA sequence and predicted amino acid sequence of human 9ql. The nucleotide sequence corresponds to nucleic acids 1 to 2009 of SEQ ID NO:13 (FIG. 7A). The amino acid sequence corresponds to amino acids 1 to 270 of SEQ ID NO:14 (FIG. 7B).

FIG. 8 depicts the cDNA sequence and predicted amino acid sequence of rat 9ql. The nucleotide sequence corresponds to nucleic acids 1 to 1247 of SEQ ID NO:15. The amino acid sequence corresponds to amino acids 1 to 257 of SEQ ID NO:16.

FIG. 9 depicts the cDNA sequence and predicted amino acid sequence of mouse 9ql. The nucleotide sequence corresponds to nucleic acids 1 to 2343 of SEQ ID NO:17. The amino acid sequence corresponds to amino acids 1 to 270 of SEQ ID NO:18.

FIG. 10 depicts the cDNA sequence and predicted amino acid sequence of human 9qm. The nucleotide sequence corresponds to nucleic acids 1 to 1955 of SEQ ID NO:19 (FIG. 10A). The amino acid sequence corresponds to amino acids 1 to 252 SEQ ID NO:20 (FIG. 10B).

FIG. 11 depicts the cDNA sequence and predicted amino acid sequence of rat 9qm. The nucleotide sequence corresponds to nucleic acids 1 to 2300 of SEQ ID NO:21. The amino acid sequence corresponds to amino acids 1 to 252 of SEQ ID NO:22.

FIG. 12 depicts the cDNA sequence and predicted amino acid sequence of human 9qs. The nucleotide sequence corresponds to nucleic acids 1 to 1859 of SEQ ID NO:23. The amino acid sequence corresponds to amino acids 1 to 220 of SEQ ID NO:24.

FIG. 13 depicts the cDNA sequence and predicted amino acid sequence of monkey 9qs. The nucleotide sequence corresponds to nucleic acids 1 to 2191 of SEQ ID NO:25. The amino acid sequence corresponds to amino acids 1 to 220 of SEQ ID NO:26.

FIG. 14 depicts the cDNA, sequence and predicted amino acid sequence of rat 9qc. The nucleotide sequence corresponds to nucleic acids 1 to 2057 of SEQ ID NO:27. The amino acid sequence corresponds to amino acids 1 to 252 of SEQ ID NO:28.

FIG. 15 depicts the cDNA, sequence and predicted amino acid sequence of rat 8t. The nucleotide sequence corresponds to nucleic acids 1 to 1904 of SEQ NO:29. The amino acid sequence corresponds to amino acids 1 to 225 of SEQ ID NO:30.

FIG. 16 depicts the cDNA sequence and predicted amino acid sequence of human p19. The nucleotide sequence corresponds to nucleic acids 1 to 619 of SEQ ID NO:31. The amino acid sequence corresponds to amino acids 1 to 200 of SEQ ID NO:32.

FIG. 17 depicts the cDNA sequence and predicted amino acid sequence of rat p19 The nucleotide sequence corresponds to nucleic acids 1 to 442 of SEQ ID NO:33. The amino acid sequence corresponds to amino acids 1 to 109 of SEQ ID NO:34.

FIG. 18 depicts the cDNA sequence and predicted amino acid sequence of mouse p19. The nucleotide sequence corresponds to nucleic acids 1 to 2644 of SEQ ID NO:35. The amino acid sequence corresponds to amino acids 1 to 256 of SEQ ID NO:36.

FIG. 19 depicts the cDNA sequence and predicted amino acid sequence of human W28559. The nucleotide sequence corresponds to nucleic acids 1 to 380 of SEQ ID NO:37. The amino acid sequence corresponds to amino acids 1 to 126 of SEQ ID NO:38.

FIG. 20 depicts the cDNA sequence and predicted amino acid sequence of human P193. The nucleotide sequence corresponds to nucleic acids 1 to 2176 of SEQ ID NO:39. The amino acid sequence corresponds to amino acids 1 to 41 of SEQ ID NO:40.

FIG. 22 depicts the genomic DNA sequence of human 9q. FIG. 22A depicts exon 1 and its flanking intron sequences (SEQ ID NO:46). FIGS. 22B and 22C depict exons 2–11 and the flanking intron sequences (SEQ ID NO:47).

FIG. 23 depicts the cDNA sequence and predicted amino acid sequence of monkey KChIP4a. The nucleotide sequence corresponds to nucleic acids 1 to 2413 of SEQ ID NO:48. The amino acid sequence corresponds to amino acids 1 to 233 of SEQ ID NO:49.

FIG. 24 depicts the cDNA sequence and predicted amino acid sequence of monkey KChIP4b. The nucleotide sequence corresponds to nucleic acids 1 to 1591 of SEQ ID NO:50. The amino acid sequence corresponds to amino acids 1 to 233 of SEQ ID NO:51.

FIG. 25 depicts an alignment of KChIP4a, KchIP4b, 9ql, 1v, p19, and related human paralog (hsnespara) W28559. Amino acids identical to the consensus are shaded in black, conserved amino acids are shaded in gray.

FIG. 26 depicts the cDNA sequence and predicted amino acid sequence of rat 33b07. The nucleotide sequence corresponds to nucleic acids 1 to 2051 of SEQ ID NO:52. The amino acid sequence corresponds to amino acids 1 to 407 of SEQ ID NO:53.

FIG. 27 depicts the cDNA sequence and predicted amino acid sequence of human 33b07. The nucleotide sequence corresponds to nucleic acids 1 to 4148 of SEQ ID NO:54 (FIG. 27A). The amino acid sequence corresponds to amino acids 1 to 414 of SEQ ID NO:55 (FIG. 27B).

FIG. 28 depicts the cDNA sequence and predicted amino acid sequence of rat 1p. The nucleotide sequence corresponds to nucleic acids 1 to 2643 of SEQ ID NO:56. The amino acid sequence corresponds to amino acids 1 to 267 of SEQ ID NO:57.

FIG. 29 depicts the cDNA sequence and predicted amino acid sequence of rat 7s. The nucleotide sequence corresponds to nucleic acids 1 to 2929 of SEQ ID NO:58. The amino acid sequence corresponds to amino acids 1 to 270 of SEQ ID NO:59.

FIG. 30 depicts the cDNA sequence and predicted amino acid sequence of rat 29x. The nucleotide sequence corresponds to nucleic acids 1 to 1489 of SEQ ID NO:60. The amino acid sequence corresponds to amino acids 1 to 351 of SEQ ID NO:61.

FIG. 31 depicts the cDNA sequence of rat 25r. The nucleotide sequence corresponds to nucleic acids 1 to 1194 of SEQ ID NO:62.

FIG. 32 depicts the cDNA sequence and predicted amino acid sequence of rat 5p. The nucleotide sequence corresponds to nucleic acids 1to 600 of SEQ ID NO:63. The amino acid sequence corresponds to amino acids 1 to 95 of SEQ ID NO:64.

FIG. 33 depicts the cDNA sequence and predicted amino acid sequence of rat 7q. The nucleotide sequence corresponds to nucleic acids 1 to 639 of SEQ ID NO:65. The amino acid sequence corresponds to amino acids 1 to 212 of SEQ ID NO:66.

FIG. 34 depicts the cDNA sequence and predicted amino acid sequence of rat 19r. The nucleotide sequence corresponds to nucleic acids 1 to 816 of SEQ ID NO:67. The amino acid sequence corresponds to amino acids 1 to 271 of SEQ ID NO:68.

FIG. 35 depicts the cDNA sequence and predicted amino acid sequence of monkey KChIP4c. The nucleotide sequence corresponds to nucleic acids 1 to 2263 of SEQ ID NO:69. The amino acid sequence corresponds to amino acids 1 to 229 of SEQ ID NO:70.

FIG. 36 depicts the cDNA sequence and predicted amino acid sequence of monkey KChIP4d. The nucleotide sequence corresponds to nucleic acids 1 to 2259 of SEQ ID NO:71. The amino acid sequence corresponds to amino acids 1 to 250 of SEQ ID NO:72.

FIG. 39 depicts a graph showing the current traces from CHO cells which express Kv4.2 with or without KChIP3 (p19). Cells are voltage clamped at −80 mV and stepped from −60 mV to +50 mV for 200 ms. Peak current amplitudes at the various test voltages are shown in the right panel. FIG. 39 further depicts a table showing the amplitude and kinetic effects of KchIP3 (p19)) on Kv4.2. KchIP3 causes alterations in peak current and inactivation and recovery from inactivation time constants.

FIG. 40 depicts results from electrophysiological experiments demonstrating that coexpression of KChIP1 dramatically alters the current density and kinetics of Kv4.2 channels expressed in CHO cells.

FIG. 41 depicts an alignment of human KChIP family members with closely related members of the recoverin family of Ca 2+ sensing proteins. HIP: human hippocalcin; NCS1: rat neuronal calcium sensor 1 ). The alignment was performed using the MegAlign program for Macintosh (version 4.00 from DNASTAR) using the Clustal method with the PAM250 residue weight table and default parameters, and shaded using BOXSHADES. Residues identical to the consensus are shaded black, conservative substitutions are shaded grey. X, Y, Z and −X, −Y, −Z denote the positions of residues which are responsible for binding to the calcium ion in the EF hand.

DETAILED DESCRIPTION OF THE INVENTION

Figure 21:
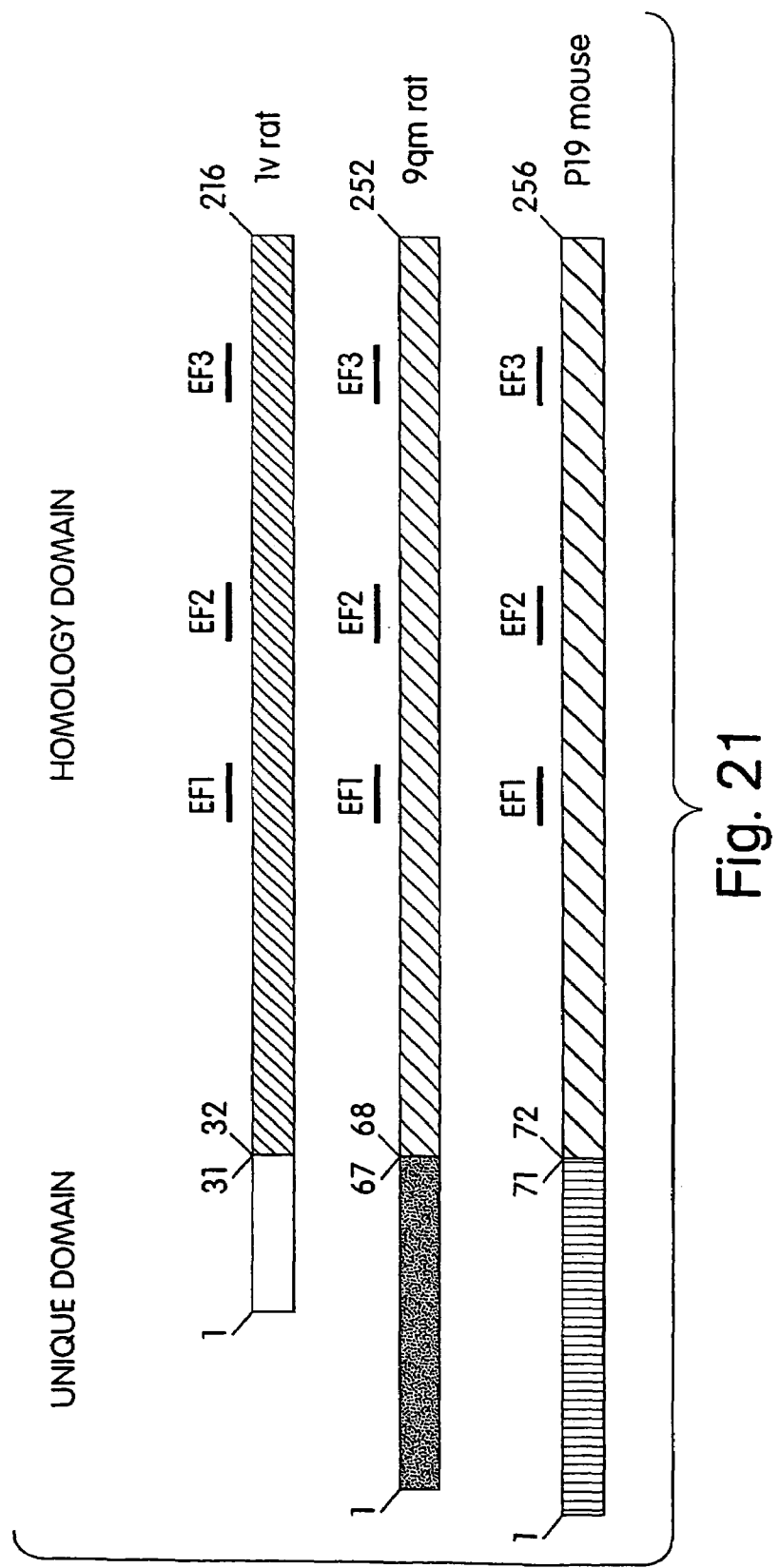
FIG. 21 depicts a schematic representation of the rat 1v, the rat 9qm, and the mouse P19 proteins, aligned to indicate the conserved domains among these proteins.

The present invention is based, at least in part, on the discovery of novel nucleic acid molecules which encode gene products that interact with potassium channel proteins or possess substantial homology to the gene products of the invention that interact with potassium channel proteins (paralogs). Potassium channel proteins are, for example, potassium channels having a Kv4.2 or Kv4.3 subunit. The nucleic acid molecules of the invention and their gene products are referred to herein as "Potassium Channel Interacting Proteins" "PCIP", or "KChIP" nucleic acid and protein molecules. The PCIP proteins of the present invention bind to and modulate a potassium channel mediated activity in a cell, e.g., a cardiac cell. Kv4 potassium channels, e.g., potassium channels having a Kv4.2 or Kv4.3 subunit, underlie the voltage-gated K+ current known as $I_{to}$ (transient outward current) in the mammalian heart (Kaab S. et al. (1998) *Circulation* 98(14):1383–93; Dixon J. E. et al. (1996) *Circulation Research* 79(4):659–68; Nerbonne J M (1998) *Journal of Neurobiology* 37(1):37–59; Barry D. M. et al. (1998) *Circulation Research* 83(5):560–7: Barry D. M. et al. (1996) *Annual Review of Physiology* 58:363–94. This current underlies the rapid repolarization of cardiac myocytes during an action potential. It also participates in the inter-beat interval by controlling the rate at which cardiac myocytes reach the threshold for firing a subsequent action potential.

This current is also known to be down regulated in patients with cardiac hypertrophy. resulting in prolongation of the cardiac action potential. In these patients, action potential prolongation is thought to produce changes in calcium load and calcium handling within the myocardium, which contributes to the progression of cardiac disease from hypertrophy to heart failure (Wickenden et al. (1998) *Cardiovascular Research* 37:312). Interestingly, several PCIPs of the present invention (e.g., 9 ql, 9 qm, 9 qs, shown in SEQ ID NOs:13, 15, 17, 19, 21, 23, and 25) bind to and modulate potassium channels containing a Kv4.2 or Kv4.3 subunit and contain calcium binding EF-hand domains. Because of mutations in these PCIP genes, defects in the expression of these calcium-binding PCIP proteins themselves, or defects in the interaction between these PCIPs and Kv4.2 or Kv4.3 channels, might be expected to lead to decreases in KV4.3 or $KV4.3(I_m)$ currents in the myocardium, therapeutic agents that alter PCIP expression or modulate the interaction between these PCIPs and Kv4.2 or Kv4.3 may be extremely valuable agents to slow or prevent the progression of disease from hypertrophy to heart failure.

Accordingly, in one aspect, this invention provides a method for identifying a compound suitable for treating a cardiovascular disorder by contacting a PCIP polypeptide. or a cell expressing a PCIP polypeptide with a test compound and determining whether the PCIP polypeptide binds to the test compound, thereby identifying a compound suitable for treating a potassium channel associated disorder such as a cardiovascular disorder. As used herein, a "potassium channel associated disorder" includes a disorder, disease or condition which is characterized by a misregulation of a potassium channel mediated activity. Potassium channel associated disorders can, for example, detrimentally affect the generation and distribution of electrical impulses that stimulate the cardiac muscle fibers to contract. Examples of potassium channel associated disorders include cardiovascular disorders such as arteriosclerosis, ischemia reperfusion injury, restenosis, arterial inflammation, vascular wall remodeling ventricular remodeling, rapid ventricular pacing, coronary microembolism, tachycardia, bradycardia, pressure overload, aortic bending, coronary artery ligation, vascular heart disease, atrial fibrillation, long-QT syndrome, congestive heart failure, sinus node disfunction, angina, heart failure, hypertension, atrial fibrillation, atrial flutter, dilated cardiomyopathy, idiopathic cardiomyopathy, myocardial infarction, coronary artery disease, coronary artery spasm, or arrhythmia. In a preferred embodiment, the cardiovascular disorder is associated with an abnormal $I_{to}$ current.

In a preferred embodiment. the binding of the test compound to the PCIP polypeptide is detected by direct detection of test compound/polypeptide binding. In another embodiment, the binding of the test compound to the PCIP polypeptide is detected by using a competition binding assay. In yet another embodiment, the binding of the test compound to the PCIP polypeptide is detected by using an assay for PCIP activity. As used interchangeably herein, a "PCIP activity". "biological activity of PCIP" or "functional activity of PCIP", refers to an activity exerted by a PCIP protein, polypeptide or nucleic acid molecule on a PCIP responsive cell or on a PCIP protein substrate, as determined in vivo, or in vitro, according to standard techniques. In one embodiment, a PCIP activity is a direct activity, such as an association with a PCIP-target molecule. As used herein, a "target molecule" or "binding partner" is a molecule with which a PCIP protein binds or interacts in nature, such that PCIP-mediated function is achieved. A PCIP target molecule can be a non-PCIP molecule or a PCIP protein or polypeptide. In an exemplary embodiment, a PCIP target molecule is a PCIP ligand. Alternatively, a PCIP activity is an indirect activity, such as a cellular signaling activity mediated by interaction of the PCIP protein with a PCIP ligand.

As used herein, a "biologically active portion" of a PCIP protein includes a fragment of a PCIP protein which participates in an interaction between a PCIP molecule and a non-PCIP molecule. Biologically active portions of a PCIP protein include peptides comprising amino acid sequences sufficiently identical to or derived from the amino acid sequence of the PCIP protein, e.g., the amino acid sequence shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, or SEQ ID NO:72, which include less amino acids than the full length PCIP proteins, and exhibit at least one activity of a PCIP protein. Typically, biologically active portions comprise a domain or motif with at least one activity of the PCIP protein, e.g., binding of a potassium channel subunit. A biologically active portion of a PCIP protein can be a polypeptide which is, for example, 10, 25, 50, 100, 200, or more amino acids in length. Biologically active portions of a PCIP protein can be used as targets for developing agents which modulate a potassium channel mediated activity.

The biological activities to PCIP are described herein. For example. the binding of the test compound to the PCIP polypeptide is detected by using an assay for one or more of the following activities: (1) interaction with (e.g. binding to) a potassium channel protein or portion thereof, e.g., a potassium channel comprising a Kv4.3 or Kv4.2 subunit; (2) regulation of the phosphorylation state to a potassium channel protein or portion thereof; (3) association with (e.g., binding to) calcium and acting as a calcium dependent kinase; (4) modulation of a potassium channel mediated activity in a cell (e.g., a cardiac cell such as a pericardial cell. a myocardial cell, or an endocardial cell); (5) modulation of chromatin formation in a cell. e.g., a cardiac cell; (6) modulation to vesicular traffic and protein transport in a cell, e.g., a cardiac cell; (7) modulation of cytokine signaling in a cell, e.g., a cardiac cell; (8) regulation of the association of a potassium channel protein or portion thereof with the cellular cytoskeleton; (9) modulation of cellular proliferation; (10) modulation of the release to neurotransmitters; (11) modulation to membrane excitability; (12) influencing the resting potential of membranes; (13) modulation of wave forms and frequencies to action potentials; and (14) modulation of thresholds of excitation.

In another aspect, the invention features a method for identifying a compound suitable for treating a cardiovascular disorder by incubating a cell expressing a potassium channel or a fragment thereof, and a PCIP polypeptide, in the presence and absence of a candidate compound; and determining whether the presence of the candidate compound modulates the interaction of the potassium channel or fragment thereof with the PCIP polypeptide, thereby identifying a compound suitable for treating a cardiovascular disorder. As used herein, a "potassium channel" includes a protein or polypeptide that is involved in receiving, conducting, and transmitting signals in an excitable cell. Potassium channels are typically expressed in electrically excitable cells, e.g., neurons, cardiac, skeletal and smooth muscle, renal, endocrine, and egg cells, and can form heteromultimeric structures, e.g., composed of pore-forming and cytoplasmic subunits. Examples of potassium channels include: (1) the voltage-gated potassium channels, (2) the ligand-gated potassium channels, and (3) the mechanically-gated potassium channels. For a detailed description of potassium channels, see Kandel E.R. Et. al., Principles of Neural Science, second edition. (Elsevier Science Publishing Co., Inc. N.Y. (1985), the contents of which are incorporated herein by reference. The PCIP proteins of the present invention have been shown to interact with, for example, potassium channels having a Kv4.3 subunit or a Kv4.2 subunit.

In yet another aspect. the invention features a method for treating a cardiovascular disorder by contacting a potassium channel with an effective amount of a compound that modulates the binding of a PCIP protein to the potassium channel.

In a further aspect, the invention features a method for determining if a subject is at risk for a cardiovascular disorder by detecting, in a sample of cells from the subject an alteration in a PCIP gene which causes a mutated PCIP polypeptide to be produced, an alteration in a PCIP gene which causes abnormal expression of a PCIP polypeptide, or an alteration in a PCIP gene which causes abnormal processing of a PCIP polypeptide.

In another aspect, the invention features a method for identifying a subject suffering from a cardiovascular disorder by detecting, in a sample of cells from the subject an alteration in a PCIP gene which causes a mutated PCIP polypeptide to be produced, an alteration in a PCIP gene which causes abnormal expression of a PCIP polypeptide, or an alteration in a PCIP gene which causes abnormal processing of a PCIP polypeptide.

The PCIP molecules of the present invention were initially identified based on their ability, as determined using yeast two-hybrid assays (described in detail in Example 1), to interact with the amino-terminal 180 amino acids of rat Kv4.3 subunit. Further binding studies with other potassium subunits were performed to demonstrate specificity of the PCIP for Kv4.3 and Kv4.2. In situ localization, immunohistochemical methods, co-immunoprecipitation and patch clamping, methods were then used to clearly demonstrate that the PCIPs of the present invention interact with and modulate the activity of potassium channels, particularly those comprising a 4.3 or 4.2 subunit.

Several novel human, mouse, monkey, and rat PCIP family members have been identified, referred to herein as 1v, 9q, p19, W28559, KChIP4, 33b07, 1p, and rat 7s proteins and nucleic acid molecules. The human, rat, and mouse cDNAs encoding the 1v polypeptide are represented by SEQ ID NOs:1, 3, and 5, and shown in FIGS. 1, 2, and 3, respectively. In the brain, 1vmRNA is highly expressed i neocortical and hippocampal interneurons, in the thalamic reticular nucleus and medial habenula, in basal forebrain and striatal cholinergic neurons, in the superior colliculus, and in cerebellar granule cells. The 1v polypeptide is highly expressed in the somata, dendrites, axons and axon terminals of cells that express 1v mRNA. Splice variants of the 1v gene have been identified in rat and mouse and are represented by SEQ ID NOs:7, 9, and 11 and shown in FIGS. 4, 5, and 6, respectively. 1v polypeptide interacts with potassium channels comprising Kv4.3 or kv4.2 subunits, but not wil Kv1.1 subunits. As determined by Northern blot, the 1v transcripts (mRNA) are expressed predominantly in the brain.

The 8t cDNA (SEQ ID NO:29) encodes a polypeptide having a molecular weight of approximately 26 kD corresponding to SFEQ ID NO:30 (see FIG. 15). The 8t polypeptide interacts with potassium channel comprising Kv4.3 or Kv4.2 subunits, but not with Kv1.1 subunits. As determined by Northern blot and in situ data, the 8t mRNA is expressed predominantly in the heart and the brain. The 8t cDNA is a splice variant of 9q.

Human, rat, monkey, and mouse 9q cDNA was also isolated. Splice variants include human 9ql (SEQ ID NO:13; FIG. 7) rat 9ql (SEQ ID NO:15; FIG. 8), mouse 9ql (SEQ ID NO:17; FIG. 9). human 9qm (SEQ ID NO:19; FIG. 10), rat 9qm (SEQ ID NO:21 FIG. 11), human 9qs (SEQ ID NO:23; FIG. 12), monkey 9qs (SEQ ID NO:25; FIG. 13), and rat 9qc (SEQ ID NO:27; FIG. 14). The genomic DNA sequence of 9q has also be determined. Exon 1 and its flanking intron sequences (SEQ ID NO:46) are shown in FIG. 22A. Exons 2–11 and the flanking intron sequences (SEQ ID NO:47) are shown in FIG. 22B. 9q polypeptides interact with potassium channels comprising Kv4.3 or Kv4.2 subunits, but not with Kv1.1 subunits. As determined by Northern blot and in situ data, the 9q proteins are expressed predominantly in the heart and the brain. In the brain, 9q mRNA is highly expressed in the neostriatum, hippocampal formation, neocortical pyramidal cells and interneurons, and in the thalamus, superior colliculus, and cerebellum.

Human, rat, and mouse P19 cDNA were also isolated. Human P19 is shown in SEQ ID NO:31 and FIG. 16; and in SEQ ID NO:39 and FIG. 20 (the 3' sequence). Rat P19 is shown in SEQ ID NO:33 and FIG. 17, and mouse P19 is shown in SEQ ID NO:35 and FIG. 18. P19 polypeptides interact with potassium channels comprising Kv4.3 or Kv4.2 subunits, but not with Kv1.1 subunits. As determined by Northern blot analysis, the P19 transcripts (mRNA) are expressed predominantly in the brain and to a much lesser degree in the heart.

A partial human paralog of the PCIP molecules was also identified. This paralog is referred to herein as W28559 and is shown in SEQ ID NO:37 and FIG. 19.

Monkey KChIP1a and its splice variants KChIP4b, KChIP4c, and KChIP4d were also identified. Monkey KChIP4a is shown in SEQ ID NO:48 and FIG. 23. Monkey KChIP4b is shown in SEQ ID NO:50 and FIG. 24. Monkey KChIP4c is shown in SEQ ID NO:69 and FIG. 35. Monkey KChIP4d is shown in SEQ ID NO:71 and FIG. 36.

The nucleotide sequence of the full length rat 33b07 cDNA and the predicted amino acid sequence of the rat 33b07 polypeptide are shown in FIG. 26 and in SEQ ID NOs:52 and 53, respectively. The rat 33b07 cDNA encodes a protein having a molecular weight of approximately 44.7 kD and which is 407 amino acid residues in length. Rat 33b07 binds rKv4.3N and rKv4.2N with slight preference for rKv4.2N in yeast 2-hybrid assays.

The nucleotide sequence of the full length human 33b07 cDNA and the predicted amino acid sequence of the human 33b07 polypeptide are shown in FIG. 27 and in SEQ ID NOs:54 and 55, respectively.

The nucleotide sequence of the partial length rat 1 p cDNA and the predicted amino acid sequence of the rat 1p polypeptide are shown in FIG. 28 and in SEQ ID NOs:56 and 57, respectively. The rat 1p cDNA encodes a protein having a molecular weight of approximately 28.6 kD and which is 267 amino acid residues in length. Rat 1p binds rKv4.3N and rKv4.2N with slight preference for rKv4.3N in yeast two-hybrid assays.

The nucleotide sequence of the partial length rat 7s cDNA and the predicted amino acid sequence of the rat 7s polypeptide are shown in FIG. 29 and in SEQ ID NOs:58 and 59, respectively. The rat 7s cDNA encodes a protein having a molecular weight of approximately 28.6 kD and which is 270 amino acid residues in length. Rat 7s binds rkv4.3N and rKv4.2N with preference for rKv4.3N in yeast two-hybrid assays.

The sequences of the PCIP molecules used in the methods of the present invention are summarized below, in Tables I and II.

TABLE I

PCIP Molecules Used in the Methods of the Present Invention

| PCIP | Nucleic Acid Molecule Form | Source | SEQ ID NO: DNA | SEQ ID NO: PROTEIN | ATCC |
|---|---|---|---|---|---|
| 1v or KChIP1 | 1v | human (225–875)* | 1 | 2 | 98994 |
| | 1v | rat (210–860) | 3 | 4 | 98946 |
| | 1v | mouse (477–1127) | 5 | 6 | 98945 |
| | 1vl | rat (31–714) | 7 | 8 | 98942 |
| | 1vl | mouse (77–760) | 9 | 10 | 98943 |
| | 1vn (partial) | rat (345–955) | 11 | 12 | 98944 |
| 9q or KChIP2 | Genomic DNA sequence (Exon 1 and flanking intron sequences) | human | 46 | | |
| | Genomic DNA sequence (Exons 2–11 and flanking intron sequences) | human | 47 | | |
| | 9ql | human (207–1019) | 13 | 14 | 98993 98991 |
| | 9ql (partial) | rat (2–775) | 15 | 16 | 98948 |
| | 9ql | mouse (181–993) | 17 | 18 | 98937 |
| | 9qm | human (207–965) | 19 | 20 | 98993 98991 |
| | 9qm | rat (214–972) | 21 | 22 | 98941 |
| | 9qs | human (207–869) | 23 | 24 | 98951 |
| | 9qs | monkey (133–795) | 2 | 26 | 98950 |
| | 9qc | rat (208–966) | 27 | 28 | 98947 |
| | 8t | rat | 29 | 30 | 98939 |

TABLE I-continued

PCIP Molecules Used in the Methods of the Present Invention

| PCIP | Nucleic Acid Molecule Form | Source | SEQ ID NO: DNA | SEQ ID NO: PROTEIN | ATCC |
|---|---|---|---|---|---|
| p19 or KChIP3 | (partial) p19 | (1–678) Human (1–771) | 31 | 32 | P1A-316 |
| | p19 (partial) | rat (1–330) | 33 | 34 | 98936 |
| | p19 | mouse (49–819) | 35 | 36 | 98940 |
| | p193 (partial) | Human (2–127) | 39 | 40 | 98949 |
| W28559 | W28559 (partial) | human (1–339) | 37 | 38 | |
| KChIP4 | KChIP4a | Monkey (265–966) | 48 | 49 | |
| | KChIP4b C–terminal splice variant | Monkey (265–966) | 50 | | |
| | KChIP4c splice variant | Monkey (122–811) | 69 | 70 | |
| | KChIP4d splice variant | Monkey (64–816) | 71 | 72 | |

*The coordinates of the coding sequence are shown in parenthesis. The first column indicates the PCIPs which were identified and column 2 indicates the various nucleic acid forms identified for each PCIP.

TABLE II

PCIP Molecules Used in the Methods of the Present Invention

| PCIP | Nucleic Acid Molecule Form | Source | SEQ ID NO: DNA | SEQ ID NO: PROTEIN | ATCC |
|---|---|---|---|---|---|
| 33b07 Novel | 33b07 | Human (88–1332) | 52 | 53 | PTA-316 |
| | 33b07 | Rat (85–1308) | 54 | 55 | |
| 1p Novel | 1p (partial) | Rat (1–804) | 56 | 57 | |
| 7s Novel | 7s (partial) | Rat (1–813) | 58 | 59 | |
| 29x | 29x | Rat (433–1071) | 60 | 61 | |
| | 25r splice variant of 29x | Rat (130–768) | 62 | | |
| 5p | 5p | Rat (52–339) | 63 | 64 | |
| 7q | 7q | Rat (1–639) | 65 | 66 | |
| 19r | 19r | Rat (1–816) | 67 | 68 | |

*The coordinates of the coding sequence are shown in parenthesis. The first column indicates the four families of PCIPs which were identified and column 2 indicates the various nucleic acid forms identified for each family. Novel molecules are also indicated.

Plasmids containing the nucleotide sequences encoding human rat and monkey PCIPs were deposited with American Type Culture Collection (ATCC) 10801 University Boulevard, Manassas, Va. 20110-2209, on Nov. 17, 1998, and assigned the Accession Numbers described above. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

Clones containing cDNA molecules encoding human p19 (clone EphP19) and human 33b07 (clone Eph33b07) were deposited with American Type Culture Collection (Manassas, Va.) on Jul. 8, 1998 as Accession Number PTA-316, as part of a composite deposit representing a mixture of two strains each carrying one recombinant plasmid harboring a particular cDNA clone. (The ATCC strain designation for the mixture of hP19 and h33b07 is EphP19h33b07mix).

To distinguish the strains and isolate a strain harboring a particular cDNA clone, an aliquot of the mixture can be streaked out to single colonies on LB plates supplemented with 100 ug/ml ampicillin. single colonies grown. and then plasmid DNA extracted using a standard minipreparation procedure. Next, a sample of the DNA minipreparation can be digested with Not1 and the resultant products resolved on a 0.8% agarose gel using standard DNA electrophoresis conditions. The digest gives the following band patterns: EphP19:7 kb 9 (single band), Eph33b07:5.8 kb (single band).

Various aspects of the invention are described in further detail in the following subsections:

I. SCREENING ASSAYS

The invention provides a method (also referred to herein as a "screening assay") for identifying modulators, i.e., candidate or test compounds or agents (e.g., peptides, peptidomimetics, small molecules or other drugs) which bind to PCIP proteins, have a stimulatory or inhibitory effect on, for example, PCIP expression or PCIP activity, or have a stimulatory or inhibitory effect on, for example, the expression or activity of a PCIP substrate.

In one embodiment, the invention provides assays for screening candidate or test compounds which are substrates of a PCIP protein or polypeptide or biologically active portion thereof. In another embodiment, the invention provides assays for screening candidate or test compounds which bind to or modulate the activity of a PCIP protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam. K. S. (1997) *Anticancer Drug Des.* 12:145).

Examples of methods for the synthesis of molecular libraries can be found in the art, for example in; DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223, 409). spores (Ladner USP '409). plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl.*

*Acad. Sci.* 87:6378–6382); (Felici (1991) *J. Mol. Biol.* 222:301–310); (Ladner supra).

In one embodiment, an assay is a cell-based assay in which a cell which expresses a PCIP protein or biologically active portion thereof is contacted with a test compound and the ability of the test compound to modulate PCIP activity, e.g., binding to a potassium channel comprising a Kv4.2 or Kv4.2 subunit, or a portion thereof, is determined. Determining the ability of the test compound to modulate PCIP activity can be accomplished by monitoring, for example, the $I_{to}$ current or the release of a neurotransmitter from a cell which expresses PCIP such as a cardiac cell. Currents in cells e.g., the $I_{to}$ current can be measured using the patch-clamp technique as described in the Examples section using the techniques described in, for example, Hamill et al. 1981. Pfluegers Arch. 391:85–100). The cell, for example, can be of mammalian origin. Determining the ability of the test compound to modulate the ability of PCIP to bind to a substrate can be accomplished, for example, by coupling the PCIP substrate with a radioisotope or enzymatic label such that binding of the PCIP substrate to PCIP can be determined by detecting the labeled PCIP substrate in a complex. For example, compounds (e.g., PCIP substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with. for example. horseradish peroxidase, alkaline phosphatase, or luciferase. and the enzymatic label detected by determination of conversion of an appropriate substrate to product.

It is also within the scope of this invention to determine the ability of a compound (e.g. PCIP substrate) to interact with PCIP without the labeling of any of the interactants. For example. a microplysiometer can be used to detect the interaction of a compound with PCIP without the labeling of either the compound or the PCIP. McConnell. H. M. et al. (1992) *Science* 257:1906–1912. As used herein, a "microphysiometer" (e.g., Cytosensor) is an analytical instrument that measures the rate at which a cell acidities its environment using a light-addressable potentiometric sensor (LAPS). Changes in this acidification rate can be used as an indicator of the interaction between a compound and PCIP.

In another embodiment, an assay is a cell-based assay comprising contacting a cell expressing a PCIP target molecule (e.g., a potassium channel comprising a Kv4.2 or Kv4.2 subunit, or a portion thereof, is determined. Determining the ability of the test compound to modulate, or a fragment thereof) with a test compound and determining the ability of the test compound to modulate (e.g., stimulate or inhibit) the activity of the PCIP target molecule. Determining the ability of the test compound to modulate the activity of a PCIP target molecule can be accomplished, for example, by determining the ability of the PCIP protein to bind to or interact with the PCIP target molecule, e.g., a potassium channel or a fragment thereof.

Determining the ability of the PCIP protein or a biologically active fragment thereof, to bind to or interact with a PCIP target molecule can be accomplished by one of the methods described above for determining direct binding. In a preferred embodiment, determining the ability of the PCIP protein to bind to or interact with a target molecule can be accomplished by determining the activity of the target molecule. For example, the activity of the target molecule can be determined by detecting induction of a cellular second messenger of the target (i.e.,intracellular $Ca^{2+}$, diacylglycerol, $IP_3$, and the like), detecting catalytic/enzymatic activity of the target an appropriate substrate, detecting the induction of a reporter gene (comprising a target-responsive regulatory element operatively linked to a nucleic acid encoding a detectable marker, e.g., luciferase), or detecting a target-regulated cellular response such as the release of a neurotransmitter.

In yet another embodiment, an assay of the present invention is a cell-tree assay in which a PCIP protein or biologically active portion thereof is contacted with a test compound and the ability of the test compound to bind to the PCIP protein or biologically active portion thereof is determined. Preferred biologically active portions of the PCIP proteins to be used in assays of the present invention include fragments which participate in interactions with non-PCIP molecules, e.g., potassium channels comprising a Kv4.2 or Kv4.2 subunit, or a portion thereof, is determined. Determining the ability of the test compound to modulate, or fragments thereof, or fragments with high surface probability scores. Binding of the test compound to the PCIP protein can be determined either directly or indirectly as described above. In a preferred embodiment, the assay includes contacting the PCIP protein or biologically active portion thereof with a known compound which binds PCIP to form an assay mixture, contacting the assay mixture with a test compound, and determining the ability of the test compound to interact with a PCIP protein, wherein determining the ability of the test compound to interact with a PCIP protein comprises determining the ability of the test compound to preferentially bind to PCIP or biologically active portion thereof as compared to the known compound.

In another embodiment, the assay is a cell-free assay in which a PCIP protein or biologically active portion thereof is contacted with a test compound and the ability of the test compound to modulate (e.g., stimulate or inhibit) the activity of the PCIP protein or biologically active portion thereof is determined. Determining the ability of the test compound to modulate the activity of a PCIP protein can be accomplished, for example, by determining the ability of the PCIP protein to bind to a PCIP target molecule by one of the methods described above for determining direct binding. Determining the ability of the PCIP protein to bind to a PCIP target molecule can also be accomplished using a technology such as real-time Biomolecular Interaction Analysis (BIA). Sjolander, S. and Urbaniezky, C. (1991) *Anal. Chem.* 63:2338–2345 and Szabo et al. (1995) *Curr. opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a PCIP protein can be accomplished by determining the ability of the PCIP protein to further modulate the activity of a downstream effector of a PCIP target molecule. For example, the activity of the effector molecule on an appropriate target can be determined or the binding of the effector to an appropriate target can be determined as previously described.

In yet another embodiment the cell-free assay involves contacting a PCIP protein or biologically active portion thereof with a known compound which binds the PCIP protein to form an assay mixture, contacting the assay mixture with a test compound, and determining the ability of the test compound to interact with the PCIP protein, wherein determining the ability of the test compound to interact with the PCIP protein comprises determining the ability of the PCIP protein to preferentially bind to or modulate the activity of a PCIP target molecule.

The cell-free assays of the present invention are amenable to use of both soluble and/or membrane-bound forms of isolated proteins. In the case of cell-free assays in which a membrane-bound form of an isolated protein is used (e.g., a potassium channel) it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100 Triton® X-114. Thesit®, Isotridecypoly( ethlylene glycol ether)$_n$3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention. it may be desirable to immobilize either PCIP or its target molecule to facilitate separation of complexed from uncomplexed forms of one or both of the proteins, as well as to accommodate automation of the assay. Binding of a test compound to a PCIP protein, or interaction of a PCIP protein with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/PCIP fusion proteins or glutathione-S-transferase/target fusion proteins can be adsorbed onto glutathione sepharose beads (Sigma Chemical, St. Louis, Mo.) or glutathione derivatized microtitre plates. which are then combined with the test compound or the test compound and either the non-adsorbed target protein or PCIP protein. and the mixture incubated under conditions conducive to complex formation (e.g., at physiological conditions for salt and pH). Following incubation, the beads or microtitre plate wells are washed to remove any unbound components. the matrix immobilized in the case of beads. complex determined either directly or indirectly. tor example. as described above. Alternatively, the complexes can be dissociated from the matrix, and the level of PCIP binding or activity determined using standard techniques.

Other techniques for immobilizing, proteins on matrices can also be used in the screening assays of the invention. For example, either a PCIP protein or a PCIP target molecule can be immobilized utilizing conjugation of biotin and streptavidn. Biotinylated PCIP protein or target molecules can be prepared from biotin-NHS (N-hydroxy-succinimide) using techniques known in the art (e.g., biotinylation kit. Pierce Chemicals, Rockford, Ill.), and immobilized in the wells of streptavidin-coated 96 well plates (Pierce Chemical). Alternatively, antibodies reactive with PCIP protein or target molecules but which do not interfere with binding of the PCIP protein to its target molecule can be derivatized to the wells of the plate, and unbound target or PCIP protein trapped in the wells by antibody conjugation. Methods for detecting such complexes, in addition to those described above for the GSI-immobilized complexes, include immunodetection of complexes using antibodies reactive with the PCIP protein or target molecule, as well as enzyme-linked assays which rely on detecting an enzymatic activity associated with the PCIP protein or target molecule.

In a preferred embodiment, candidate or test compounds or agents are tested for their ability to inhibit or stimulate a PCIP molecule's ability to modulate vesicular traffic and protein transport in a cell, e.g., a cardiac cell, using the assays described in, for example, Komada M. et al. (1999) *Genes Dev.* 13(11):1475–85, and Roth M. G. et al. (1999) *Chem Phys. Lipids,* 98(1–2):141–52, the contents of which are incorporated herein by reference.

In another preferred embodiment, candidate or test compounds or agents are tested for their ability to inhibit or stimulate a PCIP molecule's ability to regulate the phosphorylation state of a potassium channel protein or portion thereof, using for example, an in vitro kinase assay. Briefly, a PCIP target molecule, e.g., an immunoprecipitated potassium channel from a cell line expressing such a molecule, can be incubated with the PCIP protein and radioactive ATP, e.g., [γ-$^{32}$P]ATP, in a buffer containing $MgCl_2$ and $MnCl_2$, e.g., 10 mM $MgCl_2$ and 5 mM $MnCl_2$. Following the incubation, the immunoprecipitated PCIP target molecule, e.g., the potassium channel, can be separated by SDS-polyacrlamide gel eletrophoresis under reducing conditions, transferred to a membrane, e.g., a PVDF membrane, and autoradiographed. The appearance of detectable bands on the autoradiograph indicates that the PCIP substrate, e. g., the potassium channel, has been phosphorylated. Phosphoaminoacid analysis of the phosphorylated substrate can also be performed in order to determine which residues on the PCIP substrate are phosphorylated. Briefly, the radiophosphorylated protein band can be excised from the SDS gel and subjected to partial acid hydrolysis. The products can then be separated by one-dimensional electrophoresis and analyzed on, for example, phosphoimager and compared to ninhydrin-stained phosphoaminoacid standards. Assays such as those described in, for example. Tamaskovic R. et al. (1999) *Biol Chem* 380(5):569–78, the contents of which are incorporated herein by reference, can also be used.

In another preferred embodiment, candidate or test compounds or agents are tested for their ability to inhibit or stimulate a PCIP molecule's ability to associate with (e g., bind) calcium, using for example, the assays described in Liu L. (1999) *Cell Signal.* 11(5):317–24 and Kawai T. et al. (1999) *Oncogene* 18(23):3471–80, the contents of which are incorporated herein by reference.

In another preferred embodiment, candidate or test compounds or agents are tested for their ability to inhibit or stimulate a PCIP molecule's ability to modulate chromatin formation in a cell, using for example, the assays described in Okuwaki M. et al. (1998) *J. Biol. Chem.* 273(51):34511-8 and Miyaji-Yamaguchi M. (1999) J. Mol. Biol. 290(2): 547–557, the contents of which are incorporated herein by reference.

In yet another preferred embodiment, candidate or test compounds or agents are tested for their ability to inhibit or stimulate a PCIP molecule's ability to modulate cellular proliferation, using for example, the assays described in Baker F. I., et al. (1995) *Cell Prolif.* 28(1):1–15, Cheviron N. et al. (1996) *Cell Prolif.* 29(8):437–46. Hu Z. W. et al. (1999) *J. Pharmacol. Exp. Ther.* 290(1):28–37 and Elliott K. et al. (1999) *Oncogene* 18(24):3564–73, the contents of which are incorporated herein by reference.

In a preferred embodiment, candidate or test compounds or agents are tested for their ability to inhibit or stimulate a PCIP molecule's ability to regulate the association of a potassium channel protein or portion thereof with the cellular cytoskeleton, using for example, the assays described in Gonzalez C. et al. (1998) *Cell. Mol. Biol.* 44(7):1117–27 and Chia C. P. et al. (1998) *Exp. Cell Res.* 244(1):340–8, the contents of which are incorporated herein by reference.

In another preferred embodiment, candidate or test compounds or agents are tested for their ability to inhibit or stimulate a PCIP molecule's ability to modulate membrane excitability, using for example, the assays described in Bar-Sagi D. et al. (1985) *J Biol. Chem.* 260(8):4740–4 and Barker J. I. et al. (1984) *Neurosci. Lett.* 47(3):313-8, the contents of which are incorporated herein by reference.

In another preferred embodiment, candidate or test compounds or agents are tested for their ability to inhibit or stimulate a PCIP molecule's ability to modulate cytokine signaling in a cell, e.g., a cardiac cell, the assays described in Nakashimia Y. et al. (1999) *J. Bone Joint Surg. Am.* 81(5): 603–15, the contents of which are incorporated herein by reference.

In another embodiment. modulators of PCIP expression are identified in a method wherein a cell is contacted with a candidate compound and the expression of PCIP mRNA or protein in the cell is determined. The level to expression of PCIP mRNA or protein in the presence of the candidate compound is compared to the level of expression of PCIP mRNA or protein in the absence to the candidate compound. The candidate compound can then be identified as a modulator of PCIP expression based on this comparison. For example, when expression of PCIP mRNA or protein is greater (statistically significantly greater) in the presence of the candidate compound than in its absence, the candidate compound is identified as a stimulator of PCIP mRNA or protein expression. Alternatively, when expression of PCIP mRNA or protein is less (statistically significantly less) in the presence of the candidate compound than in its absence, the candidate compound is identified as an inhibitor of PCIP mRNA or protein expression. The level of PCIP mRNA or protein expression in the cells can he determined by methods described herein for detecting PCIP mRNA or protein.

In yet another aspect of the invention, the PCIP proteins can be used as "bait proteins" in a two-hybrid assay or three-hybrid assay (see. e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with PCIP ("PCIP-binding proteins" or "PCIP-bp") and are involved in PCIP activity (described in more detail in the Examples section below). Such PCIP-binding proteins are also likely to be involved in the propagation of signals by the PCIP proteins or PCIP targets as, for example, downstream elements of a PCIP-mediated signaling pathway. Alternatively, such PCIP-binding proteins are likely to be PCIP inhibitors.

The two-hybrid system is based on the modular nature of most transcription factors. which consist of separable DNA-binding and activation domains. Briefly. the assay utilizes two different DNA constructs. In one construct. the gene that codes for a PCIP protein is fused to a gene encoding the DNA binding domain of a known transcription factor (e.g., (GAL-4). In the other construct. a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a PCIP-dependent complex, the DNA-binding and activation domains of the transcription factor are brought into close proximity. This proximity allows transcription to a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the PCIP protein.

This invention further pertains to novel agents identified by the above-described screening assays. Accordingly. it is within the scope of this invention to further use an agent identified is described herein in an appropriate animal model. For example, an agent identified as described herein (e.g., a PCIP modulating agent, an antisense PCIP nucleic acid molecule, a PCIP-specific antibody, or a PCIP-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

II. PREDICTIVE MEDICINE

The present invention also pertains to the field of predictive medicine in which diagnostic assays, prognostic assays. and monitoring clinical trials are used for prognostic (predictive) purposes to thereby treat an individual prophylactically. Accordingly, one aspect of the present invention relates to diagnostic assays for determining PCIP protein and/or nucleic acid expression as well as PCIP activity. in the context of a biological sample (e.g., blood, serum, cells, tissue) to thereby determine whether an individual is afflicted with a disease or disorder, or is at risk of developing a disorder, associated with aberrant PCIP expression or activity. The invention also provides for prognostic (or predictive) assays for determining whether an individual is at risk of developing a disorder associated with PCIP protein, nucleic acid expression or activity. For example. mutations in a PCIP gene can be assayed in a biological sample. Such assays can be used for prognostic or predictive purpose to thereby phophylactically treat an individual prior to the onset of a disorder characterized by or associated with PCIP protein, nucleic acid expression or activity.

Another aspect of the invention pertains to monitoring the influence of agents (e.g., drugs, compounds) on the expression or activity of PCIP in clinical trials.

These and other agents are described in further detail in the following sections.

1. Diagnostic Assays

An exemplary method for detecting the presence or absence of PCIP protein or nucleic acid in a biological sample involves obtaining a biological sample from a test subject and contacting the biological sample with a compound or an agent capable of detecting PCIP protein or nucleic acid (e.g., mRNA. genomic DNA) that encodes PCIP protein such that the presence of PCIP protein or nucleic acid is detected in the biological sample. A preferred agent for detecting PCIP mRNA or genomic DNA is a labeled nucleic acid probe capable of hybridizing to PCIP mRNA or genomic DNA. The nucleic acid probe can be. tor example. a full-length PCIP nucleic acid. such as the nucleic acid of SEQ ID NO: 1, SEQ ID NO:3 SEQ ID NO:5, SEQ ID NO:7, SEQ ID NO:9, SEQ ID NO:11, SEQ ID NO:13, SEQ ID NO: 15, SEQ ID NO:17, SEQ ID NO:19, SEQ ID NO:21, SEQ ID NO:23, SEQ ID NO: 25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:51, SEQ ID NO:36, SEQ ID NO:58, SEQ ID NO:69, or SEQ ID NO:71, or the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, 98994, or PTA-316, or a portion thereof, such as an oligonucleotide of at least 15, 30, 50, 100, 250 or 500 nucleotides in length and sufficient to specifically hybridize under stringent conditions to PCIP mRNA or genomic DNA. Other suitable probes tor use in the diagnostic assays of the invention are described herein.

A preferred agent for detecting PCIP protein is an antibody capable of binding to PCIP protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e physically linking) a detectable substance to the probe or antibody. as well as indirect labeling of the probe or antibody by reactivity with another reagent that is directly labeled. Examples of indirect labeling include detection of a primary antibody using a tluorescentlv labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect PCIP mRNA. protein. or genomic DNA in a biological sample in vitro as well as in vivo. For example. in vitro techniques for detection of PCIP mRNA include Northern hybridizations and in situ hybridizations. In vitro techniques for detection of PCIP protein include enzyme linked immunosorbent assays (ELISAs). Western blots, immunoprecipitations and immunofluorescence. In vitro techniques for detection of PCIP genomic DNA include Southern hybridizations. Furthermore, in vivo techniques for detection of PCIP protein include introducing into a subject a labeled anti-PCIP antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting PCIP protein, mRNA, or genomic DNA, such that the presence of PCIP protein, mRNA or genomic DNA is detected in the biological sample, and comparing the presence of PCIP protein, mRNA or genomic DNA in the control sample with the presence of PCIP protein, mRNA on genomic DNA in the test sample.

The invention also encompasses kits for detecting the presence of PCIP in a biological sample. For example, the kit can comprise a labeled compound or agent capable of detecting PCIP protein or mRNA in a biological sample: means tor determining the amount of PCIP in the sample: and means for comparing the amount of PCIP in the sample with a standard. The compound or agent can be packaged in a suitable container. The kit can further comprise instructions for using the kit to detect PCIP protein or nucleic acid.

2. Prognostic Assays

The diagnostic methods described herein can furthermore be utilized to identify subjects having or at risk of developing a disease or disorder associated with aberrant PCIP expression or activity. For example, the assays described herein, such as the preceding diagnostic assays or the following assays, can be utilized to identity a subject having or at risk of developing a disorder associated with a misregulation in PCIP protein activity or nucleic acid expression. such as a cardiovascular disorders such as sinus node disfunction. angina, heart failure, hypertension, atrial fibrillation, atrial flutter, dilated cardiomyopathy, idiopathic cardiomyopathy, myocardial infarction, coronary artery disease, coronary artery spasm, or arrythmia.

Alternatively, the prognostic assays can be utilized to identify a subject having or at risk for developing a disorder associated with a misregulation in PCIP protein activity or nucleic acid expression, such as a potassium channel associated disorder. Thus, the present invention provides a method for identifying a disease or disorder associated with aberrant PCIP expression or activity in which a test sample is obtained from a subject and PCIP protein or nucleic acid (e.g., mRNA or genomic DNA) is detected, wherein the presence of PCIP protein or nucleic acid is diagnostic for a subject having or at risk to developing a disease or disorder associated with aberrant PCIP expression or activity. As used herein, a "test sample" refers to a biological sample obtained from a subject of interest. For example, a test sample can be a biological fluid (e.g., serum), cell sample or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant PCIP expression or activity. For example, such methods can be used to determine whether a subject can be effectively treated with an agent for a cardiovascular disorder. Thus, the present invention provides methods for determining whether a subject can be effectively treated with an agent for a disorder associated with aberrant PCIP expression or activity in which a test sample is obtained and PCIP protein or nucleic acid expression or activity is detected (e.G., wherein the abundance of PCIP protein or nucleic acid expression or activity is diagnostic for a subject that can be administered the agent to treat a disorder associated with aberrant PCIP expression or activity).

The methods of the invention can also be used to detect genetic alterations in a PCIP gene, thereby determining if a subject with the altered gene is at risk for a disorder characterized by misregulation in PCIP protein activity or nucleic acid expression, such as a cardiovascular disorder. In preferred embodiments, the methods include detecting, in a sample of cells from the subject, the presence or absence of a genetic alteration characterized by at least one of an alteration affecting the integrity of a gene encoding a PCIP-protein, or the mis-expression of the PCIP gene. For example, such genetic alterations can be detected by ascertaining the existence of at least one of 1) a deletion of one or more nucleotides from a PCIP gene; 2) an addition of one or more nucleotides to a PCIP gene; 3) a substitution of one or more nucleotides of a PCIP gene; 4) a chromosomal rearrangement of a PCIP gene; 5) an alteration in the level of a messenger RNA transcript of a PCIP gene, 6) aberrant modification of a PCIP gene, such as of the methylation pattern of the genomic DNA, 7) the presence of a non-wild type splicing pattern of a messenger RNA transcript of a PCIP gene, 8) a non-wild type level of a PCIP-protein, 9) allelic loss of a PCIP gene and 10) inappropriate post-translational modification of a PCIP-protein. As described herein, there are a large number of assays know in the art which can be used for detecting alterations in a PCIP gene. A preferred biological sample is a tissue or serum sample isolated by conventional means from a subject.

In certain embodiments, detection of the alteration involves the use of a probe/primer in a polymerase chain reaction (PCR) (see. eg. U.S. Pat. Nos. 4,683,195 and 4,683,202). such as anchor PCR or RACE PCR, or, alternatively, in a ligation chain reaction (LCR) (see, e.g., Landegran et al. (1988) Science 241:1077–1080; and Nakazawa et al. (1994) Proc. Natl. Acad. Sci. USA 91: 360–364), the latter of which can be particularly useful for detecting point mutations in the PCIP-gene (see Abravaya et al. (1995) Nucleic Acids Res. 23:675–682). This method can include the steps of collecting a sample of cells from a subject, isolating nucleic acid (e.g., genomic, mRNA or both) from the cells of the sample, contacting the nucleic acid sample with one or more primers which specifically hybridize to a PCIP gene under conditions such that hybridization and amplification of the PCIP-gene (if present) occurs, and detecting the presence or absence of an amplification product, or detecting the size of the amplification product and comparing the length to a control sample. It is anticipated that PCR and/or LCR may be desirable to use as a preliminary amplification step in conjullctiol with any of the techniques used for detecting mutations described herein.

Alternative amplification methods include: self sustained sequence replication (Guatelli, J. C. et al., (1990) Proc. Natl. Acad. Sci. USA 87: 1874–1878), transcriptional amplification system (Kwoh. D. Y. et al., (1989) Proc. Natl. Acad. Sci. USA 86:1173–1177). Q-Beta Replicase (Lizardi, P. M. et al. (1988) Bio-Technology 6: 1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a PCIP gene from a sample cell can be identified by alterations in restriction enzyme cleavage patterns. For example, sample and control DNA is isolated. amplified (optionally), divested with one or more restriction endonucleases, and fragment length sizes are determined by gel electrophoresis and compared. Differences in fragment length sizes between sample and control DNA indicates mutations in the sample DNA. Moreover. the use of sequence specific ribozynes (see, for example, U.S. Pat. No. 5,498,531) can be used to score for the presence of specific mutations by development or loss of a ribozyme cleavage site.

In other embodiments, genetic mutations in PCIP can be identified by hybridizing a sample and control nucleic acids, e.g., DNA or RNA, to high density arrays containing hundreds or thousands of oligonucleotides probes (Cronin. M. T. et al. (1996) Human Mutation 7:244–255; Kozal, M. J. et al. (1996) Nature Medicine 2: 753–759). For example, genetic mutations in PCIP can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets. one complementary to the wild-type gene and the other complementary to the mutant gene.

In yet another embodiment, any of a variety of sequencing reactions known in the art can be used to directly sequence the PCIP gene and detect mutations by comparing the sequence of the sample PCIP with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74: 5463). It is also contemplated that any of a variety of automated sequencing procedures can be utilized when performing the diagnostic assays ((1995) Biotechniques 19:448), including sequencing by mass spectrometry (see. e.g., PCT International Publication No. WO 94/16101: Cohen et al. (1996) Adv. Chromatogr. 36: 127–162; and Griffin et al. (1993) Appl. Biochem. Biotechnol. 38: 147–159).

Other methods tor detecting mutations in the PCIP gene include methods in which protection from cleavage agents is used to detect mismatched bases in RNA/RNA or RNA/DNA heteroduplexes (Myers et al. (1985) Science 230: 1242). In general, the art technique of "mismatch cleavage" starts by providing heteroduplexes of formed by hybridizing (labeled) RNA or DNA containing the wild-type PCIP sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resultillg material is then separated by size on denaturing polyacrylamide gels to determine the site of mutation. See, for example, Cotton et al. (1988) Proc. Natl Acad Sci USA 85:4397; Saleeba et al. (1992) Methods Enzymol. 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems tor detecting and mapping point mutations in PCIP cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15: 1657–1662). According to an exemplary embodiment, a probe based on a PCIP sequence, e.g., a wild-type PCIP sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in PCIP genes. For example, single strand conformation polymorphism (SSCP) may be used to detect differences in electrophoretic mobility between mutant and wild type nucleic acids (Orita et al. (1989) *Proc. Natl. Acad. Sci USA:* 86: 2766, see also Cotton (1993) *Mutat. Res.* 285: 125–144; and Hayashi (1992) *Genet. Anal. Tech. Appl.* 9: 73–79). Single-stranded DNA fragments of sample and control PCIP nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313: 495). When DGGE is used as the method of analysis. DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology Which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6: 1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a PCIP gene.

Furthermore, any cell type or tissue in which PCIP is expressed may be utilized in the prognostic assays described herein.

3. Monitoring of Effects During Clinical Trials

Monitoring the influence of agents (e.g., drugs) on the expression or activity of a PCIP protein (e.g., the modulation of membrane excitability or resting potential) can be applied not only in basic drug screening, but also in clinical trials. For example, the effectiveness of an agent determined by a screening assay as described herein to increase PCIP gene expression, protein levels, or upregulate PCIP activity, can be monitored in clinical trials of subjects exhibiting decreased PCIP gene expression, protein levels, or down-regulated PCIP activity. Alternatively, the effectiveness of an agent determined by a screening assay to decrease PCIP gene expression, protein levels, or downregulate PCIP activity, can be monitored in clinical trials of subjects exhibiting increased PCIP gene expression, protein levels, or upregulated PCIP activity. In such clinical trials, the expression or activity of a PCIP gene, and preferably, other genes that have been implicated in, for example, a potassium channel associated disorder can be used as a "read out" or markers of the phenotype of a particular cell.

For example, and not by way of limitation, genes, including PCIP, that are modulated in cells by treatment with an agent (e.g., compound, drug or small molecule) which modulates PCIP activity (e.g., identified in a screening assay as described herein) can be identified. Thus, to study the effect of agents on potassium channel associated disorders, for example, in a clinical trial, cells can be isolated and RNA prepared and analyzed for the levels of expression of PCIP and other genes implicated in the potassium channel associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of PCIP or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent: (ii) detecting the level of expression of a PCIP protein, mRNA, or genomic DNA in the preadministration sample; (iii) obtaining one or more post-administration samples from the subject: (iv) detecting the level of expression or activity of the PCIP protein, mRNA, or genomic DNA in the post-administration samples: (v) comparing the level of expression or activity of the PCIP protein, mRNA, or genomic DNA in the pre-administration sample with the PCIP protein, mRNA, or genomic DNA in the post administration sample or samples; and (vi) altering the administration of the agent to the subject accordingly. For example, increased administration of the agent may be desirable to increase the expression or activity of PCIP to higher levels than detected, i.e., to increase the effectiveness of the agent. Alternatively, decreased administration of the agent may be desirable to decrease expression or activity of PCIP to lower levels than detected, i.e. to decrease the effectiveness of the agent. According to such an embodiment, PCIP expression or activity may be used as an indicator of the effectiveness of an agent, even in the absence of an observable phenotypic response.

METHODS OF TREATMENT

The present invention provides for both prophylactic and therapeutic methods of treating a subject at risk of (or susceptible to) a disorder or having a disorder associated with aberrant PCIP expression or activity such as a cardiovascular disorder. With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the PCIP molecules of the present invention or PCIP modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant PCIP expression or activity such as a cardiovascular disorder, by administering to the subject a PCIP or an agent which modulates PCIP expression or at least one PCIP activity. Subjects at risk for a disease which is caused or contributed to by aberrant PCIP expression or activity can be identified by, for example, any or a combination of diagnostic or prognostic assays as described herein. Administration of a prophylactic agent can occur prior to the manifestation of symptoms characteristic of the PCIP aberrancy, such that a disease or disorder is prevented or, alteratively, delayed in its progression. Depending on the type of PCIP aberrancy, for example, a PCIP, PCIP agonist or PCIP antagonist agent can be used for treating the subject. The appropriate agent can be determined based on screening assays described herein.

2. Therapeutic Methods

Another aspect of the invention pertains to methods of modulating PCIP expression or activity tor therapeutic purposes. Accordingly, in an exemplary embodiment, the modulatory method of the invention involves contacting a cell with a PCIP or agent that modulates one or more of the activities of PCIP protein activity associated with the cell.

An agent that modulates PCIP protein activity can be an agent as described herein, such as a nucleic acid or a protein, a naturally-occurring target molecule of a PCIP protein (e.g., a PCIP substrate), a PCIP antibody, a PCIP agonist or antagonist, a peptidomimetic of a PCIP agonist or antagonist, or other small molecule. In one embodiment, the agent stimulates one or more PCIP activities. Examples of Such stimulatory agents include active PCIP protein and a nucleic acid molecule encoding PCIP that has been introduced into the cell. In another embodiment, the agent inhibits one or more PCIP activities. Examples of such inhibitory agents include antisense PCIP nucleic acid molecules, anti-PCIP antibodies, and PCIP inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a PCIP protein or nucleic acid molecule. Examples of such disorders include cardiovascular disorders such as long-QT syndrome, sinus node disfunction, angina, heart failure, hypertension, atrial fibrillation, atrial flutter, dilated cardiomyopathy, idiopathic cardiomyopathy, myocardial infarction, coronary artery disease, coronary artery spasm, or arrythmia. In one embodiment, the method involves administering an agent (e.g., an agent identified by a screening assay described herein). or combination of agents that modulates (e.g., upregulates or downregulates) PCIP expression or activity. In another embodiment, the method involves administering a PCIP protein or nucleic acid molecule as therapy to compensate for reduced or aberrant PCIP expression or activity.

Stimulation of PCIP activity is desirable in situations in which PCIP is abnormally downregulated and/or in which increased PCIP activity is likely to have a beneficial effect. For example, stimulation of PCIP activity is desirable in situations in which a PCIP is downregulated and/or in which increased PCIP activity is likely to have a beneficial effect. Likewise, inhibition of PCIP activity is desirable in situations in which PCIP is abnormally upregulated and/or in which decreased PCIP activity is likely to have a beneficial effect.

A PCIP molecule or an agent that modulates one or more of the activities of PCIP protein activity associated with the cell can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition used in the methods of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents: antibacterial agents such as benzyl alcohol or methyl parabens: antioxidants such as ascorbic acid or sodium bisulfite: chelating agents such as ethylenediaminetetraacetic acid: buffers such as acetates, citrates or phosphates and agents tor the adjustment of tonicity such as sodium chloride or dextrose, pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany. N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent ethical delays absorption, for example, aluminum monostearate and gelatin.

Sterile injectable solutions can be prepared by incorporating the active compound (e.g., a fragment of a PCIP protein or an anti-PCIP antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin: an excipient such as starch or lactose, a disintegrating agent such as alginic acid. Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions used in the methods of the invention can also be prepared in the form of suppositories (e.g., with conventional suppository bases such as cocoa butter and other glycerides) or retention enemas for rectal delivery.

In one embodiment, pharmaceutical compositions used in the methods of the invention are prepared with carriers that will protect the active compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polyacetic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound tor the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography. As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The methods of the present invention encompasses the use of agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothiosphamide, busulfan, dibromomannitol, streptozotocin. mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vineristine and vinblastine).

The conjugates can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, .alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., "Monoclonal Antibodies For Immunotargeting Of Drugs in Cancer Therapy", in Monoclonal Antibodies and Cancer Therapy, Reisteld et al. (eds.), pp. 243–56 (Alan R. Liss. Inc. 1985): Hellstrom et al., "Antibodies for Drug Delivery", in Controlled Drug Delivery (2nd Ed.), Robinson et al. (eds.), pp. 623–53 (Marcel Dekker, Inc. 1987): Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985): "Analysis, Results, And Future Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62: 119–58 (1982), Alternatively, an antibody can be conjugated to a second antibody to Form an antibody heteroconjugate as described by Segal in U.S. Pat. No. 4,676,980.

The nucleic acid molecules used in the methods of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

3. Pharmacogenomics

The PCIP molecules of the present invention, as well as agents, or modulators which have a stimulatory or inhibitory effect on PCIP activity (e.g., PCIP gene expression) as identified by a screening assay described herein can be administered to individuals to treat (prophylactically or therapeutically) potassium channel associated disorders associated with aberrant PCIP activity (e.g. cardiovascular disorders such as long-QT syndrome, sinus node disfunction, angina, heart failure, hypertension, atrial fibrillation, atrial flutter, dilated cardiomyopathy, idiopathic cardiomyopathy, myocardial infarction, coronary artery disease, coronary artery spasm, or arrythmia). In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a PCIP molecule or PCIP modulator as well as tailoring the dosage and/or therapeutic regimen of treatment with a PCIP molecule or PCIP modulator.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23(10–11): 983–985 and Linder. M. W. et al. (1997) Clin. Chem. 43(2): 254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic detects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a PCIP protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding tor CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a PCIP molecule or PCIP modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a PCIP molecule or PCIP modulator, such as a modulator identified by one of the exemplary screening assays described herein.

This invention is further illustrated by the following examples which should not be construed as limiting. The contents of all references, patents and published patent applications cited throughout this application, as well as the Figures and the Sequence Listing are incorporated herein by reference.

EXAMPLES

The following materials and methods were used in the Examples.

Strains, plasmids Bait cDNAs and General Microbiological Techniques

Basic yeast strains (HF7c, Y187.) bait (pGB19) and fish (pACT2) plasmids used in this work were purchased from Clontech (Palo Alto, Calif.), cDNAs encoding rat Kv4.3, Kv4.2, and Kv1.1, were provided by Wyeth-Ayerst Research (865 Ridge Rd., Monmouth Junction, N.J. 08852) Standard yeast media including synthetic complete medium lacking L-leucine, L-tryptophan, and L-histidine were prepared and yeast genetic manipulations were performed as described (Sherman (1991) *Meth. Enzymol.* 194:3–21). Yeast transformations were performed using standard protocols (Gietz et al. (1992) *Nucleic Acids Res.* 20:1425; Ito et al (1983) *J. Bacteriol.* 153 163–168). Plasmid DNAs were isolated from yeast strains by a standard method (Hoffmann and Winston (1987) *Gene* 57:267–272).

Bait and Yeast Strain Construction

The first 180 amino acids of rKv4.3 (described in Serdio P. et al. (1996) *J. Neurophys* 75: 2174–2179) were amplified by PCR and cloned in frame into pGBT9 resulting in plasmid pHWA2, (hereinafter "bait"). This bait was transformed into the two-hybrid screening strain HF7c and tested tor expression and self-activation. The bait was validated for expression by Western blotting. The rKv4.3 bait did not self-activate in the presence of 10 mM 3-amino-1,2,3-Triazole (3-AT).

Library Construction

Rat mid brain tissue was provided by Wyeth-Ayerst Research (Monmouth Junction, N.J.). Total cellular RNA was extracted from the tissues using standard techniques (Sambrook. J., Fritsh, E. F. and Maniatis, T. *Molecular Cloning: A Laboratory Manual.* 2nd ed., Cold Spring Harbor Laboratory: Cold Spring Harbor Laboratory Press, Cold Spring Harbor, N.Y. (1989)). mRNA was prepared using a Poly-A Spin mRNA Isolation Kit from New England Biolabs (Beverly, Mass.). cDNA from the mRNA sample was synthesized using a cDNA Synthesis Kit from Stratagene (La Jolla, Calif.) and ligated into pACT2's EcoR1 and Xhol sites, giving rise to a two-hybrid library.

Two-Hybrid Screening

Two-hybrid screens were carried out essentially as described in Bartel, P. et al. (1993) "Using the Two-Hybrid System to Detect Polypeptide-Polypeptide Interactions" in Cellular Interactions in Development: A Practical Approach, Hartley, D. A. ed. Oxford University Press, Oxford, Pp. 153–179, with a bait-library pair of rk4.3 bait-rat mid brain library. A filter disk beta-galactosidase (beta-gal) assay was performed essentially as previously described (Brill et al. (1994) *Mol. Biol. Cell* 5: 297–312). Clones that were positive for both reporter gene activity (His and beta-galactosidase) were scored and fish, plasmids were isolated from yeast transformed into *E. Coli* strain KC8. DNA plasmids were purified and the resulting plasmids were sequenced by conventional methods (Sanger F. et al. (1977) *PNAS,* 74: 5463–67).

Specificity Test

Positive interactor clones were subjected to a binding specificity test where they were exposed to a panel of related and unrelated baits by a mating scheme previously described (Finley R. I., Jr. et al. (1994) *PNAS* 91(26):12980–12984). Briefly, positive fish plasmids were transformed into Y187 and the panel of baits were transformed into HF7c. Transformed fish and bait cells were streaked out as stripes on selective medium plates, mated on YPAD plates, and tested tor reporter gene activity.

Analysis

PCIP nucleotides were analyzed for nucleic acid hits by the BLASTN 1.4.8 MP program (Altschul et al. (1990) Basic Local Alignment Search Tool, *J Mol. Biol.* 215: 403–410). PCIP proteins were analyzed for polypeptide hits by the BLASTP 1.4.9 MP program.

Example 1

Identification of Rat PCIP cDNAs

The Kv4.3 gene coding sequence (coding for the first 180 amino acids) was amplified by PCR and cloned into pGBT9 creating a GAL4 DNA-binding domain-Kv4.3(1–180) gene fusion (plasmid pFWA2). HF7c was transformed with this construct. The resulting strain grew on synthetic complete medium lacking L-tryptophan but not on synthetic complete medium lacking L-tryptophan and L-histidine in the presence of 10 mM 3-AT demonstrating that the :GAL4 DNA-binding domain:-: vKv4.3(1–180): gene fusion does not have intrinsic transcriptional activation activity higher than the threshold allowed by 10 mM 3-AT.

In this example, a yeast two-hybrid assay was performed in which a plasmid containing a :GAL4 DNA-binding domain:-:rKv4.3(1–180): gene fusion was introduced into the yeast two-hybrid screening strain HF7c described above.

HF7c was then transformed with the rat mid brain two-hybrid library. Approximately six million transformants were obtained and plated in selection medium. Colonies that grew in the selection medium and expressed the beta-galactosidase reporter gene were further characterized and subjected to retransformation and specificity assays. The retransformation and specificity tests yielded three PCIP clones (rat 1v, 8t, and 9qm ) that were able to bind to the Kv4.3 polypeptide.

The full length sequences for the rat 1v gene and partial sequences tor 8t and 9q genes were derived as follows. The partial rat PCIP sequences were used to prepare probes, which were then used to screen, for example, rat mid brain cDNA libraries. Positive clones were identified, amplified and sequenced using standard techniques, to obtain the full length sequence. Additionally, a rapid amplification of the existing rat PCIP cDNA ends (using for example, 5' RACE, by Gibco, BRL) was used to complete the 5' end of the transcript.

Example 2

Identification of Human 1v cDNA

To obtain the human 1v nucleic acid molecule, a cDNA library made from a human hippocampus (Clontech, Palo Alto, Calif.) was screened under low stringency conditions as follows: Prehybridization for 4 hours at 42° C. in Clontech Express Hyb solution, followed by overnight hybridization at 42° C. The probe used was a PCR-generated fragment including nucletides 49–711 of the rat sequence labeled with $^{32}$P dCTP. The filters were washed 6 times in 2XSSC/0.1% SDS at 55° C. The same conditions were used for secondary screening of the positive isolates. Clones thus obtained were sequenced using an ABI automated DNA Sequencing system, and compared to the rat sequences shown in SEQ ID NO:3 as well as to known sequences from the GenBank database. The largest clone from the library screen was subsequently subcloned into pBS-KS+ (Stratagene, La Jolla, Calif.) for sequence verification. The 515 base pair clone was determined to represent the human homolog of the 1v gene, encompassing 211 base pairs of 5' UTR and a 304 base pair coding region. To generate the full-length cDNA, 3' RACE was used according to the manufacturers instructions (Clontech Advantage PCR kit).

Example 3

Isolation and Characterization of 1v Splice Variants

The mouse 1v shown in SEQ ID NO:5 and the rat 1vl splice variant shown in SEQ ID NO:7 was isolated using a two-hybrid assay as described in Example 1. The mouse 1vl splice variant shown in SEQ ID NO: 7 was isolated by screening a mouse brain cDNA library, and the rat 1vn splice variant shown in SEQ ID NO:11 was isolated by BLAST searching.

Example 4

Isolation and Identification of 9q and Other PCIPs

Rat 9ql (SEQ ID NO: 15) was isolated by database mining, rat 9qm (SEQ ID NO: 21) was isolated by a two-hybrid assay, and rat 9qc (SEQ ID NO:27) was identified by database mining. Human 9ql (SEQ ID NO: 13), and human 9qs (SEQ ID NO: 23) were identified as described in Example 2. Mouse 9ql (SEQ ID NO: 17), monkey 9qs (SEQ ID NO:25), human p195 (SEQ ID NO:31), W28559 (SEQ ID NO:37), human p193 (SEQ ID NO:39), rat p19 (SEQ ID NO:33), and mouse p19 (SEQ ID NO:35) were identified by database mining. Rat 8t (SEQ ID NO:29) was identified using a two-hybrid assay.

The human genomic 9q sequence SEQ ID NOs:46 and 47) was isolated by screening a BAC genomic DNA library (Research Genetics) using primers which were designed based on the sequence of the human 9qm cDNA. Two positive clones were identified (448O2 and 721117) and sequenced.

Example 5

Expression of p19, 1v, 8t, and 9q mRNA in Rat Tissues

PCIP molecules, e.g., 9q and 8t, were demonstrated to be predominantly expressed in the heart. Briefly, rat or mouse multiple tissue Northern blots (Clontech) were probed with a l$^{32}$Pl-labeled cDNA probe directed at the p19 sequence, the 5'-untranslated and 5'-coding region of the rat 1v sequence (nucleotides 35–124; SEQ ID NO:3) (this probe is specified for rat 1v and rat 1vl, the 5' coding region of the 8t sequence (nucleotides 1–88: SEQ ID NO:29) (this probe is specific for 8t), or the 5' end of the rat 9qm sequence (nucleotides 1–195: SEQ ID NO:21) (this probe is specific for all 9q isoforms, besides 8t). Blots were hybridized using standard techniques.

The results indicated that p19 is expressed predominantly in the brain, but also in the heart. Moreover, northern blots hybridized with the rat 1v probe revealed a single band at 2.3 kb only in the lane containing brain RNA, suggesting that 1v expression is brain specific. Northern blots probed with the rat 8t probe revealed a major band at 2.4 kb. The rat 8t band was most intense in the lane containing heart RNA and there was also a weaker band in the lane containing brain RNA. Northern blots hybridized with the 9q cDNA probe revealed a major band at 2.5 kb and a minor band at over 4 kb with predominant expression in heart and brain. The minor band may represent incompletely spliced or processed 9q mRNA.

Example 6

Expression of 1v, 8t, and 9q in Brain

Expression of the rat 1v and 8t/9q genes in the brain was examined by in situ hybridization histochemistry (ISHH) using l$^{35}$Sl-labeled cRNA probes and a hybridization procedure identical to that described in Rhodes et al. (1996) J. Neurosci., 16:4846–4860. Templates for preparing the cRNA probes were generated by standard PCR methods. Briefly, oligonucleotide primers were designed to amplify a fragment of 3'- or 5'-untranslated region of the target cDNA and in addition, add the promoter recognition sequences for T7 and T3 polymerase. Thus, to generate a 300 nucleotide probe directed at the 3'-untranslated region of the 1v mRNA, we used the following primers: 5-TAATACGACTCACTAT-AGGGACTGGCCATCCTGCTCTCAG-3 (T7, forward, sense: SEQ ID NO:42) 5-ATTAACCCTCACTAAAGGGA-CACTACTGTTTAAGCTCAAG-3 (T3, reverse, antisense: SEQ ID NO:43). The underlined bases correspond to the T7 and T3 promoter sequences. To generate a probe directed at a 325 bp region of 3'-untranslated sequence shared by the 8t and 9q mRNAs, the following primers were used: 5-TAATACGACTCACTATAGGGCACCTC- CCCTCCGGCTGTTC-3 (T7, forward, sense: SEQ ID NO:44) 5-ATTAACCCTCACTAAAGGAGAGCAGCAG-CATGGCAGGGT-3 (T3, reverse, antisense: SEQ ID NO:45).

Autoradiograms of rat brain tissue sections processed for ISHH localization of 1v or 8t/9q mRNA expression revealed that 1v mRNA is expressed widely in brain in a pattern consistent with labeling of neurons as opposed to glial or endothelial cells. 1v mRNA is highly expressed in cortical, hippocampal, and striatal interneurons, the reticlar nucleus of the thalamus, the medial habernula, and in cerebellar granule cells. 1v mRNA is expressed at moderate levels in midbrain nuclei including the substantia nigra and superior colliculus, in several other thalamic nuclei, and in the medial septal and diagonal band nuclei of the basal forebrain.

Because the probe used to analyze the expression of 8t and 9q hybridizes to a region of the 3-untranslated region that is identical in the 8t and 9q mRNAs, this probe generates a composite image that reveals that 8t/9q mRNA is expressed widely in brain in a pattern that partly overlaps with that for 1v as described above. However, 8t/9q mRNA is highly expressed in the striatum, hippocampal formation, cerebellar granule cells, and neocortex. 8t/9q mRNA is expressed at moderate levels in the midbrain, thalamus, and brainstem. In may of these areas. 8t/9q mRNA appears to be concentrated in interneurons in addition to principal cells, and in all regions 8t/9q expression appears to be concentrated in neurons as apposed to glial cells.

Single- and double-label immunohistochemistry revealed that the PCIP and Kv4 polypeptides are precisely colocalized in many of the cell types and brain regions where PCIP and Kv4 mRNAs are coexpressed. For example, 9qm colocalized with Kv4.2 in the somata and dendrites of hippocampal granule and pyramidal cells, neurons in the medial habenular nucleus and in cerebellar basket cells, while 1v colocalized with Kv4.3 in layer II neurons of posterior cingulate cortex, hippocampal interneurons, and in a subset of cerebellar granule cells. Immunoprecipitation analyses indicated that 1v and 9qm are coassociated with Kv4 α-subunits in rat brain membranes.

Example 7

Co-Association of PCIPs and Kv4 Channels in COS and CHO Cells

COS1 and CHO cells were transiently transfected with individual PCIPs (KChIP1, KChIP2, KChIP3) alone or together with Kv4.2 or Kv4.3 using the lipofectamine plus procedure essentially as described by the manufacturer (Boehringer Mannheim). Forty-eight hours after the transfection, cells were washed, fixed, and processed for immunofluorescent visualization as described previously (Bekele-Arcuri et al. (1996) Neuropharmacology, 35:851–865). Affinity-purified rabbit polyclonal or mouse monoclonal antibodies to the Kv4 channel or the PCIP protein were used tor immunofluorescent detection of the target proteins.

When expressed alone, the PCIPs were diffusely distributed throughout the cytoplasm of COS-1 and CHO cells, as would be expected for cytoplasmic proteins. In contrast, when expressed alone, the Kv4.2 and Kv4.3 polypeptides were concentrated within the perinuclear ER and Golgi compartments, with some immunoreactivity concentrated in the outer margins of the cell. When the PCIPs were coexpressed with Kv4 α-subunits, the characteristic diffuse PCIP distribution changed dramatically, such that the PCIPs precisely colocalized with the Kv4 α-subunits. This redistribution of the PCIPs did not occur when they were coexpressed with the Kv1.4 α-subunit, indicating that altered PCIP localization is not a consequence of overexpression and that these PCIPs associate specifically with Kv4-family α-subunits.

To verify that the PCIP and Kv4 polypeptides are tightly associated and not simply colocalized in co-transfected cells, reciprocal immunoprecipitation analyses were performed using the PCIP and channel-specific antibodies described above. All three PCIP polypeptides coassociated with Kv4 α-subunits in cotransfected cells, as evidenced by the ability of anti-Kv4.2 and anti-Kv4.3 antibodies to immunoprecipitate the KChIP1, KChIP2, and KChIP3 proteins from lysates prepared from cotransfected cells, and by the ability of anti-PCIP antibodies to immunoprecipitate Kv4.2 and Kv4.3 α-subunits from these same lysates. The cells were lysed in buffer containing detergent and protease inhibitors, and prepared for immunoprecipitation reactions essentially as described previously (Nakahira et al. (1996) J. Biol. Chem. 271:7084–7089). Immunoprecipitations were performed as described in Nakahira et al. (1996) J. Biol. Chem., 271: 7084–7089 and in Harlow E. and Lane, D., Antibodies: A Laboratory Manual, Cold Spring Harbor Laboratory, c1988. The products resulting from the immunoprecipitation were size fractionated by SDS-PAGE and transferred to nitrocellulose filters using standard procedures.

To confirm that the cytoplasmic N-terminus of Kv4 channels is sufficient for the interaction with the PCIPs KChIP1 or KChIP2 were co-expressed with a Kv4.3 mutant (Kv4.3ΔC) that lacks the entire 219 amino acid cytoplasmic C-terminal tail. In transiently transfected COS-1 cells, the Kv4.3ΔC mutant was extensively trapped within the perinuclear ER and Golgi: little or no staining was observed at the outer margins of the cell. Nonetheless, KChIP1 and KChIP2 precisely colocalized with Kv4.3ΔC in cotransfected cells, and moreover, Kv4.3ΔC was efficiently coimmunoprecipitated by PCIP antibodies. indicating that the interaction of these PCIPs with Kv4 α-subunits does not require the cytoplasmic C-terminus of the channel.

Example 8

Co-Association of PCIPs and Kv4 Channels in Native Tissues

To determine whether PCIPs colocalize and co-associate with Kv4 subunits in native tissues, Kv4- and PCIP-specific antibodies were used for single and double-label immunohistochemical analyses and for reciprocal coimmunoprecipitation analyses of rat brain membranes. Immunohistochemical staining of rat brain sections indicated that KChIP1 and KChIP2 colocalize with Kv4.2 and Kv4.3 in a region and cell type-specific manner. For example, KChIP1 colocalized with Kv4.3 in hippocampal interneurons, cerebellar granule cells, and cerebellar glomeruli, a specialized synaptic arrangement between the dendrites of cerebellar basket and golgi cells and mossy fiber terminals. KChIP2 colocalized with Kv4.3 and Kv4.2 in the dendrites of granule cells in the dentate gyrus, in the apical and basal dendrites of hippocampal and neocortical pyramidal cells, and in several subcortical structures including the striatum and superior colliculus. Co-immunoprecipitation analyses performed using synaptic membranes prepared from whole rat brain revealed that the PCIPs (KChIPs 1, 2, and 3) are tightly associated with Kv4.2 and Kv4.3 in brain K+ channel complexes. Anti-PCIP antibodies immunoprecipitated Kv4.2 and Kv4.3 from brain membranes, and anti-Kv4.2 and Kv4.3 antibodies immunoprecipitated the PCIPs. None of the PCIP polypeptides were immunoprecipitated by anti-Kv2.1 antibodies, indicating that the association of these PCIPs with brain Kv channels may be specific for Kv4 α-subunits. Taken together, these anatomical and biochemical analyses indicate that these PCIPs are integral components of native Kv4 channel complexes.

Example 9

PCIPs are Cacium Binding proteins

To determine whether KChIPs 1, 2, and 3 bind Ca2+, GST-fusion proteins were generated for each PCIP and the ability of the GST-PCIP proteins, as well as the recombinant PCIP polypeptides enzymatically cleaved from GST, to bind $^{45}$Ca2+ was examined using a filter overlay assay (described in, for example, Kobayashi et al. (1993) Biochem. Biophys. Res. Commun. 189(1): 511-7). All three PCIP polypeptides, but not an unrelated GST-fusion protein, display strong $^{45}$Ca2+ binding in this assay. Moreover, all three PCIP polypeptides display a Ca2+-dependent mobility shift on SDS-PAGE, indicating that like the other members of this family, KChIPs 1, 2 and 3 are in fact Ca2+-binding proteins (Kobuyashi et al. (1993) supra. Buxbaum et al. Nef (1996). Neuron-specific calcium sensors (the NCS-1 subfamily). In: Celio MR (ed) Guidebook to the calcium-binding proteins. Oxford University Press, New York. pp 94–98; Buxbaum J. D., et al. (1998) *Nature Med.* 4(10): 1177–81.

Example 10

Electrophysiological Characterization of PCIPs

Because PCIPs, e.g., KCIP1 (1v), KChIP2 (9ql), and KChIP3 (p19), colocalize and coassociate with Kv4 α-subunits in brain another critical question was to determine whether these PCIPs alter the conductance properties of Kv4 channels. To address this issue, Kv4.2 and Kv4.3 were expressed alone and in combination with individual PCIPs.

CHO cells were transiently-transfected with cDNA using the DOTAP lipofection method as described by the manufacturer (Boehringer Mannheim, Inc.). Transfected cells were identified by cotransfecting enhanced GFP along with the genes of interest and subsequently determining if the cells contained green GFP fluorescence. Currents in CHO cells were measured using the patch-clamp technique (Hamill et al. 1981, Pfluegers Arch. 391: 85–100).

Transient transfection of the rat Kv4.2 α-subunit in CHO cells resulted in expression of a typical A-type K+ conductance. Coexpression of Kv4.2 with KChIP1 revealed several dramatic effects of KChIP1 on the channel (FIG. 41 and Table 1). First, the amplitude of the Kv4.2 current increased approximately 7.5 fold in the presence of KChIP1 (amplitude of Kv4.2 alone=0.60+/−0.096 nA/cell: Kv4.2+KChIP1=4.5+/−0.55 nA/cell). When converted into current density by correcting or cell capacitance, a measure of cell surface membrane area, the Kv4.2 current density increased 12 fold with coexpression of KChIP1 (Kv4.2 alone=25.5+/− 3.2 pA/pF: Kv4.2+KChIP1=306.9 +/−57.9 pA/pF), indicating that KChIPs promote and/or stabilize Kv4.2 surface expression. Together with this increase in current density, a dramatic leftward shift in the threshold for activation of Kv4.2 currents was observed in cells expressing Kv4.2 and KChIP1 (activation V1/2 for Kv4.2 alone=20.8+/−7.0 mV.

Kv4.2+KChIP1=−12.1+/−1.4 mV). Finally, the kinetics of Kv4.2 inactivation slowed considerably when Kv4.2 was coexpressed with KChIP1 (inactivation time constant of Kv4.2 alone=28.2+/−2.6 ms; Kv4.2+KChIP1=104.1+/−10.4 ms), while channels recovered from inactivation much more rapidly in cells expressing both Kv4.2 and KChIP1 (recovery tau−53.6+/−7.6 ms) versus cells expressing Kv4.2 alone (recovery tau=272.2+/−26.1 ms).

KChIPs1, 2 and 3 have distinct N-termini but share considerable amino acid identity within the C-terminal "core" domain. Despite their distinct N-termini, the effects of KChIP2 and KChIP3 on Kv4.2 current density and kinetics were strikingly similar to those produced by KChIP1 (Table 1). Thus to confirm that the conserved C-terminal core domain, which contains all three EF-hands, is sufficient to modulate Kv4 current density and kinetics. N-terminal truncation mutants of KChIP1 and KChIP2 were prepared. The KChIP1ΔN2-31 and KChIP2ΔN2-67 mutants truncated KCh1P1 and KChIP2, respectively, to the C-terminal 185 amino acid core sequence. Coexpression of KChIP1ΔN2-31 or KChIP2ΔN2-67 with Kv4.2 in CHO cells produced changes in Kv4.2 current density and kinetics that were indistinguishable from the effects produced by full-length KChIP1 or KChIP2 (Table 1).

To investigate whether the modulatory effects of these KChIPs are specific for Kv4 channels. KChIP1 was coexpressed with Kv1.4 and Kv2.1 in Xenopus oocytes. Xenopus oocytes were injected with 1–3 ng/oocyte of cRNA which was prepared using standard in vitro transcription techniques (Sambrook et al. 1989. Molecular Cloning: a laboratory manual. Cold Spring Harbor Press). Currents in oocytes were measured with a two-electrode voltage clamp. KChIP1 did not appear to have any effect on Kv1.4 or Kv2.1 currents (Table 2), indicating that these functional effects may be specific tor Kv4 channels. As a final control tor the KChIP effects and to verify that the KChIPs effects on Kv4 currents are independent of expression system, the above kinetic analyses were repeated after expressing Kv4.3 and KChIP mRNAs in Xenopus oocytes. The effects KChIP1 on for Kv4.3 in the oocyte system were strikingly similar to those on Kv4.2 in CHO cells (Table 1).

Since these KChIPs bind Ca2+, another important question is to determine whether the effects of KChIP1 on Kv4.2 currents are Ca2+-dependent. This question was addressed indirectly by introducing point mutations within each of KChIP1's EF-hand domains: one mutant has point mutations in the first two EF hands ($D_{199}$ to A, $G_{104}$ to A, and $G_{140}$ to A) and the other one has point mutations in all three EF hands ($D_{199}$ to A, $G_{104}$ to A, $D_{135}$ to A, $G_{140}$ to A, $D_{183}$ to A, and $G_{188}$ to A). These mutations substituted alanine for the two most highly conserved amino acids within the EF-hand consensus (FIG. 25; Linse, S. and Forsen, S. (1995) Determinants that govern high-affinity Calcium binding. In Means, S. (Ed.)Advances in second messenger and phosphoprotein research. New York. Ravens Press., 30: 89–150). Coexpression of this KChIP1 triple EF-hand mutant with Kv4.2 or Kv4.3 in COS cells indicated that this mutant colocalizes and is efficiently coimmunoprecipitated with Kv4 α-subunits in COS-1 cells. However, these EF-hand point mutations completely eliminated the effects of KChIP1 on Kv4.2 kinetics (Table 1). Taken together, these results indicate that the binding interaction between KChIP1 and Kv4.2 is Ca2+ independent, while modulation of Kv4.2 kinetics by KChIP1 is either Ca2+-dependent or sensitive to structural changes induced by point mutations within the EF-hand domains.

TABLE 1

Functional effect of KchIPs on Kv4 channels

| Current Parameter | rKv4.2-vector | rKv4.2-KchIP1 | rKv4.2-KchIP1 ΔN2–31 | rKv4.2-KchIP2 | rKv4.2-KchIP2 ΔN2–67 | rKv4.2-KchIP3 | rKv4.3 | rKv4.3-KchIP1 |
|---|---|---|---|---|---|---|---|---|
| Peak Current (nA/cell at 50 MV) | 0.60* ±0.096 | 4.5* ±0.0055 | 6.0* ±1.1 | 3.3* ±0.45 | 5.8* ±1.1 | 3.5* ±0.99 | 7.7µA ±2.6 | 18.1 µA* ±3.8 |
| Peak Current Density (pA/pF at 50 mV) | 25.5 ±3.2 | 306.9* ±57.9 | 407.2* ±104.8 | 196.6* ±26.6 | 202.6* ±27.5 | 161.7* ±21.8 | — | — |
| Inactivation time constant (ms, at 50 mV) | 28.2 ±2.6 | 104.1 ±10.4 | 129.2 ±14.2 | 95.1* ±8.3 | 109.5* ±9.6 | 67.2* ±14.1 | 56.3 ±6.6 | 135.0 ±15.1 |
| Recovery from Inactivation Time constant | 272.2 | 53.6* | 98.1* | 49.5* | 36.1* | 126.1* | 327.0 | 34.5* |

*Significantly different from control.

TABLE 2

Functional effects of KChIPs on other Kv channels

| | Oocytes | | Oocytes | |
|---|---|---|---|---|
| Current Parameter | HKv1.4 | hKv1.4 + 1v | HKv2.1 | HKv2.1 + 1v |
| Peak Current (µA/cell at 50 MV) | 8.3 ±2.0 | 6.5 ±0.64 | 3.7 ±0.48 | 2.9 ±0.37 |
| Inactivation time constant (ms. at 50 mV) | 53.2 ±2.8 | 58.2 ±6.6 | 1.9 s ±0.079 | 1.7 s 0.078 |
| Recovery from Inactivation time constant (sec. at −80 mV) | 1.9 | 1.6 | 7.6 | 7.7 |
| Activation $V_{12}$ (mV) | −21.0 | −20.9 | 12.0 | 12.4 |
| Steady-state Inactivation V1/2 (mV) | −48.1 | −47.5 | −25.3 | −23.9 |

Example 11

Effects of KChIP1 and KChIP2 on Surface Expression of KV4-αSubunits in COS-1 Cells To examine the ability of KChIP1 to enhance the surface expression of Kv4 channels, the ability of KChIP1 to promote the formation of surface co-clusters of Kv4 channels and PSD-95 was monitored. PSD-95 is used to facilitate the visualization of the complex.

To facilitate the interaction between Kv4.3 and PSD-95, a chimeric Kv4.3 subunit (Kv4.3ch) was generated in which the C-terminal 10 amino acids from rKv1.4 (SNAKAVETDV, SEQ ID NO:73) were appended to the C-terminus of Kv4.3. The C-terminal 10 amino acids from rKv1.4 were used because they associate with PSD-95 and confer the ability to associate with PSD-95 to the Kv4.3 protein when fused to the Kv4.3 C-terminus. Expression of Kv4.3ch in COS-1 cells revealed that the Kv4.3ch polypeptide was trapped in the perinuclear cytoplasm, with minimal detectable Kv4.3ch immunoreactivity at the outer margins of the cell. When Kv4.3ch was co-expressed with PSD-95, PSD-95 became trapped in the perinuclear cytoplasm and co-localized with Kv4.3ch. However, when KChIP1 was co-expressed with Kv4.3ch and PSD-95, large plaque-like surface co-clusters of Kv4.3ch, KChIP1 and PSD-95 were observed. Triple-label immunofluorescence confirmed that these surface clusters contain all three polypeptides, and reciprocal co-immunoprecipitation analyses indicated that the three polypeptides are co-associated in these surface clusters. Control experiments indicated that KChI1 does not interact with PSD-95 alone, and does not co-localize with Kv1.4 and PSD-95 in surface clusters. Taken together, these data indicate that KChIP1 may promote the transit of the Kv4.3 subunits to the cell surface.

Example 12

Characterization of the PCIP Proteins

In this example, the amino acid sequences of the PCIP proteins were compared to amino acid sequences of known proteins and various motifs were identified.

The 1v polypeptide, the amino acid sequence of which is shown in SEQ ID NO:3 is a novel polypeptide which includes 216 amino acid residues. Domains that are putatively involved in calcium binding (Linse, S. and Forsen, S. (1995), *Advances in Second Messenger and Phosphoprotein Research* 30, Chapter 3, p 89–151, edited by Means, AR., Raven Press, Ltd., New York), were identified by sequence alignment (see FIG. 21).

The 8t polypeptide, the amino acid sequence of which is shown in SEQ ID NO:30 is a novel polypeptide which includes 225 amino acid residues. Calcium binding domains that are putatively involved in calcium binding (Linse, S. and Forsen, S. (1995) *Advances in Second Messenger and Phosphoprotein Research* 30, Chapter 3, p 89–151, edited by Means, AR., Raven Press. Ltd., New York), were identified by sequence alignment (see FIG. 21)

The 9q polypeptide is a novel polypeptide which includes calcium binding domains that are putatively involved in calcium binding (Linse, S. and Forsen, S (1995) *Advances in Second Messenger and Phosphoprotein Research* 30, Chapter 3, p 89–151, edited by Means, AR., Raven Press, Ltd., New York (see FIG. 21).

The p19 polypeptide is a novel polypeptide which includes calcium binding domains that are putatively involved in calcium binding (Linse. S. and Forsen, S. (1995) *Advances in Second Messenger and Phosphoprotein Research* 30, Chapter 3, p 89–151, edited by Means, AR., Raven Press, Ltd., New York (see FIG. 21).

A BLASTN 2.0.7 search (Altschul et al. (1990) *J. Mol. Biol.* 215:403) of the nucleotide sequence of rat 1vl revealed that the rat 1vl is similar to the rat cDNA clone RMUAH89 (Accession Number AA849706). The rat 1 vl nucleic acid molecule is 98% identical to the rat cDNA clone RMUAH89 (Accession Number AA849706) over nucleotides 1063 to 1488.

A BLASTN 2.0.7 search (Altschul et al. (1990) *J. Mol. Biol.* 215: 403) of the nucleotide sequence of human 9ql revealed that the human 9ql is similar to the human cDNA clone 1309405 (Accession Number AA757119). The human 9 ql nucleic acid molecule is 98% identical to the human cDNA clone 1309405 (Accession Number AA757119) over nucleotides 937 to 1405.

A BLASTN 2.0.7 search (Altschul et al. (1990) *J Mol. Biol.* 215: 403) of the nucleotide sequence of mouse P19 revealed that the mouse P19 is similar to the Mus musculus cDNA clone MNCb-7005 (Accession Number AU035979). The mouse P19 nucleic acid molecule is 98% identical to the Mus musculus cDNA clone MNCb-7005 (Accession Number AU035979) over nucleotides 1 to 583.

Example 13

Expression of Recombinant PCIP Proteins in Bacterial Cells

In this example, PCIP is expressed as a recombinant glutathione-S-transferase (GST) fusion polypeptide in *E. coli* and the fusion polypeptide is isolated and characterized. Specifically, PCIP is fused to GST and this fusion polypeptide is expressed in *E. coli*, e.g., strain B121. Expression of the GST-PCIP fusion protein in B121 is induced with IPTG. The recombinant fusion polypeptide is purified from crude bacterial lysates of the induced B121 strain by affinity chromatography on glutathione beads. Using polyacrylamide gel electrophoretic analysis of the polypeptide purified from the bacterial lysates, the molecular weight of the resultant fusion polypeptide is determined.

Rat 1v and 9ql were cloned into pGEX-6p-2 (Pharmacia). The resulting recombinant fusion proteins were expressed in *E. coli* cells and purified following art known methods (described in, for example, *Current Protocols in Molecular Biology*, eds. Ausubel et al. John Wiley & Sons: 1992). The identities of the purified proteins were verified by western blot analysis using antibodies raised against peptide epitopes of rat 1v and 9ql.

Example 14

Expression of Recombinant PCIP Proteins in COS Cells

To express the PCIP gene in COS cells, the pcDNA/Amp vector by Invitrogen Corporation (San Diego. Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire PCIP protein and an HA tag (Wilson et al. (1984) *Cell* 3:767) or a FLAG tag fused in-frame to its 3' end of the fragment is cloned into the polylinker region of the vector, thereby placing the expression of the recombinant protein under the control of the CMV promoter.

To construct the plasmid, the PCIP DNA sequence is amplified by PCR using two primers. The 5' primer contains the restriction site of interest followed by approximately twenty nucleotides of the PCIP coding sequence starting from the initiation codon; the 3' end sequence contains complementary sequences to the other restriction site of interest, a translation stop codon, the HA tag or FLAG tag and the last 20 nucleotides of the PCIP coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the PCIP gene is inserted in the correct orientation. The ligation mixture is transformed into *E. coli* cells (strains HB101, DH5a, SURE, available from Stratagene Cloning Systems, La Jolla, Calif. can be used), the transformed culture is plated on ampicillin media plates, and resistant colonies are selected. Plasmid DNA is isolated from transformants and examined by restriction analysis for the presence of the correct fragment.

COS cells are subsequently transfected with the PCIP-pcDNA/Amp plasmid DNA using the calcium phosphate or calcium chloride co-precipitation methods. DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd. ed.* Cold Spring Harbor Laboratory, Cold Spring Harbor Laboratory Press, Cold Spring Harbor, N.Y., 1989. The expression of the PCIP polypeptide is detected by radiolabelling ($^{35}$S-methionine or $^{35}$S-cysteine available from NEN. Boston, Mass. can be used) and immunoprecipitation (Harlow, E. and Lane, D. *Antibodies: A Laboratory Manual*, Cold Spring Harbor Laboratory Press, Cold Spring Harbor, N.Y. 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1% NP-40. 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the PCIP coding sequence is cloned directly into the polylinker of the pCDNA/Amp vector using the appropriate restriction sites. The resulting plasmid is transfected into COS cells in the manner described above, and the expression of the PCIP polypeptide is detected by radiolabelling and immunoprecipitation using a PCIP specific monoclonal antibody.

Rat 1 v was cloned into the mammalian expression vector pRBG4. Transfections into COS cells were performed using LipofectAmine Plus (Gibco BRL) following the manufacturer's instructions. The expressed 1v protein was detected by immunocytochemistry and/or western blot analysis using antibodies raised against 1 v in rabbits or mice.

Example 15

Identification and Characterization of Human Full Length p19

The human full length p19 sequence was identified using RACE PCR. The sequence of p19 (also referred to as KChIP3) is shown in FIG. 16. The amino acid sequence of human p19 is 92% identical to the mouse p19 gene (SEQ ID NO:35).

TBLASTN searches using the protein sequence of human p19 revealed that human p19 is homologous to two sequences. Calsenilin (described in (1998) *Nature Medicine* 4: 1177–1181) and DREAM, a Ca2+-dependent regulator of prodynorphin and c-fos transcription (described in Carrion el al. (1999) *Nature* 398:80–84), Human p19 is 100% identical at the nucleotide level to Calsenilin (but extends 3' to the published sequence) and 99% identical at the nucleotide level to DREAM.

The ability of p19 (as well as other PCIP family members) to co-localize with presenilin and act as transcription factors is determined using art known techniques such as northern blots, in situ hybridization, β-gal assays, DNA mobility assays (described in , for example. Carrion et al (1999) *Nature* 398: 80) and DNA mobility supershift assays, using antibodies specific for KchIPs.

Other assays suitable for evaluating the association of PCIP family members with presenilins is co-immunoprecipitation (described in, for example, Buxbaum et al. (1998) *Nature Medicine* 4: 1177).

Example 16

Identification and Characterization of Monkey KChIP4

In this example, the identification and characterization of the genes encoding monkey KChIP4a (jlkbd352e0ltl ) and alternatively spliced monkey KChIP4b (jlkbb231c04t1), KChIP4c (jlkxa053c02), and KChIP4d (jlkx015b10) is described. TBLASTN searches in proprietary databases with the sequence of the known PCIP family members, lead to the identification of four clones jlkbb231c04tl, jlkbd352e01tl, jlkxa053c02, and jlkx015b10. The four monkey clones were obtained and sequenced.

The sequences of proprietary monkey clones jlkbb231c04tl and jlkbd352e01tl were found to correspond to alternately spliced variants of an additional PCIP family member, referred to herein as KChIP4. Clone jlkbb231c04tl contains a 822bp deletion relative to jlkbd352e01tl (presumably due to splicing out of an exon), resulting in the loss of the final EF hand domain. In clone jlkbd352e01tl, the final EF hand domain is preserved, and the C-terminus is highly homologous to that of PCIP family members 1v, 9ql, and p19. Overall identity in the homologous C-termini among KChIP4. 1v, 9ql, and p19 ranged from 71%–80% at the amino acid level (alignments were performed using the CLUSTALW).

Monkey KChIP4c and KChIP4d were discovered by BLASTN search using monkey KChIP4a as a query for searching a proprietary database.

The nucleotide sequence of the monkey KChIP4a cDNA and the predicted amino acid sequence of the KChIP4a polypeptide are shown in FIG. 23 and in SEQ ID NOs:48 and 49, respectively.

The nucleotide sequence of the monkey KChIP4b cDNA and the predicted amino acid sequence of the KChIP4b polypeptide are shown in FIG. 24 and in SEQ ID NOs:50 and 51, respectively.

The nucleotide sequence of the monkey KChIP4c cDNA and the predicted amino acid sequence of the KChIP4c polypeptide are shown in FIG. 35 and in SEQ ID NOs:69 and 70, respectively.

he nucleotide sequence of the monkey KChIP4d cDNA and the predicted amino acid sequence of the KChIP4d polypeptide are shown in FIG. 36 and in SEQ ID NOs:71 and 72, respectively.

Figure 37:
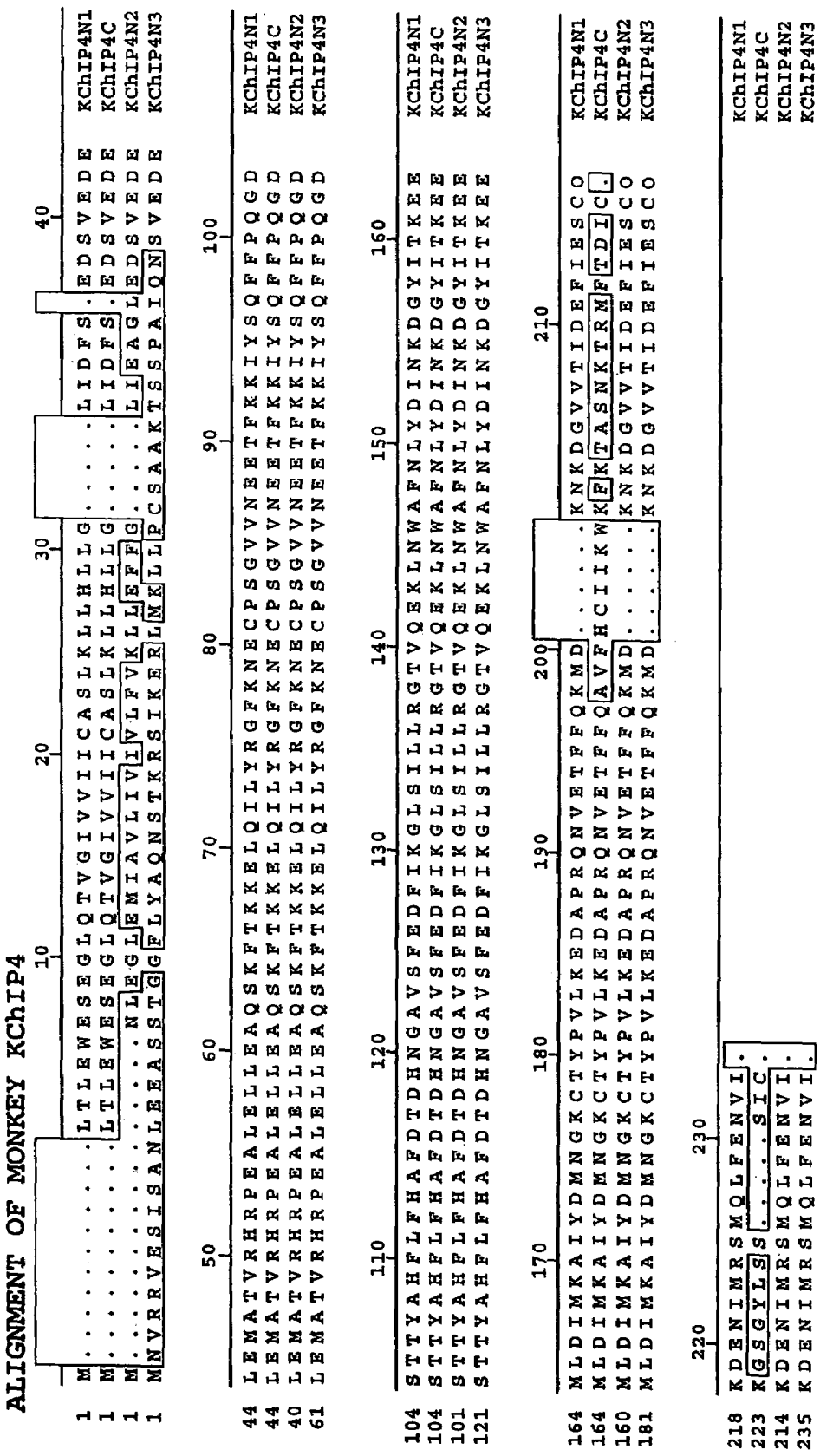
FIG. 37 depicts an alignment of KChIP4a, KChIP4b, KChIP4c, and KChIP4d.
Figure 38:
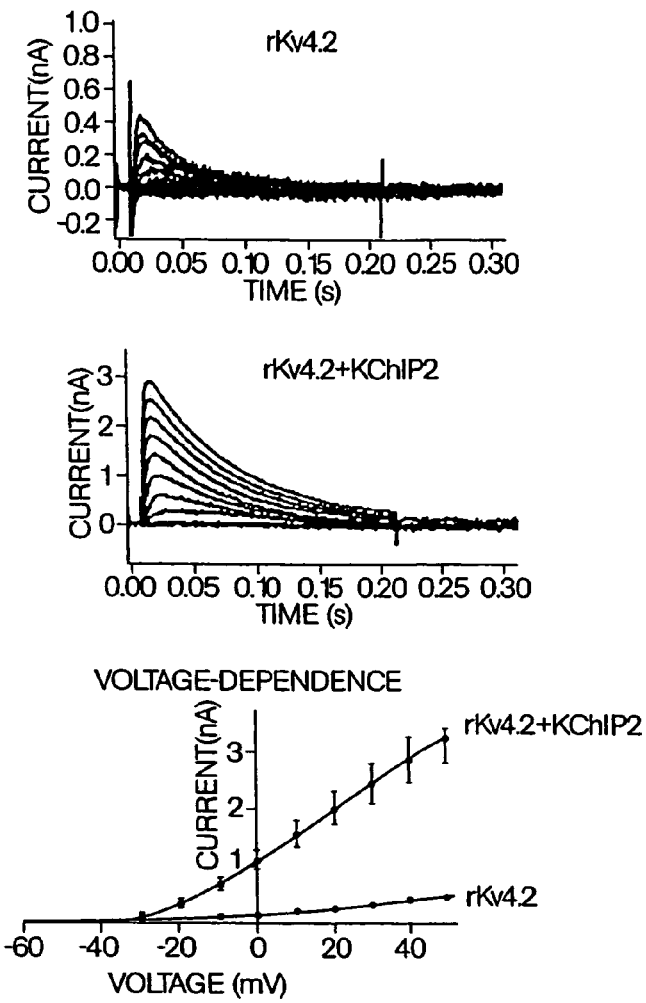
FIG. 38 depicts a graph showing the current traces from CHO cells which express Kv4.2 with or without KChIP3 (p19). Cells are voltage clamped at −80 mV and stepped from −60 mV to +50 mV for 200 ms. Peak current amplitudes at the various test voltages are shown in the right panel.
Figure 39:
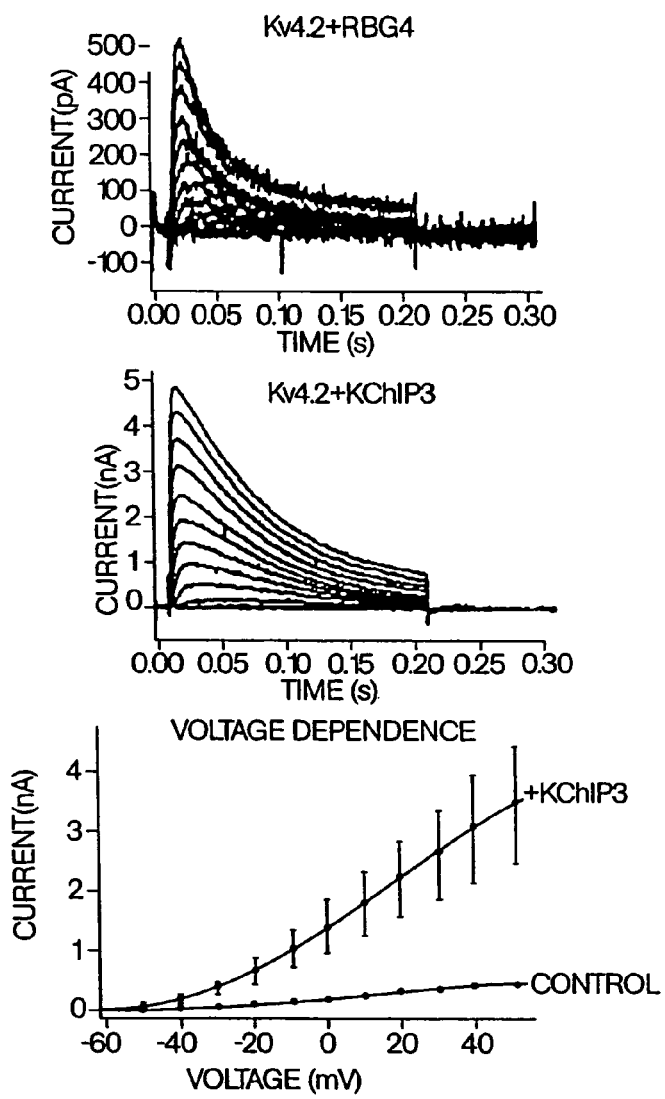
FIG. 39 further depicts a table showing the amplitude and kinetic effects of KchIP3 (p19) on Kv4.2. KchIP3 causes alterations in peak current and amplitude, inactivation and recovery from inactivation time constants, and activation $V_{12}$.
Figure 40A:
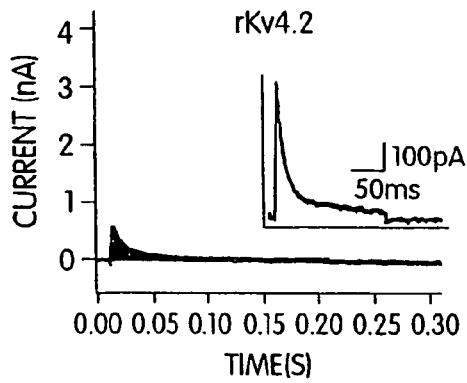
FIG. 40A depicts current traces from a Kv4.2 transfected CHO cell. Current was evoked by depolarizing the cell sequentially from a holding potential of −80 mV to test potentials from −60 to 50 mV. Current traces are leak subtracted using a p/5 protocol. The current axis is shown at the same magnification as in (b) to emphasize the change in current amplitudes. Inset-Single current trace at 50 mV at an expanded current axis to show the kinetics of current activation and inactivation.
Figure 40B:
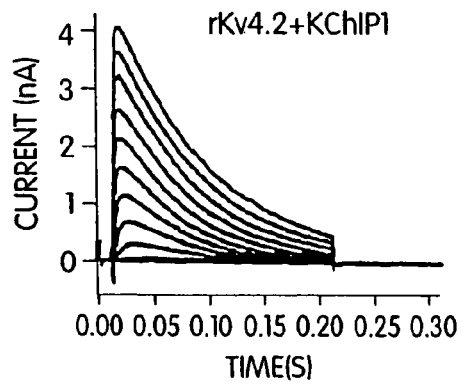
FIG. 40B depicts current traces as in (a), but from a cell transfected with equal amounts of DNA for Kv4.2 and KChIP1.
Figure 40C:
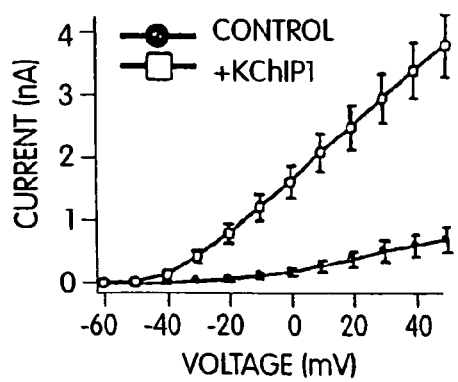
FIG. 40C depicts peak current amplitude at all voltages from cells transfected with Kv4.2 alone (n=11) or cotransfected with KChIP1 (n=9).
Figure 40D:
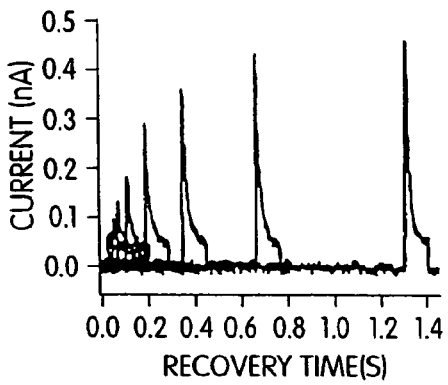
FIGS. 40D and 40E depict recovery from inactivation using a two pulse protocol. Kv4.2 alone (D) or coexpressed with KChIP1 (E) is driven into the inactivated state using a first pulse to 50 mV, then a second pulse to 50 mV is applied at varying times after the first pulse. Holding potential is −80 mV before and after all pulses.
Figure 40E:
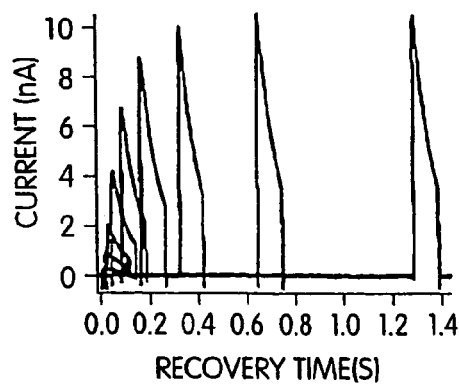
Figure 40F:
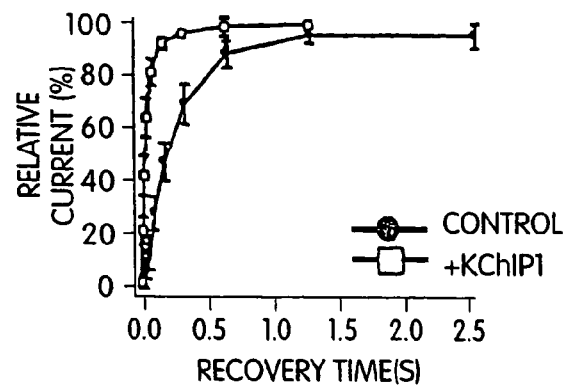
FIG. 40F depicts a summary of the percentage the peak current recovers between pulses for Kv4.2 (n=8) and Kv4.2 plus KChIP1 (n=5) transfected cells. The time constant of recovery from inactivation is fit to a single exponential.

FIG. 37 depicts an alignment of the protein sequences of KChIP4a, KChIP4b, KChIP4c, and KChIP4d.

Rat KChIP4 is predominantly expressed in the brain, and weakly in the kidney, but not in the heart, brain, spleen, lung, liver, skeletal muscle or testes, as indicated by northern blot experiments in which a northern blot purchased from Clontech was probed with a DNA fragment from the 3'-untranslated region of rat KChIP4.

Example 17

Identification and Characterization of Human and Rat 33b07

In this example, the identification and characterization of the genes encoding rat and human 33b07 is described. Partial rat 33b07 (clone name 9o) was isolated as a positive clone from the yeast two-hybrid screen described above, using rKv4.3N as bait. The full length rat 33b07 clone was identified by mining of proprietary databases.

The nucleotide sequence of the full length rat 33b07 cDNA and the predicted amino acid sequence of the rat 33b07 polypeptide are shown in FIG. 26 and in SEQ ID NOs:52 and 53, respectively. The rat 33b07 cDNA encodes a protein having a molecular weight of approximately 44.7 kD and which is 407 amino acid residues in length.

Rat 33b07 binds rKv4.3N and rKv4.2N with slight preference for rKv4.2N in yeast 2-hybrid assays. In contrast, rat 33b07 does not bind rKv1.1N, indicating that the rat 33b07-Kv4N interaction is specific.

Rat 33b07 is expressed predominantly in the brain as determined by northern blot analysis.

The human 33b07 ortholog (clone 106d5) was also identified by mining of proprietary databases. The nucleotide sequence of the full length human 33b07 cDNA and the predicted amino acid sequence of the human 33b07 polypeptide are shown in FIG. 27 and in SEQ ID NOs:54 and 55, respectively. The human 33b07 cDNA encodes a protein having a molecular weight of approximately 45.1 kD and which is 414 amino acid residues in length.

Human 33b07 is 99% identical to the human KIAA0721 protein (GenBank Accession Number: AB018264) at the amino acid level. However, Genbank Accession Number: AB018264 does not have a functional annotation. Human 33b07 is also homologous to Testes-specific (Y-encoded) proteins (TSP(Y)s). SET, and Nucleosome Assembly Proteins (NAPs). The human 33b07 is 38% identical to human SET protein (GenBank Accession Number Q01105=U51924) over amino acids 204 to 337 and 46% identical over amino acids 334 to 387.

Human SET is also called HLA-DR associated protein II (PHAPH) (Hoppe-Seyler (1994) *Biol. Chem.* 375:113–126) and in some cases is associated with acute undifferentiated leukemia (AUL) as a result of a translocation event resulting in the formation of a SET-CAN fusion gene (Von Lindern M.

et al. (1992) *Mol. Cell. Biol.* 12:3346–3355). An alternative spliced form of SET is also called Template Activating Factor-1 alpha (TAF). TAF is found to be associated with myeloid leukemogenesis (Nagata K. et al. (1995) *Proc. Natl. Acad. Sci. U.S.A.* 92 (10),4279–4283). Human SET is also a potent protein inhibitor of phosphatase 2A (Adachi Y. et al. (1994) *J. Biol. Chem.* 269:2258–2262). NAPs may be involved in modulating chromatin formation and contribute to regulation of cell proliferation (Simon H. U. et al. (1994) *Biochem. J.* 297:389–397).

Thus, due to its homology to the above identified proteins, 33b07 may function as a protein inhibitor of phosphatase, an oncogene, and/or a chromatin modulator. The homology of 33b07 to SET, a protein phosphatase inhibitor, is of particular interest. Many channels, in particular the Kv4 channels (with which 33b07 is associated), are known to be regulated by phosphorylation by PKC and PKA ((1998) *J. Neuroscience* 18(10): 3521–3528: Am J Physiol 273: H1775–86 (1997)). Thus, 33b07 may modulate Kv4 activity by regulating the phosphorylation status of the potassium channel.

Example 18

Identification and Characterization of Rat 1p

In this example, the identification and characterization of the gene encoding rat 1p is described. Partial rat 1p was isolated as a positive clone from the yeast two-hybrid screen described above, using rKv4.3N as a bait.

The nucleotide sequence of the partial length rat 1p cDNA and the predicted amino acid sequence of the rat 1 p polypeptide are shown in FIG. 28 and in SEQ ID NOs:56 and 57, respectively. The rat 1p cDNA encodes a protein having a molecular weight of approximately 28.6 kD and which is 267 amino acid residues in length.

Rat 1p binds rKv4.3N and rKv4.2N with slight preference for rKv4.3N in yeast two-hybrid assays. In contrast, 1p does not bind rKv1.1N, indicating that the 1p-Kv4N interaction is specific.

Rat 1p is predominantly expressed in the brain as determined by northern blot analysis.

A BLASTP 1.4 search, using a score of 100 and a word length of 3 (Altschul et al (1990) *J. Mol. Biol.* 215: 403) of the amino acid sequences of rat 1p revealed that rat 1p is similar to the human Restin (GenBank Accession Number P30622; also named cytoplasmic linker protein-170 alpha-2 (CLIP-170), M97501)). The rat 1p protein is 58% identical to the human Restin over amino acid residues 105 to 182.55% identical to the human Restin over amino acid residues 115 to 186. 22% identical to the human Restin over amino acid residues 173 to 246. 22% identical to the human Restin over amino acid residues 169 to 218, and 58% identical to the human Restin over amino acid residues 217 to 228.

Restin is also named Reed-Sternberg intermediate filament associated protein. Reed-Sternberg cells are the tumoral cells diagnostic for Hodgkin's disease. It is suggested that Restin overexpression may be a contributing factor in the progression of Hodgkin's disease (Bilbe G. et al (1992) *EMBO J* 11: 2103–13) and Restin appears to be an intermediate filament associated protein that links endocytic vesicles to microtubules (Pierre P. et al. (1992) *Cell* 70 (6), 887–900).

The cytoskeleton regulates the activity of potassium channels (see, for example, Honore F. et al. (1992) *EMBO J.* 11:2465–2471 and Levin G. et al. (1996) *J. Biol. Chem.* 271:29321–29328), as well as the activity of other channels, e.g., Ca channels (Johnson B. D. et al (1993) *Neuron* 10:797–804): or Na channels (Fukuda J. et al. (1981) *Nature* 294: 82–85).

Accordingly, based on its homology to the Restin protein, the rat 1p protein may be associated with the cytoskeleton and may modulate the activity of potassium channels, e.g., Kv4, via its association to the cytoskeleton.

Example 19

Identification and Characterization of Rat 7s

In this example, the identification and characterization of the gene encoding rat 7s is described. Partial rat 7s was isolated as a positive clone from the yeast two-hybrid screen described above, using rKv4.3N as a bait. Rat 7s is the rat ortholog of the human vacuolar H(+)-ATPase catalytic subunit A (Accession Number P38606 and B46091) described in, for example, van Hille B. et al. (1993) *J. Biol. Chem.* 268 (10), 7075–7080.

The nucleotide sequence of the partial length rat 7s cDNA and the predicted amino acid sequence of the rat 7s polypeptide are shown in FIG. 29 and in SEQ ID NOs:58 and 59, respectively. The rat 7s cDNA encodes a protein having a molecular weight of approximately 28.6 kD and which is 270 amino acid residues in length.

Rat 7s binds rKv4.3N and rKv4.2N with preference for rKv4.3N in yeast two-hybrid assays. In contrast, 7s does not bind rKv1.1N, indicating that the 7s-Kv4N interaction is specific.

Rat 7s is expressed at significantly higher levels in the brain and the kidney than in the lung, liver, heart, testes, and skeletal muscle, as determined by northern blot analysis.

Example 20

Identification and Characterization of Rat 29x and 25r

In this example, the identification and characterization of the gene encoding rat 29x is described. Rat 29x was isolated as a positive clone from the yeast two-hybrid screen described above, using rKv4.3N as a bait. Rat 25r is a splice variant of 29x. They differ in the 5' untranslated region, but are identical in the coding region and at the amino acid level.

The nucleotide sequence of the rat 29x cDNA and the predicted amino acid sequence of the rat 29x polypeptide are shown in FIG. 30 and in SEQ ID NOs:60 and 61. respectively. The rat 29x cDNA encodes a protein having a molecular weight of approximately 40.4 kD and which is 351 amino acid residues in length.

The nucleotide sequence of the rat 25r cDNA is shown in FIG. 31 and in SEQ ID NO:62. The rat 25r cDNA encodes a protein having a molecular weight of approximately 40.4 kD and which is 351 amino acid residues in length.

Rat 29x is expressed in the spleen, lung, kidney, heart, brain, testes, skeletal muscle and liver, with the highest level of expression being in the spleen and the lowest being in the liver.

Rat 29x binds rKv4.3N and rKv4.2N with slight preference tor rKv4.3N in yeast two-hybrid assays. In contrast, 29x does not bind rKv1.1N, indicating that the 29x-Kv4N interaction is specific.

Rat 29x is identical at the amino acid level to rat SOCS-1 (Suppressor Of Cytokine Signaling) described in Starr R. et al. (1997) *Nature* 387: 917–921 to JAB described in Endo T. A. et al. (1997) *Nature* 387: 921–924; and to SSI-1 (STAT-induced STAT inhibitor-1) described in Naka T. et al. (1997) *Nature* 387:924–928. These proteins are characterized in that they have an SH2 domain, bind to and inhibit JAK kinase, and, as a result, regulate cytokine signaling. Rat 29x contains an SH2 domain at amino acid residues 219–308 of SEQ ID NO:61.

Tyrosine phosphorylation regulates potassium channel activity (Prevarskaya N. B. et al. (1995) *J. Biol. Chem.* 270:24292–24299). JAK kinase phoshorylates proteins at tyrosines and is implicated in the regulation of channel activity (Prevarskaya N. B. et al. supra). Accordingly, based on its homology to SOCS-1, JAB, and SSI-1, rat 29x may modulate the activity of potassium channels, e.g., Kv4, by modulating JAK kinase activity.

Example 21

Identification and Characterization of Rat 5p

In this example, the identification and characterization of the gene encoding rat 5p is described. Rat 5p was isolated as a positive clone from the yeast two-hybrid screen described above, using rKv4.3N as a bait.

The nucleotide sequence of the rat 5pc DNA and the predicted amino acid sequence of the rat 5p polypeptide are shown in FIG. 32 and in SEQ ID NOs:63 and 64, respectively. The rat 5p cDNA encodes a protein having a molecular weight of approximately 11.1 kD and which is 95 amino acid residues in length.

Rat 5p binds rKv4.3N and rKv4.2N with similar strength in yeast two-hybrid assays. In contrast, 5p does not bind rKv1.1N, indicating that the 5p-Kv4N interaction is specific.

Rat 5p is expressed in the spleen, lung, skeletal muscle, heart, kidney, brain, liver, and testes, as determined by northern blot analysis.

The rat 5p is identical to rat Calpactin I light chain or P10 (Accession Number P05943). P10 binds and induces the dimerization of annexin II (p36). P10 may function as a regulator of protein phosphorylation in that the p36 monomer is the preferred target of a tyrosine-specific kinase (Masiakowski P. et al. (1998) *Proc. Natl. Acad. Sci U.S.A.* 85 (4):1277–1281).

Tyrosine phosphorylation regulates the activity potassium channels (Prevarskaya N. B. et al. supra), Thus, due to its identity to P10, rat 5p may modulate the activity of potassium channels, e.g., Kv4, by modulating the activity of a tyrosine-specific kinase.

Example 22

Identification and Characterization of Rat 7q

In this example, the identification and characterization of the gene encoding rat 7q is described. Rat 7q as isolated as a positive clone from the yeast two-hybrid screen described above, using rK4.3N as a bait. Full length rat 7q was obtained by RACE PCR.

The nucleotide sequence of the rat 7q cDNA and the predicted amino acid sequence of the rat 7q polypeptide are shown in FIG. 33 and in SEQ ID NOs:65 and 66, respectively. The rat 7q cDNA encodes a protein having a molecular weight of approximately 23.5 kD and which is 212 amino acid residues in length.

Rat 7q binds rKv4.3N and rKv4.2N with same strength in yeast two-hybrid assays. In contrast, 7q does not bind rKv1.1N, indicating that the 7q-Kv4N interaction is specific.

Rat 7q is expressed in the heart, brain, spleen, lung, liver, skeletal muscle, kidney, and testes, as determined by northern blot analysis.

Rat 7q is identical to RAB2 (rat RAS-related protein. Accession Number P05712) at the amino acid level. RAB2 appears to be involved in vesicular traffic and protein transport (Touchot N. et al. (1987) *Proc. Natl. Acad. Sci. U.S.A.* 84 (23): 8210–8214). Accordingly, based on its homology to RAB2, rat 7q may be involved in potassium channel, e.g., Kv4, trafficking.

Example 23

Identification and Characterization of Rat 19r

In this example, the identification and characterization of the gene encoding rat 19r is described. Partial rat 19r was isolated as a positive clone from the yeast two-hybrid screen described above, using rKv4.3N as a bait. Full length rat 19r was obtained by RACE PCR.

The nucleotide sequence of the rat 19r cDNA and the predicted amino acid sequence of the rat 19r polypeptide are shown in FIG. 34 and in SEQ ID NOs:67 and 68, respectively. The rat 19r cDNA encodes a protein having a molecular weight of approximately 31.9 kD and which is 271 amino acid residues in length.

Rat 19r is expressed in the heart, brain, spleen, lung, liver, skeletal muscle, kidney, and testes, as determined by northern blot analysis.

Rat 19r binds rKv4.3N and rK4.2N with slight preference for rKv4.3N in yeast two-hybrid assays. In contrast, 19r does not bind rKv1.1N, indicating that the 19r-Kv4N interaction is specific.

Rat 19r is identical to Rat phosphatidylinositol (PTDINS) transfer protein alpha (PTDINSTP, Accession Number M25758 or P16446) described in Dickeson S. K. et al. (1989) *J Biol. Chem.* 264:16557–16564. PTDINSTP is believed to be involved in phospholipase C-beta (PLC-beta) signaling, phosphatidylinositol transfer protein (Ptdlns-TP) synthesis, secrettory vesicle formation, and enhancement of phosphatidylinositol 3-kinase (Ptdlns 3-kinase) activity (Cunningham E. et al. (1995) *Curr. Biol.* 5 (7):775–783: (1995) *Nature* 377(6549):544–547; and Panaretou C. et al. (1997) *J. Biol. Chem.* 272(4): 2477–2485).

Accordingly, based on its homology with PTDINSTP, rat 19r may modulate potassium channel, e.g., Kv4, activity via the PLC-beta signaling pathway and/or the Ptdlns 3-kinase signaling pathway. Rat p19r may also be involved in potassium channel, e.g., Kv4, trafficking.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for identifying a compound that binds to and/or modulates the activity of a Kv4.2 or Kv4.3 potassium channel by binding to and/or modulating the activity of a PCIP polypeptide comprising:

a) contacting a 9q PCIP polypeptide comprising an amino acid sequence selected from the group consisting of SEQ ID NOs: 14, 16, 18, 20, 22, 24, 26, and 28, or a cell expressing said 9q PCIP polypeptide, with a test compound; and b) determining whether said test compound binds to and/or modulates the activity of said 9q PCIP polypeptide, wherein said activity is selected from the group consisting of regulation of $I_{to}$ currents, regulation of peak current amplitudes, regulation of current density, regulation of inactivation time constants, regulation of recovery from inactivation time constants, regulation of current activation threshold, regulation of the kinetics of inactivation, regulation of the repolarization of the membrane during an action potential, interaction with a potassium channel or portion thereof, modulation of neuronal excitability, modulation of action potential conduction, modulation of somatodendritic excitability, modulation of neurotransmitter release, regulation of the phosphorylation state of a potassium channel or portion thereof, binding to calcium, acting as a calcium dependent kinase, modulation of chromatin formation in a cell, modulation of vesicular traffic, modulation of protein transport in a cell, modulation of cytokine signaling in a cell, regulation of the association of a potassium channel or portion thereof with the cellular cytoskeleton, modulation of cellular proliferation, modulation of membrane excitability, influencing the resting potential of membranes, modulation of wave forms of action potentials, modulation of wave frequencies of action potentials and modulation of excitation thresholds, thereby identifying a compound that binds to and/or modulates the activity of a Kv4.2 or Kv4.3 potassium channel.

2. The method of claim 1, wherein the binding of said test compound to said 9q PCIP polypeptide, is detected by a method selected from the group consisting of:
   a) detection of binding by direct detection of test compound/polypeptide binding;
   b) detection of binding using a competition binding assay; and
   c) detection of binding using an assay for PCIP activity.

3. A method for identifying a compound that binds to and/or modulates the activity of a Kv4.2 or Kv4.3 potassium channel by binding to and/or modulating the activity of a PCIP polypeptide, comprising:
   a) incubating a cell expressing i) a potassium channel comprising a Kv4.3 or Kv4.2 subunit, or a fragment thereof that functions as a potassium channel and ii) a 9q PCIP polypeptide comprising an amino acid sequence selected from the group consisting of SEQ ID NOs: 14, 16, 18, 20, 22, 24, 26, and 28, in the presence and absence of a test compound; and
   b) determining whether the test compound binds to/and or modulates the activity of said 9q PCIP polypeptide wherein said activity is selected from the group consisting of regulation of $I_{to}$ currents, regulation of peak current amplitudes, regulation of current density, regulation of inactivation time constants, regulation of recovery from inactivation time constants, regulation of current activation threshold, regulation of the kinetics of inactivation, regulation of the repolarization of the membrane during an action potential, interaction with a potassium channel or portion thereof, modulation of neuronal excitability, modulation of action potential conduction, modulation of somatodendritic excitability, modulation of neurotransmitter release, regulation of the phosphorylation state of a potassium channel or portion thereof, binding to calcium, acting as a calcium dependent kinase, modulation of chromatin formation in a cell, modulation of vesicular traffic, modulation of protein transport in a cell, modulation of cytokine signaling in a cell, regulation of the association of a potassium channel or portion thereof with the cellular cytoskeleton, modulation of cellular proliferation, modulation of membrane excitability, influencing the resting potential of membranes, modulation of wave forms of action potentials, modulation of wave frequencies of action potentials and modulation of excitation thresholds, thereby identifying a compound that binds to and/or modulates the activity of a Kv4.2 or Kv4.3 potassium channel.

4. A method for identifying a compound that binds to and/or modulates the activity of a Kv4.2 or Kv4.3 potassium channel by binding to and/or modulating the activity of a PCIP polypeptide, comprising:
   a) contacting a polypeptide comprising an EF domain, a Kv4.3 or Kv4.2 potassium channel α subunit binding domain, or a C-terminal core domain of a 9q PCIP polypeptide comprising an amino acid sequence selected from the group consisting of SEQ ID NOs: 14, 16, 18, 20, 22, 24, 26, and 28, or a cell expressing said polypeptide, with a test compound; and
   b) determining whether said test compound binds to and/or modulates the activity of said polypeptide, wherein said activity is selected from the group consisting of regulation of $I_{to}$ currents, regulation of peak current amplitudes, regulation of current density, regulation of inactivation time constants, regulation of recovery from inactivation time constants, regulation of current activation threshold, regulation of the kinetics of inactivation, regulation of the repolarization of the membrane during an action potential, interaction with a potassium channel or portion thereof, modulation of neuronal excitability, modulation of action potential conduction, modulation of somatodendritic excitability, modulation of neurotransmitter release, regulation of the phosphorylation state of a potassium channel or portion thereof, binding to calcium, acting as a calcium dependent kinase, modulation of chromatin formation in a cell, modulation of vesicular traffic, modulation of protein transport in a cell, modulation of cytokine signaling in a cell, regulation of the association of a potassium channel or portion thereof with the cellular cytoskeleton, modulation of cellular proliferation, modulation of membrane excitability, influencing the resting potential of membranes, modulation of wave forms of action potentials, modulation of wave frequencies of action potentials and modulation of excitation thresholds, thereby identifying a compound that binds to and/or modulates the activity of a Kv4.2 or Kv4.3 potassium channel.

5. A method for identifying a compound that binds to and/or modulates the activity of a Kv4.2 or Kv4.3 potassium channel, comprising:
   a) incubating a cell expressing i) a potassium channel comprising a Kv4.3 or Kv4.2 subunit, or a fragment thereof that functions as a potassium channel, and ii) a polypeptide comprising an EF domain, a Kv4.3 or Kv4.2 potassium channel α subunit binding domain, or a C-terminal core domain of a 9q PCIP polypeptide comprising an amino acid sequence selected from the group consisting of SEQ ID NOs: 14, 16, 18, 20, 22, 24, 26, and 28, in the presence and absence of a Θ test compound; and
   b) determining whether the test compound binds to and/or modulates the activity of said polypeptide, wherein said activity is selected from the group consisting of regulation of $I_{to}$ currents, regulation of peak current amplitudes, regulation of current density, regulation of inactivation time constants, regulation of recovery from inactivation time constants, regulation of current activation threshold, regulation of the kinetics of inactivation, regulation of the repolarization of the membrane during an action potential, interaction with a potassium channel or portion thereof, modulation of neuronal excitability, modulation of action potential conduction, modulation of somatodendritic excitability, modulation of neurotransmitter release, regulation of the phosphorylation state of a potassium channel or portion thereof, binding to calcium, acting as a calcium dependent kinase, modulation of chromatin formation in a cell, modulation of vesicular traffic, modulation of protein transport in a cell, modulation of cytokine signaling in a cell, regulation of the association of a potassium channel or portion thereof with the cellular cytoskeleton, modulation of cellular proliferation, modulation of membrane excitability, influencing the resting potential of membranes, modulation of wave forms of action potentials, modulation of wave frequencies of action potentials and modulation of excitation thresholds, thereby identifying a compound that binds to and/or modulates the activity of a Kv4.2 or Kv4.3 potassium channel.

6. The method of any one of claims 1, 3, 4 or 5 wherein said compound is useful in treating a subject suffering from a cardiovascular disorder is associated with an abnormal $I_{to}$ current.

7. The method of any one of claims 1, 3, 4 or 5, wherein said 9q PCIP is a human 9q.

8. The method of any one of claims 1, 3, 4 or 5, wherein said compound is useful in treating a subject suffering from long-QT syndrome.

9. The method of any one of claims 1, 3, 4 or 5, wherein said compound is useful in treating a subject suffering from congestive heart failure.

10. The method of claim 4, wherein the binding of said test compound to said biologically active fragment of said 9q PCIP polypeptide, is detected by a method selected from the group consisting of:
   a) detection of binding by direct detection of test compound/biologically active fragment binding;
   b) detection of binding using a competition binding assay; and
   c) detection of binding using an assay for PCIP activity.

11. The method of claims 4 or 5, wherein the EF domain is selected from the group consisting of:
   a) residues 116–127, 153–164, 189–200, or 237–248 of SEQ ID NO:14;
   b) residues 103–114, 140–151, 176–187, or 224–235 of SEQ ID NO:16;
   c) residues 116–127, 153–164, 189–200, or 237–248 of SEQ ID NO:18;
   d) residues 98–109, 135–146, 171–182, or 219–230 of SEQ ID NO:20;
   e) residues 98–109, 135–146, 171–182, or 219–230 of SEQ ID NO:22;
   f) residues 116–127, 103–114, 139–150, or 187–198 of SEQ ID NO:24;
   g) residues 66–77, 103–114, 189–200 or 237–248 of SEQ ID NO:26; and
   h) residues 98–109, 135–146, 171–182, or 219–230 of SEQ ID NO:28.

12. A method for identifying a compound that binds to and/or modulates the activity of a Kv4.2 or Kv4.3 potassium channel by binding to and/or modulating the activity of a PCIP polypeptide comprising:
   a) contacting a polypeptide that is at least 95% identical to a 9q PCIP polypeptide comprising an amino acid sequence selected from the group consisting of SEQ ID NOs: 14, 16, 18, 20, 22, 24, 26, and 28 and retains the ability to bind to a Kv4 channel, or a cell expressing said polypeptide, with a test compound; and
   b) determining whether said test compound binds to and/or modulates the activity of said polypeptide, wherein said activity is selected from the group consisting of regulation of Ito currents, regulation of peak current amplitudes, regulation of current density, regulation of inactivation time constants, regulation of recovery from inactivation time constants, regulation of current activation threshold, regulation of the kinetics of inactivation, regulation of the repolarization of the membrane during an action potential, interaction with a potassium channel or portion thereof, modulation of neuronal excitability, modulation of action potential conduction, modulation of somatodendritic excitability, modulation of neurotransmitter release, regulation of the phosphorylation state of a potassium channel or portion thereof, binding to calcium, acting as a calcium dependent kinase, modulation of chromatin formation in a cell, modulation of vesicular traffic, modulation of protein transport in a cell, modulation of cytokine signaling in a cell, regulation of the association of a potassium channel or portion thereof with the cellular cytoskeleton, modulation of cellular proliferation, modulation of membrane excitability, influencing the resting potential of membranes, modulation of wave forms of action potentials, modulation of wave frequencies of action potentials and modulation of excitation thresholds, thereby identifying a compound that binds to and/or modulates the activity of a Kv4.2 or Kv4.3 potassium channel.

* * * * *

SEQUENCE LISTING

<160> NUMBER OF SEQ ID NOS: 73

<210> SEQ ID NO 1
<211> LENGTH: 1463
<212> TYPE: DNA
<213> ORGANISM: Homo sapiens
<220> FEATURE:
<221> NAME/KEY: CDS
<222> LOCATION: (225)..(872)

<400> SEQUENCE: 1

```
gaatagcccc ctttcacttc tgagtccctg catgtgcggg gctgaagaag gaagccagaa      60
gcctcctagc ctcgcctcca cgtttgctga ataccaagct gcaggcgagc tgccgggcgc     120
ttttctctcc tccaattcag agtagacaaa ccacgtggat ttctttccag ggtaggggag     180
gggccgggcc cggggtccca actcgcactc aagtcttcgc tgcc atg ggg gcc gtc     236
                                                 Met Gly Ala Val
                                                   1 atg ggc acc ttc tca tct ctg caa acc aaa caa agg cga ccc tcg aaa      284
Met Gly Thr Phe Ser Ser Leu Gln Thr Lys Gln Arg Arg Pro Ser Lys
  5                  10                  15                  20 gat aag att gaa gat gag ctg gag atg acc atg gtt tgc cat cgg ccc      332
Asp Lys Ile Glu Asp Glu Leu Glu Met Thr Met Val Cys His Arg Pro
                 25                  30                  35 gag gga ctg gag cag ctc gag gcc cag acc aac ttc acc aag agg gag      380
Glu Gly Leu Glu Gln Leu Glu Ala Gln Thr Asn Phe Thr Lys Arg Glu
             40                  45                  50 ctg cag gtc ctt tat cga ggc ttc aaa aat gag tgc ccc agt ggt gtg      428
Leu Gln Val Leu Tyr Arg Gly Phe Lys Asn Glu Cys Pro Ser Gly Val
         55                  60                  65 gtc aac gaa gac aca ttc aag cag atc tat gct cag ttt ttc cct cat      476
Val Asn Glu Asp Thr Phe Lys Gln Ile Tyr Ala Gln Phe Phe Pro His
 70                  75                  80 gga gat gcc agc acg tat gcc cat tac ctc ttc aat gcc ttc gac acc      524
Gly Asp Ala Ser Thr Tyr Ala His Tyr Leu Phe Asn Ala Phe Asp Thr
 85                  90                  95                 100 act cag aca ggc tcc gtg aag ttc gag gac ttt gta acc gct ctg tcg      572
Thr Gln Thr Gly Ser Val Lys Phe Glu Asp Phe Val Thr Ala Leu Ser
                105                 110                 115 att tta ttg aga gga act gtc cac gag aaa cta agg tgg aca ttt aat      620
Ile Leu Leu Arg Gly Thr Val His Glu Lys Leu Arg Trp Thr Phe Asn
            120                 125                 130 ttg tat gac atc aac aag gac gga tac ata aac aaa gag gag atg atg      668
Leu Tyr Asp Ile Asn Lys Asp Gly Tyr Ile Asn Lys Glu Glu Met Met
        135                 140                 145 gac att gtc aaa gcc atc tat gac atg atg ggg aaa tac aca tat cct      716
Asp Ile Val Lys Ala Ile Tyr Asp Met Met Gly Lys Tyr Thr Tyr Pro
    150                 155                 160 gtg ctc aaa gag gac act cca agg cag cat gtg gac gtc ttc ttc cag      764
Val Leu Lys Glu Asp Thr Pro Arg Gln His Val Asp Val Phe Phe Gln
165                 170                 175                 180 aaa atg gac aaa aat aaa gat ggc atc gta act tta gat gaa ttt ctt      812
Lys Met Asp Lys Asn Lys Asp Gly Ile Val Thr Leu Asp Glu Phe Leu
                185                 190                 195 gaa tca tgt cag gag gac gac aac atc atg agg tct ctc cag ctg ttt      860
Glu Ser Cys Gln Glu Asp Asp Asn Ile Met Arg Ser Leu Gln Leu Phe
            200                 205                 210 caa aat gtc atg taactggtga cactcagcca ttcagctctc agagacattg           912
Gln Asn Val Met
```

-continued

```
                215 tactaaacaa ccaccttaac accctgatct gcccttgttc tgattttaca caccaactct    972 tgggacagaa acaccttta cactttggaa gaattctctg ctgaagactt tcttatggaa    1032 cccagcatca tgtggctcag tctctgattg ccaactcttc ctctttcttc ttcttgagag    1092 agacaagatg aaatttgagt ttgttttgga agcatgctca tctcctcaca ctgctgccct    1152 atggaaggtc cctctgctta agcttaaaca gtagtgcaca aaatatgctg cttacgtgcc    1212 cccagcccac tgcctccaag tcaggcagac cttggtgaat ctggaagcaa gaggacctga    1272 gccagatgca caccatctct gatggcctcc caaaccaatg tgcctgtttc tcttcctttg    1332 gtgggaagaa tgagagttat ccagaacaat taggatctgt catgaccaga ttgggagagc    1392 cagcacctaa catatgtggg ataggactga attattaagc atgacattgt ctgatgaccc    1452 aaactgcccc g                                                        1463
```

<210> SEQ ID NO 2
<211> LENGTH: 216
<212> TYPE: PRT
<213> ORGANISM: Homo sapiens

<400> SEQUENCE: 2

```
Met Gly Ala Val Met Gly Thr Phe Ser Ser Leu Gln Thr Lys Gln Arg
  1               5                  10                  15

Arg Pro Ser Lys Asp Lys Ile Glu Asp Glu Leu Glu Met Thr Met Val
             20                  25                  30

Cys His Arg Pro Glu Gly Leu Glu Gln Leu Glu Ala Gln Thr Asn Phe
         35                  40                  45

Thr Lys Arg Glu Leu Gln Val Leu Tyr Arg Gly Phe Lys Asn Glu Cys
     50                  55                  60

Pro Ser Gly Val Val Asn Glu Asp Thr Phe Lys Gln Ile Tyr Ala Gln
 65                  70                  75                  80

Phe Phe Pro His Gly Asp Ala Ser Thr Tyr Ala His Tyr Leu Phe Asn
                 85                  90                  95

Ala Phe Asp Thr Thr Gln Thr Gly Ser Val Lys Phe Glu Asp Phe Val
            100                 105                 110

Thr Ala Leu Ser Ile Leu Leu Arg Gly Thr Val His Glu Lys Leu Arg
        115                 120                 125

Trp Thr Phe Asn Leu Tyr Asp Ile Asn Lys Asp Gly Tyr Ile Asn Lys
    130                 135                 140

Glu Glu Met Met Asp Ile Val Lys Ala Ile Tyr Asp Met Met Gly Lys
145                 150                 155                 160

Tyr Thr Tyr Pro Val Leu Lys Glu Asp Thr Pro Arg Gln His Val Asp
                165                 170                 175

Val Phe Phe Gln Lys Met Asp Lys Asn Lys Asp Gly Ile Val Thr Leu
            180                 185                 190

Asp Glu Phe Leu Glu Ser Cys Gln Glu Asp Asp Asn Ile Met Arg Ser
        195                 200                 205

Leu Gln Leu Phe Gln Asn Val Met
    210                 215
```

<210> SEQ ID NO 3
<211> LENGTH: 1856
<212> TYPE: DNA
<213> ORGANISM: Rattus sp.
<220> FEATURE:
<221> NAME/KEY: CDS

<222> LOCATION: (300)..(1034)

<400> SEQUENCE: 3

```
ggcacacaac ccctggattc ttcggagaat atgccgtgag gtgttgccaa ttattagttc      60
tcttggctag cagatgttta gggactggtt aagcctttgg agaaattacc ttaggaaaac     120
ggggaaataa aagcaaagat taccatgaat tgcaagatta cctagcaatt gcaaggtagg     180
aggagagagg tggagggcgg agtagacagg agggagggga aaagtgagag gaagctaggc     240
tggtggaaat aaccctgcac ttggaacagc gcaaagaag cgcgattttc cagctttaa      299
```

| | | | | | | | | | | | | | | | | |
|---|---|---|---|---|---|---|---|---|---|---|---|---|---|---|---|---|
| atg | cct | gcc | cgc | gtt | ctg | ctt | gcc | tac | ccg | gga | acg | gag | atg | ttg | acc | 347 |
| Met | Pro | Ala | Arg | Val | Leu | Leu | Ala | Tyr | Pro | Gly | Thr | Glu | Met | Leu | Thr | |
| 1 | | | | 5 | | | | | 10 | | | | | 15 | | |

| cag | ggc | gag | tct | gaa | ggg | ctc | cag | acc | ttg | ggg | ata | gta | gtg | gtc | ctg | 395 |
|---|---|---|---|---|---|---|---|---|---|---|---|---|---|---|---|---|
| Gln | Gly | Glu | Ser | Glu | Gly | Leu | Gln | Thr | Leu | Gly | Ile | Val | Val | Val | Leu | |
| | | | 20 | | | | | 25 | | | | | 30 | | | |

| tgt | tcc | tct | ctg | aaa | cta | ctg | cac | tac | ctc | ggg | ctg | att | gac | ttg | tcg | 443 |
|---|---|---|---|---|---|---|---|---|---|---|---|---|---|---|---|---|
| Cys | Ser | Ser | Leu | Lys | Leu | Leu | His | Tyr | Leu | Gly | Leu | Ile | Asp | Leu | Ser | |
| | 35 | | | | | 40 | | | | | 45 | | | | | |

| gat | gac | aag | atc | gag | gat | gat | ctg | gag | atg | acc | atg | gtt | tgc | cat | cgg | 491 |
|---|---|---|---|---|---|---|---|---|---|---|---|---|---|---|---|---|
| Asp | Asp | Lys | Ile | Glu | Asp | Asp | Leu | Glu | Met | Thr | Met | Val | Cys | His | Arg | |
| 50 | | | | | 55 | | | | | 60 | | | | | | |

| cct | gag | gga | ctg | gag | cag | ctt | gag | gca | cag | acg | aac | ttc | acc | aag | aga | 539 |
|---|---|---|---|---|---|---|---|---|---|---|---|---|---|---|---|---|
| Pro | Glu | Gly | Leu | Glu | Gln | Leu | Glu | Ala | Gln | Thr | Asn | Phe | Thr | Lys | Arg | |
| 65 | | | | | 70 | | | | | 75 | | | | | 80 | |

| gaa | ctg | caa | gtc | ctt | tac | cgg | gga | ttc | aaa | aac | gag | tgc | ccc | agt | ggt | 587 |
|---|---|---|---|---|---|---|---|---|---|---|---|---|---|---|---|---|
| Glu | Leu | Gln | Val | Leu | Tyr | Arg | Gly | Phe | Lys | Asn | Glu | Cys | Pro | Ser | Gly | |
| | | | | 85 | | | | | 90 | | | | | 95 | | |

| gtg | gtt | aac | gaa | gag | aca | ttc | aag | cag | atc | tac | gct | cag | ttt | ttc | cct | 635 |
|---|---|---|---|---|---|---|---|---|---|---|---|---|---|---|---|---|
| Val | Val | Asn | Glu | Glu | Thr | Phe | Lys | Gln | Ile | Tyr | Ala | Gln | Phe | Phe | Pro | |
| | | | 100 | | | | | 105 | | | | | 110 | | | |

| cat | gga | gat | gcc | agc | aca | tac | gca | cat | tac | ctc | ttc | aat | gcc | ttc | gac | 683 |
|---|---|---|---|---|---|---|---|---|---|---|---|---|---|---|---|---|
| His | Gly | Asp | Ala | Ser | Thr | Tyr | Ala | His | Tyr | Leu | Phe | Asn | Ala | Phe | Asp | |
| | 115 | | | | | 120 | | | | | 125 | | | | | |

| acc | acc | cag | aca | ggc | tct | gta | aag | ttc | gag | gac | ttt | gtg | act | gct | ctg | 731 |
|---|---|---|---|---|---|---|---|---|---|---|---|---|---|---|---|---|
| Thr | Thr | Gln | Thr | Gly | Ser | Val | Lys | Phe | Glu | Asp | Phe | Val | Thr | Ala | Leu | |
| 130 | | | | | 135 | | | | | 140 | | | | | | |

| tcg | att | tta | ctg | aga | gga | acg | gtc | cat | gaa | aaa | ctg | agg | tgg | acg | ttt | 779 |
|---|---|---|---|---|---|---|---|---|---|---|---|---|---|---|---|---|
| Ser | Ile | Leu | Leu | Arg | Gly | Thr | Val | His | Glu | Lys | Leu | Arg | Trp | Thr | Phe | |
| 145 | | | | | 150 | | | | | 155 | | | | | 160 | |

| aat | ttg | tac | gac | atc | aat | aaa | gac | ggc | tac | ata | aac | aaa | gag | gag | atg | 827 |
|---|---|---|---|---|---|---|---|---|---|---|---|---|---|---|---|---|
| Asn | Leu | Tyr | Asp | Ile | Asn | Lys | Asp | Gly | Tyr | Ile | Asn | Lys | Glu | Glu | Met | |
| | | | 165 | | | | | 170 | | | | | 175 | | | |

| atg | gac | ata | gtg | aaa | gcc | atc | tat | gac | atg | atg | ggg | aaa | tac | acc | tat | 875 |
|---|---|---|---|---|---|---|---|---|---|---|---|---|---|---|---|---|
| Met | Asp | Ile | Val | Lys | Ala | Ile | Tyr | Asp | Met | Met | Gly | Lys | Tyr | Thr | Tyr | |
| | | | 180 | | | | | 185 | | | | | 190 | | | |

| cct | gtg | ctc | aaa | gag | gac | act | ccc | agg | cag | cac | gtg | gac | gtc | ttc | ttc | 923 |
|---|---|---|---|---|---|---|---|---|---|---|---|---|---|---|---|---|
| Pro | Val | Leu | Lys | Glu | Asp | Thr | Pro | Arg | Gln | His | Val | Asp | Val | Phe | Phe | |
| | 195 | | | | | 200 | | | | | 205 | | | | | |

| cag | aaa | atg | gat | aaa | aat | aaa | gat | ggc | att | gta | acg | tta | gac | gaa | ttt | 971 |
|---|---|---|---|---|---|---|---|---|---|---|---|---|---|---|---|---|
| Gln | Lys | Met | Asp | Lys | Asn | Lys | Asp | Gly | Ile | Val | Thr | Leu | Asp | Glu | Phe | |
| 210 | | | | | 215 | | | | | 220 | | | | | | |

| ctc | gag | tcc | tgt | cag | gag | gat | gac | aac | atc | atg | agg | tct | cta | cag | ctg | 1019 |
|---|---|---|---|---|---|---|---|---|---|---|---|---|---|---|---|---|
| Leu | Glu | Ser | Cys | Gln | Glu | Asp | Asp | Asn | Ile | Met | Arg | Ser | Leu | Gln | Leu | |
| 225 | | | | | 230 | | | | | 235 | | | | | 240 | |

| ttc | caa | aat | gtc | atg | taactgagga cactggccat cctgctctca gagacactga | | | | | | | | | | | 1074 |
|---|---|---|---|---|---|---|---|---|---|---|---|---|---|---|---|---|
| Phe | Gln | Asn | Val | Met | | | | | | | | | | | | |
| | | | | 245 | | | | | | | | | | | | |

```
caaacacctc aatgccctga tctgcccttg ttccagtttt acacatcaac tctcgggaca    1134
```

-continued

```
gaaataccctt ttacactttg gaagaattct ctgctgaaga ctttctacaa aacctggcac   1194
cgagtggctc agtctctgat tgccaactct tcctccctcc tcctcttgag agggacgagc   1254
tgaaatccga agtttgtttt ggaagcatgc ccatctctcc atgctgctgc tgccctgtgg   1314
aaggcccctc tgcttgagct taaacagtag tgcacagttt tctgcgtata cagatcccca   1374
actcactgcc tctaagtcag gcagaccctg atcaatctga accaaatgtg caccatcctc   1434
cgatggcctc ccaagccaat gtgcctgctt ctcttcctct ggtgggaaga agaacgctc    1494 tacagagcac ttagagctta ccatgaaaat actgggagag gcagcaccta acacatgtag   1554
aataggactg aattattaag catggtggta tcagatgatg caaacagccc atgtcatttt   1614
tttttccaga ggtagggact aataattctc ccacactagc acctacgatc atagaacaag   1674
tcttttaaca catccaggag ggaaaccgct gcccagtggt ctatcccttc tctccatccc   1734
ctgctcaagc ccagcactgc atgtctctcc cggaaggtcc agaatgcctg tgaaatgctg   1794
taacttttat accctgttat aatcaataaa cagaactatt tcgtacaaaa aaaaaaaaa    1854 aa                                                                 1856
```

<210> SEQ ID NO 4
<211> LENGTH: 245
<212> TYPE: PRT
<213> ORGANISM: Rattus sp.

<400> SEQUENCE: 4

```
Met Pro Ala Arg Val Leu Leu Ala Tyr Pro Gly Thr Glu Met Leu Thr
 1               5                  10                  15

Gln Gly Glu Ser Glu Gly Leu Gln Thr Leu Gly Ile Val Val Leu
                20                  25                  30

Cys Ser Ser Leu Lys Leu Leu His Tyr Leu Gly Leu Ile Asp Leu Ser
                35                  40                  45

Asp Asp Lys Ile Glu Asp Leu Glu Met Thr Met Val Cys His Arg
 50                  55                  60

Pro Glu Gly Leu Glu Gln Leu Glu Ala Gln Thr Asn Phe Thr Lys Arg
 65                  70                  75                  80

Glu Leu Gln Val Leu Tyr Arg Gly Phe Lys Asn Glu Cys Pro Ser Gly
                85                  90                  95

Val Val Asn Glu Glu Thr Phe Lys Gln Ile Tyr Ala Gln Phe Phe Pro
            100                 105                 110

His Gly Asp Ala Ser Thr Tyr Ala His Tyr Leu Phe Asn Ala Phe Asp
            115                 120                 125

Thr Thr Gln Thr Gly Ser Val Lys Phe Glu Asp Phe Val Thr Ala Leu
        130                 135                 140

Ser Ile Leu Leu Arg Gly Thr Val His Glu Lys Leu Arg Trp Thr Phe
145                 150                 155                 160

Asn Leu Tyr Asp Ile Asn Lys Asp Gly Tyr Ile Asn Lys Glu Glu Met
                165                 170                 175

Met Asp Ile Val Lys Ala Ile Tyr Asp Met Met Gly Lys Tyr Thr Tyr
            180                 185                 190

Pro Val Leu Lys Glu Asp Thr Pro Arg Gln His Val Asp Val Phe Phe
            195                 200                 205

Gln Lys Met Asp Lys Asn Lys Asp Gly Ile Val Thr Leu Asp Glu Phe
        210                 215                 220

Leu Glu Ser Cys Gln Glu Asp Asp Asn Ile Met Arg Ser Leu Gln Leu
225                 230                 235                 240
```

Phe Gln Asn Val Met
                245

<210> SEQ ID NO 5
<211> LENGTH: 1907
<212> TYPE: DNA
<213> ORGANISM: Mus musculus
<220> FEATURE:
<221> NAME/KEY: CDS
<222> LOCATION: (477)..(1124)

<400> SEQUENCE: 5

| | | |
|---|---|---|
| cggccccctg agatccagcc cgagcgcggg gcggagcggc cgggtggcag caggggcggg | 60 | |
| cgggcggagc gcagctcccg caccgcacgc ggcgcgggct cggcagcctc ggccgtgcgg | 120 | |
| gcacgccggc cccgtgtcca acatcaggca ggctttgggg ctcggggctc gggcctcgga | 180 | |
| gaagccagtg gcccggctgg gtgcccgcac cgggggggcgc ctgtgaaggc tcccgcgagc | 240 | |
| ctctggccct gggagtcagt gcatgtgcct ggctgaagaa ggcagcagcc acgagctcca | 300 | |
| ggcgccccgg cccacgtttt tctgaatacc aagctgcagg cgagctgctc ggggcttttt | 360 | |
| tgctttctcg cttttcctct cctccaattc aaagtgggca atccacaccg atttctttc | 420 | |
| aggggaggga agagacaggg cctggggtcc aagacgcac acaagtcttc gctgcc atg | 479 |
| | | Met
                                                                   1 |

| | |
|---|---|
| ggg gcc gtc atg ggc act ttc tcc tcc ctg cag acc aaa caa agg cga | 527 |
| Gly Ala Val Met Gly Thr Phe Ser Ser Leu Gln Thr Lys Gln Arg Arg | |
|       5                  10                  15 | |

| | |
|---|---|
| ccc tct aaa gac aag att gag gat gag cta gag atg acc atg gtt tgc | 575 |
| Pro Ser Lys Asp Lys Ile Glu Asp Glu Leu Glu Met Thr Met Val Cys | |
|  20                  25                  30 | |

| | |
|---|---|
| cac cgg cct gag gga ctg gag cag ctt gag gca cag acg aac ttc acc | 623 |
| His Arg Pro Glu Gly Leu Glu Gln Leu Glu Ala Gln Thr Asn Phe Thr | |
| 35                  40                  45 | |

| | |
|---|---|
| aag aga gaa ctg caa gtc ttg tac cgg gga ttc aaa aac gag tgc cct | 671 |
| Lys Arg Glu Leu Gln Val Leu Tyr Arg Gly Phe Lys Asn Glu Cys Pro | |
| 50                  55                  60                  65 | |

| | |
|---|---|
| agc ggt gtg gtc aat gaa gaa aca ttc aag cag atc tac gct cag ttt | 719 |
| Ser Gly Val Val Asn Glu Glu Thr Phe Lys Gln Ile Tyr Ala Gln Phe | |
|              70                  75                  80 | |

| | |
|---|---|
| ttc cct cac gga gat gcc agc aca tat gca cat tac ctc ttc aat gcc | 767 |
| Phe Pro His Gly Asp Ala Ser Thr Tyr Ala His Tyr Leu Phe Asn Ala | |
|          85                  90                  95 | |

| | |
|---|---|
| ttc gac acc acc cag aca ggc tct gta aag ttc gag gac ttt gtg act | 815 |
| Phe Asp Thr Thr Gln Thr Gly Ser Val Lys Phe Glu Asp Phe Val Thr | |
|      100                 105                 110 | |

| | |
|---|---|
| gct ctg tcg att tta ctg aga ggg aca gtc cat gaa aaa cta agg tgg | 863 |
| Ala Leu Ser Ile Leu Leu Arg Gly Thr Val His Glu Lys Leu Arg Trp | |
| 115                 120                 125 | |

| | |
|---|---|
| acg ttt aat ttg tat gac atc aat aaa gac ggc tac ata aac aaa gag | 911 |
| Thr Phe Asn Leu Tyr Asp Ile Asn Lys Asp Gly Tyr Ile Asn Lys Glu | |
| 130                 135                 140                 145 | |

| | |
|---|---|
| gag atg atg gac ata gtc aaa gcc atc tat gac atg atg ggg aaa tac | 959 |
| Glu Met Met Asp Ile Val Lys Ala Ile Tyr Asp Met Met Gly Lys Tyr | |
|              150                 155                 160 | |

| | |
|---|---|
| acc tat cct gtg ctc aaa gag gac act ccc agg cag cat gtg gat gtc | 1007 |
| Thr Tyr Pro Val Leu Lys Glu Asp Thr Pro Arg Gln His Val Asp Val | |
|          165                 170                 175 | |

| | |
|---|---|
| ttc ttc cag aaa atg gat aaa aat aaa gat ggc att gta acg tta gat | 1055 |
| Phe Phe Gln Lys Met Asp Lys Asn Lys Asp Gly Ile Val Thr Leu Asp | |

-continued

```
                180                 185                 190
gaa ttt ctt gaa tca tgt cag gag gat gac aac atc atg aga tct cta       1103
Glu Phe Leu Glu Ser Cys Gln Glu Asp Asp Asn Ile Met Arg Ser Leu
195                 200                 205 cag ctg ttc caa aat gtc atg taactgagga cactggccat tctgctctca         1154
Gln Leu Phe Gln Asn Val Met
210                 215 gagacactga caaacacctt aatgccctga tctgcccttg ttccaatttt acacaccaac    1214
tcttgggaca gaaataccct ttacactttg gaagaattct ctgctgaaga ctttctacaa    1274
aacctggcac acgtggctc tgtctctgag ggacgagcgg agatccgact ttgttttgga    1334
agcatgccca tctcttcatg ctgctgccct gtggaaggcc cctctgcttg agcttaatca    1394
atagtgcaca gttttatgct tacacatatc cccaactcac tgcctccaag tcaggcagac    1454
tctgatgaat ctgagccaaa tgtgcaccat cctccgatgg cctcccaagc caatgtgcct    1514
gcttctcttc ctctggtggg aagaaagagt gttctacgga caattagag cttaccatga     1574
aaatattggg agaggcagca cctaacacat gtagaatagg actgaattat taagcatggt    1634
gatatcagat gatgcaaatt gcccatgtca tttttttcaa aggtagggac aaatgattct    1694
cccacactag cacctgtggt catagagcaa gtctcttaac atgcccagaa ggggaaccac    1754
tgtccagtgg tctatccctc ctctccatcc cctgctcaaa cccagcactg catgtccctc    1814
caagaaggtc cagaatgcct gcgaaacgct gtactttat accctgttct aatcaataaa     1874
cagaactatt tcgtaaaaaa aaaaaaaaaa aaa                                 1907
```

<210> SEQ ID NO 6
<211> LENGTH: 216
<212> TYPE: PRT
<213> ORGANISM: Mus musculus

<400> SEQUENCE: 6

```
Met Gly Ala Val Met Gly Thr Phe Ser Ser Leu Gln Thr Lys Gln Arg
  1               5                  10                  15

Arg Pro Ser Lys Asp Lys Ile Glu Asp Glu Leu Glu Met Thr Met Val
                 20                  25                  30

Cys His Arg Pro Glu Gly Leu Glu Gln Leu Glu Ala Gln Thr Asn Phe
             35                  40                  45

Thr Lys Arg Glu Leu Gln Val Leu Tyr Arg Gly Phe Lys Asn Glu Cys
         50                  55                  60

Pro Ser Gly Val Val Asn Glu Gly Thr Phe Lys Gln Ile Tyr Ala Gln
 65                  70                  75                  80

Phe Phe Pro His Gly Asp Ala Ser Thr Tyr Ala His Tyr Leu Phe Asn
                 85                  90                  95

Ala Phe Asp Thr Thr Gln Thr Gly Ser Val Lys Phe Glu Asp Phe Val
                100                 105                 110

Thr Ala Leu Ser Ile Leu Leu Arg Gly Thr Val His Glu Lys Leu Arg
            115                 120                 125

Trp Thr Phe Asn Leu Tyr Asp Ile Asn Lys Asp Gly Tyr Ile Asn Lys
        130                 135                 140

Glu Glu Met Met Asp Ile Val Lys Ala Ile Tyr Asp Met Met Gly Lys
145                 150                 155                 160

Tyr Thr Tyr Pro Val Leu Lys Glu Asp Thr Pro Arg Gln His Val Asp
                165                 170                 175

Val Phe Phe Gln Lys Met Asp Lys Asn Lys Asp Gly Ile Val Thr Leu
            180                 185                 190
```

```
Asp Glu Phe Leu Glu Ser Cys Gln Glu Asp Asp Asn Ile Met Arg Ser
        195                 200                 205

Leu Gln Leu Phe Gln Asn Val Met
    210                 215

<210> SEQ ID NO 7
<211> LENGTH: 1534
<212> TYPE: DNA
<213> ORGANISM: Rattus sp.
<220> FEATURE:
<221> NAME/KEY: CDS
<222> LOCATION: (31)..(711)

<400> SEQUENCE: 7
gtcccaagtc gcacacaagt cttcgctgcc atg ggg gcc gtc atg ggt acc ttc     54
                                 Met Gly Ala Val Met Gly Thr Phe
                                  1               5 tcg tcc ctg cag acc aaa caa agg cga ccc tct aaa gac atc gcc tgg    102
Ser Ser Leu Gln Thr Lys Gln Arg Arg Pro Ser Lys Asp Ile Ala Trp
     10                  15                  20 tgg tat tac cag tat cag aga gac aag atc gag gat gat ctg gag atg    150
Trp Tyr Tyr Gln Tyr Gln Arg Asp Lys Ile Glu Asp Asp Leu Glu Met
 25                  30                  35                  40 acc atg gtt tgc cat cgg cct gag gga ctg gag cag ctt gag gca cag    198
Thr Met Val Cys His Arg Pro Glu Gly Leu Glu Gln Leu Glu Ala Gln
                 45                  50                  55 acg aac ttc acc aag aga gaa ctg caa gtc ctt tac cgg gga ttc aaa    246
Thr Asn Phe Thr Lys Arg Glu Leu Gln Val Leu Tyr Arg Gly Phe Lys
             60                  65                  70 aac gag tgc ccc agt ggt gtg gtt aac gaa gag aca ttc aag cag atc    294
Asn Glu Cys Pro Ser Gly Val Val Asn Glu Glu Thr Phe Lys Gln Ile
         75                  80                  85 tac gct cag ttt ttc cct cat gga gat gcc agc aca tac gca cat tac    342
Tyr Ala Gln Phe Phe Pro His Gly Asp Ala Ser Thr Tyr Ala His Tyr
     90                  95                 100 ctc ttc aat gcc ttc gac acc acc cag aca ggc tct gta aag ttc gag    390
Leu Phe Asn Ala Phe Asp Thr Thr Gln Thr Gly Ser Val Lys Phe Glu
105                 110                 115                 120 gac ttt gtg act gct ctg tcg att tta ctg aga gga acg gtc cat gaa    438
Asp Phe Val Thr Ala Leu Ser Ile Leu Leu Arg Gly Thr Val His Glu
                125                 130                 135 aaa ctg agg tgg acg ttt aat ttg tac gac atc aat aaa gac ggc tac    486
Lys Leu Arg Trp Thr Phe Asn Leu Tyr Asp Ile Asn Lys Asp Gly Tyr
            140                 145                 150 ata aac aaa gag gag atg atg gac ata gtg aaa gcc atc tat gac atg    534
Ile Asn Lys Glu Glu Met Met Asp Ile Val Lys Ala Ile Tyr Asp Met
        155                 160                 165 atg ggg aaa tac acc tat cct gtg ctc aaa gag gac act ccc agg cag    582
Met Gly Lys Tyr Thr Tyr Pro Val Leu Lys Glu Asp Thr Pro Arg Gln
    170                 175                 180 cac gtg gac gtc ttc ttc cag aaa atg gat aaa aat aaa gat ggc att    630
His Val Asp Val Phe Phe Gln Lys Met Asp Lys Asn Lys Asp Gly Ile
185                 190                 195                 200 gta acg tta gac gaa ttt ctc gag tcc tgt cag gag gat gac aac atc    678
Val Thr Leu Asp Glu Phe Leu Glu Ser Cys Gln Glu Asp Asp Asn Ile
                205                 210                 215 atg agg tct cta cag ctg ttc caa aat gtc atg taactgagga cactggccat    731
Met Arg Ser Leu Gln Leu Phe Gln Asn Val Met
            220                 225 cctgctctca gagacactga caaacacctc aatgccctga tctgcccttg ttccagtttt    791
```

```
acacatcaac tctcgggaca gaaatacctt ttacactttg gaagaattct ctgctgaaga    851
ctttctacaa aacctggcac cgcgtggctc agtctctgat tgccaactct tcctccctcc    911
tcctcttgag agggacgagc tgaaatccga agtttgtttt ggaagcatgc ccatctctcc    971
atgctgctgc tgccctgtgg aaggcccctc tgcttgagct taaacagtag tgcacagttt   1031
tctgcgtata cagatcccca actcactgcc tctaagtcag gcagaccctg atcaatctga   1091
accaaatgtg caccatcctc cgatggcctc ccaagccaat gtgcctgctt ctcttcctct   1151
ggtgggaaga agaacgctc tacagagcac ttagagctta ccatgaaaat actgggagag    1211
gcagcaccta acacatgtag aataggactg aattattaag catggtggta tcagatgatg   1271
caaacagccc atgtcatttt ttttccagag gtagggacta ataattctcc cacactagca   1331
cctacgatca tagaacaagt cttttaacac atccaggagg gaaaccgctg cccagtggtc   1391
tatcccttct ctccatcccc tgctcaagcc cagcactgca tgtctctccc ggaaggtcca   1451
gaatgcctgt gaaatgctgt aacttttata ccctgttata atcaataaac agaactattt   1511
cgtacaaaaa aaaaaaaaaa aaa                                           1534
```

<210> SEQ ID NO 8
<211> LENGTH: 227
<212> TYPE: PRT
<213> ORGANISM: Rattus sp.

<400> SEQUENCE: 8

```
Met Gly Ala Val Met Gly Thr Phe Ser Ser Leu Gln Thr Lys Gln Arg
 1               5                  10                  15

Arg Pro Ser Lys Asp Ile Ala Trp Trp Tyr Gln Tyr Gln Arg Asp
            20                  25                  30

Lys Ile Glu Asp Asp Leu Glu Met Thr Met Val Cys His Arg Pro Glu
        35                  40                  45

Gly Leu Glu Gln Leu Glu Ala Gln Thr Asn Phe Thr Lys Arg Glu Leu
    50                  55                  60

Gln Val Leu Tyr Arg Gly Phe Lys Asn Glu Cys Pro Ser Gly Val Val
65                  70                  75                  80

Asn Glu Glu Thr Phe Lys Gln Ile Tyr Ala Gln Phe Phe Pro His Gly
                85                  90                  95

Asp Ala Ser Thr Tyr Ala His Tyr Leu Phe Asn Ala Phe Asp Thr Thr
            100                 105                 110

Gln Thr Gly Ser Val Lys Phe Glu Asp Phe Val Thr Ala Leu Ser Ile
        115                 120                 125

Leu Leu Arg Gly Thr Val His Glu Lys Leu Arg Trp Thr Phe Asn Leu
    130                 135                 140

Tyr Asp Ile Asn Lys Asp Gly Tyr Ile Asn Lys Glu Glu Met Met Asp
145                 150                 155                 160

Ile Val Lys Ala Ile Tyr Asp Met Met Gly Lys Tyr Thr Tyr Pro Val
                165                 170                 175

Leu Lys Glu Asp Thr Pro Arg Gln His Val Asp Val Phe Phe Gln Lys
            180                 185                 190

Met Asp Lys Asn Lys Asp Gly Ile Val Thr Leu Asp Glu Phe Leu Glu
        195                 200                 205

Ser Cys Gln Glu Asp Asp Asn Ile Met Arg Ser Leu Gln Leu Phe Gln
    210                 215                 220

Asn Val Met
225
```

-continued

```
<210> SEQ ID NO 9
<211> LENGTH: 1540
<212> TYPE: DNA
<213> ORGANISM: Mus musculus
<220> FEATURE:
<221> NAME/KEY: CDS
<222> LOCATION: (77)..(757)

<400> SEQUENCE: 9
atccacaccg atttctttc aggggaggga agagacaggg cctggggtcc caagacgcac      60
acaagtcttc gctgcc atg ggg gcc gtc atg ggc act ttc tcc tcc ctg cag   112
               Met Gly Ala Val Met Gly Thr Phe Ser Ser Leu Gln
                 1               5                  10 acc aaa caa agg cga ccc tct aaa gac atc gcc tgg tgg tat tac cag      160
Thr Lys Gln Arg Arg Pro Ser Lys Asp Ile Ala Trp Trp Tyr Tyr Gln
         15                  20                  25 tat cag aga gac aag att gag gat gag cta gag atg acc atg gtt tgc     208
Tyr Gln Arg Asp Lys Ile Glu Asp Glu Leu Glu Met Thr Met Val Cys
 30                  35                  40 cac cgg cct gag gga ctg gag cag ctt gag gca cag acg aac ttc acc     256
His Arg Pro Glu Gly Leu Glu Gln Leu Glu Ala Gln Thr Asn Phe Thr
 45                  50                  55                  60 aag aga gaa ctg caa gtc ttg tac cgg gga ttc aaa aac gag tgc cct     304
Lys Arg Glu Leu Gln Val Leu Tyr Arg Gly Phe Lys Asn Glu Cys Pro
             65                  70                  75 agc ggt gtg gtc aat gaa gaa aca ttc aag cag atc tac gct cag ttt     352
Ser Gly Val Val Asn Glu Glu Thr Phe Lys Gln Ile Tyr Ala Gln Phe
         80                  85                  90 ttc cct cac gga gat gcc agc aca tat gca cat tac ctc ttc aat gcc     400
Phe Pro His Gly Asp Ala Ser Thr Tyr Ala His Tyr Leu Phe Asn Ala
     95                  100                 105 ttc gac acc acc cag aca ggc tct gta aag ttc gag gac ttt gtg act     448
Phe Asp Thr Thr Gln Thr Gly Ser Val Lys Phe Glu Asp Phe Val Thr
110                 115                 120 gct ctg tcg att tta ctg aga ggg aca gtc cat gaa aaa cta agg tgg     496
Ala Leu Ser Ile Leu Leu Arg Gly Thr Val His Glu Lys Leu Arg Trp
125                 130                 135                 140 acg ttt aat ttg tat gac atc aat aaa gac ggc tac ata aac aaa gag     544
Thr Phe Asn Leu Tyr Asp Ile Asn Lys Asp Gly Tyr Ile Asn Lys Glu
                145                 150                 155 gag atg atg gac ata gtc aaa gcc atc tat gac atg atg ggg aaa tac     592
Glu Met Met Asp Ile Val Lys Ala Ile Tyr Asp Met Met Gly Lys Tyr
            160                 165                 170 acc tat cct gtg ctc aaa gag gac act ccc agg cag cat gtg gat gtc     640
Thr Tyr Pro Val Leu Lys Glu Asp Thr Pro Arg Gln His Val Asp Val
        175                 180                 185 ttc ttc cag aaa atg gat aaa aat aaa gat ggc att gta acg tta gat     688
Phe Phe Gln Lys Met Asp Lys Asn Lys Asp Gly Ile Val Thr Leu Asp
    190                 195                 200 gaa ttt ctt gaa tca tgt cag gag gat gac aac atc atg aga tct cta     736
Glu Phe Leu Glu Ser Cys Gln Glu Asp Asp Asn Ile Met Arg Ser Leu
205                 210                 215                 220 cag ctg ttc caa aat gtc atg taactgagga cactggccat tctgctctca        787
Gln Leu Phe Gln Asn Val Met
                225 gagacactga caaacacctt aatgccctga tctgcccttg ttccaatttt acacaccaac    847 tcttgggaca gaaataccct ttacactttg gaagaattct ctgctgaaga ctttctacaa    907 aacctggcac cacgtggctc tgtctctgag ggacgagcgg agatccgact ttgttttgga    967
```

-continued

```
agcatgccca tctcttcatg ctgctgccct gtggaaggcc cctctgcttg agcttaatca    1027
atagtgcaca gttttatgct tacacatatc cccaactcac tgcctccaag tcaggcagac    1087
tctgatgaat ctgagccaaa tgtgcaccat cctccgatgg cctcccaagc caatgtgcct    1147
gcttctcttc ctctggtggg aagaaagagt gttctacgga acaattagag cttaccatga    1207
aaatattggg agaggcagca cctaacacat gtagaatagg actgaattat taagcatggt    1267
gatatcagat gatgcaaatt gcccatgtca ttttttcaa aggtagggac aaatgattct     1327
cccacactag cacctgtggt catagagcaa gtctcttaac atgcccagaa ggggaaccac    1387
tgtccagtgg tctatccctc ctctccatcc cctgctcaaa cccagcactg catgtccctc    1447
caagaaggtc cagaatgcct gcgaaacgct gtacttttat accctgttct aatcaataaa    1507
cagaactatt tcgtacaaaa aaaaaaaaaa aaa                                 1540
```

<210> SEQ ID NO 10
<211> LENGTH: 227
<212> TYPE: PRT
<213> ORGANISM: Mus musculus

<400> SEQUENCE: 10

```
Met Gly Ala Val Met Gly Thr Phe Ser Ser Leu Gln Thr Lys Gln Arg
  1               5                  10                  15

Arg Pro Ser Lys Asp Ile Ala Trp Trp Tyr Gln Tyr Gln Arg Asp
             20                  25                  30

Lys Ile Glu Asp Glu Leu Glu Met Thr Met Val Cys His Arg Pro Glu
         35                  40                  45

Gly Leu Glu Gln Leu Glu Ala Gln Thr Asn Phe Thr Lys Arg Glu Leu
     50                  55                  60

Gln Val Leu Tyr Arg Gly Phe Lys Asn Glu Cys Pro Ser Gly Val Val
 65                  70                  75                  80

Asn Glu Glu Thr Phe Lys Gln Ile Tyr Ala Gln Phe Phe Pro His Gly
                 85                  90                  95

Asp Ala Ser Thr Tyr Ala His Tyr Leu Phe Asn Ala Phe Asp Thr Thr
            100                 105                 110

Gln Thr Gly Ser Val Lys Phe Glu Asp Phe Val Thr Ala Leu Ser Ile
        115                 120                 125

Leu Leu Arg Gly Thr Val His Glu Lys Leu Arg Trp Thr Phe Asn Leu
130                 135                 140

Tyr Asp Ile Asn Lys Asp Gly Tyr Ile Asn Lys Glu Glu Met Met Asp
145                 150                 155                 160

Ile Val Lys Ala Ile Tyr Asp Met Met Gly Lys Tyr Thr Tyr Pro Val
                165                 170                 175

Leu Lys Glu Asp Thr Pro Arg Gln His Val Asp Val Phe Phe Gln Lys
            180                 185                 190

Met Asp Lys Asn Lys Asp Gly Ile Val Thr Leu Asp Glu Phe Leu Glu
        195                 200                 205

Ser Cys Gln Glu Asp Asp Asn Ile Met Arg Ser Leu Gln Leu Phe Gln
    210                 215                 220

Asn Val Met
225
```

<210> SEQ ID NO 11
<211> LENGTH: 955
<212> TYPE: DNA
<213> ORGANISM: Rattus sp.

```
<220> FEATURE:
<221> NAME/KEY: CDS
<222> LOCATION: (345)..(953)
<220> FEATURE:
<223> OTHER INFORMATION: Xaa at position 92 of the corresponding amino
      acid sequence may be any amino acid

<400> SEQUENCE: 11
gtccgggcac acaacccctg gattcttcgg agaatatgcc gtgacggtgt tgccaattat      60
tagttctctt ggctagcaga tgtttaggga ctggttaagc ctttggagaa attaccttag     120
gaaaacgggg aaataaaagc aaagattacc atgaattgca agattaccta gcaattgcaa     180
ggtaggagga gagaggtgga gggcggagta gacaggaggg agggagaaag tgagaggaag     240
ctaggctggt ggaaataacc ctgcacttgg aacagcggca aagaagcgcg attttccagc     300
tttaaatgcc tgcccgcgtt ctgcttgcct acccgggaac ggag atg ttg acc cag     356
                                                    Met Leu Thr Gln
                                                      1 ggc gag tct gaa ggg ctc cag acc ttg gga ata gta gtg gtc ctg tgt      404
Gly Glu Ser Glu Gly Leu Gln Thr Leu Gly Ile Val Val Val Leu Cys
 5                  10                  15                  20 tcc tct ctg aaa cta ctg cac tac ctc ggg ctg att gac ttg tcg gat      452
Ser Ser Leu Lys Leu Leu His Tyr Leu Gly Leu Ile Asp Leu Ser Asp
             25                  30                  35 gac aag atc gag gat gat ctg gag atg acc atg gtt tgc cat cgg cct      500
Asp Lys Ile Glu Asp Asp Leu Glu Met Thr Met Val Cys His Arg Pro
         40                  45                  50 gag gga ctg gag cag ctt gag gca cag acg aac ttc acc aag aga gaa      548
Glu Gly Leu Glu Gln Leu Glu Ala Gln Thr Asn Phe Thr Lys Arg Glu
     55                  60                  65 ctg caa gtc ctt tac cgg gga ttc aaa aac gag tgc ccc agt ggt gtg      596
Leu Gln Val Leu Tyr Arg Gly Phe Lys Asn Glu Cys Pro Ser Gly Val
 70                  75                  80 gtt aac gaa gag aca ttc aag cng atc tac gct cag ttt ttc cct cat      644
Val Asn Glu Glu Thr Phe Lys Xaa Ile Tyr Ala Gln Phe Phe Pro His
 85                  90                  95                 100 gga gat gcc agc aca tac gca cat tac ctc ttc aat gcc ttc gac acc      692
Gly Asp Ala Ser Thr Tyr Ala His Tyr Leu Phe Asn Ala Phe Asp Thr
            105                 110                 115 acc cag aca ggc tct gta aag ttc gag gac ttt gtg act gct ctg tcg      740
Thr Gln Thr Gly Ser Val Lys Phe Glu Asp Phe Val Thr Ala Leu Ser
        120                 125                 130 att tta ctg aga gga acg gtc cat gaa aaa ctg aag tgg acg ttt aat      788
Ile Leu Leu Arg Gly Thr Val His Glu Lys Leu Lys Trp Thr Phe Asn
    135                 140                 145 ttg tac gac atc aat aaa gac ggc tac ata aac aaa gag gag atg atg      836
Leu Tyr Asp Ile Asn Lys Asp Gly Tyr Ile Asn Lys Glu Glu Met Met
150                 155                 160 gac ata gtg aaa gcc atc tat gac atg atg ggg aaa tac acc tat ctt      884
Asp Ile Val Lys Ala Ile Tyr Asp Met Met Gly Lys Tyr Thr Tyr Leu
165                 170                 175                 180 gtg ctc aaa gag gac act tcc agg cag cac gtg gac gtc ttc ttc cag      932
Val Leu Lys Glu Asp Thr Ser Arg Gln His Val Asp Val Phe Phe Gln
                185                 190                 195 aaa atg gat aaa aat aaa gat gg                                        955
Lys Met Asp Lys Asn Lys Asp
            200

<210> SEQ ID NO 12
<211> LENGTH: 203
<212> TYPE: PRT
```

<213> ORGANISM: Rattus sp.

<400> SEQUENCE: 12

```
Met Leu Thr Gln Gly Glu Ser Glu Gly Leu Gln Thr Leu Gly Ile Val
 1               5                  10                  15

Val Val Leu Cys Ser Ser Leu Lys Leu Leu His Tyr Leu Gly Leu Ile
                20                  25                  30

Asp Leu Ser Asp Asp Lys Ile Glu Asp Leu Glu Met Thr Met Val
            35                  40                  45

Cys His Arg Pro Glu Gly Leu Glu Gln Leu Glu Ala Gln Thr Asn Phe
        50                  55                  60

Thr Lys Arg Glu Leu Gln Val Leu Tyr Arg Gly Phe Lys Asn Glu Cys
65                  70                  75                  80

Pro Ser Gly Val Val Asn Glu Glu Thr Phe Lys Xaa Ile Tyr Ala Gln
                85                  90                  95

Phe Phe Pro His Gly Asp Ala Ser Thr Tyr Ala His Tyr Leu Phe Asn
            100                 105                 110

Ala Phe Asp Thr Thr Gln Thr Gly Ser Val Lys Phe Glu Asp Phe Val
        115                 120                 125

Thr Ala Leu Ser Ile Leu Leu Arg Gly Thr Val His Glu Lys Leu Lys
130                 135                 140

Trp Thr Phe Asn Leu Tyr Asp Ile Asn Lys Asp Gly Tyr Ile Asn Lys
145                 150                 155                 160

Glu Glu Met Met Asp Ile Val Lys Ala Ile Tyr Asp Met Met Gly Lys
                165                 170                 175

Tyr Thr Tyr Leu Val Leu Lys Glu Asp Thr Ser Arg Gln His Val Asp
            180                 185                 190

Val Phe Phe Gln Lys Met Asp Lys Asn Lys Asp
        195                 200
```

<210> SEQ ID NO 13
<211> LENGTH: 2009
<212> TYPE: DNA
<213> ORGANISM: Homo sapiens
<220> FEATURE:
<221> NAME/KEY: CDS
<222> LOCATION: (207)..(1016)

<400> SEQUENCE: 13

```
ctcacctgct gcctagtgtt ccctctcctg ctccaggacc tccgggtaga cctcagaccc      60
cgggcccatt cccagactca gcctcagccc ggacttcccc agccccgaca gcacagtagg     120
ccgccagggg gcgccgtgtg agcgccctat cccggccacc cggcgccccc tcccacggcc     180
cgggcgggag cggggcgccg ggggcc atg cgg ggc cag ggc cgc aag gag agt     233
               Met Arg Gly Gln Gly Arg Lys Glu Ser
                 1               5 ttg tcc gat tcc cga gac ctg gac ggc tcc tac gac cag ctc acg ggc     281
Leu Ser Asp Ser Arg Asp Leu Asp Gly Ser Tyr Asp Gln Leu Thr Gly
 10                  15                  20                  25 cac cct cca ggg ccc act aaa aaa gcg ctg aag cag cga ttc ctc aag     329
His Pro Pro Gly Pro Thr Lys Lys Ala Leu Lys Gln Arg Phe Leu Lys
                30                  35                  40 ctg ctg ccg tgc tgc ggg ccc caa gcc ctg ccc tca gtc agt gaa aca     377
Leu Leu Pro Cys Cys Gly Pro Gln Ala Leu Pro Ser Val Ser Glu Thr
            45                  50                  55 tta gcc gcc cca gcc tcc ctc cgc ccc cac aga ccc cgc ctg ctg gac     425
Leu Ala Ala Pro Ala Ser Leu Arg Pro His Arg Pro Arg Leu Leu Asp
        60                  65                  70
```

```
cca gac agc gtg gac gat gaa ttt gaa ttg tcc acc gtg tgt cac cgg    473
Pro Asp Ser Val Asp Asp Glu Phe Glu Leu Ser Thr Val Cys His Arg
 75                  80                  85 cct gag ggt ctg gag cag ctg cag gag caa acc aaa ttc acg cgc aag    521
Pro Glu Gly Leu Glu Gln Leu Gln Glu Gln Thr Lys Phe Thr Arg Lys
 90                  95                 100                 105 gag ttg cag gtc ctg tac cgg ggc ttc aag aac gaa tgt ccc agc gga    569
Glu Leu Gln Val Leu Tyr Arg Gly Phe Lys Asn Glu Cys Pro Ser Gly
                110                 115                 120 att gtc aat gag gag aac ttc aag cag att tac tcc cag ttc ttt cct    617
Ile Val Asn Glu Glu Asn Phe Lys Gln Ile Tyr Ser Gln Phe Phe Pro
            125                 130                 135 caa gga gac tcc agc acc tat gcc act ttt ctc ttc aat gcc ttt gac    665
Gln Gly Asp Ser Ser Thr Tyr Ala Thr Phe Leu Phe Asn Ala Phe Asp
        140                 145                 150 acc aac cat gat ggc tcg gtc agt ttt gag gac ttt gtg gct ggt ttg    713
Thr Asn His Asp Gly Ser Val Ser Phe Glu Asp Phe Val Ala Gly Leu
    155                 160                 165 tcc gtg att ctt cgg gga act gta gat gac agg ctt aat tgg gcc ttc    761
Ser Val Ile Leu Arg Gly Thr Val Asp Asp Arg Leu Asn Trp Ala Phe
170                 175                 180                 185 aac ctg tat gac ctt aac aag gac ggc tgc atc acc aag gag gaa atg    809
Asn Leu Tyr Asp Leu Asn Lys Asp Gly Cys Ile Thr Lys Glu Glu Met
                190                 195                 200 ctt gac atc atg aag tcc atc tat gac atg atg ggc aag tac acg tac    857
Leu Asp Ile Met Lys Ser Ile Tyr Asp Met Met Gly Lys Tyr Thr Tyr
            205                 210                 215 cct gca ctc cgg gag gag gcc cca agg gaa cac gtg gag agc ttc ttc    905
Pro Ala Leu Arg Glu Glu Ala Pro Arg Glu His Val Glu Ser Phe Phe
        220                 225                 230 cag aag atg gac aga aac aag gat ggt gtg gtg acc att gag gaa ttc    953
Gln Lys Met Asp Arg Asn Lys Asp Gly Val Val Thr Ile Glu Glu Phe
    235                 240                 245 att gag tct tgt caa aag gat gag aac atc atg agg tcc atg cag ctc   1001
Ile Glu Ser Cys Gln Lys Asp Glu Asn Ile Met Arg Ser Met Gln Leu
250                 255                 260                 265 ttt gac aat gtc atc tagccccag gagagggggt cagtgtttcc tgggggacc     1056
Phe Asp Asn Val Ile
                270 atgctctaac cctagtccag gcggacctca cccttctctt cccaggtcta tcctcatcct   1116 acgcctccct gggggctgga gggatccaag agcttgggga ttcagtagtc cagatctctg   1176 gagctgaagg ggccagagag tgggcagagt gcatctcggg gggtgttccc aactcccacc   1236 agctctcacc cccttcctgc ctgacaccca gtgttgagag tgcccctcct gtaggaattg   1296 agcggttccc cacctcctac cctactctag aaacacacta gagcgatgtc tcctgctatg   1356 gtgcttcccc catccctgac ctcataaaca tttcccctaa gactcccctc tcagagagaa   1416 tgctccattc ttggcactgg ctggcttctc agaccagcca ttgagagccc tgtgggaggg   1476 ggacaagaat gtatagggag aaatcttggg cctgagtcaa tggataggtc ctaggaggtg   1536 ggtggggttg agaatagaag ggcctggaca gattatgatt gctcaggcat accaggttat   1596 agctccaagt tccacaggtc tgctaccaca ggccatcaaa atataagttt ccaggctttg   1656 cagaagacct tgtctcctta gaaatgcccc agaaattttc cacaccctcc tcggtatcca   1716 tggagagcct ggggccagat atctggctca tctctggcat tgcttcctct ccttccttcc   1776 tgcatgtgtt ggtggtggtt gtggtggggg aatgtggatg gggatgtcc tggctgatgc    1836
```

```
ctgccaaaat tcatcccac cctccttgct tatcgtccct gttttgaggg ctatgacttg    1896 agttttgtt tcccatgttc tctatagact tgggaccttc ctgaacttgg ggcctatcac    1956
tccccacagt ggatgcctta gaagggagag ggaaggaggg aggcaggcat agc           2009
```

```
<210> SEQ ID NO 14
<211> LENGTH: 270
<212> TYPE: PRT
<213> ORGANISM: Homo sapiens

<400> SEQUENCE: 14
```

Met Arg Gly Gln Gly Arg Lys Glu Ser Leu Ser Asp Ser Arg Asp Leu
 1               5                  10                  15

Asp Gly Ser Tyr Asp Gln Leu Thr Gly His Pro Pro Gly Pro Thr Lys
            20                  25                  30

Lys Ala Leu Lys Gln Arg Phe Leu Lys Leu Leu Pro Cys Cys Gly Pro
        35                  40                  45

Gln Ala Leu Pro Ser Val Ser Glu Thr Leu Ala Ala Pro Ala Ser Leu
    50                  55                  60

Arg Pro His Arg Pro Arg Leu Leu Asp Pro Asp Ser Val Asp Asp Glu
65                  70                  75                  80

Phe Glu Leu Ser Thr Val Cys His Arg Pro Glu Gly Leu Glu Gln Leu
                85                  90                  95

Gln Glu Gln Thr Lys Phe Thr Arg Lys Glu Leu Gln Val Leu Tyr Arg
            100                 105                 110

Gly Phe Lys Asn Glu Cys Pro Ser Gly Ile Val Asn Glu Glu Asn Phe
        115                 120                 125

Lys Gln Ile Tyr Ser Gln Phe Phe Pro Gln Gly Asp Ser Ser Thr Tyr
    130                 135                 140

Ala Thr Phe Leu Phe Asn Ala Phe Asp Thr Asn His Asp Gly Ser Val
145                 150                 155                 160

Ser Phe Glu Asp Phe Val Ala Gly Leu Ser Val Ile Leu Arg Gly Thr
                165                 170                 175

Val Asp Asp Arg Leu Asn Trp Ala Phe Asn Leu Tyr Asp Leu Asn Lys
            180                 185                 190

Asp Gly Cys Ile Thr Lys Glu Glu Met Leu Asp Ile Met Lys Ser Ile
        195                 200                 205

Tyr Asp Met Met Gly Lys Tyr Thr Tyr Pro Ala Leu Arg Glu Glu Ala
    210                 215                 220

Pro Arg Glu His Val Glu Ser Phe Phe Gln Lys Met Asp Arg Asn Lys
225                 230                 235                 240

Asp Gly Val Val Thr Ile Glu Glu Phe Ile Glu Ser Cys Gln Lys Asp
                245                 250                 255

Glu Asn Ile Met Arg Ser Met Gln Leu Phe Asp Asn Val Ile
            260                 265                 270

```
<210> SEQ ID NO 15
<211> LENGTH: 1247
<212> TYPE: DNA
<213> ORGANISM: Rattus sp.
<220> FEATURE:
<221> NAME/KEY: CDS
<222> LOCATION: (2)..(772)

<400> SEQUENCE: 15
``` c cga gat ctg gac ggc tcc tat gac cag ctt acg ggc cac cct cca ggg    49
  Arg Asp Leu Asp Gly Ser Tyr Asp Gln Leu Thr Gly His Pro Pro Gly
   1               5                  10                  15

| | |
|---|---|
| ccc agt aaa aaa gcc ctg aag cag cgt ttc ctc aag ctg ctg ccg tgc<br>Pro Ser Lys Lys Ala Leu Lys Gln Arg Phe Leu Lys Leu Leu Pro Cys<br>20 25 30 | 97 |
| tgc ggg ccc caa gcc ctg ccc tca gtc agt gaa aca tta gct gcc cca<br>Cys Gly Pro Gln Ala Leu Pro Ser Val Ser Glu Thr Leu Ala Ala Pro<br>35 40 45 | 145 |
| gcc tcc ctc cgc ccc cac aga ccc cgc ccg ctg gac cca gac agc gta<br>Ala Ser Leu Arg Pro His Arg Pro Arg Pro Leu Asp Pro Asp Ser Val<br>50 55 60 | 193 |
| gag gat gag ttt gaa tta tcc acg gtg tgt cac cga cct gag ggc ctg<br>Glu Asp Glu Phe Glu Leu Ser Thr Val Cys His Arg Pro Glu Gly Leu<br>65 70 75 80 | 241 |
| gaa caa ctc cag gaa cag acc aag ttc aca cgc aga gag ctg cag gtc<br>Glu Gln Leu Gln Glu Gln Thr Lys Phe Thr Arg Arg Glu Leu Gln Val<br>85 90 95 | 289 |
| ctg tac cga ggc ttc aag aac gaa tgc ccc agt ggg att gtc aac gag<br>Leu Tyr Arg Gly Phe Lys Asn Glu Cys Pro Ser Gly Ile Val Asn Glu<br>100 105 110 | 337 |
| gag aac ttc aag cag att tat tct cag ttc ttt ccc caa gga gac tcc<br>Glu Asn Phe Lys Gln Ile Tyr Ser Gln Phe Phe Pro Gln Gly Asp Ser<br>115 120 125 | 385 |
| agc aac tat gct act ttt ctc ttc aat gcc ttt gac acc aac cac gat<br>Ser Asn Tyr Ala Thr Phe Leu Phe Asn Ala Phe Asp Thr Asn His Asp<br>130 135 140 | 433 |
| ggc tct gtc agt ttt gag gac ttt gtg gct ggt ttg tcg gtg att ctt<br>Gly Ser Val Ser Phe Glu Asp Phe Val Ala Gly Leu Ser Val Ile Leu<br>145 150 155 160 | 481 |
| cgg ggg acc ata gat gat aga ctg agc tgg gct ttc aac tta tat gac<br>Arg Gly Thr Ile Asp Asp Arg Leu Ser Trp Ala Phe Asn Leu Tyr Asp<br>165 170 175 | 529 |
| ctc aac aag gac ggc tgt atc aca aag gag gaa atg ctt gac att atg<br>Leu Asn Lys Asp Gly Cys Ile Thr Lys Glu Glu Met Leu Asp Ile Met<br>180 185 190 | 577 |
| aag tcc atc tat gac atg atg ggc aag tac aca tac cct gcc ctc cgg<br>Lys Ser Ile Tyr Asp Met Met Gly Lys Tyr Thr Tyr Pro Ala Leu Arg<br>195 200 205 | 625 |
| gag gag gcc cca aga gaa cac gtg gag agc ttc ttc cag aag atg gac<br>Glu Glu Ala Pro Arg Glu His Val Glu Ser Phe Phe Gln Lys Met Asp<br>210 215 220 | 673 |
| agg aac aag gac ggc gtg gtg acc atc gag gaa ttc atc gag tct tgt<br>Arg Asn Lys Asp Gly Val Val Thr Ile Glu Glu Phe Ile Glu Ser Cys<br>225 230 235 240 | 721 |
| caa cag gac gag aac atc atg agg tcc atg cag ctc ttt gat aat gtc<br>Gln Gln Asp Glu Asn Ile Met Arg Ser Met Gln Leu Phe Asp Asn Val<br>245 250 255 | 769 |
| atc tagctcccca gggagagggg ttagtgtgtc ctagggtgac caggctgtag<br>Ile | 822 |
| tcctagtcca gacgaaccta accctctctc tccaggcctg tcctcatctt acctgtaccc | 882 |
| tggggctgt agggattcaa tatcctgggg cttcagtagt ccagatccct gagctaagtc | 942 |
| acaaagtag gcaagagtag gcaagctaaa tctgggggct tcccaacccc cgacagctct | 1002 |
| caccccttct caactgatac ctagtgctga ggacacccct ggtgtaggga ccaagtggtt | 1062 |
| ctccaccttc tagtcccact ctagaaacca cattagacag aaggtctcct gctatggtgc | 1122 |
| tttccccatc cctaatctct tagattttcc tcaagactcc cttctcagag aacacgctct | 1182 |
| gtccatgtcc ccagctgggg acatggacag agcgtgttct ctagttctag atcgcgagcg | 1242 |
| gccgc | 1247 |

<210> SEQ ID NO 16
<211> LENGTH: 257
<212> TYPE: PRT
<213> ORGANISM: Rattus sp.

<400> SEQUENCE: 16

```
Arg Asp Leu Asp Gly Ser Tyr Asp Gln Leu Thr Gly His Pro Pro Gly
  1               5                  10                  15

Pro Ser Lys Lys Ala Leu Lys Gln Arg Phe Leu Lys Leu Leu Pro Cys
             20                  25                  30

Cys Gly Pro Gln Ala Leu Pro Ser Val Ser Glu Thr Leu Ala Ala Pro
         35                  40                  45

Ala Ser Leu Arg Pro His Arg Pro Arg Pro Leu Asp Pro Asp Ser Val
     50                  55                  60

Glu Asp Glu Phe Glu Leu Ser Thr Val Cys His Arg Pro Gly Gly Leu
 65                  70                  75                  80

Glu Gln Leu Gln Glu Gln Thr Lys Phe Thr Arg Arg Glu Leu Gln Val
                 85                  90                  95

Leu Tyr Arg Gly Phe Lys Asn Glu Cys Pro Ser Gly Ile Val Asn Glu
            100                 105                 110

Glu Asn Phe Lys Gln Ile Tyr Ser Gln Phe Phe Pro Gln Gly Asp Ser
        115                 120                 125

Ser Asn Tyr Ala Thr Phe Leu Phe Asn Ala Phe Asp Thr Asn His Asp
    130                 135                 140

Gly Ser Val Ser Phe Glu Asp Phe Val Ala Gly Leu Ser Val Ile Leu
145                 150                 155                 160

Arg Gly Thr Ile Asp Asp Arg Leu Ser Trp Ala Phe Asn Leu Tyr Asp
                165                 170                 175

Leu Asn Lys Asp Gly Cys Ile Thr Lys Glu Glu Met Leu Asp Ile Met
            180                 185                 190

Lys Ser Ile Tyr Asp Met Met Gly Lys Tyr Thr Tyr Pro Ala Leu Arg
        195                 200                 205

Glu Glu Ala Pro Arg Glu His Val Glu Ser Phe Gln Lys Met Asp
    210                 215                 220

Arg Asn Lys Asp Gly Val Val Thr Ile Glu Glu Phe Ile Glu Ser Cys
225                 230                 235                 240

Gln Gln Asp Glu Asn Ile Met Arg Ser Met Gln Leu Phe Asp Asn Val
                245                 250                 255

Ile
```

<210> SEQ ID NO 17
<211> LENGTH: 2343
<212> TYPE: DNA
<213> ORGANISM: Mus musculus
<220> FEATURE:
<221> NAME/KEY: CDS
<222> LOCATION: (181)..(990)

<400> SEQUENCE: 17

```
cgggactctg aggtgggccc taaaatccag cgctccccag agaaaagcct tgccagcccc    60 tactccggc ccccagcccc agcaggtcgc tgcgccgcca gggggcactg tgtgagcgcc    120
ctatcctggc cacccggcgc ccctcccac ggcccaggcg ggagcggggc gccgggggcc    180 atg cgg ggc caa ggc cga aag gag agt ttg tcc gaa tcc cga gat ttg    228
Met Arg Gly Gln Gly Arg Lys Glu Ser Leu Ser Glu Ser Arg Asp Leu
  1               5                  10                  15
```

-continued

| | |
|---|---|
| gac ggc tcc tat gac cag ctt acg ggc cac cct cca ggg ccc agt aaa<br>Asp Gly Ser Tyr Asp Gln Leu Thr Gly His Pro Pro Gly Pro Ser Lys<br>20 25 30 | 276 |
| aaa gcc ctg aag cag cgt ttc ctc aag ctg ctg ccg tgc tgc ggg ccc<br>Lys Ala Leu Lys Gln Arg Phe Leu Lys Leu Leu Pro Cys Cys Gly Pro<br>35 40 45 | 324 |
| caa gcc ctg ccc tca gtc agt gaa aca tta gct gcc cca gcc tcc ctc<br>Gln Ala Leu Pro Ser Val Ser Glu Thr Leu Ala Ala Pro Ala Ser Leu<br>50 55 60 | 372 |
| cgc ccc cac aga ccc cgc ccg ctg gac cca gac agc gtg gag gat gag<br>Arg Pro His Arg Pro Arg Pro Leu Asp Pro Asp Ser Val Glu Asp Glu<br>65 70 75 80 | 420 |
| ttt gaa cta tcc acg gtg tgc cac cgg cct gag ggt ctg gaa caa ctc<br>Phe Glu Leu Ser Thr Val Cys His Arg Pro Glu Gly Leu Glu Gln Leu<br>85 90 95 | 468 |
| cag gaa caa acc aag ttc aca cgc aga gag ttg cag gtc ctg tac aga<br>Gln Glu Gln Thr Lys Phe Thr Arg Arg Glu Leu Gln Val Leu Tyr Arg<br>100 105 110 | 516 |
| ggc ttc aag aac gaa tgt ccc agc gga att gtc aac gag gag aac ttc<br>Gly Phe Lys Asn Glu Cys Pro Ser Gly Ile Val Asn Glu Glu Asn Phe<br>115 120 125 | 564 |
| aag caa att tat tct cag ttc ttt ccc caa gga gac tcc agc aac tac<br>Lys Gln Ile Tyr Ser Gln Phe Phe Pro Gln Gly Asp Ser Ser Asn Tyr<br>130 135 140 | 612 |
| gct act ttt ctc ttc aat gcc ttt gac acc aac cat gat ggc tct gtc<br>Ala Thr Phe Leu Phe Asn Ala Phe Asp Thr Asn His Asp Gly Ser Val<br>145 150 155 160 | 660 |
| agt ttt gag gac ttt gtg gct ggt ttg tca gtg att ctt cgg gga acc<br>Ser Phe Glu Asp Phe Val Ala Gly Leu Ser Val Ile Leu Arg Gly Thr<br>165 170 175 | 708 |
| ata gat gat aga ctg aac tgg gct ttc aac tta tat gac ctc aac aag<br>Ile Asp Asp Arg Leu Asn Trp Ala Phe Asn Leu Tyr Asp Leu Asn Lys<br>180 185 190 | 756 |
| gat ggc tgt atc acg aag gag gaa atg ctc gac atc atg aag tcc atc<br>Asp Gly Cys Ile Thr Lys Glu Glu Met Leu Asp Ile Met Lys Ser Ile<br>195 200 205 | 804 |
| tat gac atg atg ggc aag tac acc tac cct gcc ctc cgg gag gag gcc<br>Tyr Asp Met Met Gly Lys Tyr Thr Tyr Pro Ala Leu Arg Glu Glu Ala<br>210 215 220 | 852 |
| ccg agg gaa cac gtg gag agc ttc ttc cag aag atg gac aga aac aag<br>Pro Arg Glu His Val Glu Ser Phe Phe Gln Lys Met Asp Arg Asn Lys<br>225 230 235 240 | 900 |
| gac ggc gtg gtg acc att gag gaa ttc att gag tct tgt caa cag gac<br>Asp Gly Val Val Thr Ile Glu Glu Phe Ile Glu Ser Cys Gln Gln Asp<br>245 250 255 | 948 |
| gag aac atc atg agg tcc atg caa ctc ttt gat aat gtc atc<br>Glu Asn Ile Met Arg Ser Met Gln Leu Phe Asp Asn Val Ile<br>260 265 270 | 990 |
| tagctcccca gggagagggg ttagtgtgtc ccagggtaac catgctgtag ccctagtcca | 1050 |
| ggcaaaccta accctcctct ccccgggtct gtcctcatcc tacctgtacc ctggggggctg | 1110 |
| tagggattca acatcctggc gcttcagtag tccagatccc tgagctaagt ggcgagagta | 1170 |
| ggcaagctaa gtctttggag ggtgggtggg ggcgcgcaga ttcccaaccc ccgacgactc | 1230 |
| tcaccccttt ctcgactgat acccagtgct gaggctaccc tggtgtcgg gaacgaccaa | 1290 |
| agtggttctc tgcctcccca gcccactcta gagacccaca ctagacggga atatctcctg | 1350 |
| ctatggtgct tccccatcc ctgaccgcag attttcctcc taagactccc ttctcagaga | 1410 |

-continued

```
atatgctttt gtcccttgtc cctggctggc ttttcagcct agcctttgag gaccctgtgg    1470 gagggagaa taagaaagca gacaaaatct tggccctgag ccagtggtta ggtcctagga    1530
atcaggctgg agtggagacc agaaagcctg ggcaggctat gagagcccca ggttggcttg    1590
tcaccgccag gttccacagg gctgctgctc tgggtcagca gagtatgagt ttccagactt    1650
tccagaaggc cttatgtcct tagcaatgtc ccagaaattc accatacact tctcagtgtc    1710
ttaggatcca gatgtccggt ccatccctga aacctctccc tcctccttgc tcctatggtg    1770
ggagtggtgg ccaggggacg atgagtgagc cggtgtcctg gatgatgcct gtcaaggtcc    1830
cacctaccct ccggctgtca agccgttctg gtgaccctgt tgattctcc atgaccctg     1890 tctagatgta gaggtgtgga gtgagtctag tggcagcctt aggggaatgg gaagaacgag    1950
aggggcactc catctgaacc cagtgtgggg gcatccattc gaatctttgc ctggctcccc    2010
acaatgccct aggatcctct agggtcccca ccccactct ttagtctacc cagagatgct     2070
ccagagctca cctagagggc aggaccata ggatccaggt ccaacctgtc atcagcatcc      2130
ggccatgctg ctgctgctta ttaataaacc tgcttgtcgt tcagcgcccc ttcccagtca    2190 gccaggtct gaggggaagg ccccacttt cccgcctcct gtcagacatt gttgactgct      2250
ttgcattttg ggctcttcta cctatatttt gtataataag aaagacacca gatccaataa    2310
aacacatggc tatgcacaaa aaaaaaaaaa aaa                                 2343
```

<210> SEQ ID NO 18
<211> LENGTH: 270
<212> TYPE: PRT
<213> ORGANISM: Mus musculus

<400> SEQUENCE: 18

```
Met Arg Gly Gln Gly Arg Lys Glu Ser Leu Ser Glu Ser Arg Asp Leu
 1               5                  10                  15

Asp Gly Ser Tyr Asp Gln Leu Thr Gly His Pro Pro Gly Pro Ser Lys
             20                  25                  30

Lys Ala Leu Lys Gln Arg Phe Leu Lys Leu Pro Cys Cys Gly Pro
         35                  40                  45

Gln Ala Leu Pro Ser Val Ser Glu Thr Leu Ala Ala Pro Ala Ser Leu
     50                  55                  60

Arg Pro His Arg Pro Arg Pro Leu Asp Pro Asp Ser Val Glu Asp Glu
 65                  70                  75                  80

Phe Glu Leu Ser Thr Val Cys His Arg Pro Glu Gly Leu Glu Gln Leu
                 85                  90                  95

Gln Glu Gln Thr Lys Phe Thr Arg Arg Glu Leu Gln Val Leu Tyr Arg
            100                 105                 110

Gly Phe Lys Asn Glu Cys Pro Ser Gly Ile Val Asn Glu Glu Asn Phe
        115                 120                 125

Lys Gln Ile Tyr Ser Gln Phe Phe Pro Gln Gly Asp Ser Ser Asn Tyr
    130                 135                 140

Ala Thr Phe Leu Phe Asn Ala Phe Asp Thr Asn His Asp Gly Ser Val
145                 150                 155                 160

Ser Phe Glu Asp Phe Val Ala Gly Leu Ser Val Ile Leu Arg Gly Thr
                165                 170                 175

Ile Asp Asp Arg Leu Asn Trp Ala Phe Asn Leu Tyr Asp Leu Asn Lys
            180                 185                 190

Asp Gly Cys Ile Thr Lys Glu Glu Met Leu Asp Ile Met Lys Ser Ile
        195                 200                 205
```

```
Tyr Asp Met Met Gly Lys Tyr Thr Tyr Pro Ala Leu Arg Glu Glu Ala
        210                 215                 220

Pro Arg Glu His Val Glu Ser Phe Phe Gln Lys Met Asp Arg Asn Lys
225                 230                 235                 240

Asp Gly Val Val Thr Ile Glu Glu Phe Ile Glu Ser Cys Gln Gln Asp
                245                 250                 255

Glu Asn Ile Met Arg Ser Met Gln Leu Phe Asp Asn Val Ile
            260                 265                 270

<210> SEQ ID NO 19
<211> LENGTH: 1955
<212> TYPE: DNA
<213> ORGANISM: Homo sapiens
<220> FEATURE:
<221> NAME/KEY: CDS
<222> LOCATION: (207)..(962)

<400> SEQUENCE: 19
ctcacctgct gcctagtgtt ccctctcctg ctccaggacc tccgggtaga cctcagaccc      60
cgggcccatt cccagactca gcctcagccc ggacttcccc agccccgaca gcacagtagg     120
ccgccagggg gcgccgtgtg agcgccctat cccggccacc cggcgccccc tcccacggcc     180
cgggcgggag cggggcgccg ggggcc atg cgg ggc cag ggc cgc aag gag agt     233
                             Met Arg Gly Gln Gly Arg Lys Glu Ser
                              1               5
```

| | | |
|---|---|---|
| ttg tcc gat tcc cga gac ctg gac ggc tcc tac gac cag ctc acg ggc | 281 |
| Leu Ser Asp Ser Arg Asp Leu Asp Gly Ser Tyr Asp Gln Leu Thr Gly | |
| 10              15                  20                  25 | |

```
cac cct cca ggg ccc act aaa aaa gcg ctg aag cag cga ttc ctc aag    329
His Pro Pro Gly Pro Thr Lys Lys Ala Leu Lys Gln Arg Phe Leu Lys
            30                  35                  40 ctg ctg ccg tgc tgc ggg ccc caa gcc ctg ccc tca gtc agt gaa aac    377
Leu Leu Pro Cys Cys Gly Pro Gln Ala Leu Pro Ser Val Ser Glu Asn
                45                  50                  55 agc gtg gac gat gaa ttt gaa ttg tcc acc gtg tgt cac cgg cct gag    425
Ser Val Asp Asp Glu Phe Glu Leu Ser Thr Val Cys His Arg Pro Glu
        60                  65                  70 ggt ctg gag cag ctg cag gag caa acc aaa ttc acg cgc aag gag ttg    473
Gly Leu Glu Gln Leu Gln Glu Gln Thr Lys Phe Thr Arg Lys Glu Leu
 75                  80                  85 cag gtc ctg tac cgg ggc ttc aag aac gaa tgt ccc agc gga att gtc    521
Gln Val Leu Tyr Arg Gly Phe Lys Asn Glu Cys Pro Ser Gly Ile Val
 90                  95                 100                 105 aat gag gag aac ttc aag cag att tac tcc cag ttc ttt cct caa gga    569
Asn Glu Glu Asn Phe Lys Gln Ile Tyr Ser Gln Phe Phe Pro Gln Gly
                110                 115                 120 gac tcc agc acc tat gcc act ttt ctc ttc aat gcc ttt gac acc aac    617
Asp Ser Ser Thr Tyr Ala Thr Phe Leu Phe Asn Ala Phe Asp Thr Asn
            125                 130                 135 cat gat ggc tcg gtc agt ttt gag gac ttt gtg gct ggt ttg tcc gtg    665
His Asp Gly Ser Val Ser Phe Glu Asp Phe Val Ala Gly Leu Ser Val
        140                 145                 150 att ctt cgg gga act gta gat gac agg ctt aat tgg gcc ttc aac ctg    713
Ile Leu Arg Gly Thr Val Asp Asp Arg Leu Asn Trp Ala Phe Asn Leu
155                 160                 165 tat gac ctt aac aag gac ggc tgc atc acc aag gag gaa atg ctt gac    761
Tyr Asp Leu Asn Lys Asp Gly Cys Ile Thr Lys Glu Glu Met Leu Asp
170                 175                 180                 185 atc atg aag tcc atc tat gac atg atg ggc aag tac acg tac cct gca    809
Ile Met Lys Ser Ile Tyr Asp Met Met Gly Lys Tyr Thr Tyr Pro Ala
```

```
ctc cgg gag gag gcc cca agg gaa cac gtg gag agc ttc ttc cag aag      857
Leu Arg Glu Glu Ala Pro Arg Glu His Val Glu Ser Phe Phe Gln Lys
            205                 210                 215 atg gac aga aac aag gat ggt gtg gtg acc att gag gaa ttc att gag      905
Met Asp Arg Asn Lys Asp Gly Val Val Thr Ile Glu Glu Phe Ile Glu
            220                 225                 230 tct tgt caa aag gat gag aac atc atg agg tcc atg cag ctc ttt gac      953
Ser Cys Gln Lys Asp Glu Asn Ile Met Arg Ser Met Gln Leu Phe Asp
        235                 240                 245 aat gtc atc tagcccccag gagaggggt cagtgtttcc tgggggacc               1002
Asn Val Ile
250 atgctctaac cctagtccag gcggacctca cccttctctt cccaggtcta tcctcatcct    1062 acgcctccct gggggctgga gggatccaag agcttgggga ttcagtagtc cagatctctg    1122 gagctgaagg ggccagagag tgggcagagt gcatctcggg gggtgttccc aactcccacc    1182 agctctcacc cccttcctgc ctgacaccca gtgttgagag tgcccctcct gtaggaattg    1242 agcggttccc cacctcctac cctactctag aaacacacta gagcgatgtc tcctgctatg    1302 gtgcttcccc catccctgac ctcataaaca tttcccctaa gactcccctc tcagagagaa    1362 tgctccattc ttggcactgg ctggcttctc agaccagcca ttgagagccc tgtgggaggg    1422 ggacaagaat gtatagggag aaatcttggg cctgagtcaa tggataggtc ctaggaggtg    1482 ggtgggttg agaatagaag ggcctggaca gattatgatt gctcaggcat accaggttat     1542 agctccaagt tccacaggtc tgctaccaca ggccatcaaa atataagttt ccaggctttg    1602 cagaagacct tgtctcctta gaaatgcccc agaaattttc cacaccctcc tcggtatcca    1662 tggagagcct ggggccagat atctggctca tctctggcat tgcttcctct ccttccttcc    1722 tgcatgtgtt ggtggtggtt gtggtggggg aatgtggatg ggggatgtcc tggctgatgc    1782 ctgccaaaat ttcatcccac cctccttgct tatcgtccct gttttgaggg ctatgacttg    1842 agttttttgtt tccatgttc tctatagact tgggaccttc ctgaacttgg ggcctatcac    1902 tccccacagt ggatgcctta gaagggagag ggaaggaggg aggcaggcat agc           1955

<210> SEQ ID NO 20
<211> LENGTH: 252
<212> TYPE: PRT
<213> ORGANISM: Homo sapiens

<400> SEQUENCE: 20

Met Arg Gly Gln Gly Arg Lys Glu Ser Leu Ser Asp Ser Arg Asp Leu
 1               5                  10                  15

Asp Gly Ser Tyr Asp Gln Leu Thr Gly His Pro Pro Gly Pro Thr Lys
             20                  25                  30

Lys Ala Leu Lys Gln Arg Phe Leu Lys Leu Leu Pro Cys Cys Gly Pro
         35                  40                  45

Gln Ala Leu Pro Ser Val Ser Glu Asn Ser Val Asp Asp Glu Phe Glu
     50                  55                  60

Leu Ser Thr Val Cys His Arg Pro Glu Gly Leu Glu Gln Leu Gln Glu
 65                  70                  75                  80

Gln Thr Lys Phe Thr Arg Lys Glu Leu Gln Val Leu Tyr Arg Gly Phe
                 85                  90                  95

Lys Asn Glu Cys Pro Ser Gly Ile Val Asn Glu Glu Asn Phe Lys Gln
            100                 105                 110
```

-continued

```
Ile Tyr Ser Gln Phe Phe Pro Gln Gly Asp Ser Ser Thr Tyr Ala Thr
        115                 120                 125
Phe Leu Phe Asn Ala Phe Asp Thr Asn His Asp Gly Ser Val Ser Phe
130                 135                 140
Glu Asp Phe Val Ala Gly Leu Ser Val Ile Leu Arg Gly Thr Val Asp
145                 150                 155                 160
Asp Arg Leu Asn Trp Ala Phe Asn Leu Tyr Asp Leu Asn Lys Asp Gly
                165                 170                 175
Cys Ile Thr Lys Glu Glu Met Leu Asp Ile Met Lys Ser Ile Tyr Asp
            180                 185                 190
Met Met Gly Lys Tyr Thr Tyr Pro Ala Leu Arg Glu Glu Ala Pro Arg
        195                 200                 205
Glu His Val Glu Ser Phe Phe Gln Lys Met Asp Arg Asn Lys Asp Gly
    210                 215                 220
Val Val Thr Ile Glu Glu Phe Ile Glu Ser Cys Gln Lys Asp Glu Asn
225                 230                 235                 240
Ile Met Arg Ser Met Gln Leu Phe Asp Asn Val Ile
                245                 250
```

<210> SEQ ID NO 21
<211> LENGTH: 2300
<212> TYPE: DNA
<213> ORGANISM: Rattus sp.
<220> FEATURE:
<221> NAME/KEY: CDS
<222> LOCATION: (214)..(969)

<400> SEQUENCE: 21

```
ctcacttgct gcccaaggct cctgctcctg ccccaggact ctgaggtggg ccctaaaacc      60
cagcgctctc taaagaaaag ccttgccagc ccctactccc ggcccccaac cccagcaggt     120
cgctgcgccg ccaggggggcg ctgtgtgagc gccctattct ggccacccgg cgccccctcc    180
cacggcccag gcgggagcgg ggcgccgggg gcc atg cgg ggc caa ggc aga aag     234
                                    Met Arg Gly Gln Gly Arg Lys
                                     1               5 gag agt ttg tcc gaa tcc cga gat ctg gac ggc tcc tat gac cag ctt     282
Glu Ser Leu Ser Glu Ser Arg Asp Leu Asp Gly Ser Tyr Asp Gln Leu
         10                  15                  20 acg ggc cac cct cca ggg ccc agt aaa aaa gcc ctg aag cag cgt ttc     330
Thr Gly His Pro Pro Gly Pro Ser Lys Lys Ala Leu Lys Gln Arg Phe
 25                  30                  35 ctc aag ctg ctg ccg tgc tgc ggg ccc caa gcc ctg ccc tca gtc agt     378
Leu Lys Leu Leu Pro Cys Cys Gly Pro Gln Ala Leu Pro Ser Val Ser
 40                  45                  50                  55 gaa aac agc gta gag gat gag ttt gaa tta tcc acg gtg tgt cac cga     426
Glu Asn Ser Val Glu Asp Glu Phe Glu Leu Ser Thr Val Cys His Arg
                 60                  65                  70 cct gag ggc ctg gaa caa ctc cag gaa cag acc aag ttc aca cgc aga     474
Pro Glu Gly Leu Glu Gln Leu Gln Glu Gln Thr Lys Phe Thr Arg Arg
             75                  80                  85 gag ctg cag gtc ctg tac cga ggc ttc aag aac gaa tgc ccc agt ggg     522
Glu Leu Gln Val Leu Tyr Arg Gly Phe Lys Asn Glu Cys Pro Ser Gly
         90                  95                 100 att gtc aac gag gag aac ttc aag cag att tat tct cag ttc ttt ccc     570
Ile Val Asn Glu Glu Asn Phe Lys Gln Ile Tyr Ser Gln Phe Phe Pro
105                 110                 115 caa gga gac tcc agc aac tat gct act ttt ctc ttc aat gcc ttt gac     618
Gln Gly Asp Ser Ser Asn Tyr Ala Thr Phe Leu Phe Asn Ala Phe Asp
120                 125                 130                 135
```

-continued

```
acc aac cac gat ggc tct gtc agt ttt gag gac ttt gtg gct ggt ttg      666
Thr Asn His Asp Gly Ser Val Ser Phe Glu Asp Phe Val Ala Gly Leu
            140                 145                 150 tcg gtg att ctt cgg ggg acc ata gat gat aga ctg agc tgg gct ttc      714
Ser Val Ile Leu Arg Gly Thr Ile Asp Asp Arg Leu Ser Trp Ala Phe
        155                 160                 165 aac tta tat gac ctc aac aag gac ggc tgt atc aca aag gag gaa atg      762
Asn Leu Tyr Asp Leu Asn Lys Asp Gly Cys Ile Thr Lys Glu Glu Met
        170                 175                 180 ctt gac att atg aag tcc atc tat gac atg atg ggc aag tac aca tac      810
Leu Asp Ile Met Lys Ser Ile Tyr Asp Met Met Gly Lys Tyr Thr Tyr
    185                 190                 195 cct gcc ctc cgg gag gag gcc cca aga gaa cac gtg gag agc ttc ttc      858
Pro Ala Leu Arg Glu Glu Ala Pro Arg Glu His Val Glu Ser Phe Phe
200                 205                 210                 215 cag aag atg gac agg aac aag gac ggc gtg gtg acc atc gag gaa ttc      906
Gln Lys Met Asp Arg Asn Lys Asp Gly Val Val Thr Ile Glu Glu Phe
                220                 225                 230 atc gag tct tgt caa cag gac gag aac atc atg agg tcc atg cag ctc      954
Ile Glu Ser Cys Gln Gln Asp Glu Asn Ile Met Arg Ser Met Gln Leu
                235                 240                 245 ttt gat aat gtc atc tagctcccca gggagagggg ttagtgtgtc ctagggtgac     1009
Phe Asp Asn Val Ile
            250 caggctgtag tcctagtcca gacgaaccta accctctctc tccaggcctg tcctcatctt   1069 acctgtaccc tgggggctgt agggattcaa tatcctgggg cttcagtagt ccagatccct   1129 gagctaagtc acaaaagtag gcaagagtag gcaagctaaa tctgggggct tcccaacccc   1189 cgacagctct cacccctcct caactgatac ctagtgctga ggacacccct ggtgtaggga   1249 ccaagtggtt ctccaccttc tagtcccact ctagaaacca cattagacag aaggtctcct   1309 gctatggtgc tttccccatc cctaatctct tagattttcc tcaagactcc cttctcagag   1369 aacacgctct gtccatgtcc ccagctggct tctcagccta gcctttgagg gccctgtggg   1429 gaggcgggga caagaaagca gaaaagtctt ggccccgagc cagtggttag gtcctaggaa   1489 ttggctggag tggaggccag aaagcctggg cagatgatga gagcccagct gggctgtcac   1549 tgcaggttcc ggggcctaca gccctgggtc agcagagtat gagttcccag actttccaga   1609 aggtccttag caatgtccca gaaattcacc gtacacttct cagtgtctta ggagggcccg   1669 ggatccagat gtctggttca tccctgaatc ctctccctcc ttcttgctcg tatggtggga   1729 gtggtggcca ggggaagatg agtggtgtcc cggatgatgc ctgtcaaggt cccacctccc   1789 ctccggctgt tctcatgaca gctgtttggt tctccatgac ccctatctag atgtagaggc   1849 atggagtgag tcagggattt cccgaacttg agttttacca ctcctcctag tggctgcctt   1909 agggaatgg gaagaaccca gtgtgggggc acccattaga atctttgccc ggctcctcac    1969 aatgccctag ggtccctag ggtacccgct ccctctgttt agtctaccca gagatgctcc    2029 tgagctcacc tagagggtag ggacggtagg ctccaggtcc aacctctcca ggtcagcacc   2089 ctgccatgct gctgctcctc attaacaaac ctgcttgtct cctcctgcgc cccttctcag   2149 tcagccaggg tctgagggga agggcctccc gtttccccat ccgtcagaca tggttgactg   2209 cttttgcattt tgggctcttc tatctatttt gtaaaataag acatcagatc caataaaaca   2269 cacggctatg cacaaaaaaa aaaaaaaaaa a                                  2300
```

<210> SEQ ID NO 22

-continued

```
<211> LENGTH: 252
<212> TYPE: PRT
<213> ORGANISM: Rattus sp.

<400> SEQUENCE: 22
```

| | | | | | | | | | | | | | | |
|---|---|---|---|---|---|---|---|---|---|---|---|---|---|---|
| Met | Arg | Gly | Gln | Gly | Arg | Lys | Glu | Ser | Leu | Ser | Glu | Ser | Arg | Asp | Leu |
| 1 | | | | 5 | | | | | 10 | | | | | 15 | |
| Asp | Gly | Ser | Tyr | Asp | Gln | Leu | Thr | Gly | His | Pro | Pro | Gly | Pro | Ser | Lys |
| | | | 20 | | | | | 25 | | | | | 30 | | |
| Lys | Ala | Leu | Lys | Gln | Arg | Phe | Leu | Lys | Leu | Leu | Pro | Cys | Cys | Gly | Pro |
| | | 35 | | | | | 40 | | | | | 45 | | | |
| Gln | Ala | Leu | Pro | Ser | Val | Ser | Glu | Asn | Ser | Val | Glu | Asp | Glu | Phe | Glu |
| | 50 | | | | | 55 | | | | | 60 | | | | |
| Leu | Ser | Thr | Val | Cys | His | Arg | Pro | Glu | Gly | Leu | Glu | Gln | Leu | Gln | Glu |
| 65 | | | | | 70 | | | | | 75 | | | | | 80 |
| Gln | Thr | Lys | Phe | Thr | Arg | Arg | Glu | Leu | Gln | Val | Leu | Tyr | Arg | Gly | Phe |
| | | | | 85 | | | | | 90 | | | | | 95 | |
| Lys | Asn | Glu | Cys | Pro | Ser | Gly | Ile | Val | Asn | Glu | Glu | Asn | Phe | Lys | Gln |
| | | | 100 | | | | | 105 | | | | | 110 | | |
| Ile | Tyr | Ser | Gln | Phe | Phe | Pro | Gln | Gly | Asp | Ser | Ser | Asn | Tyr | Ala | Thr |
| | | | 115 | | | | | 120 | | | | | 125 | | |
| Phe | Leu | Phe | Asn | Ala | Phe | Asp | Thr | Asn | His | Asp | Gly | Ser | Val | Ser | Phe |
| | | 130 | | | | | 135 | | | | | 140 | | | |
| Glu | Asp | Phe | Val | Ala | Gly | Leu | Ser | Val | Ile | Leu | Arg | Gly | Thr | Ile | Asp |
| 145 | | | | | 150 | | | | | 155 | | | | | 160 |
| Asp | Arg | Leu | Ser | Trp | Ala | Phe | Asn | Leu | Tyr | Asp | Leu | Asn | Lys | Asp | Gly |
| | | | | 165 | | | | | 170 | | | | | 175 | |
| Cys | Ile | Thr | Lys | Glu | Glu | Met | Leu | Asp | Ile | Met | Lys | Ser | Ile | Tyr | Asp |
| | | | 180 | | | | | 185 | | | | | 190 | | |
| Met | Met | Gly | Lys | Tyr | Thr | Tyr | Pro | Ala | Leu | Arg | Glu | Glu | Ala | Pro | Arg |
| | | | 195 | | | | | 200 | | | | | 205 | | |
| Glu | His | Val | Glu | Ser | Phe | Phe | Gln | Lys | Met | Asp | Arg | Asn | Lys | Asp | Gly |
| | | 210 | | | | | 215 | | | | | 220 | | | |
| Val | Val | Thr | Ile | Glu | Glu | Phe | Ile | Glu | Ser | Cys | Gln | Gln | Asp | Glu | Asn |
| 225 | | | | | 230 | | | | | 235 | | | | | 240 |
| Ile | Met | Arg | Ser | Met | Gln | Leu | Phe | Asp | Asn | Val | Ile | | | | |
| | | | | 245 | | | | | 250 | | | | | | |

```
<210> SEQ ID NO 23
<211> LENGTH: 1859
<212> TYPE: DNA
<213> ORGANISM: Homo sapiens
<220> FEATURE:
<221> NAME/KEY: CDS
<222> LOCATION: (207)..(866)

<400> SEQUENCE: 23
ctcacctgct gcctagtgtt ccctctcctg ctccaggacc tccgggtaga cctcagaccc      60
cgggcccatt cccagactca gcctcagccc ggacttcccc agccccgaca gcacagtagg     120
ccgccagggg gcgccgtgtg agcgccctat cccggccacc cggcgccccc tcccacggcc     180
cgggcgggag cggggcgccg ggggcc atg cgg ggc cag ggc cgc aag gag agt     233
                                Met Arg Gly Gln Gly Arg Lys Glu Ser
                                  1               5 ttg tcc gat tcc cga gac ctg gac ggc tcc tac gac cag ctc acg gac     281
Leu Ser Asp Ser Arg Asp Leu Asp Gly Ser Tyr Asp Gln Leu Thr Asp
    10                  15                  20                  25
```

| | | |
|---|---|---|
| agc gtg gac gat gaa ttt gaa ttg tcc acc gtg tgt cac cgg cct gag<br>Ser Val Asp Asp Glu Phe Glu Leu Ser Thr Val Cys His Arg Pro Glu<br>30 35 40 | | 329 |
| ggt ctg gag cag ctg cag gag caa acc aaa ttc acg cgc aag gag ttg<br>Gly Leu Glu Gln Leu Gln Glu Gln Thr Lys Phe Thr Arg Lys Glu Leu<br>45 50 55 | | 377 |
| cag gtc ctg tac cgg ggc ttc aag aac gaa tgt ccc agc gga att gtc<br>Gln Val Leu Tyr Arg Gly Phe Lys Asn Glu Cys Pro Ser Gly Ile Val<br>60 65 70 | | 425 |
| aat gag gag aac ttc aag cag att tac tcc cag ttc ttt cct caa gga<br>Asn Glu Glu Asn Phe Lys Gln Ile Tyr Ser Gln Phe Phe Pro Gln Gly<br>75 80 85 | | 473 |
| gac tcc agc acc tat gcc act ttt ctc ttc aat gcc ttt gac acc aac<br>Asp Ser Ser Thr Tyr Ala Thr Phe Leu Phe Asn Ala Phe Asp Thr Asn<br>90 95 100 105 | | 521 |
| cat gat ggc tcg gtc agt ttt gag gac ttt gtg gct ggt ttg tcc gtg<br>His Asp Gly Ser Val Ser Phe Glu Asp Phe Val Ala Gly Leu Ser Val<br>110 115 120 | | 569 |
| att ctt cgg gga act gta gat gac agg ctt aat tgg gcc ttc aac ctg<br>Ile Leu Arg Gly Thr Val Asp Asp Arg Leu Asn Trp Ala Phe Asn Leu<br>125 130 135 | | 617 |
| tat gac ctt aac aag gac ggc tgc atc acc aag gag gaa atg ctt gac<br>Tyr Asp Leu Asn Lys Asp Gly Cys Ile Thr Lys Glu Glu Met Leu Asp<br>140 145 150 | | 665 |
| atc atg aag tcc atc tat gac atg atg ggc aag tac acg tac cct gca<br>Ile Met Lys Ser Ile Tyr Asp Met Met Gly Lys Tyr Thr Tyr Pro Ala<br>155 160 165 | | 713 |
| ctc cgg gag gag gcc cca agg gaa cac gtg gag agc ttc ttc cag aag<br>Leu Arg Glu Glu Ala Pro Arg Glu His Val Glu Ser Phe Phe Gln Lys<br>170 175 180 185 | | 761 |
| atg gac aga aac aag gat ggt gtg gtg acc att gag gaa ttc att gag<br>Met Asp Arg Asn Lys Asp Gly Val Val Thr Ile Glu Glu Phe Ile Glu<br>190 195 200 | | 809 |
| tct tgt caa aag gat gag aac atc atg agg tcc atg cag ctc ttt gac<br>Ser Cys Gln Lys Asp Glu Asn Ile Met Arg Ser Met Gln Leu Phe Asp<br>205 210 215 | | 857 |
| aat gtc atc tagcccccag gagagggggt cagtgtttcc tgggggacc<br>Asn Val Ile<br>220 | | 906 |
| atgctctaac cctagtccag gcggacctca cccttctctt cccaggtcta tcctcatcct | | 966 |
| acgcctccct gggggctgga gggatccaag agcttgggga ttcagtagtc cagatctctg | | 1026 |
| gagctgaagg ggccagagag tgggcagagt gcatctcggg gggtgttccc aactcccacc | | 1086 |
| agctctcacc cccttcctgc ctgacaccca gtgttgagag tgcccctcct gtaggaattg | | 1146 |
| agcggttccc cacctcctac cctactctag aaacacacta gagcgatgtc tcctgctatg | | 1206 |
| gtgcttcccc catccctgac ctcataaaca tttcccctaa gactcccctc tcagagagaa | | 1266 |
| tgctccattc ttggcactgg ctggcttctc agaccagcca ttgagagccc tgtgggaggg | | 1326 |
| ggacaagaat gtatagggag aaatcttggg cctgagtcaa tggataggtc ctaggaggtg | | 1386 |
| ggtggggttg agaatagaag ggcctggaca gattatgatt gctcaggcat accaggttat | | 1446 |
| agctccaagt tccacaggtc tgctaccaca ggccatcaaa atataagttt ccaggctttg | | 1506 |
| cagaagacct tgtctcctta gaaatgcccc agaaattttc cacaccctcc tcggtatcca | | 1566 |
| tggagagcct ggggccagat atctggctca tctctggcat tgcttcctct ccttccttcc | | 1626 |
| tgcatgtgtt ggtggtggtt gtggtggggg aatgtggatg gggatgtcc tggctgatgc | | 1686 |
| ctgccaaaat ttcatcccac cctccttgct tatcgtccct gttttgaggg ctatgacttg | | 1746 |

```
agtttttgtt tcccatgttc tctatagact tgggaccttc ctgaacttgg ggcctatcac   1806
tccccacagt ggatgcctta aagggagag ggaaggaggg aggcaggcat agc           1859
```

<210> SEQ ID NO 24
<211> LENGTH: 220
<212> TYPE: PRT
<213> ORGANISM: Homo sapiens

<400> SEQUENCE: 24

```
Met Arg Gly Gln Gly Arg Lys Glu Ser Leu Ser Asp Ser Arg Asp Leu
 1               5                  10                  15

Asp Gly Ser Tyr Asp Gln Leu Thr Asp Ser Val Asp Asp Glu Phe Glu
            20                  25                  30

Leu Ser Thr Val Cys His Arg Pro Glu Gly Leu Glu Gln Leu Gln Glu
        35                  40                  45

Gln Thr Lys Phe Thr Arg Lys Glu Leu Gln Val Leu Tyr Arg Gly Phe
    50                  55                  60

Lys Asn Glu Cys Pro Ser Gly Ile Val Asn Glu Glu Asn Phe Lys Gln
65                  70                  75                  80

Ile Tyr Ser Gln Phe Phe Pro Gln Gly Asp Ser Ser Thr Tyr Ala Thr
                85                  90                  95

Phe Leu Phe Asn Ala Phe Asp Thr Asn His Asp Gly Ser Val Ser Phe
            100                 105                 110

Glu Asp Phe Val Ala Gly Leu Ser Val Ile Leu Arg Gly Thr Val Asp
        115                 120                 125

Asp Arg Leu Asn Trp Ala Phe Asn Leu Tyr Asp Leu Asn Lys Asp Gly
    130                 135                 140

Cys Ile Thr Lys Glu Glu Met Leu Asp Ile Met Lys Ser Ile Tyr Asp
145                 150                 155                 160

Met Met Gly Lys Tyr Thr Tyr Pro Ala Leu Arg Glu Glu Ala Pro Arg
                165                 170                 175

Glu His Val Glu Ser Phe Phe Gln Lys Met Asp Arg Asn Lys Asp Gly
            180                 185                 190

Val Val Thr Ile Glu Glu Phe Ile Glu Ser Cys Gln Lys Asp Glu Asn
        195                 200                 205

Ile Met Arg Ser Met Gln Leu Phe Asp Asn Val Ile
    210                 215                 220
```

<210> SEQ ID NO 25
<211> LENGTH: 2191
<212> TYPE: DNA
<213> ORGANISM: Simian sp.
<220> FEATURE:
<221> NAME/KEY: CDS
<222> LOCATION: (133)..(792)

<400> SEQUENCE: 25

```
cccacgcgtc cgcccacgcg tccgcggacg cgtggggtgc actaggccgc caggggcgc    60 cgtgtgagcg ccctatcccg gccacccggc gcccctccc acggaccggg cgggagcggg   120
gcgccggggg cc atg cgg ggc cag ggc cgc aag gag agt ttg tcc gat tcc   171
              Met Arg Gly Gln Gly Arg Lys Glu Ser Leu Ser Asp Ser
                1               5                   10 cga gac ctg gac gga tcc tac gac cag ctc acg gac agc gtg gag gat   219
Arg Asp Leu Asp Gly Ser Tyr Asp Gln Leu Thr Asp Ser Val Glu Asp
 15                  20                  25 gaa ttt gaa ttg tcc acc gtg tgt cac cgg cct gag ggt ctg gag cag   267
```

```
                Glu Phe Glu Leu Ser Thr Val Cys His Arg Pro Glu Gly Leu Glu Gln
                 30                  35                  40                  45 ctg cag gag caa acc aaa ttc acg cgc aag gag ttg cag gtc ctg tac         315
Leu Gln Glu Gln Thr Lys Phe Thr Arg Lys Glu Leu Gln Val Leu Tyr
                 50                  55                  60 cgg ggc ttc aag aac gaa tgt ccg agc gga att gtc aat gag gag aac         363
Arg Gly Phe Lys Asn Glu Cys Pro Ser Gly Ile Val Asn Glu Glu Asn
                 65                  70                  75 ttc aag caa att tac tcc cag ttc ttt cct caa gga gac tcc agc acc         411
Phe Lys Gln Ile Tyr Ser Gln Phe Phe Pro Gln Gly Asp Ser Ser Thr
                 80                  85                  90 tat gcc act ttt ctc ttc aat gcc ttt gac acc aac cat gat ggc tcg         459
Tyr Ala Thr Phe Leu Phe Asn Ala Phe Asp Thr Asn His Asp Gly Ser
                 95                 100                 105 gtc agt ttt gag gac ttt gtg gct ggt ttg tcc gtg att ctt cgg gga         507
Val Ser Phe Glu Asp Phe Val Ala Gly Leu Ser Val Ile Leu Arg Gly
110                 115                 120                 125 act gta gat gac agg ctt aat tgg gcc ttc aac ttg tat gac ctc aac         555
Thr Val Asp Asp Arg Leu Asn Trp Ala Phe Asn Leu Tyr Asp Leu Asn
                130                 135                 140 aag gac ggc tgc atc acc aag gag gaa atg ctt gac atc atg aag tcc         603
Lys Asp Gly Cys Ile Thr Lys Glu Glu Met Leu Asp Ile Met Lys Ser
                145                 150                 155 atc tat gac atg atg ggc aag tac aca tac cct gca ctc cgg gag gag         651
Ile Tyr Asp Met Met Gly Lys Tyr Thr Tyr Pro Ala Leu Arg Glu Glu
                160                 165                 170 gcc cca agg gaa cat gtg gag aac ttc ttc cag aag atg gac aga aac         699
Ala Pro Arg Glu His Val Glu Asn Phe Phe Gln Lys Met Asp Arg Asn
175                 180                 185 aag gat ggc gtg gtg acc att gag gaa ttc att gag tct tgt caa aag         747
Lys Asp Gly Val Val Thr Ile Glu Glu Phe Ile Glu Ser Cys Gln Lys
190                 195                 200                 205 gat gag aac atc atg agg tcc atg cag ctc ttt gac aat gtc atc              792
Asp Glu Asn Ile Met Arg Ser Met Gln Leu Phe Asp Asn Val Ile
                210                 215                 220 tagcccccag gagaggggt cagtgtttcc tgggggacc atgctctaac cctagtccag         852
gtggacctca cccttctctt cccaggtcta tccttgtcct aggcctccct ggggctgga        912
gggatccaag agcttgggga ttcagtagtc cagatctctg gagctgaagg ggccagagag       972
tgggcagagt gcatcttggg gggtgttccc aactcccacc agctttcacc cgcttcctgc      1032
ctgacaccca gtgttgagag tgcccctcct gtaggaactg agtggttccc cacctcctac      1092
ccccactcta gaaacacact agacagatgt ctcctgctat ggtgcttccc ccatccctga      1152
cttcataaac atttcccta aaactccctt ctcagagaga atgctccatt cttggcactg       1212
gctggcttct cagaccagcc tttgagagcc ctgtgggagg gggacaagaa tgtatagggg      1272
agaaatcttg ggcctgagtc aatggatagg tcctaggagg tggctgggt tgagaataga       1332
aaggcctgga cacaatgtga ttgctcaggc ataccaagtt atagctccaa gttccacagg      1392
tctgctacca caggccatca aaatataagt ttccaggctt tgcagaagac cttgtctcct      1452
tggaaatgcc ccagatattt tccataccct cctcgatatc catggagagc ctggggctag      1512
atatctggca tatccctggc attgcttcct ctccttcctt cctgcatgtg ttggtggtgg      1572
ttgtggcagg ggaatgtgga taggagatgt cctggcagat gcctgccaaa gtttcatccc      1632
accctccctg ctcatcgccc ctgttttgag ggctgtgact tgagtttttg tttcccatgt      1692
tctctataga cttgggacct tcctgaactt ggggcctatc actccccaca gtggatgcct      1752
```

-continued

```
tagaagggag agggaaggag ggaggcaggc atagcatctg aacccagtgt gggggcattc    1812
actaggatct tcaatcaacc cgggctctcc ccaaccccc agataacctc ctcagttccc    1872
tagagtctcc tcttgctcta ctcaatctac ccagagatgc cccttagcac actcagaggg    1932
cagggaccat aggacccagg ttccaacccc attgtcagca ccccagccat gctgccatcc    1992
cttagcacac ctgctcgtcc cattcagctt accctcccag tcagccagaa tctgagggga    2052
gggcccccag agagcccct tccccatcag aagactgttg actgctttgc attttgggct    2112
cttctatata ttttgtaaaa taagaactat accagatcta ataaaacaca atggctatgc    2172
aaaaaaaaaa aaaaaaaaa                                                2191
```

<210> SEQ ID NO 26
<211> LENGTH: 220
<212> TYPE: PRT
<213> ORGANISM: Simian sp.

<400> SEQUENCE: 26

```
Met Arg Gly Gln Gly Arg Lys Glu Ser Leu Ser Asp Ser Arg Asp Leu
  1               5                  10                  15

Asp Gly Ser Tyr Asp Gln Leu Thr Asp Ser Val Glu Asp Glu Phe Glu
             20                  25                  30

Leu Ser Thr Val Cys His Arg Pro Glu Gly Leu Glu Gln Leu Gln Glu
         35                  40                  45

Gln Thr Lys Phe Thr Arg Lys Glu Leu Gln Val Leu Tyr Arg Gly Phe
     50                  55                  60

Lys Asn Glu Cys Pro Ser Gly Ile Val Asn Glu Glu Asn Phe Lys Gln
 65                  70                  75                  80

Ile Tyr Ser Gln Phe Phe Pro Gln Gly Asp Ser Ser Thr Tyr Ala Thr
                 85                  90                  95

Phe Leu Phe Asn Ala Phe Asp Thr Asn His Asp Gly Ser Val Ser Phe
            100                 105                 110

Glu Asp Phe Val Ala Gly Leu Ser Val Ile Leu Arg Gly Thr Val Asp
        115                 120                 125

Asp Arg Leu Asn Trp Ala Phe Asn Leu Tyr Asp Leu Asn Lys Asp Gly
    130                 135                 140

Cys Ile Thr Lys Glu Glu Met Leu Asp Ile Met Lys Ser Ile Tyr Asp
145                 150                 155                 160

Met Met Gly Lys Tyr Thr Tyr Pro Ala Leu Arg Glu Glu Ala Pro Arg
                165                 170                 175

Glu His Val Glu Asn Phe Phe Gln Lys Met Asp Arg Asn Lys Asp Gly
            180                 185                 190

Val Val Thr Ile Glu Glu Phe Ile Glu Ser Cys Gln Lys Asp Glu Asn
        195                 200                 205

Ile Met Arg Ser Met Gln Leu Phe Asp Asn Val Ile
    210                 215                 220
```

<210> SEQ ID NO 27
<211> LENGTH: 2057
<212> TYPE: DNA
<213> ORGANISM: Simian sp.
<220> FEATURE:
<221> NAME/KEY: CDS
<222> LOCATION: (208)..(963)

<400> SEQUENCE: 27

```
tgctgcccaa ggctcctgct cctgccccag gactctgagg tgggccctaa aacccagcgc     60
```

```
tctctaaaga aaagccttgc cagcccctac tcccggcccc caaccccagc aggtcgctgc       120
gccgccaggg ggcgctgtgt gagcgcccta ttctggccac ccggcgcccc ctcccacggg       180
ccaggcggga gcggggcgcc gggggcc atg cgg ggc caa ggc aga aag gag agt      234
                                Met Arg Gly Gln Gly Arg Lys Glu Ser
                                 1               5 ttg tcc gaa tcc cga gat ctg gac ggc tcc tat gac cag ctt acg ggc        282
Leu Ser Glu Ser Arg Asp Leu Asp Gly Ser Tyr Asp Gln Leu Thr Gly
 10              15                  20                  25 cac cct cca ggg ccc agt aaa aaa gcc ctg aag cag cgt ttc ctc aag        330
His Pro Pro Gly Pro Ser Lys Lys Ala Leu Lys Gln Arg Phe Leu Lys
                 30                  35                  40 ctg ctg ccg tgc tgc ggg ccc caa gcc ctg ccc tca gtc agt gaa aac        378
Leu Leu Pro Cys Cys Gly Pro Gln Ala Leu Pro Ser Val Ser Glu Asn
             45                  50                  55 agc gta gag gat gag ttt gaa tta tcc acg gtg tgt cac cga cct gag        426
Ser Val Glu Asp Glu Phe Glu Leu Ser Thr Val Cys His Arg Pro Glu
         60                  65                  70 ggc ctg gaa caa ctc cag gaa cag acc aag ttc aca cgc aga gag ctg        474
Gly Leu Glu Gln Leu Gln Glu Gln Thr Lys Phe Thr Arg Arg Glu Leu
     75                  80                  85 cag gtc ctg tac cga ggc ttc aag aac gaa tgc ccc agt ggg att gtc        522
Gln Val Leu Tyr Arg Gly Phe Lys Asn Glu Cys Pro Ser Gly Ile Val
 90                  95                 100                 105 aac gag gag aac ttc aag cag att tat tct cag ttc ttt ccc caa gga        570
Asn Glu Glu Asn Phe Lys Gln Ile Tyr Ser Gln Phe Phe Pro Gln Gly
                110                 115                 120 gac tcc agc aac tat gct act ttt ctc ttc aat gcc ttt gac acc aac        618
Asp Ser Ser Asn Tyr Ala Thr Phe Leu Phe Asn Ala Phe Asp Thr Asn
            125                 130                 135 cac gat ggc tct gtc agt ttt gag gac ttt gtg gct ggt ttg tcg gtg        666
His Asp Gly Ser Val Ser Phe Glu Asp Phe Val Ala Gly Leu Ser Val
        140                 145                 150 att ctt cgg ggg acc ata gat gat aga ctg agc tgg gct ttc aac tta       714
Ile Leu Arg Gly Thr Ile Asp Asp Arg Leu Ser Trp Ala Phe Asn Leu
    155                 160                 165 tat gac ctc aac aag gac ggc tgt atc aca aag gag gaa atg ctt gac       762
Tyr Asp Leu Asn Lys Asp Gly Cys Ile Thr Lys Glu Glu Met Leu Asp
170                 175                 180                 185 att atg aag tcc atc tat gac atg atg ggc aag tac aca tac cct gcc       810
Ile Met Lys Ser Ile Tyr Asp Met Met Gly Lys Tyr Thr Tyr Pro Ala
                190                 195                 200 ctc cgg gag gag gcc cca aga gaa cac gtg gag agc ttc ttc cag aag       858
Leu Arg Glu Glu Ala Pro Arg Glu His Val Glu Ser Phe Phe Gln Lys
            205                 210                 215 atg gac agg aac aag gac ggc gtg gtg acc atc gag gaa ttc atc gag       906
Met Asp Arg Asn Lys Asp Gly Val Val Thr Ile Glu Glu Phe Ile Glu
        220                 225                 230 tct tgt caa cag gac gag aac atc atg agg tcc atg cag ctc tca ccc       954
Ser Cys Gln Gln Asp Glu Asn Ile Met Arg Ser Met Gln Leu Ser Pro
    235                 240                 245 ctt ctc aac tgatacctag tgctgaggac acccctggtg tagggaccaa              1003
Leu Leu Asn
250 gtggttctcc accttctagt cccactctag aaaccacatt agacagaagg tctcctgcta     1063 tggtgctttc cccatcccta atctcttaga tttcctcaa gactcccttc tcagagaaca      1123 cgctctgtcc atgtccccag ctggcttctc agcctagcct tgagggccc tgtggggagg      1183 cggggacaag aaagcagaaa agtcttggcc ccgagccagt ggttaggtcc taggaattgg     1243
```

-continued

```
ctggagtgga ggccagaaag cctgggcaga tgatgagagc ccagctgggc tgtcactgca   1303
ggttccgggg cctacagccc tgggtcagca gagtatgagt tcccagactt tccagaaggt   1363
ccttagcaat gtcccagaaa ttcaccgtac acttctcagt gtcttaggag ggcccgggat   1423
ccagatgtct ggttcatccc tgaatcctct ccctccttct tgctcgtatg gtgggagtgg   1483
tggccagggg aagatgagtg gtgtcccgga tgatgcctgt caaggtccca cctcccctcc   1543
ggctgttctc atgacagctg tttggttctc catgacccct atctagatgt agaggcatgg   1603
agtgagtcag ggatttcccg aacttgagtt ttaccactcc tcctagtggc tgccttaggg   1663
gaatgggaag aacccagtgt gggggcaccc attagaatct ttgcccggct cctcacaatg   1723
ccctagggtc ccctagggta cccgctccct ctgtttagtc tacccagaga tgctcctgag   1783
ctcacctaga gggtagggac ggtaggctcc aggtccaacc tctccaggtc agcaccctgc   1843
catgctgctg ctcctcatta acaaacctgc ttgtctcctc ctgcgcccct tctcagtcag   1903
ccagggtctg aggggaaggg cctcccgttt ccccatccgt cagacatggt tgactgcttt   1963
gcatttgggg ctcttctatc tattttgtaa aataagacat cagatccaat aaaacacacg   2023
gctatgcaca aaaaaaaaaa aaaaaaaaaa aaaa                                2057
```

<210> SEQ ID NO 28
<211> LENGTH: 252
<212> TYPE: PRT
<213> ORGANISM: Simian sp.

<400> SEQUENCE: 28

```
Met Arg Gly Gln Gly Arg Lys Glu Ser Leu Ser Glu Ser Arg Asp Leu
  1               5                  10                  15

Asp Gly Ser Tyr Asp Gln Leu Thr Gly His Pro Pro Gly Pro Ser Lys
             20                  25                  30

Lys Ala Leu Lys Gln Arg Phe Leu Lys Leu Leu Pro Cys Cys Gly Pro
         35                  40                  45

Gln Ala Leu Pro Ser Val Ser Glu Asn Ser Val Glu Asp Glu Phe Glu
     50                  55                  60

Leu Ser Thr Val Cys His Arg Pro Glu Gly Leu Glu Gln Leu Gln Glu
 65                  70                  75                  80

Gln Thr Lys Phe Thr Arg Arg Glu Leu Gln Val Leu Tyr Arg Gly Phe
                 85                  90                  95

Lys Asn Glu Cys Pro Ser Gly Ile Val Asn Glu Glu Asn Phe Lys Gln
            100                 105                 110

Ile Tyr Ser Gln Phe Phe Pro Gln Gly Asp Ser Ser Asn Tyr Ala Thr
        115                 120                 125

Phe Leu Phe Asn Ala Phe Asp Thr Asn His Asp Gly Ser Val Ser Phe
    130                 135                 140

Glu Asp Phe Val Ala Gly Leu Ser Val Ile Leu Arg Gly Thr Ile Asp
145                 150                 155                 160

Asp Arg Leu Ser Trp Ala Phe Asn Leu Tyr Asp Leu Asn Lys Asp Gly
                165                 170                 175

Cys Ile Thr Lys Glu Glu Met Leu Asp Ile Met Lys Ser Ile Tyr Asp
            180                 185                 190

Met Met Gly Lys Tyr Thr Tyr Pro Ala Leu Arg Glu Glu Ala Pro Arg
        195                 200                 205

Glu His Val Glu Ser Phe Phe Gln Lys Met Asp Arg Asn Lys Asp Gly
    210                 215                 220
```

```
Val Val Thr Ile Glu Glu Phe Ile Glu Ser Cys Gln Gln Asp Glu Asn
225                 230                 235                 240

Ile Met Arg Ser Met Gln Leu Ser Pro Leu Leu Asn
                245                 250

<210> SEQ ID NO 29
<211> LENGTH: 1904
<212> TYPE: DNA
<213> ORGANISM: Rattus sp.
<220> FEATURE:
<221> NAME/KEY: CDS
<222> LOCATION: (1)..(675)

<400> SEQUENCE: 29 atg aac cac tgc cct cgc agg tgc cgg agc ccg ttg ggg cag gca gct       48
Met Asn His Cys Pro Arg Arg Cys Arg Ser Pro Leu Gly Gln Ala Ala
1               5                  10                  15 cga tct ctc tac cag ttg gta act ggg tcg ctg tcg cca gac agc gta       96
Arg Ser Leu Tyr Gln Leu Val Thr Gly Ser Leu Ser Pro Asp Ser Val
            20                  25                  30 gag gat gag ttt gaa tta tcc acg gtg tgt cac cga cct gag ggc ctg      144
Glu Asp Glu Phe Glu Leu Ser Thr Val Cys His Arg Pro Glu Gly Leu
        35                  40                  45 gaa caa ctc cag gaa cag acc aag ttc aca cgc aga gag ctg cag gtc      192
Glu Gln Leu Gln Glu Gln Thr Lys Phe Thr Arg Arg Glu Leu Gln Val
    50                  55                  60 ctg tac cga ggc ttc aag aac gaa tgc ccc agt ggg att gtc aac gag      240
Leu Tyr Arg Gly Phe Lys Asn Glu Cys Pro Ser Gly Ile Val Asn Glu
65                  70                  75                  80 gag aac ttc aag cag att tat tct cag ttc ttt ccc caa gga gac tcc      288
Glu Asn Phe Lys Gln Ile Tyr Ser Gln Phe Phe Pro Gln Gly Asp Ser
                85                  90                  95 agc aac tat gct act ttt ctc ttc aat gcc ttt gac acc aac cac gat      336
Ser Asn Tyr Ala Thr Phe Leu Phe Asn Ala Phe Asp Thr Asn His Asp
            100                 105                 110 ggc tct gtc agt ttt gag gac ttt gtg gct ggt ttg tcg gtg att ctt      384
Gly Ser Val Ser Phe Glu Asp Phe Val Ala Gly Leu Ser Val Ile Leu
        115                 120                 125 cgg ggg acc ata gat gat aga ctg agc tgg gct ttc aac tta tat gac      432
Arg Gly Thr Ile Asp Asp Arg Leu Ser Trp Ala Phe Asn Leu Tyr Asp
    130                 135                 140 ctc aac aag gac ggc tgt atc aca aag gag gaa atg ctt gac att atg      480
Leu Asn Lys Asp Gly Cys Ile Thr Lys Glu Glu Met Leu Asp Ile Met
145                 150                 155                 160 aag tcc atc tat gac atg atg ggc aag tac aca tac cct gcc ctc cgg      528
Lys Ser Ile Tyr Asp Met Met Gly Lys Tyr Thr Tyr Pro Ala Leu Arg
                165                 170                 175 gag gag gcc cca aga gaa cac gtg gag agc ttc ttc cag aag atg gac      576
Glu Glu Ala Pro Arg Glu His Val Glu Ser Phe Phe Gln Lys Met Asp
            180                 185                 190 agg aac aag gac ggc gtg gtg acc atc gag gaa ttc atc gag tct tgt      624
Arg Asn Lys Asp Gly Val Val Thr Ile Glu Glu Phe Ile Glu Ser Cys
        195                 200                 205 caa cag gac gag aac atc atg agg tcc atg cag ctc ttt gat aat gtc      672
Gln Gln Asp Glu Asn Ile Met Arg Ser Met Gln Leu Phe Asp Asn Val
    210                 215                 220 atc tagctcccca gggagagggg ttagtgtgtc ctagggtgac caggctgtag          725
Ile
225 tcctagtcca gacgaaccta accctctctc tccaggcctg tcctcatctt acctgtaccc   785
```

```
tgggggctgt agggattcaa tatcctgggg cttcagtagt ccagatccct gagctaagtc    845
acaaaagtag gcaagagtag gcaagctaaa tctgggggct tcccaacccc cgacagctct    905
caccccttct caactgatac ctagtgctga ggacacccct ggtgtaggga ccaagtggtt    965
ctccaccttc tagtcccact ctagaaacca cattagacag aaggtctcct gctatggtgc   1025
tttccccatc cctaatctct tagatttttcc tcaagactcc cttctcagag aacacgctct   1085
gtccatgtcc ccagctggct tctcagccta gcctttgagg gccctgtggg gaggcgggga   1145
caagaaagca gaaagtcttt ggccccgagc tagtggttag gtcctaggaa ttggctggag   1205
tggaggccag aaagcctggg cagatgatga gagcccagct gggctgtcac tgcaggttcc   1265
agggcctaca gccctgggtc agcagagtat gagttcccag actttccaga aggtccttag   1325
caatgtccca gaaattcacc atacacttct cagtgtcccg gatgatgcct gtcaaggtcc   1385
cacctcccct ccggctgttc tcatgacagc tgtttggttc tccatgaccc ctatctagat   1445
gtagaggcat ggagtgagtc agggatttcc cgaacttgag ttttaccact cctcctagtg   1505
gctgccttag gggaatggga agaacccagt gtgggggcac ccattagaat ctttgcccgg   1565
ttcctcacaa tgccctaggg tcccctaggg tacccgctcc ctctgtttag tctacccaga   1625
gatgctcctg agctcaccta gagggtaggg acggtaggct ccaggtccaa cctctccagg   1685
tcagcaccct gccatgctgc tgctcctcat taacaaacct gcttgtctcc tcctgcgccc   1745
cttctcagtc agccagggtc tgaggggaag ggcctcccgt ttccccatcc gtcagacatg   1805
gttgactgct ttgcattttg ggctcttcta tctattttgt aaaataagac atcagatcca   1865
ataaaacaca cggctatgca caaaaaaaaa aaaaaaaa                            1904
```

<210> SEQ ID NO 30
<211> LENGTH: 225
<212> TYPE: PRT
<213> ORGANISM: Rattus sp.

<400> SEQUENCE: 30

```
Met Asn His Cys Pro Arg Arg Cys Arg Ser Pro Leu Gly Gln Ala Ala
 1               5                  10                  15

Arg Ser Leu Tyr Gln Leu Val Thr Gly Ser Leu Ser Pro Asp Ser Val
                20                  25                  30

Glu Asp Glu Phe Glu Leu Ser Thr Val Cys His Arg Pro Glu Gly Leu
            35                  40                  45

Glu Gln Leu Gln Glu Gln Thr Lys Phe Thr Arg Arg Glu Leu Gln Val
        50                  55                  60

Leu Tyr Arg Gly Phe Lys Asn Glu Cys Pro Ser Gly Ile Val Asn Glu
 65                  70                  75                  80

Glu Asn Phe Lys Gln Ile Tyr Ser Gln Phe Pro Gln Gly Asp Ser
                85                  90                  95

Ser Asn Tyr Ala Thr Phe Leu Phe Asn Ala Phe Asp Thr Asn His Asp
            100                 105                 110

Gly Ser Val Ser Phe Glu Asp Phe Val Ala Gly Leu Ser Val Ile Leu
        115                 120                 125

Arg Gly Thr Ile Asp Asp Arg Leu Ser Trp Ala Phe Asn Leu Tyr Asp
    130                 135                 140

Leu Asn Lys Asp Gly Cys Ile Thr Lys Glu Glu Met Leu Asp Ile Met
145                 150                 155                 160

Lys Ser Ile Tyr Asp Met Met Gly Lys Tyr Thr Tyr Pro Ala Leu Arg
                165                 170                 175
```

```
Glu Glu Ala Pro Arg Glu His Val Glu Ser Phe Phe Gln Lys Met Asp
            180                 185                 190

Arg Asn Lys Asp Gly Val Val Thr Ile Glu Glu Phe Ile Glu Ser Cys
        195                 200                 205

Gln Gln Asp Glu Asn Ile Met Arg Ser Met Gln Leu Phe Asp Asn Val
    210                 215                 220

Ile
225

<210> SEQ ID NO 31
<211> LENGTH: 2841
<212> TYPE: DNA
<213> ORGANISM: Homo sapiens
<220> FEATURE:
<221> NAME/KEY: CDS
<222> LOCATION: (1)..(768)

<400> SEQUENCE: 31
```

| | |
|---|---|
| atg cag ccg gct aag gaa gtg aca aag gcg tcg gac ggc agc ctc ctg<br>Met Gln Pro Ala Lys Glu Val Thr Lys Ala Ser Asp Gly Ser Leu Leu<br>1              5                10               15 | 48 |
| ggg gac ctc ggg cac aca cca ctt agc aag aag gag ggt atc aag tgg<br>Gly Asp Leu Gly His Thr Pro Leu Ser Lys Lys Glu Gly Ile Lys Trp<br>               20                25              30 | 96 |
| cag agg ccg agg ctc agc cgc cag gct ttg atg aga tgc tgc ctg gtc<br>Gln Arg Pro Arg Leu Ser Arg Gln Ala Leu Met Arg Cys Cys Leu Val<br>      35               40               45 | 144 |
| aag tgg atc ctg tcc agc aca gcc cca cag ggc tca gat agc agc gac<br>Lys Trp Ile Leu Ser Ser Thr Ala Pro Gln Gly Ser Asp Ser Ser Asp<br>50              55                60 | 192 |
| agt gag ctg gag ctg tcc acg gtg cgc cac cag cca gag ggg ctg gac<br>Ser Glu Leu Glu Leu Ser Thr Val Arg His Gln Pro Glu Gly Leu Asp<br>65              70                75              80 | 240 |
| cag ctg cag gcc cag acc aag ttc acc aag aag gag ctg cag tct ctc<br>Gln Leu Gln Ala Gln Thr Lys Phe Thr Lys Lys Glu Leu Gln Ser Leu<br>               85                90              95 | 288 |
| tac agg ggc ttt aag aat gag tgt ccc acg ggc ctg gtg gac gaa gac<br>Tyr Arg Gly Phe Lys Asn Glu Cys Pro Thr Gly Leu Val Asp Glu Asp<br>             100              105             110 | 336 |
| acc ttc aaa ctc att tac gcg cag ttc ttc cct cag gga gat gcc acc<br>Thr Phe Lys Leu Ile Tyr Ala Gln Phe Phe Pro Gln Gly Asp Ala Thr<br>            115              120             125 | 384 |
| acc tat gca cac ttc ctc ttc aac gcc ttt gat gcg gac ggg aac ggg<br>Thr Tyr Ala His Phe Leu Phe Asn Ala Phe Asp Ala Asp Gly Asn Gly<br>     130              135             140 | 432 |
| gcc atc cac ttt gag gac ttt gtg gtt ggc ctc tcc atc ctg ctg cgg<br>Ala Ile His Phe Glu Asp Phe Val Val Gly Leu Ser Ile Leu Leu Arg<br>145            150              155              160 | 480 |
| ggc aca gtc cac gag aag ctc aag tgg gcc ttt aat ctc tac gac att<br>Gly Thr Val His Glu Lys Leu Lys Trp Ala Phe Asn Leu Tyr Asp Ile<br>               165             170             175 | 528 |
| aac aag gat ggc tac atc acc aaa gag gag atg ctg gcc atc atg aag<br>Asn Lys Asp Gly Tyr Ile Thr Lys Glu Glu Met Leu Ala Ile Met Lys<br>            180              185             190 | 576 |
| tcc atc tat gac atg atg ggc cgc cac acc tac ccc atc ctg cgg gag<br>Ser Ile Tyr Asp Met Met Gly Arg His Thr Tyr Pro Ile Leu Arg Glu<br>     195              200             205 | 624 |
| gac gcc ccg gcg gag cac gtg gag agg ttc ttc gag aaa atg gac cgg<br>Asp Ala Pro Ala Glu His Val Glu Arg Phe Phe Glu Lys Met Asp Arg<br>210            215              220 | 672 |

| | |
|---|---|
| aac cag gat ggg gta gtg acc att gaa gag ttc ctg gag gcc tgt cag<br>Asn Gln Asp Gly Val Val Thr Ile Glu Glu Phe Leu Glu Ala Cys Gln<br>225                  230                   235                  240 | 720 |
| aag gat gag aac atc atg agc tcc atg cag ctg ttt gag aat gtc atc<br>Lys Asp Glu Asn Ile Met Ser Ser Met Gln Leu Phe Glu Asn Val Ile<br>                  245                   250                   255 | 768 |
| taggacacgt ccaaaggagt gcatggccac agccacctcc accccaaga aacctccatc | 828 |
| ctgccaggag cagcctccaa gaaactttta aaaatagat ttgcaaaaag tgaacagatt | 888 |
| gctacacaca cacacacaca cacacacaca cacacacaca cacagccatt catctgggct | 948 |
| ggcagagggg acagagttca gggagggggct gagtctggct aggggccgag tccaggagcc | 1008 |
| ccagccagcc cttcccaggc cagcgaggcg aggctgcctc tgggtgagtg gctgacagag | 1068 |
| caggtctgca ggccaccagc tgctggatgt caccaagaag gggctcgagt gcccctgcag | 1128 |
| gggagggtcc aatctccggt gtgagcccac ctcgtcccgt tctccattct gctttcttgc | 1188 |
| cacacagtgg gccggcccca ggctcccctg gtctcctccc cgtagccact ctctgcccac | 1248 |
| tacctatgct tctagaaagc ccctcacctc aggacccccag agggaccagc tgggggggcag | 1308 |
| gggggagagg gggtaatgga ggccaagcct gcagctttct ggaaattctt ccctgggggt | 1368 |
| cccaggatcc cctgctactc cactgacctg gaagagctgg gtaccaggcc acccactgtg | 1428 |
| gggcaagcct gagtggtgag gggccactgg gccccattct ccctccatgg caggaaggcg | 1488 |
| ggggatttca gtttaggga ttgggtcgtg gtggagaatc tgagggcact ctctgccagc | 1548 |
| tccacagggt gggatgagcc tctccttgcc ccagtcctgg ttcagtggga atgcagtggg | 1608 |
| tggggctgta cacaccctcc agcacagact gttccctcca aggtcctctt aggtcccggg | 1668 |
| aggaacgtgg ttcagagact ggcagccagg gagcccgggg cagagctcag aggagtctgg | 1728 |
| gaagggggcgt gtccctcctc ttcctgtagt gcccctccca tgcccagca gcttggctga | 1788 |
| gccccctctc ctgaagcagt gtcgccgtcc ctctgccttg cacaaaaagc acaagcattc | 1848 |
| cttagcagct caggcgcagc cctagtggga gcccagcaca ctgcttctcg gaggccaggc | 1908 |
| cctcctgctg gctgaggctt gggcccagta gccccaatat ggtggccctg ggaagaggc | 1968 |
| cttgggggtc tgctctgtgc ctgggatcag tggggcccca aagcccagcc cggctgacca | 2028 |
| acattcaaaa gcacaaaccc tggggactct gcttggctgt cccctccatc tggggatgga | 2088 |
| gaatgccagc ccaaagctgg agccaatggt gagggctgag agggctgtgg ctgggtggtc | 2148 |
| agcagaaacc cccaggagga gagagatgct gctcccgcct gattgggcc tcacccagaa | 2208 |
| ggaacccggt cccaggccgc atggcccctc caggaacatt cccacataat acattccatc | 2268 |
| acagccagcc cagctccact cagggctggc ccggggagtc cccgtgtgcc ccaagaggct | 2328 |
| agccccaggg tgagcagggc cctcagagga aggcagtat ggcggaggcc atggggccc | 2388 |
| ctcggcattc acacacagcc tggcctcccc tgcggagctg catggacgcc tggctccagg | 2448 |
| ctccaggctg actgggggcc tctgcctcca ggagggcatc agctttccct ggctcaggga | 2508 |
| tcttctccct cccctcaccc gctgcccagc cctcccagct ggtgtcactc tgcctctaag | 2568 |
| gccaaggcct caggagagca tcaccaccac acccctgccg gccttggcct tggggccaga | 2628 |
| ctggctgcac agcccaacca ggagggtct gcctcccacg ctgggacaca gaccggccgc | 2688 |
| atgtctgcat ggcagaagcg tctcccttgg ccacggcctg ggagggtggt tcctgttctc | 2748 |
| agcatccact aatattcagt cctgtatatt ttaataaaat aaacttgaca aaggaaaaaa | 2808 |
| aaaaaaaaaa aattcctgcg gccgcgttct cca | 2841 |

-continued

```
<210> SEQ ID NO 32
<211> LENGTH: 256
<212> TYPE: PRT
<213> ORGANISM: Homo sapiens

<400> SEQUENCE: 32

Met Gln Pro Ala Lys Glu Val Thr Lys Ala Ser Asp Gly Ser Leu Leu
  1               5                  10                  15

Gly Asp Leu Gly His Thr Pro Leu Ser Lys Lys Glu Gly Ile Lys Trp
             20                  25                  30

Gln Arg Pro Arg Leu Ser Arg Gln Ala Leu Met Arg Cys Cys Leu Val
         35                  40                  45

Lys Trp Ile Leu Ser Ser Thr Ala Pro Gln Gly Ser Asp Ser Ser Asp
 50                  55                  60

Ser Glu Leu Glu Leu Ser Thr Val Arg His Gln Pro Glu Gly Leu Asp
 65                  70                  75                  80

Gln Leu Gln Ala Gln Thr Lys Phe Thr Lys Lys Glu Leu Gln Ser Leu
                 85                  90                  95

Tyr Arg Gly Phe Lys Asn Glu Cys Pro Thr Gly Leu Val Asp Glu Asp
            100                 105                 110

Thr Phe Lys Leu Ile Tyr Ala Gln Phe Phe Pro Gln Gly Asp Ala Thr
        115                 120                 125

Thr Tyr Ala His Phe Leu Phe Asn Ala Phe Asp Ala Asp Gly Asn Gly
    130                 135                 140

Ala Ile His Phe Glu Asp Phe Val Val Gly Leu Ser Ile Leu Leu Arg
145                 150                 155                 160

Gly Thr Val His Glu Lys Leu Lys Trp Ala Phe Asn Leu Tyr Asp Ile
                165                 170                 175

Asn Lys Asp Gly Tyr Ile Thr Lys Glu Glu Met Leu Ala Ile Met Lys
            180                 185                 190

Ser Ile Tyr Asp Met Met Gly Arg His Thr Tyr Pro Ile Leu Arg Glu
        195                 200                 205

Asp Ala Pro Ala Glu His Val Glu Arg Phe Phe Glu Lys Met Asp Arg
    210                 215                 220

Asn Gln Asp Gly Val Val Thr Ile Glu Glu Phe Leu Glu Ala Cys Gln
225                 230                 235                 240

Lys Asp Glu Asn Ile Met Ser Ser Met Gln Leu Phe Glu Asn Val Ile
                245                 250                 255

<210> SEQ ID NO 33
<211> LENGTH: 442
<212> TYPE: DNA
<213> ORGANISM: Rattus sp.
<220> FEATURE:
<221> NAME/KEY: CDS
<222> LOCATION: (1)..(327)

<400> SEQUENCE: 33 ttt gag gac ttt gtg gtt ggg ctc tcc atc ctg ctt cga ggg acc gtc      48
Phe Glu Asp Phe Val Val Gly Leu Ser Ile Leu Leu Arg Gly Thr Val
  1               5                  10                  15 cat gag aag ctc aag tgg gcc ttc aat ctc tac gac atc aac aag gac      96
His Glu Lys Leu Lys Trp Ala Phe Asn Leu Tyr Asp Ile Asn Lys Asp
             20                  25                  30 ggt tac atc acc aaa gag gag atg ctg gcc atc atg aag tcc atc tac     144
Gly Tyr Ile Thr Lys Glu Glu Met Leu Ala Ile Met Lys Ser Ile Tyr
         35                  40                  45 gac atg atg ggc cgc cac acc tac cct atc ctg cgg gag gac gca cct     192
```

```
Asp Met Met Gly Arg His Thr Tyr Pro Ile Leu Arg Glu Asp Ala Pro
     50                  55                  60 ctg gag cat gtg gag agg ttc ttc cag aaa atg gac agg aac cag gat      240
Leu Glu His Val Glu Arg Phe Phe Gln Lys Met Asp Arg Asn Gln Asp
 65                  70                  75                  80 gga gta gtg act att gat gaa ttt ctg gag act tgt cag aag gac gag      288
Gly Val Val Thr Ile Asp Glu Phe Leu Glu Thr Cys Gln Lys Asp Glu
                 85                  90                  95 aac atc atg agc tcc atg cag ctg ttt gag aac gtc atc taggacatgt       337
Asn Ile Met Ser Ser Met Gln Leu Phe Glu Asn Val Ile
                100                 105 aggagggggac cctgggtggc catgggttct caacccagag aagcctcaat cctgacagga   397
gaagcctcta tgagaaacat ttttctaata tatttgcaaa aagtg                    442

<210> SEQ ID NO 34
<211> LENGTH: 109
<212> TYPE: PRT
<213> ORGANISM: Rattus sp.

<400> SEQUENCE: 34

Phe Glu Asp Phe Val Val Gly Leu Ser Ile Leu Leu Arg Gly Thr Val
 1               5                  10                  15

His Glu Lys Leu Lys Trp Ala Phe Asn Leu Tyr Asp Ile Asn Lys Asp
                 20                  25                  30

Gly Tyr Ile Thr Lys Glu Glu Met Leu Ala Ile Met Lys Ser Ile Tyr
             35                  40                  45

Asp Met Met Gly Arg His Thr Tyr Pro Ile Leu Arg Glu Asp Ala Pro
     50                  55                  60

Leu Glu His Val Glu Arg Phe Phe Gln Lys Met Asp Arg Asn Gln Asp
 65                  70                  75                  80

Gly Val Val Thr Ile Asp Glu Phe Leu Glu Thr Cys Gln Lys Asp Glu
                 85                  90                  95

Asn Ile Met Ser Ser Met Gln Leu Phe Glu Asn Val Ile
                100                 105

<210> SEQ ID NO 35
<211> LENGTH: 2644
<212> TYPE: DNA
<213> ORGANISM: Mus musculus
<220> FEATURE:
<221> NAME/KEY: CDS
<222> LOCATION: (49)..(816)

<400> SEQUENCE: 35
cgggctgcaa agcgggaaga ttagtgacgg tcccttcag cagcagag atg cag agg      57
                                                    Met Gln Arg
                                                     1 acc aag gaa gcc gtg aag gca tca gat ggc aac ctc ctg gga gat cct      105
Thr Lys Glu Ala Val Lys Ala Ser Asp Gly Asn Leu Leu Gly Asp Pro
 5                  10                  15 ggg cgc ata cca ctg agc aag agg gaa agc atc aag tgg caa agg cca      153
Gly Arg Ile Pro Leu Ser Lys Arg Glu Ser Ile Lys Trp Gln Arg Pro
 20                  25                  30                  35 cgg ttc acc cgc cag gcc ctg atg cgt tgc tgc tta atc aag tgg atc      201
Arg Phe Thr Arg Gln Ala Leu Met Arg Cys Cys Leu Ile Lys Trp Ile
                 40                  45                  50 ctg tcc agt gct gcc cca caa ggc tca gac agc agt gac agt gaa ctg      249
Leu Ser Ser Ala Ala Pro Gln Gly Ser Asp Ser Ser Asp Ser Glu Leu
             55                  60                  65
```

```
gag tta tcc acg gtg cgc cat cag cca gag ggc ttg gac cag cta caa      297
Glu Leu Ser Thr Val Arg His Gln Pro Glu Gly Leu Asp Gln Leu Gln
            70                  75                  80 gct cag acc aag ttc acc aag aag gag ctg cag tcc ctt tac cga ggc      345
Ala Gln Thr Lys Phe Thr Lys Lys Glu Leu Gln Ser Leu Tyr Arg Gly
85                  90                  95 ttc aag aat gag tgt ccc aca ggc ctg gtg gat gaa gac acc ttc aaa      393
Phe Lys Asn Glu Cys Pro Thr Gly Leu Val Asp Glu Asp Thr Phe Lys
100                 105                 110                 115 ctc att tat tcc cag ttc ttc cct cag gga gat gcc acc acc tat gca      441
Leu Ile Tyr Ser Gln Phe Phe Pro Gln Gly Asp Ala Thr Thr Tyr Ala
                120                 125                 130 cac ttc ctc ttc aat gcc ttt gat gct gat ggg aac ggg gcc atc cac      489
His Phe Leu Phe Asn Ala Phe Asp Ala Asp Gly Asn Gly Ala Ile His
            135                 140                 145 ttt gag gac ttt gtg gtt ggg ctc tcc atc ctg ctt cga ggg acg gtc      537
Phe Glu Asp Phe Val Val Gly Leu Ser Ile Leu Leu Arg Gly Thr Val
        150                 155                 160 cat gag aag ctc aag tgg gcc ttc aat ctc tat gac att aac aag gat      585
His Glu Lys Leu Lys Trp Ala Phe Asn Leu Tyr Asp Ile Asn Lys Asp
    165                 170                 175 ggt tgc atc acc aag gag gag atg ctg gcc atc atg aag tcc atc tac      633
Gly Cys Ile Thr Lys Glu Glu Met Leu Ala Ile Met Lys Ser Ile Tyr
180                 185                 190                 195 gac atg atg ggc cgc cac acc tac ccc atc ctg cgg gag gat gca ccc      681
Asp Met Met Gly Arg His Thr Tyr Pro Ile Leu Arg Glu Asp Ala Pro
                200                 205                 210 ctg gag cat gtg gag agg ttc ttt cag aaa atg gac agg aac cag gat      729
Leu Glu His Val Glu Arg Phe Phe Gln Lys Met Asp Arg Asn Gln Asp
            215                 220                 225 gga gtg gtg acc att gat gaa ttt ctg gag act tgt cag aag gat gag      777
Gly Val Val Thr Ile Asp Glu Phe Leu Glu Thr Cys Gln Lys Asp Glu
        230                 235                 240 aac atc atg aac tcc atg cag ctg ttt gag aac gtc atc taggacatgt       826
Asn Ile Met Asn Ser Met Gln Leu Phe Glu Asn Val Ile
    245                 250                 255 gggagggggac cccagtggtc attgcttctc aacccagaga agcctcaatc ctgacaggag   886
aagcctctat gagaaacatt tttctaatat atttgcaaaa agtgagcagt ttacttccaa    946
gacacagcca ccgtcacaca cagacacaga catacagaca cacacacaca cacacacaca   1006
tggttcctct ggcttggcca aggaagtggc agccagaagg caccccgcc  tattcctagg   1066 tcaataaaaa aggctgcctc tgggatggcc agccctggct agatgttacc cacaaggaac   1126
tcagagatcg agaggaccag gtctacaaag ctaaggtccc tgtgtctttt ctaccactcg   1186
ggagatcaaa ctactccctg cctatggacc catgctctta ggaagctccc agaaactcca   1246 agggacaaa  gaggggagag gtctatagga agaaatggtt ttggaagctg gcttgcagc    1306 cttatgctaa tgatcacctg gggtcctgga acccgagtgc caggctacct actatgccgt   1366
gagcttagat agtgaggggc cattggacta agacctcctg taagagtggg gcaggattga   1426 ggttttttgga gaaactgagg aaacaatttg tccataccac tgggtgaaga ctgctggcca  1486
gtgggaatgt ggctggtgga gatttcccaa cttccagcac caggatggcc tctccaaggt   1546
cctctttgat tccctgggga gatcacctgg ctcatagact gacaaccagg gaactgggct   1606
gaaatgggag gtctggtagg gggcatcccc ctccttttcc ctggccactt gccacccagt   1666
tccttaacac agtggatcgg ccacacctct gtggctgccc ttgaacagac tcatcccgac   1726
caagacaaaa aagcacaaac tcctagcagc tcaggccaag cccacaaggg aaggcctggg   1786
```

-continued

```
tccctgcagc cctgattcag tggccgagga agacgctcag acatccatcc tgtacctcgg      1846
agccttgggg gtctcacagc cctttcccag cccagctcgc caacattcta aagcacaaac      1906
ctgcggattc tgcttgcttg ggctgcgccc tggggattga aggccactgt taaccctaag      1966
ctggagctag ccctgagggc tggggacctg tgaccaggca acaggtcagc agaccctcag      2026
gaggagagag agctgttcct gcctccccag gcctcgccca gaaggaacag tgtcccaaga      2086
agcatgtttc ctggaggaac atccccacaa aagtacattc catcatctga agcccggtct      2146
ctgctcaggc ctgcctctga aagtccacgt gtgttcccca gaaggccagc cccaagataa      2206
gggaggtcct tagaggaagg acagggtgac aacaccccta tacacaggtg gaccccccct      2266
ctgaggactg tactgacccc atctccatcc tgaccggggc cttcctttac ccgatctaca      2326
gaccaccagt tctccctggc tcaggaccc cctgtcccc agtctgactc ttcccatcga       2386
ggtccctgtc ttgtgaaaag ccaaggccac gggaaaaggc caccactcta acctgctgca      2446
tcccttagcc tctggctgca cgcccaacct ggaggggtct gtccccttg cagggacaca       2506 gactggccgc atgtccgcat ggcagaagcg tctcccttgg gtgcagcctg gaagggtggt      2566
ttctgtctca gcgcccacca atattcagtc ctatatattt taataaaaga aacttgacaa      2626
aggaaaaaaa aaaaaaaa                                                   2644
```

<210> SEQ ID NO 36
<211> LENGTH: 256
<212> TYPE: PRT
<213> ORGANISM: Mus musculus

<400> SEQUENCE: 36

```
Met Gln Arg Thr Lys Glu Ala Val Lys Ala Ser Asp Gly Asn Leu Leu
 1               5                  10                  15

Gly Asp Pro Gly Arg Ile Pro Leu Ser Lys Arg Glu Ser Ile Lys Trp
             20                  25                  30

Gln Arg Pro Arg Phe Thr Arg Gln Ala Leu Met Arg Cys Cys Leu Ile
         35                  40                  45

Lys Trp Ile Leu Ser Ser Ala Pro Gln Gly Ser Asp Ser Ser Asp
     50                  55                  60

Ser Glu Leu Glu Leu Ser Thr Val Arg His Gln Pro Glu Gly Leu Asp
 65                  70                  75                  80

Gln Leu Gln Ala Gln Thr Lys Phe Thr Lys Lys Glu Leu Gln Ser Leu
                 85                  90                  95

Tyr Arg Gly Phe Lys Asn Glu Cys Pro Thr Gly Leu Val Asp Glu Asp
            100                 105                 110

Thr Phe Lys Leu Ile Tyr Ser Gln Phe Phe Pro Gln Gly Asp Ala Thr
        115                 120                 125

Thr Tyr Ala His Phe Leu Phe Asn Ala Phe Asp Ala Asp Gly Asn Gly
    130                 135                 140

Ala Ile His Phe Glu Asp Phe Val Val Gly Leu Ser Ile Leu Leu Arg
145                 150                 155                 160

Gly Thr Val His Glu Lys Leu Lys Trp Ala Phe Asn Leu Tyr Asp Ile
                165                 170                 175

Asn Lys Asp Gly Cys Ile Thr Lys Glu Glu Met Leu Ala Ile Met Lys
            180                 185                 190

Ser Ile Tyr Asp Met Met Gly Arg His Thr Tyr Pro Ile Leu Arg Glu
        195                 200                 205

Asp Ala Pro Leu Glu His Val Glu Arg Phe Phe Gln Lys Met Asp Arg
```

```
                210                 215                 220
Asn Gln Asp Gly Val Val Thr Ile Asp Glu Phe Leu Glu Thr Cys Gln
225                 230                 235                 240

Lys Asp Glu Asn Ile Met Asn Ser Met Gln Leu Phe Glu Asn Val Ile
                245                 250                 255

<210> SEQ ID NO 37
<211> LENGTH: 531
<212> TYPE: DNA
<213> ORGANISM: Homo sapiens
<220> FEATURE:
<221> NAME/KEY: CDS
<222> LOCATION: (1)..(336)
<220> FEATURE:
<223> OTHER INFORMATION: At position 495, n=any amino acid

<400> SEQUENCE: 37 cac gag gtg gaa agc att tcg gct cag ctg gag gag gcc agc tct aca      48
His Glu Val Glu Ser Ile Ser Ala Gln Leu Glu Glu Ala Ser Ser Thr
  1               5                  10                  15 ggc ggt ttc ctg tac gct cag aac agc acc aag cgc agc att aaa gag      96
Gly Gly Phe Leu Tyr Ala Gln Asn Ser Thr Lys Arg Ser Ile Lys Glu
                 20                  25                  30 cgg ctc atg aag ctc ttg ccc tgc tca gct gcc aaa acg tcg tct cct     144
Arg Leu Met Lys Leu Leu Pro Cys Ser Ala Ala Lys Thr Ser Ser Pro
             35                  40                  45 gct att caa aac agc gtg gaa gat gaa ctg gag atg gcc acc gtc agg     192
Ala Ile Gln Asn Ser Val Glu Asp Glu Leu Glu Met Ala Thr Val Arg
         50                  55                  60 cat cgg ccc gaa gcc ctt gag ctt ctg gaa gcc cag agc aaa ttt acc     240
His Arg Pro Glu Ala Leu Glu Leu Leu Glu Ala Gln Ser Lys Phe Thr
 65                  70                  75                  80 aag aaa gag ctt cag atc ctt tac aga gga ttt aag aac gta aga act     288
Lys Lys Glu Leu Gln Ile Leu Tyr Arg Gly Phe Lys Asn Val Arg Thr
                 85                  90                  95 ttc ttt ttg act tta cct tca cac aat tcc cag agg agc att gag aaa     336
Phe Phe Leu Thr Leu Pro Ser His Asn Ser Gln Arg Ser Ile Glu Lys
                100                 105                 110 tgagaggaaa agggggaaaa tatcccattc tatgagaagc cccatcatat gtatatttca    396
tactgatcct tcccagatag gaatataatc agtatctgtg gactttgaat ctctgtggca    456
cacccatgct ggcatactgt aattgcccat taaacaaana gttttgaga aaaaaaaaa      516 aaaaaaaaaa aaaaa                                                      531

<210> SEQ ID NO 38
<211> LENGTH: 112
<212> TYPE: PRT
<213> ORGANISM: Homo sapiens

<400> SEQUENCE: 38

His Glu Val Glu Ser Ile Ser Ala Gln Leu Glu Glu Ala Ser Ser Thr
  1               5                  10                  15

Gly Gly Phe Leu Tyr Ala Gln Asn Ser Thr Lys Arg Ser Ile Lys Glu
                 20                  25                  30

Arg Leu Met Lys Leu Leu Pro Cys Ser Ala Ala Lys Thr Ser Ser Pro
             35                  40                  45

Ala Ile Gln Asn Ser Val Glu Asp Glu Leu Glu Met Ala Thr Val Arg
         50                  55                  60

His Arg Pro Glu Ala Leu Glu Leu Leu Glu Ala Gln Ser Lys Phe Thr
 65                  70                  75                  80
```

```
Lys Lys Glu Leu Gln Ile Leu Tyr Arg Gly Phe Lys Asn Val Arg Thr
             85                  90                  95
Phe Phe Leu Thr Leu Pro Ser His Asn Ser Gln Arg Ser Ile Glu Lys
            100                 105                 110

<210> SEQ ID NO 39
<211> LENGTH: 2176
<212> TYPE: DNA
<213> ORGANISM: Homo sapiens
<220> FEATURE:
<221> NAME/KEY: CDS
<222> LOCATION: (2)..(124)

<400> SEQUENCE: 39 t gaa agg ttc ttc gag aaa atg gac cgg aac cag gat ggg gta gtg acc       49
  Glu Arg Phe Phe Glu Lys Met Asp Arg Asn Gln Asp Gly Val Val Thr
   1               5                  10                  15 att gaa gag ttc ctg gag gcc tgt cag aag gat gag aac atc atg agc        97
Ile Glu Glu Phe Leu Glu Ala Cys Gln Lys Asp Glu Asn Ile Met Ser
             20                  25                  30 tcc atg cag ctg ttt gag aat gtc atc taggacacgt ccaaggagt              144
Ser Met Gln Leu Phe Glu Asn Val Ile
         35                  40 gcatggccac agccacctcc accccaaga aacctccatc ctgccaggag cagcctccaa      204 gaaacttta aaaatagat ttgcaaaaag tgaacagatt gctacacaca cacacacaca       264
cacacacaca cacacacaca cacagccatt catctgggct ggcagagggg acagagttca    324
gggaggggct gagtctggct aggggccgag tccaggagcc ccagccagcc cttcccaggc    384
cagcgaggcg aggctgcctc tgggtgagtg gctgacagag caggtctgca ggccaccagc    444
tgctggatgt caccaagaag gggctcgagt gcccctgcag ggagggtcc aatctccggt    504 gtgagcccac ctcgtcccgt tctccattct gctttcttgc cacacagtgg gccggcccca    564
ggctcccctg gtctcctccc cgtagccact ctctgcccac tacctatgct tctagaaagc    624
ccctcacctc aggaccccag agggaccagc tgggggcag ggggagagg gggtaatgga    684 ggccaagcct gcagctttct ggaaattctt ccctgggggt cccaggatcc cctgctactc    744
cactgacctg gaagagctgg gtaccaggcc acccactgtg gggcaagcct gagtggtgag    804
gggccactgg gccccattct ccctccatgg caggaaggcg ggggatttca agtttaggga    864
ttgggtcgtg gtggagaatc tgagggcact ctctgccagc tccacagggt gggatgagcc    924
tctccttgcc ccagtcctgg ttcagtggga atgcagtggg tgggctgta cacaccctcc    984 agcacagact gttccctcca aggtcctctt aggtcccggg aggaacgtgg ttcagagact   1044
ggcagccagg gagcccgggg cagagctcag aggagtctgg gaagggcgt gtccctcctc   1104 ttcctgtagt gcccctccca tggcccagca gcttggctga ccccctctc ctgaagcagt    1164 gtcgccgtcc ctctgccttg cacaaaaagc acaagcattc cttagcagct caggcgcagc   1224
cctagtggga gcccagcaca ctgcttctcg gaggccaggc cctcctgctg gctgaggctt   1284
gggcccagta gccccaatat ggtggccctg ggaagaggc cttggggtc tgctctgtgc    1344 ctgggatcag tggggcccca aagcccagcc cggctgacca acattcaaaa gcacaaaccc   1404
tggggactct gcttggctgt cccctccatc tggggatgga gaatgccagc caaagctgg    1464 agccaatggt gagggctgag agggctgtgg ctgggtggtc agcagaaacc cccaggagga   1524
gagagatgct gctcccgcct gattggggcc tcacccagaa ggaacccggt cccaggccgc   1584
atggcccctc caggaacatt cccacataat acattccatc acagccagcc cagctccact   1644
```

-continued

```
cagggctggc ccggggagtc cccgtgtgcc ccaagaggct agccccaggg tgagcagggc    1704
cctcagagga aaggcagtat ggcggaggcc atggggggccc ctcggcattc acacacagcc   1764
tggcctcccc tgcggagctg catggacgcc tggctccagg ctccaggctg actgggggcc    1824
tctgcctcca ggagggcatc agctttccct ggctcaggga tcttctccct ccctcaccc    1884 gctgcccagc cctcccagct ggtgtcactc tgcctctaag ccaaggcct caggagagca    1944 tcaccaccac accctgccg ccttggcct tggggccaga ctggctgcac agcccaacca    2004
ggaggggtct gcctcccacg ctgggacaca gaccggccgc atgtctgcat ggcagaagcg    2064
tctcccttgg ccacggcctg ggagggtggt tcctgttctc agcatccact aatattcagt   2124
cctgtatatt ttaataaaat aaacttgaca aaggaaaaaa aaaaaaaaaa aa            2176
```

<210> SEQ ID NO 40
<211> LENGTH: 41
<212> TYPE: PRT
<213> ORGANISM: Homo sapiens

<400> SEQUENCE: 40

```
Glu Arg Phe Phe Glu Lys Met Asp Arg Asn Gln Asp Gly Val Val Thr
 1               5                  10                  15

Ile Glu Glu Phe Leu Glu Ala Cys Gln Lys Asp Glu Asn Ile Met Ser
            20                  25                  30

Ser Met Gln Leu Phe Glu Asn Val Ile
         35                  40
```

<210> SEQ ID NO 41
<211> LENGTH: 2057
<212> TYPE: DNA
<213> ORGANISM: Rattus sp.
<220> FEATURE:
<221> NAME/KEY: CDS
<222> LOCATION: (208)..(963)

<400> SEQUENCE: 41

```
tgctgcccaa ggctcctgct cctgccccag gactctgagg tgggccctaa aacccagcgc    60
tctctaaaga aaagccttgc cagccctac tcccggcccc caaccccagc aggtcgctgc     120
gccgccaggg ggcgctgtgt gagcgcccta ttctggccac ccggcgcccc ctcccacggc    180
ccaggcggga gcggggcgcc gggggcc atg cgg ggc caa ggc aga aag gag agt    234
                               Met Arg Gly Gln Gly Arg Lys Glu Ser
                                 1               5 ttg tcc gaa tcc cga gat ctg gac ggc tcc tat gac cag ctt acg ggc      282
Leu Ser Glu Ser Arg Asp Leu Asp Gly Ser Tyr Asp Gln Leu Thr Gly
 10              15                  20                  25 cac cct cca ggg ccc agt aaa aaa gcc ctg aag cag cgt ttc ctc aag      330
His Pro Pro Gly Pro Ser Lys Lys Ala Leu Lys Gln Arg Phe Leu Lys
            30                  35                  40 ctg ctg ccg tgc tgc ggg ccc caa gcc ctg ccc tca gtc agt gaa aac      378
Leu Leu Pro Cys Cys Gly Pro Gln Ala Leu Pro Ser Val Ser Glu Asn
        45                  50                  55 agc gta gag gat gag ttt gaa tta tcc acg gtg tgt cac cga cct gag      426
Ser Val Glu Asp Glu Phe Glu Leu Ser Thr Val Cys His Arg Pro Glu
    60                  65                  70 ggc ctg gaa caa ctc cag gaa cag acc aag ttc aca cgc aga gag ctg      474
Gly Leu Glu Gln Leu Gln Glu Gln Thr Lys Phe Thr Arg Arg Glu Leu
 75                  80                  85 cag gtc ctg tac cga ggc ttc aag aac gaa tgc ccc agt ggg att gtc      522
Gln Val Leu Tyr Arg Gly Phe Lys Asn Glu Cys Pro Ser Gly Ile Val
            90                  95                 100
```

```
               90                  95                 100                 105
aac gag gag aac ttc aag cag att tat tct cag ttc ttt ccc caa gga              570
Asn Glu Glu Asn Phe Lys Gln Ile Tyr Ser Gln Phe Phe Pro Gln Gly
                    110                 115                 120 gac tcc agc aac tat gct act ttt ctc ttc aat gcc ttt gac acc aac              618
Asp Ser Ser Asn Tyr Ala Thr Phe Leu Phe Asn Ala Phe Asp Thr Asn
            125                 130                 135 cac gat ggc tct gtc agt ttt gag gac ttt gtg gct ggt ttg tcg gtg              666
His Asp Gly Ser Val Ser Phe Glu Asp Phe Val Ala Gly Leu Ser Val
            140                 145                 150 att ctt cgg ggg acc ata gat gat aga ctg agc tgg gct ttc aac tta              714
Ile Leu Arg Gly Thr Ile Asp Asp Arg Leu Ser Trp Ala Phe Asn Leu
    155                 160                 165 tat gac ctc aac aag gac ggc tgt atc aca aag gag gaa atg ctt gac              762
Tyr Asp Leu Asn Lys Asp Gly Cys Ile Thr Lys Glu Glu Met Leu Asp
170                 175                 180                 185 att atg aag tcc atc tat gac atg atg ggc aag tac aca tac cct gcc              810
Ile Met Lys Ser Ile Tyr Asp Met Met Gly Lys Tyr Thr Tyr Pro Ala
                190                 195                 200 ctc cgg gag gag gcc cca aga gaa cac gtg gag agc ttc ttc cag aag              858
Leu Arg Glu Glu Ala Pro Arg Glu His Val Glu Ser Phe Phe Gln Lys
            205                 210                 215 atg gac agg aac aag gac ggc gtg gtg acc atc gag gaa ttc atc gag              906
Met Asp Arg Asn Lys Asp Gly Val Val Thr Ile Glu Glu Phe Ile Glu
            220                 225                 230 tct tgt caa cag gac gag aac atc atg agg tcc atg cag ctc tca ccc              954
Ser Cys Gln Gln Asp Glu Asn Ile Met Arg Ser Met Gln Leu Ser Pro
    235                 240                 245 ctt ctc aac tgatacctag tgctgaggac accctggtg tagggaccaa                      1003
Leu Leu Asn
250 gtggttctcc accttctagt cccactctag aaaccacatt agacagaagg tctcctgcta           1063 tggtgctttc cccatcccta atctcttaga ttttcctcaa gactcccttc tcagagaaca           1123 cgctctgtcc atgtccccag ctggcttctc agcctagcct ttgagggccc tgtggggagg           1183 cggggacaag aaagcagaaa agtcttggcc ccgagccagt ggttaggtcc taggaattgg           1243 ctggagtgga ggccagaaag cctgggcaga tgatgagagc ccagctgggc tgtcactgca           1303 ggttccgggg cctacagccc tgggtcagca gagtatgagt tcccagactt tccagaaggt           1363 ccttagcaat gtcccagaaa ttcaccgtac acttctcagt gtcttaggag ggcccgggat           1423 ccagatgtct ggttcatccc tgaatcctct ccctccttct tgctcgtatg gtgggagtgg           1483 tggccagggg aagatgagtg gtgtcccgga tgatgcctgt caaggtccca cctcccctcc           1543 ggctgttctc atgacagctg tttggttctc catgacccct atctagatgt agaggcatgg           1603 agtgagtcag ggatttcccg aacttgagtt ttaccactcc tcctagtggc tgccttaggg           1663 gaatgggaag aacccagtgt gggggcaccc attagaatct ttgcccggct cctcacaatg           1723 ccctagggtc ccctagggta cccgctccct ctgtttagtc tacccagaga tgctcctgag           1783 ctcacctaga gggtagggac ggtaggctcc aggtccaacc tctccaggtc agcaccctgc           1843 catgctgctg ctcctcatta acaaacctgc ttgtctcctc ctgcgcccct tctcagtcag           1903 ccagggtctg aggggaaggg cctcccgttt cccatccgt cagacatggt tgactgcttt            1963 gcattttggg ctcttctatc tattttgtaa aataagacat cagatccaat aaaacacacg           2023 gctatgcaca aaaaaaaaaa aaaaaaaaaa aaaa                                       2057
```

```
<210> SEQ ID NO 42
<211> LENGTH: 252
<212> TYPE: PRT
<213> ORGANISM: Rattus sp.

<400> SEQUENCE: 42
```

Met Arg Gly Gln Gly Arg Lys Glu Ser Leu Ser Glu Ser Arg Asp Leu
1               5                   10                  15

Asp Gly Ser Tyr Asp Gln Leu Thr Gly His Pro Pro Gly Pro Ser Lys
            20                  25                  30

Lys Ala Leu Lys Gln Arg Phe Leu Lys Leu Leu Pro Cys Cys Gly Pro
        35                  40                  45

Gln Ala Leu Pro Ser Val Ser Glu Asn Ser Val Glu Asp Phe Glu
    50                  55                  60

Leu Ser Thr Val Cys His Arg Pro Glu Gly Leu Glu Gln Leu Gln Glu
65                  70                  75                  80

Gln Thr Lys Phe Thr Arg Arg Glu Leu Gln Val Leu Tyr Arg Gly Phe
                85                  90                  95

Lys Asn Glu Cys Pro Ser Gly Ile Val Asn Glu Glu Asn Phe Lys Gln
            100                 105                 110

Ile Tyr Ser Gln Phe Phe Pro Gln Gly Asp Ser Ser Asn Tyr Ala Thr
        115                 120                 125

Phe Leu Phe Asn Ala Phe Asp Thr Asn His Asp Gly Ser Val Ser Phe
    130                 135                 140

Glu Asp Phe Val Ala Gly Leu Ser Val Ile Leu Arg Gly Thr Ile Asp
145                 150                 155                 160

Asp Arg Leu Ser Trp Ala Phe Asn Leu Tyr Asp Leu Asn Lys Asp Gly
                165                 170                 175

Cys Ile Thr Lys Glu Glu Met Leu Asp Ile Met Lys Ser Ile Tyr Asp
            180                 185                 190

Met Met Gly Lys Tyr Thr Tyr Pro Ala Leu Arg Glu Glu Ala Pro Arg
        195                 200                 205

Glu His Val Glu Ser Phe Phe Gln Lys Met Asp Arg Asn Lys Asp Gly
    210                 215                 220

Val Val Thr Ile Glu Glu Phe Ile Glu Ser Cys Gln Gln Asp Glu Asn
225                 230                 235                 240

Ile Met Arg Ser Met Gln Leu Ser Pro Leu Leu Asn
                245                 250

```
<210> SEQ ID NO 43
<211> LENGTH: 26
<212> TYPE: PRT
<213> ORGANISM: Artificial Sequence
<220> FEATURE:
<223> OTHER INFORMATION: Xaas at positions 2,5,6,9,17,25 and 26 may be
      Ile, Leu, Val or Met
<220> FEATURE:
<223> OTHER INFORMATION: Xaas at positions 3,4,7,8,16,18-20,23 and 24
      may be any amino acid
<220> FEATURE:
<223> OTHER INFORMATION: Description of Artificial Sequence: consensus
      motif

<400> SEQUENCE: 43
```

Glu Xaa Xaa Xaa Xaa Xaa Xaa Xaa Xaa Asp Lys Asp Gly Asp Gly Xaa
1               5                   10                  15

Xaa Xaa Xaa Xaa Glu Phe Xaa Xaa Xaa Xaa
            20                  25

```
<210> SEQ ID NO 44
<211> LENGTH: 40
<212> TYPE: DNA
<213> ORGANISM: Rattus sp.

<400> SEQUENCE: 44
taatacgact cactataggg actggccatc ctgctctcag                              40

<210> SEQ ID NO 45
<211> LENGTH: 40
<212> TYPE: DNA
<213> ORGANISM: Rattus sp.

<400> SEQUENCE: 45
attaaccctc actaaaggga cactactgtt taagctcaag                              40

<210> SEQ ID NO 46
<211> LENGTH: 40
<212> TYPE: DNA
<213> ORGANISM: Rattus sp.

<400> SEQUENCE: 46
taatacgact cactataggg cacctcccct ccggctgttc                              40

<210> SEQ ID NO 47
<211> LENGTH: 40
<212> TYPE: DNA
<213> ORGANISM: Rattus sp.

<400> SEQUENCE: 47
attaaccctc actaaaggga gagcagcagc atggcagggt                              40

<210> SEQ ID NO 48
<211> LENGTH: 2413
<212> TYPE: DNA
<213> ORGANISM: Simian sp.
<220> FEATURE:
<221> NAME/KEY: CDS
<222> LOCATION: (265)..(963)

<400> SEQUENCE: 48
gtcgacccac gcgtccggtg cgctgtggtt gcggggggga gccccgccag ccaaatgcca        60
ggatcagcat gagaggctgg actttagtcc aggtctgtcc tcaccccggg ggaccgccgg       120
ctttgcaggg tgcagctgcg aggaactgct cactttttc ccttgcaag tctttgttcc        180 aagcctgacg ttgctacgat tctgtaatta actccctcca ctccaaaggg gtctggaggc       240
tgggatgctc tgccagctca gagg atg ttg act ctg gag tgg gag tcc gaa          291
                          Met Leu Thr Leu Glu Trp Glu Ser Glu
                            1               5 gga ctg caa aca gtg ggt att gtt gtg att ata tgt gca tct ctg aag         339
Gly Leu Gln Thr Val Gly Ile Val Val Ile Ile Cys Ala Ser Leu Lys
 10                  15                  20                  25 ctg ctt cat ttg ctg gga ctg att gat ttt cg gaa gac agc gtg gaa          387
Leu Leu His Leu Leu Gly Leu Ile Asp Phe Ser Glu Asp Ser Val Glu
             30                  35                  40 gat gaa ctg gag atg gcc act gtc agg cat cgg cct gag gcc ctt gag         435
Asp Glu Leu Glu Met Ala Thr Val Arg His Arg Pro Glu Ala Leu Glu
         45                  50                  55 ctt ctg gaa gcc cag agc aaa ttt acc aag aaa gag ctt cag atc ctt         483
Leu Leu Glu Ala Gln Ser Lys Phe Thr Lys Lys Glu Leu Gln Ile Leu
     60                  65                  70 tac aga gga ttt aag aac gaa tgc ccc agt ggt gtt gtt aat gaa gaa         531
```

```
Tyr Arg Gly Phe Lys Asn Glu Cys Pro Ser Gly Val Val Asn Glu Glu
        75                  80                  85 acc ttc aaa gag att tac tcg cag ttc ttt cca cag gga gac tct aca    579
Thr Phe Lys Glu Ile Tyr Ser Gln Phe Phe Pro Gln Gly Asp Ser Thr
 90                  95                 100                 105 aca tat gca cat ttt ctg ttc aat gcg ttt gat acg gac cac aat gga    627
Thr Tyr Ala His Phe Leu Phe Asn Ala Phe Asp Thr Asp His Asn Gly
                110                 115                 120 gct gtg agt ttc gag gat ttc atc aaa ggt ctt tcc att ttg ctc cgg    675
Ala Val Ser Phe Glu Asp Phe Ile Lys Gly Leu Ser Ile Leu Leu Arg
            125                 130                 135 ggg aca gta caa gaa aaa ctc aat tgg gca ttt aat ctg tat gat ata    723
Gly Thr Val Gln Glu Lys Leu Asn Trp Ala Phe Asn Leu Tyr Asp Ile
        140                 145                 150 aat aaa gat ggc tac atc act aaa gag gaa atg ctt gat ata atg aaa    771
Asn Lys Asp Gly Tyr Ile Thr Lys Glu Glu Met Leu Asp Ile Met Lys
    155                 160                 165 gca ata tac gac atg atg ggt aaa tgt aca tat cct gtc ctc aaa gaa    819
Ala Ile Tyr Asp Met Met Gly Lys Cys Thr Tyr Pro Val Leu Lys Glu
170                 175                 180                 185 gat gca ccc aga caa cac gtc gaa aca ttt ttt cag aaa atg gac aaa    867
Asp Ala Pro Arg Gln His Val Glu Thr Phe Phe Gln Lys Met Asp Lys
                190                 195                 200 aat aaa gat ggg gtt gtt acc ata gat gag ttc att gaa agc tgc caa    915
Asn Lys Asp Gly Val Val Thr Ile Asp Glu Phe Ile Glu Ser Cys Gln
            205                 210                 215 aaa gat gaa aac ata atg cgc tcc atg cag ctc ttt gaa aat gtg att    963
Lys Asp Glu Asn Ile Met Arg Ser Met Gln Leu Phe Glu Asn Val Ile
        220                 225                 230 taacttgtca actagatcct gaatccaaca gacaaatgtg aactattcta ccacccttaa   1023
agtcggagct accactttta gcatagattg ctcagcttga cactgaagca tattatgcaa   1083
acaagctttg ttttaatata aagcaatccc caaaagattt gagtttctca gttataaatt   1143
tgcatccttt ccataatgcc actgagttca tgggatgttc taactcattt catactctgt   1203
gaatattcaa aagtaataga atctggcata tagttttatt gattccttag ccatgggatt   1263
attgaggctt tcacatatca gtgattttaa ataccagtg ttttttgctc tcatttgtat    1323
gtattcagtc ctaggatttt gaatggtttt ctaatatact gacatctgca tttaatttcc   1383
agaaattaaa ttaattttca tgtctgaatg ctgtaattcc atttatatac tttaagtaaa   1443
caaataagat tactacaatt aaacacatag ttccagtttc tatggccttc ccttcccacc   1503
ttctattata aattaatttt atctggtatt tttaaacatt taaaaattta tcatcagata   1563
tcagcatatg cctaattatg cctaatgaaa cttaataagc atttaatttt ccatcataca   1623
ttatagccaa ggcctatata ctatatataa ttttggattt gtttaatctt acaggctgtt   1683
ttccattgta tcatcaagtg gaagttcaag acggcatcaa acaaaacaag gatgtttaca   1743
gacatatgca aagggtcagg atatctatcc tccagtatat gttaatgctt aataacaagt   1803
aatcctaaca gcattaaagg ccaaatctgt cctctttccc ctgacttcct tacagcatgt   1863
ttatattaca agccattcag ggacaaagaa accttgacta ccccactgtc tactaggaac   1923
aaacaaacag caagcaaaat tcactttgaa agcaccagtg gttccattac attgacaact   1983
actaccaaga ttcagtagaa ataagtgct caacaactaa tccagattac aatatgattt    2043
agtgcatcat aaaattccaa caattcgat tatttttaat catctcagcc acaactgtaa    2103
agttgccaca ttactaaaga cacacacatc gtccctgttt tgtagaaata tcacaaagac   2163
```

-continued

```
caagaggcta cagaaggagg aaatttgcaa ctgtctttgc aacaataaat caggtatcta    2223
ttctggtgta gagataggat gttgaaagct gccctgctat caccagtgta gaaattaaga    2283
gtagtacaat acatgtacac tgaaatttgc catcgcgtgt ttgtgtaaac tcaatgtgca    2343
cattttgtat ttcaaaaaga aaaataaaa gcaaataaaa atgttwawaa mwmwaaaaaa     2403
aaaaaaaaaa                                                           2413
```

<210> SEQ ID NO 49
<211> LENGTH: 233
<212> TYPE: PRT
<213> ORGANISM: Simian sp.

<400> SEQUENCE: 49

```
Met Leu Thr Leu Glu Trp Glu Ser Glu Gly Leu Gln Thr Val Gly Ile
 1               5                  10                  15

Val Val Ile Ile Cys Ala Ser Leu Lys Leu Leu His Leu Leu Gly Leu
                20                  25                  30

Ile Asp Phe Ser Glu Asp Ser Val Glu Asp Glu Leu Glu Met Ala Thr
            35                  40                  45

Val Arg His Arg Pro Glu Ala Leu Glu Leu Leu Glu Ala Gln Ser Lys
        50                  55                  60

Phe Thr Lys Lys Glu Leu Gln Ile Leu Tyr Arg Gly Phe Lys Asn Glu
 65                  70                  75                  80

Cys Pro Ser Gly Val Val Asn Glu Glu Thr Phe Lys Glu Ile Tyr Ser
                85                  90                  95

Gln Phe Phe Pro Gln Gly Asp Ser Thr Thr Tyr Ala His Phe Leu Phe
            100                 105                 110

Asn Ala Phe Asp Thr Asp His Asn Gly Ala Val Ser Phe Glu Asp Phe
        115                 120                 125

Ile Lys Gly Leu Ser Ile Leu Leu Arg Gly Thr Val Gln Glu Lys Leu
    130                 135                 140

Asn Trp Ala Phe Asn Leu Tyr Asp Ile Asn Lys Asp Gly Tyr Ile Thr
145                 150                 155                 160

Lys Glu Glu Met Leu Asp Ile Met Lys Ala Ile Tyr Asp Met Met Gly
                165                 170                 175

Lys Cys Thr Tyr Pro Val Leu Lys Glu Asp Ala Pro Arg Gln His Val
            180                 185                 190

Glu Thr Phe Phe Gln Lys Met Asp Lys Asn Lys Asp Gly Val Val Thr
        195                 200                 205

Ile Asp Glu Phe Ile Glu Ser Cys Gln Lys Asp Glu Asn Ile Met Arg
    210                 215                 220

Ser Met Gln Leu Phe Glu Asn Val Ile
225                 230
```

<210> SEQ ID NO 50
<211> LENGTH: 1591
<212> TYPE: DNA
<213> ORGANISM: Simian sp.
<220> FEATURE:
<221> NAME/KEY: CDS
<222> LOCATION: (265)..(963)

<400> SEQUENCE: 50

```
gtcgacccac gcgtccggtg cgctgtggtt gcggggggga gccccgccag ccaaatgcca     60
ggatcagcat gagaggctgg actttagtcc aggtctgtcc tcaccccggg ggaccgccgg    120
ctttgcaggg tgcagctgcg aggaactgct cactttttc cccttgcaag tctttgttcc    180
```

```
aagcctgacg ttgctacgat tctgtaatta actccctcca ctccaaaggg gtctggaggc    240
tgggatgctc tgccagctca gagg atg ttg act ctg gag tgg gag tcc gaa      291
                           Met Leu Thr Leu Glu Trp Glu Ser Glu
                            1               5 gga ctg caa aca gtg ggt att gtt gtg att ata tgt gca tct ctg aag      339
Gly Leu Gln Thr Val Gly Ile Val Val Ile Ile Cys Ala Ser Leu Lys
 10              15                  20                  25 ctg ctt cat ttg ctg gga ctg att gat ttt tcg gaa gac agc gtg gaa      387
Leu Leu His Leu Leu Gly Leu Ile Asp Phe Ser Glu Asp Ser Val Glu
                 30                  35                  40 gat gaa ctg gag atg gcc act gtc agg cat cgg cct gag gcc ctt gag      435
Asp Glu Leu Glu Met Ala Thr Val Arg His Arg Pro Glu Ala Leu Glu
             45                  50                  55 ctt ctg gaa gcc cag agc aaa ttt acc aag aaa gag ctt cag atc ctt      483
Leu Leu Glu Ala Gln Ser Lys Phe Thr Lys Lys Glu Leu Gln Ile Leu
         60                  65                  70 tac aga gga ttt aag aac gaa tgc ccc agt ggt gtt gtt aat gaa gaa      531
Tyr Arg Gly Phe Lys Asn Glu Cys Pro Ser Gly Val Val Asn Glu Glu
     75                  80                  85 acc ttc aaa gag att tac tcg cag ttc ttt cca cag gga gac tct aca      579
Thr Phe Lys Glu Ile Tyr Ser Gln Phe Phe Pro Gln Gly Asp Ser Thr
 90                  95                 100                 105 aca tat gca cat ttt ctg ttc aat gcg ttt gat acg gac cac aat gga      627
Thr Tyr Ala His Phe Leu Phe Asn Ala Phe Asp Thr Asp His Asn Gly
                110                 115                 120 gct gtg agt ttc gag gat ttc atc aaa ggt ctt tcc att ttg ctc cgg      675
Ala Val Ser Phe Glu Asp Phe Ile Lys Gly Leu Ser Ile Leu Leu Arg
            125                 130                 135 ggg aca gta caa gaa aaa ctc aat tgg gca ttt aat ctg tat gat ata      723
Gly Thr Val Gln Glu Lys Leu Asn Trp Ala Phe Asn Leu Tyr Asp Ile
        140                 145                 150 aat aaa gat ggc tac atc act aaa gag gaa atg ctt gat ata atg aaa      771
Asn Lys Asp Gly Tyr Ile Thr Lys Glu Glu Met Leu Asp Ile Met Lys
155                 160                 165 gca ata tac gac atg atg ggt aaa tgt aca tat cct gtc ctc aaa gaa      819
Ala Ile Tyr Asp Met Met Gly Lys Cys Thr Tyr Pro Val Leu Lys Glu
170                 175                 180                 185 gat gca ccc aga caa cac gtc gaa aca ttt ttt cag gct gtt ttc cat      867
Asp Ala Pro Arg Gln His Val Glu Thr Phe Phe Gln Ala Val Phe His
                190                 195                 200 tgt atc atc aag tgg aag ttc aag acg gca tca aac aaa aca agg atg      915
Cys Ile Ile Lys Trp Lys Phe Lys Thr Ala Ser Asn Lys Thr Arg Met
            205                 210                 215 ttt aca gac ata tgc aaa ggg tca gga tat cta tcc tcc agt ata tgt      963
Phe Thr Asp Ile Cys Lys Gly Ser Gly Tyr Leu Ser Ser Ser Ile Cys
        220                 225                 230 taatgcttaa taacaagtaa tcctaacagc attaaaggcc aaatctgtcc tctttcccct   1023
gacttcctta cagcatgttt atattacaag ccattcaggg acaagaaac cttgactacc    1083 ccactgtcta ctaggaacaa acaaacagca agcaaaattc actttgaaag caccagtggt   1143
tccattacat tgacaactac taccaagatt cagtagaaaa taagtgctca acaactaatc   1203
cagattacaa tatgatttag tgcatcataa aattccaaca attcagatta tttttaatca   1263
tctcagccac aactgtaaag ttgccacatt actaaagaca cacacatcgt ccctgttttg   1323
tagaaatatc acaaagacca agaggctaca gaaggaggaa atttgcaact gtctttgcaa   1383
caataaatca ggtatctatt ctggtgtaga gataggatgt tgaaagctgc cctgctatca   1443
```

-continued

```
ccagtgtaga aattaagagt agtacaatac atgtacactg aaatttgcca tcgcgtgttt    1503
gtgtaaactc aatgtgcaca ttttgtattt caaaaagaaa aaataaaagc aaaataaaat    1563
gttwawaamw mwaaaaaaaa aaaaaaaa                                        1591
```

<210> SEQ ID NO 51
<211> LENGTH: 233
<212> TYPE: PRT
<213> ORGANISM: Simian sp.

<400> SEQUENCE: 51

```
Met Leu Thr Leu Glu Trp Glu Ser Glu Gly Leu Gln Thr Val Gly Ile
 1               5                  10                  15

Val Val Ile Ile Cys Ala Ser Leu Lys Leu Leu His Leu Leu Gly Leu
                20                  25                  30

Ile Asp Phe Ser Glu Asp Ser Val Glu Asp Glu Leu Glu Met Ala Thr
            35                  40                  45

Val Arg His Arg Pro Glu Ala Leu Glu Leu Leu Glu Ala Gln Ser Lys
        50                  55                  60

Phe Thr Lys Lys Glu Leu Gln Ile Leu Tyr Arg Gly Phe Lys Asn Glu
65                  70                  75                  80

Cys Pro Ser Gly Val Val Asn Glu Glu Thr Phe Lys Glu Ile Tyr Ser
                85                  90                  95

Gln Phe Phe Pro Gln Gly Asp Ser Thr Thr Tyr Ala His Phe Leu Phe
            100                 105                 110

Asn Ala Phe Asp Thr Asp His Asn Gly Ala Val Ser Phe Glu Asp Phe
        115                 120                 125

Ile Lys Gly Leu Ser Ile Leu Leu Arg Gly Thr Val Gln Glu Lys Leu
    130                 135                 140

Asn Trp Ala Phe Asn Leu Tyr Asp Ile Asn Lys Asp Gly Tyr Ile Thr
145                 150                 155                 160

Lys Glu Glu Met Leu Asp Ile Met Lys Ala Ile Tyr Asp Met Met Gly
                165                 170                 175

Lys Cys Thr Tyr Pro Val Leu Lys Glu Asp Ala Pro Arg Gln His Val
            180                 185                 190

Glu Thr Phe Phe Gln Ala Val Phe His Cys Ile Ile Lys Trp Lys Phe
        195                 200                 205

Lys Thr Ala Ser Asn Lys Thr Arg Met Phe Thr Asp Ile Cys Lys Gly
    210                 215                 220

Ser Gly Tyr Leu Ser Ser Ile Cys
225                 230
```

<210> SEQ ID NO 52
<211> LENGTH: 2051
<212> TYPE: DNA
<213> ORGANISM: Rattus sp.
<220> FEATURE:
<221> NAME/KEY: CDS
<222> LOCATION: (85)..(1305)

<400> SEQUENCE: 52

```
ggtggagcta agcactcact gcggtgctgc cctgcgtctg cagagaacaa ggaaagcttc     60
tctgcagggc tgtcagctgc caaa atg aac ggc gtg gaa ggg aac aac gag       111
                             Met Asn Gly Val Glu Gly Asn Asn Glu
                               1               5 ctc cct ctc gct aac acc tcg acc tcc gcc ctt gtc ccg gaa gat ctg      159
Leu Pro Leu Ala Asn Thr Ser Thr Ser Ala Leu Val Pro Glu Asp Leu
 10              15                  20                  25
```

-continued

| | |
|---|---|
| gat ctg aag caa gac cag ccg ctc agc gag gaa act gac acg gtg cgg<br>Asp Leu Lys Gln Asp Gln Pro Leu Ser Glu Glu Thr Asp Thr Val Arg<br>30                                  35                               40 | 207 |
| gag atg gag gct gca ggt gag gcc ggt gcg gag gga ggc gcg tcc ccc<br>Glu Met Glu Ala Ala Gly Glu Ala Gly Ala Glu Gly Gly Ala Ser Pro<br>                45                            50                            55 | 255 |
| gat tcg gag cac tgc gac ccc cag ctc tgc ctc cga gtg gct gag aat<br>Asp Ser Glu His Cys Asp Pro Gln Leu Cys Leu Arg Val Ala Glu Asn<br>               60                            65                            70 | 303 |
| ggc tgt gct gcc gca gcg gga gag ggg ctg gag gat ggt ctg tct tca<br>Gly Cys Ala Ala Ala Ala Gly Glu Gly Leu Glu Asp Gly Leu Ser Ser<br>75                                  80                                85 | 351 |
| tca aag tgt ggg gac gca ccc ttg gcg tct gtg gca gcc aac gac agc<br>Ser Lys Cys Gly Asp Ala Pro Leu Ala Ser Val Ala Ala Asn Asp Ser<br>90                                  95                           100                         105 | 399 |
| aat aaa aat ggc tgt cag ctt gca ggg ccg ctc agc cct gct aag cca<br>Asn Lys Asn Gly Cys Gln Leu Ala Gly Pro Leu Ser Pro Ala Lys Pro<br>                           110                               115                           120 | 447 |
| aaa act ctg gaa gcc agt ggt gca gtg ggc ctg ggg tcg cag atg atg<br>Lys Thr Leu Glu Ala Ser Gly Ala Val Gly Leu Gly Ser Gln Met Met<br>                      125                              130                             135 | 495 |
| cca ggg ccg aag aag acc aag gta atg act acc aag ggc gcc atc tct<br>Pro Gly Pro Lys Lys Thr Lys Val Met Thr Thr Lys Gly Ala Ile Ser<br>140                              145                              150 | 543 |
| gcg act aca ggc aag gaa gga gaa gca ggg gcg gca atg cag gaa aag<br>Ala Thr Thr Gly Lys Glu Gly Glu Ala Gly Ala Ala Met Gln Glu Lys<br>               155                             160                           165 | 591 |
| aag ggg gtg cag aaa gaa aaa aag gca gct gga gga ggg aaa gac gag<br>Lys Gly Val Gln Lys Glu Lys Lys Ala Ala Gly Gly Gly Lys Asp Glu<br>170                              175                              180                         185 | 639 |
| act cgt cct aga gcc cct aag atc aat aac tgc atg gac tcc ctg gaa<br>Thr Arg Pro Arg Ala Pro Lys Ile Asn Asn Cys Met Asp Ser Leu Glu<br>                      190                               195                           200 | 687 |
| gcc atc gat caa gag ctg tca aat gta aat gcg caa gct gac agg gcc<br>Ala Ile Asp Gln Glu Leu Ser Asn Val Asn Ala Gln Ala Asp Arg Ala<br>                         205                             210                         215 | 735 |
| ttc ctc cag ctg gaa cgc aaa ttt ggg cgg atg aga agg ctc cac atg<br>Phe Leu Gln Leu Glu Arg Lys Phe Gly Arg Met Arg Arg Leu His Met<br>220                              225                              230 | 783 |
| cag cgc cga agt ttc atc atc caa aac atc cca ggt ttc tgg gtc aca<br>Gln Arg Arg Ser Phe Ile Ile Gln Asn Ile Pro Gly Phe Trp Val Thr<br>               235                             240                           245 | 831 |
| gcg ttt cgg aac cac ccg caa ctg tca ccg atg atc agt ggc caa gat<br>Ala Phe Arg Asn His Pro Gln Leu Ser Pro Met Ile Ser Gly Gln Asp<br>250                              255                              260                         265 | 879 |
| gaa gac atg atg agg tac atg atc aat tta gag gtg gag gag ctt aag<br>Glu Asp Met Met Arg Tyr Met Ile Asn Leu Glu Val Glu Glu Leu Lys<br>                      270                               275                           280 | 927 |
| cac cca aga gca ggg tgc aaa ttt aag ttc atc ttc caa agc aac ccc<br>His Pro Arg Ala Gly Cys Lys Phe Lys Phe Ile Phe Gln Ser Asn Pro<br>                         285                             290                         295 | 975 |
| tac ttc cga aat gag ggg ctg gtc aaa gag tac gag cgc aga tcc tca<br>Tyr Phe Arg Asn Glu Gly Leu Val Lys Glu Tyr Glu Arg Arg Ser Ser<br>300                              305                              310 | 1023 |
| ggt cga gtg gtg tcg ctc tct acg cca atc cgc tgg cac cgg ggt caa<br>Gly Arg Val Val Ser Leu Ser Thr Pro Ile Arg Trp His Arg Gly Gln<br>315                              320                           325 | 1071 |
| gaa ccc cag gcc cat atc cac agg aat aga gag ggg aac acg att ccc<br>Glu Pro Gln Ala His Ile His Arg Asn Arg Glu Gly Asn Thr Ile Pro | 1119 |

```
                330             335             340             345
agt ttc ttc aat tgg ttc tca gac cac agc ctc cta gaa ttc gac aga        1167
Ser Phe Phe Asn Trp Phe Ser Asp His Ser Leu Leu Glu Phe Asp Arg
                350             355             360 ata gct gaa att atc aaa ggg gag ctt tgg tcc aat ccc cta caa tac        1215
Ile Ala Glu Ile Ile Lys Gly Glu Leu Trp Ser Asn Pro Leu Gln Tyr
            365             370             375 tac ctg atg ggc gat ggg cca cgc aga gga gtt cga gtc cca cca agg        1263
Tyr Leu Met Gly Asp Gly Pro Arg Arg Gly Val Arg Val Pro Pro Arg
        380             385             390 cag cca gtg gag agt ccc agg tcc ttc agg ttc cag tct ggc                1305
Gln Pro Val Glu Ser Pro Arg Ser Phe Arg Phe Gln Ser Gly
    395             400             405 taagctctgc cctcgtgaga agctcttaca gaagagtcct taccaccttc tcagcttggc      1365
tagcagcatg cagccttctg tctgctttct cttccttgga ttgtgtcctt tggttcttct      1425
aagtctccgg tagtttcaag gttgtggctt ccaagtcttt gctcttcttt ctcttggcca      1485
tcacgatgtc ctgcatagtg ttaatggtgt tccaagtgca tggcctccaa actgcttcta      1545
tgccaagctc acgtgctgta gtttgtactg cttttctttg catggcttgg ttcctgtctg      1605
tgatcttcta ggttttttgt tttctttttt aaaagtggtt ctctatcaaa agaaagcttg      1665
acatatcctt accaagaact agccagattt catactgtgt tcccgatatc tatgtactgt      1725
gaagaactgt gagtttcgcc actgcaagat gggactgtat cccaatccag ccatcagccc      1785
aacaggacat tccaagctgt caccaactga tcctagctgt cttcctgggc ctttgccatt      1845
taccctgctt tttatctata gaatgagcag gtggctggta ggtgactact aggtaagagt      1905
gaagtattag gtgaggagtg ttttctgtca ccacattgtt cttgtaccaa tgcatcatga      1965
tcagcttgga tcagctactg actgtctgat atttctaacc cccaacacaa aaaaaaaaaa      2025
aaaaaaaaaa aaaaaaaaaa aaaaaa                                           2051

<210> SEQ ID NO 53
<211> LENGTH: 407
<212> TYPE: PRT
<213> ORGANISM: Rattus sp.

<400> SEQUENCE: 53

Met Asn Gly Val Glu Gly Asn Asn Glu Leu Pro Leu Ala Asn Thr Ser
 1               5                  10                  15

Thr Ser Ala Leu Val Pro Glu Asp Leu Asp Leu Lys Gln Asp Gln Pro
            20                  25                  30

Leu Ser Glu Glu Thr Asp Thr Val Arg Glu Met Glu Ala Ala Gly Glu
        35                  40                  45

Ala Gly Ala Glu Gly Gly Ala Ser Pro Asp Ser Glu His Cys Asp Pro
    50                  55                  60

Gln Leu Cys Leu Arg Val Ala Glu Asn Gly Cys Ala Ala Ala Gly
65                  70                  75                  80

Glu Gly Leu Glu Asp Gly Leu Ser Ser Lys Cys Gly Asp Ala Pro
                85                  90                  95

Leu Ala Ser Val Ala Ala Asn Asp Ser Asn Lys Asn Gly Cys Gln Leu
            100                 105                 110

Ala Gly Pro Leu Ser Pro Ala Lys Pro Lys Thr Leu Glu Ala Ser Gly
        115                 120                 125

Ala Val Gly Leu Gly Ser Gln Met Met Pro Gly Pro Lys Lys Thr Lys
    130                 135                 140
```

-continued

```
Val Met Thr Thr Lys Gly Ala Ile Ser Ala Thr Thr Gly Lys Glu Gly
145                 150                 155                 160

Glu Ala Gly Ala Ala Met Gln Glu Lys Lys Gly Val Gln Lys Glu Lys
                165                 170                 175

Lys Ala Ala Gly Gly Lys Asp Glu Thr Arg Pro Arg Ala Pro Lys
            180                 185                 190

Ile Asn Asn Cys Met Asp Ser Leu Glu Ala Ile Asp Gln Glu Leu Ser
        195                 200                 205

Asn Val Asn Ala Gln Ala Asp Arg Ala Phe Leu Gln Leu Glu Arg Lys
    210                 215                 220

Phe Gly Arg Met Arg Arg Leu His Met Gln Arg Ser Phe Ile Ile
225                 230                 235                 240

Gln Asn Ile Pro Gly Phe Trp Val Thr Ala Phe Arg Asn His Pro Gln
                245                 250                 255

Leu Ser Pro Met Ile Ser Gly Gln Asp Glu Asp Met Met Arg Tyr Met
            260                 265                 270

Ile Asn Leu Glu Val Glu Glu Leu Lys His Pro Arg Ala Gly Cys Lys
        275                 280                 285

Phe Lys Phe Ile Phe Gln Ser Asn Pro Tyr Phe Arg Asn Glu Gly Leu
    290                 295                 300

Val Lys Glu Tyr Glu Arg Arg Ser Ser Gly Arg Val Val Ser Leu Ser
305                 310                 315                 320

Thr Pro Ile Arg Trp His Arg Gly Gln Glu Pro Gln Ala His Ile His
                325                 330                 335

Arg Asn Arg Glu Gly Asn Thr Ile Pro Ser Phe Phe Asn Trp Phe Ser
            340                 345                 350

Asp His Ser Leu Leu Glu Phe Asp Arg Ile Ala Glu Ile Ile Lys Gly
        355                 360                 365

Glu Leu Trp Ser Asn Pro Leu Gln Tyr Tyr Leu Met Gly Asp Gly Pro
    370                 375                 380

Arg Arg Gly Val Arg Val Pro Pro Arg Gln Pro Val Glu Ser Pro Arg
385                 390                 395                 400

Ser Phe Arg Phe Gln Ser Gly
                405
```

<210> SEQ ID NO 54
<211> LENGTH: 4148
<212> TYPE: DNA
<213> ORGANISM: Homo sapiens
<220> FEATURE:
<221> NAME/KEY: CDS
<222> LOCATION: (88)..(1329)

<400> SEQUENCE: 54

```
ggggtggtgc tagacgtttc gggcagagct cggccgctgc ggaggacaag gaactctccc      60
tctcccacta gtctgacttc ttccaaa atg agc ggc ctg gat ggg ggc aac aag     114
                                Met Ser Gly Leu Asp Gly Gly Asn Lys
                                  1               5 ctc cct ctc gcc caa acc ggc ggc ctg gct gct ccc gac cat gcc tca       162
Leu Pro Leu Ala Gln Thr Gly Gly Leu Ala Ala Pro Asp His Ala Ser
 10                  15                  20                  25 gga gat ccg gac cta gac cag tgc caa ggg ctc cgt gaa gaa acc gag       210
Gly Asp Pro Asp Leu Asp Gln Cys Gln Gly Leu Arg Glu Glu Thr Glu
                 30                  35                  40 gcg aca cag gtg atg gcg aac aca ggt ggg ggc agc ctg gag acc gtt       258
Ala Thr Gln Val Met Ala Asn Thr Gly Gly Gly Ser Leu Glu Thr Val
             45                  50                  55
```

-continued

| | |
|---|---|
| gcg gag ggg ggt gca tcc cag gat cct gtc gac tgt ggc ccc gcg ctc<br>Ala Glu Gly Gly Ala Ser Gln Asp Pro Val Asp Cys Gly Pro Ala Leu<br>60 65 70 | 306 |
| cgc gtc cca gtt gcc ggg agt cgc ggc ggt gca gcg acc aaa gcc ggg<br>Arg Val Pro Val Ala Gly Ser Arg Gly Gly Ala Ala Thr Lys Ala Gly<br>75 80 85 | 354 |
| cag gag gat gct cca cct tct acg aaa ggt ctg gaa gca gcc tct gcc<br>Gln Glu Asp Ala Pro Pro Ser Thr Lys Gly Leu Glu Ala Ala Ser Ala<br>90 95 100 105 | 402 |
| gcc gag gct gct gac agc agc cag aaa aat ggc tgt cag ctt gga gag<br>Ala Glu Ala Ala Asp Ser Ser Gln Lys Asn Gly Cys Gln Leu Gly Glu<br>110 115 120 | 450 |
| ccc cgt ggc cct gct ggg cag aag gct cta gaa gcc tgt ggc gca ggg<br>Pro Arg Gly Pro Ala Gly Gln Lys Ala Leu Glu Ala Cys Gly Ala Gly<br>125 130 135 | 498 |
| ggc ttg ggg tct cag atg ata ccg ggg aag aag gcc aag gaa gtg acg<br>Gly Leu Gly Ser Gln Met Ile Pro Gly Lys Lys Ala Lys Glu Val Thr<br>140 145 150 | 546 |
| act aaa aaa cgc gcc atc tcg gca gca gtg gaa aag gag gga gaa gca<br>Thr Lys Lys Arg Ala Ile Ser Ala Ala Val Glu Lys Glu Gly Glu Ala<br>155 160 165 | 594 |
| ggg gcg gcg atg gag gaa aag aag gta gtg cag aag gaa aaa aag gtg<br>Gly Ala Ala Met Glu Glu Lys Lys Val Val Gln Lys Glu Lys Lys Val<br>170 175 180 185 | 642 |
| gca gga ggg gtg aaa gag gag aca cgg ccc agg gcc ccg aag atc aat<br>Ala Gly Gly Val Lys Glu Glu Thr Arg Pro Arg Ala Pro Lys Ile Asn<br>190 195 200 | 690 |
| aac tgc atg gac tca ctg gag gcc atc gat caa gag ttg tca aac gta<br>Asn Cys Met Asp Ser Leu Glu Ala Ile Asp Gln Glu Leu Ser Asn Val<br>205 210 215 | 738 |
| aat gcc cag gct gac agg gcc ttc ctt cag ctt gag cgc aag ttt ggc<br>Asn Ala Gln Ala Asp Arg Ala Phe Leu Gln Leu Glu Arg Lys Phe Gly<br>220 225 230 | 786 |
| cgc atg cga agg ctc cac atg cag cgc aga agt ttc att atc cag aat<br>Arg Met Arg Arg Leu His Met Gln Arg Arg Ser Phe Ile Ile Gln Asn<br>235 240 245 | 834 |
| atc cca ggt ttc tgg gtt act gcc ttt cga aac cac ccc cag ctg tca<br>Ile Pro Gly Phe Trp Val Thr Ala Phe Arg Asn His Pro Gln Leu Ser<br>250 255 260 265 | 882 |
| cct atg atc agt ggc caa gat gaa gac atg ctg agg tac atg atc aat<br>Pro Met Ile Ser Gly Gln Asp Glu Asp Met Leu Arg Tyr Met Ile Asn<br>270 275 280 | 930 |
| ttg gag gtg gag gag ctt aaa cac ccc aga gca ggc tgc aaa ttc aag<br>Leu Glu Val Glu Glu Leu Lys His Pro Arg Ala Gly Cys Lys Phe Lys<br>285 290 295 | 978 |
| ttc atc ttt cag ggc aac ccc tac ttc cga aat gag ggg ctt gtc aag<br>Phe Ile Phe Gln Gly Asn Pro Tyr Phe Arg Asn Glu Gly Leu Val Lys<br>300 305 310 | 1026 |
| gaa tat gaa cgc aga tcc tct ggc cgg gtg gtg tct ctt tcc act cca<br>Glu Tyr Glu Arg Arg Ser Ser Gly Arg Val Val Ser Leu Ser Thr Pro<br>315 320 325 | 1074 |
| atc cgc tgg cac cga ggc caa gac ccc cag gct cat atc cac aga aac<br>Ile Arg Trp His Arg Gly Gln Asp Pro Gln Ala His Ile His Arg Asn<br>330 335 340 345 | 1122 |
| cgg gaa ggg aac act atc cct agt ttc ttc aac tgg ttt tca gac cac<br>Arg Glu Gly Asn Thr Ile Pro Ser Phe Phe Asn Trp Phe Ser Asp His<br>350 355 360 | 1170 |
| agc ctt cta gaa ttc gac aga att gca gag att atc aaa gga gaa ctg<br>Ser Leu Leu Glu Phe Asp Arg Ile Ala Glu Ile Ile Lys Gly Glu Leu | 1218 |

-continued

|  |  |
|---|---:|
| ```
                   365                 370                 375
tgg ccc aat ccc cta caa tac tac ctg atg ggt gaa ggg ccc cgt aga
Trp Pro Asn Pro Leu Gln Tyr Tyr Leu Met Gly Glu Gly Pro Arg Arg
        380                 385                 390
``` | 1266 |
| ```
gga att cga ggc cca cca agg cag cca gtg gag agc gcc aga tcc ttc
Gly Ile Arg Gly Pro Pro Arg Gln Pro Val Glu Ser Ala Arg Ser Phe
    395                 400                 405
``` | 1314 |
| ```
agg ttc cag tct ggc taatctctgt cctgtgagaa gcttctgcac aagtttcctt
Arg Phe Gln Ser Gly
410
``` | 1369 |
| accacctcct cttggaccta tgcttggcca acagcatgca gtcttccatc tgctttctct | 1429 |
| tcatactgtg gattatcttt tcctttggtt ctaaatcttc agtaatcggt tgcaagattg | 1489 |
| ttggcttacc tgcctgtgcc attcttcctc tgggccttca tgcttttctg cattgtgtta | 1549 |
| acatgtttca gtgcatggc cttctacggc ttctatgcca agcgtatgat actatagata | 1609 |
| tagtgtacca tactgccttt cttgcatgg cttggaccct atctgtgacc atgctcttct | 1669 |
| cccaatttaa gtggttctgt accacaaaga atcttgatac attttcacaa ataactgatt | 1729 |
| gggcttcata ctttatgctg gctgtgtcct gatacccatg tacttatggt aagctatttg | 1789 |
| ggtattacca ctgcaagaca aaactgatat cttaacccgg ccatcaaccc aaattggaca | 1849 |
| ttccagacta ccaccaactg gatcccagct gccttcctgg gcttgtgcca tccaccctac | 1909 |
| tggttatctg atagaacaag ctggtggctg atgggtgact gctaggcgtg actgaggtaa | 1969 |
| tagatgaaaa gtgttctatg ttatcacatt ggttttcctg tacctttggt tactctacgt | 2029 |
| catgaccagc tgctggtgag tatgaagcct gtgctatagc ccaccctac tcactctcac | 2089 |
| cttctggttg aactttgctt aggccaccat tgtctgcctc atcaggaact atctgtagac | 2149 |
| gtagctccca gggagctcac agcaacaccc cctaccacca ggatgggcag taatatgtga | 2209 |
| cagagcccaa agcaaggctg gaacgcagtc ccttccagct tagtctttct gactcctagc | 2269 |
| caacaaacca tccttaatgt gagcaacttc tttaggcatt tcctctttc cccgcctgca | 2329 |
| cccactctga acatgacaaa agttgccaga gttggggcat tgaggaagag atatttctgg | 2389 |
| aatgtgagac ttgttatgcc tctgtctctt tctctccctc cccctcccct ctccctcccc | 2449 |
| ctctccctcc catcccttt cttcccttc actctgaagc agttttagct tattaacaga | 2509 |
| aaacaaaact ggcaaagcag gcttttgtt taatttgctc tttccctgat tgtgttcaga | 2569 |
| gagaaaggtt atgattaaat gggctccaga tctcttattg cccttattcc tccaccccac | 2629 |
| ttctttagc aaggtctgaa agtttcaaag ggagacctat aggttaattg tttagttata | 2689 |
| ggcagtgtta aattaggcag atttgacat atttatcttt ttaccccatc cattctacca | 2749 |
| aaacctgtgt atttcttgag tttttagttt gagaagctgg aaagagagag aagggcctca | 2809 |
| cagtgatggg ttcaggacgg gtcaaaggca aaggcctttg tgatgtgagc aaaggcaacc | 2869 |
| aaaacttagc ctcactccac ttttctaaag atggaaattc tttttgggc cttgactgc | 2929 |
| ttctagggta gcattttgta ggtcactctt ctcctttgta ctattttgtt tctgccctga | 2989 |
| tgtcccttgg gtctccatcc tactgcctgg ctttcttggc cctcatttct cagcttctgc | 3049 |
| atttccttcc ctgctcctaa caaatgaaga agcaggctgc agcctgcatt gtggaagatc | 3109 |
| tccagcctcc ttgtagggga taaggggatg tgtagcatct gtgtggattt tcacggacaa | 3169 |
| gttccagtag gtgggacagt gatgccgtca aggcttagtt atgatcatgt gtggtgataa | 3229 |
| agaccatcca ccatcacccct ttccccttt ggttttgaag gccttgccct aagctacctg | 3289 |
| agggtttagg aggtctgaac acacacagtg gagaggttaa tctaggttgg gaaactgagt | 3349 |

-continued

```
aaaagtccag agcaggaatg agcctgctgt ggcgtgggtt tggaaaggct cacaggaaag    3409
aacctgcagg atcaggggtg ggaggggagg ccctgaggt gctctccagg gaagaggggc    3469
tggggtttaa atagcatgct tggaggaaga ttttccttca atttttccta agtccttgaa    3529
ttcaccagta gattttgta aacaaaatgt aagtcgatgt tttctctcaa ttatcctagg    3589 agtgacctt atatgtgtgg aagattaatg gtatatgctc cttatgtcac tgttttgag    3649 taaaatccat ttcctttctc tgtttcagcc tatgacaaaa ttgatgttta caggcctgct    3709
ttttgcttat aattgacaac atgtgcaaaa ataccaaatt tgtgtcctgt gcagtatgaa    3769
gaattcagtg aatattcatt aatgtattag cttgttttgc tctctgttca tatatggctc    3829
tattcttaga aatataattt gaatgtgatc tttcaatagt ctgaatattt tacaaattat    3889
agctatgtct tgtgaaaata acctcaaaaa gaaaaatacg actctgttgt cttacttgat    3949
atttcttgcc ctagtaatgt acttgacatt tatgttccta agcagtgtaa gtaccagtag    4009
aatttctctg tcaaactcaa tgatcattta gtacttttgt cttctcccat gtgcttgaag    4069
gaaaaataaa gtgtcactac cgtatttctt gttttcatca aaaaataaaa ataatttaaa    4129
aaacaaaaaa aaaaaaaaa                                                 4148
```

<210> SEQ ID NO 55
<211> LENGTH: 414
<212> TYPE: PRT
<213> ORGANISM: Homo sapiens

<400> SEQUENCE: 55

```
Met Ser Gly Leu Asp Gly Gly Asn Lys Leu Pro Leu Ala Gln Thr Gly
 1               5                  10                  15

Gly Leu Ala Ala Pro Asp His Ala Ser Gly Asp Pro Asp Leu Asp Gln
            20                  25                  30

Cys Gln Gly Leu Arg Glu Glu Thr Glu Ala Thr Gln Val Met Ala Asn
        35                  40                  45

Thr Gly Gly Gly Ser Leu Glu Thr Val Ala Glu Gly Gly Ala Ser Gln
    50                  55                  60

Asp Pro Val Asp Cys Gly Pro Ala Leu Arg Val Pro Val Ala Gly Ser
65                  70                  75                  80

Arg Gly Gly Ala Ala Thr Lys Ala Gly Gln Glu Asp Ala Pro Pro Ser
                85                  90                  95

Thr Lys Gly Leu Glu Ala Ala Ser Ala Ala Glu Ala Ala Asp Ser Ser
            100                 105                 110

Gln Lys Asn Gly Cys Gln Leu Gly Glu Pro Arg Gly Pro Ala Gly Gln
        115                 120                 125

Lys Ala Leu Glu Ala Cys Gly Ala Gly Gly Leu Gly Ser Gln Met Ile
    130                 135                 140

Pro Gly Lys Lys Ala Lys Glu Val Thr Thr Lys Lys Arg Ala Ile Ser
145                 150                 155                 160

Ala Ala Val Glu Lys Glu Gly Glu Ala Gly Ala Met Glu Glu Lys
                165                 170                 175

Lys Val Val Gln Lys Glu Lys Lys Val Ala Gly Gly Val Lys Glu Glu
            180                 185                 190

Thr Arg Pro Arg Ala Pro Lys Ile Asn Asn Cys Met Asp Ser Leu Glu
        195                 200                 205

Ala Ile Asp Gln Glu Leu Ser Asn Val Asn Ala Gln Ala Asp Arg Ala
    210                 215                 220
```

```
Phe Leu Gln Leu Glu Arg Lys Phe Gly Arg Met Arg Arg Leu His Met
225                 230                 235                 240

Gln Arg Arg Ser Phe Ile Ile Gln Asn Ile Pro Gly Phe Trp Val Thr
            245                 250                 255

Ala Phe Arg Asn His Pro Gln Leu Ser Pro Met Ile Ser Gly Gln Asp
        260                 265                 270

Glu Asp Met Leu Arg Tyr Met Ile Asn Leu Glu Val Glu Glu Leu Lys
    275                 280                 285

His Pro Arg Ala Gly Cys Lys Phe Lys Phe Ile Phe Gln Gly Asn Pro
290                 295                 300

Tyr Phe Arg Asn Glu Gly Leu Val Lys Glu Tyr Glu Arg Arg Ser Ser
305                 310                 315                 320

Gly Arg Val Val Ser Leu Ser Thr Pro Ile Arg Trp His Arg Gly Gln
                325                 330                 335

Asp Pro Gln Ala His Ile His Arg Asn Arg Glu Gly Asn Thr Ile Pro
            340                 345                 350

Ser Phe Phe Asn Trp Phe Ser Asp His Ser Leu Leu Glu Phe Asp Arg
        355                 360                 365

Ile Ala Glu Ile Ile Lys Gly Glu Leu Trp Pro Asn Pro Leu Gln Tyr
    370                 375                 380

Tyr Leu Met Gly Glu Gly Pro Arg Arg Gly Ile Arg Gly Pro Pro Arg
385                 390                 395                 400

Gln Pro Val Glu Ser Ala Arg Ser Phe Arg Phe Gln Ser Gly
                405                 410

<210> SEQ ID NO 56
<211> LENGTH: 2643
<212> TYPE: DNA
<213> ORGANISM: Rattus sp.
<220> FEATURE:
<221> NAME/KEY: CDS
<222> LOCATION: (1)..(801)

<400> SEQUENCE: 56 ctg aaa ggg gcg agg ccc agg gtg gtg aac tcc acc tgc agt gac ttc      48
Leu Lys Gly Ala Arg Pro Arg Val Val Asn Ser Thr Cys Ser Asp Phe
1               5                   10                  15 aac cat ggc tca gct ctg cac atc gct gcc tcg aat ctg tgc ctg ggc      96
Asn His Gly Ser Ala Leu His Ile Ala Ala Ser Asn Leu Cys Leu Gly
            20                  25                  30 gcc gcc aaa tgt tta ctg gag cat ggt gcc aac cca gcg ctg agg aat     144
Ala Ala Lys Cys Leu Leu Glu His Gly Ala Asn Pro Ala Leu Arg Asn
        35                  40                  45 cga aaa gga cag gta cca gcg gaa gtg gtc cca gac ccc atg gac atg     192
Arg Lys Gly Gln Val Pro Ala Glu Val Val Pro Asp Pro Met Asp Met
    50                  55                  60 tcc ctt gac aag gca gag gca gcc ctg gtg gcc aag gaa ttg cgg acg     240
Ser Leu Asp Lys Ala Glu Ala Ala Leu Val Ala Lys Glu Leu Arg Thr
65                  70                  75                  80 ctg cta gaa gag gct gtg cca ctg tcc tgc acc ctt cct aaa gtc aca     288
Leu Leu Glu Glu Ala Val Pro Leu Ser Cys Thr Leu Pro Lys Val Thr
                85                  90                  95 cta ccc aac tat gac aac gtc cca ggc aat ctc atg ctc agc gcg ctg     336
Leu Pro Asn Tyr Asp Asn Val Pro Gly Asn Leu Met Leu Ser Ala Leu
            100                 105                 110 ggc ctg cgt cta gga gac cga gtg ctc ctc gat ggc cag aag acg ggc     384
Gly Leu Arg Leu Gly Asp Arg Val Leu Leu Asp Gly Gln Lys Thr Gly
        115                 120                 125
```

-continued

| | |
|---|---|
| acg ctg agg ttc tgc ggg acc acc gag ttc gcc agt ggc cag tgg gtg<br>Thr Leu Arg Phe Cys Gly Thr Thr Glu Phe Ala Ser Gly Gln Trp Val<br>130                             135                        140 | 432 |
| ggc gtg gag cta gat gaa ccg gaa ggc aag aac gac ggc agc gtt ggg<br>Gly Val Glu Leu Asp Glu Pro Glu Gly Lys Asn Asp Gly Ser Val Gly<br>145                           150                       155                   160 | 480 |
| ggt gtc cgg tac ttc atc tgc cct ccc aag cag ggt ctc ttt gca tct<br>Gly Val Arg Tyr Phe Ile Cys Pro Pro Lys Gln Gly Leu Phe Ala Ser<br>                          165                       170                   175 | 528 |
| gtg tcc aag gtc tcc aag gca gtg gat gca ccc ccc tca tct gtt acc<br>Val Ser Lys Val Ser Lys Ala Val Asp Ala Pro Pro Ser Ser Val Thr<br>           180                       185                       190 | 576 |
| tcc acg ccc cgc act ccc cgg atg gac ttc tcc cgt gta acg ggc aaa<br>Ser Thr Pro Arg Thr Pro Arg Met Asp Phe Ser Arg Val Thr Gly Lys<br>       195                       200                     205 | 624 |
| ggc cgg agg gaa cac aaa ggg aag aag aag tcc cca tct tcc cca tct<br>Gly Arg Arg Glu His Lys Gly Lys Lys Lys Ser Pro Ser Ser Pro Ser<br>210                             215                        220 | 672 |
| ctg ggc agc ctg cag cag cgt gaa ggg gcc aaa gct gaa gtt gga gac<br>Leu Gly Ser Leu Gln Gln Arg Glu Gly Ala Lys Ala Glu Val Gly Asp<br>225                             230                       235                   240 | 720 |
| caa gtc ctt gtg gca ggc cag aac agg gat tgt gcg ttt cta tgg gaa<br>Gln Val Leu Val Ala Gly Gln Asn Arg Asp Cys Ala Phe Leu Trp Glu<br>                         245                       250                   255 | 768 |
| gac aga ctt tgc tcc agg tta ctg gta tgg cat tgaactggac cagcccacgg<br>Asp Arg Leu Cys Ser Arg Leu Leu Val Trp His<br>           260                       265 | 821 |
| gcaagcatga cggctctgtg ttcggtgtcc ggtactttac ctgtgccccg aggcacgggg | 881 |
| tctttgcacc agcatctcgt atccagagga ttggtggatc cactgatccc cctggagaca | 941 |
| gtgttggagc aaaaaaagtg catcaagtga caatgacaca gcccaaacgc accttcacaa | 1001 |
| cagtccggac cccaaaggac attgcatcag agaactctat ctccaggtta ctcttctgct | 1061 |
| gctggtttcc ttggatgctg agggcggaga tgcagtctta gagacctgga tacctgacac | 1121 |
| agagacagag tccctctag catctcctga cacaaggaga ccccagtcac ctaagatag | 1181 |
| agattcccag tgacacctcc agaatagaaa ccccgttagc cagccctcga ttactgaggt | 1241 |
| cccattatta acagatctcc catgacgact cccccaaata cagacctcat gttaccccaa | 1301 |
| aagagattcc ctgagtagca ccttcaggct agtccctgtc ccctacccct cagagcagat | 1361 |
| ttcccccaat aaacattttc cacatcaccc aagggatgct gaccctctcc acgacaggac | 1421 |
| gttcttgagt taccagtgga ttagagtccc atgaatgaag accccccca ccccggttct | 1481 |
| ccttaagcat aggtcatacc tccagaatag ccagccacat cactatcccc atgtaacatc | 1541 |
| agtctcctca aaatggcgtg aggtcactag aaagacctta tactctcctc tccttctcag | 1601 |
| agatgccctc cattcactta agtccctgtt ctcaccctg aacaagacac ctaattaacc | 1661 |
| ggcccactca cctcaattac aaacaccaaa atcgtcctgg aagcatgaat tacaggacag | 1721 |
| caagtcttcc tgccctctgc acccttgaga accccagt gccttgtatg aagcccaccc | 1781 |
| cacatggccc acagtccctg tgctggccaa ggctcccaga aaattctcta tttttttaag | 1841 |
| taataacttc ccccccttg gggggatccc caaatttgga gaccccattc tagaacactg | 1901 |
| gggagttcaa attccagaga gaatatatat tatatataat ccccaattcc ccatgcttcc | 1961 |
| aagccctaca atctctagaa gaccccaaat ttctaattcc caggacttcc cctacccaag | 2021 |
| tcacagaatc ttcaaatccc cagggaatcc caaacttaag ataccaatcc caaaccctca | 2081 |
| ggaaatcccc caacacaagg tccttaggac cgggaggaag gaacctgttg ccaggagaac | 2141 |

-continued

```
atcccaggct ctcagggcat ctcaaacctg actcccaggc accaggagac cccaaacaga    2201
aagtcccatc tttggaacaa ggataggact ctaatacccct tagtccatgg atctttaatt    2261
tcccaacctc caaactccat gggcccacc ctcaagggaa ccccaagat ccaaatctct       2321 gataactaat atgtgcaggg ccccagggct ctaacaggac cccaaatcat ggagtcccta    2381
cttcaatcta ccttctggtc acaggtccaa gacactaaat ctgagtcatt ggccccaaag    2441
gacttcacag cacctgggcc agactaacag cctgagggag aacctgaggg ccccgtgggt    2501
ccagagcaga cctggggccc tgaccaccaa ggacagctca cgactgcccc ttcactgcat    2561
gtccctaaac tcagcatgac tcctgtcctc ttcaataaag acgtttctat ggcaaaaaaa    2621
aaaaaaaaaa aaaaaaaaaa aa                                              2643
```

<210> SEQ ID NO 57
<211> LENGTH: 267
<212> TYPE: PRT
<213> ORGANISM: Rattus sp.

<400> SEQUENCE: 57

```
Leu Lys Gly Ala Arg Pro Arg Val Val Asn Ser Thr Cys Ser Asp Phe
  1               5                  10                  15

Asn His Gly Ser Ala Leu His Ile Ala Ala Ser Asn Leu Cys Leu Gly
             20                  25                  30

Ala Ala Lys Cys Leu Leu Glu His Gly Ala Asn Pro Ala Leu Arg Asn
         35                  40                  45

Arg Lys Gly Gln Val Pro Ala Glu Val Val Pro Asp Pro Met Asp Met
     50                  55                  60

Ser Leu Asp Lys Ala Glu Ala Leu Val Ala Lys Glu Leu Arg Thr
 65                  70                  75                  80

Leu Leu Glu Glu Ala Val Pro Leu Ser Cys Thr Leu Pro Lys Val Thr
                 85                  90                  95

Leu Pro Asn Tyr Asp Asn Val Pro Gly Asn Leu Met Leu Ser Ala Leu
            100                 105                 110

Gly Leu Arg Leu Gly Asp Arg Val Leu Leu Asp Gly Gln Lys Thr Gly
        115                 120                 125

Thr Leu Arg Phe Cys Gly Thr Thr Glu Phe Ala Ser Gly Gln Trp Val
    130                 135                 140

Gly Val Glu Leu Asp Glu Pro Glu Gly Lys Asn Asp Gly Ser Val Gly
145                 150                 155                 160

Gly Val Arg Tyr Phe Ile Cys Pro Pro Lys Gln Gly Leu Phe Ala Ser
                165                 170                 175

Val Ser Lys Val Ser Lys Ala Val Asp Ala Pro Ser Ser Val Thr
            180                 185                 190

Ser Thr Pro Arg Thr Pro Arg Met Asp Phe Ser Arg Val Thr Gly Lys
        195                 200                 205

Gly Arg Arg Glu His Lys Gly Lys Lys Ser Pro Ser Ser Pro Ser
    210                 215                 220

Leu Gly Ser Leu Gln Gln Arg Glu Gly Ala Lys Ala Glu Val Gly Asp
225                 230                 235                 240

Gln Val Leu Val Ala Gly Gln Asn Arg Asp Cys Ala Phe Leu Trp Glu
                245                 250                 255

Asp Arg Leu Cys Ser Arg Leu Leu Val Trp His
            260                 265
```

-continued

<210> SEQ ID NO 58
<211> LENGTH: 2929
<212> TYPE: DNA
<213> ORGANISM: Rattus sp.
<220> FEATURE:
<221> NAME/KEY: CDS
<222> LOCATION: (1)..(810)

<400> SEQUENCE: 58

| gct | gac | tct | acc | tct | aga | tgg | gct | gag | gcc | ctc | aga | gaa | atc | tct | ggt | 48 |
|---|---|---|---|---|---|---|---|---|---|---|---|---|---|---|---|---|
| Ala | Asp | Ser | Thr | Ser | Arg | Trp | Ala | Glu | Ala | Leu | Arg | Glu | Ile | Ser | Gly | |
| 1 | | | | 5 | | | | | 10 | | | | | 15 | | |

| cgc | tta | gct | gaa | atg | cct | gca | gat | agt | gga | tac | cct | gca | tac | ctt | ggt | 96 |
|---|---|---|---|---|---|---|---|---|---|---|---|---|---|---|---|---|
| Arg | Leu | Ala | Glu | Met | Pro | Ala | Asp | Ser | Gly | Tyr | Pro | Ala | Tyr | Leu | Gly | |
| | | 20 | | | | | 25 | | | | | 30 | | | | |

| gcc | cga | ctg | gct | tct | ttc | tat | gag | cga | gca | ggc | aga | gtg | aaa | tgt | ctt | 144 |
|---|---|---|---|---|---|---|---|---|---|---|---|---|---|---|---|---|
| Ala | Arg | Leu | Ala | Ser | Phe | Tyr | Glu | Arg | Ala | Gly | Arg | Val | Lys | Cys | Leu | |
| | | | 35 | | | | | 40 | | | | | 45 | | | |

| gga | aac | cct | gag | aga | gaa | ggg | agt | gtc | agc | att | gta | gga | gca | gtt | tct | 192 |
|---|---|---|---|---|---|---|---|---|---|---|---|---|---|---|---|---|
| Gly | Asn | Pro | Glu | Arg | Glu | Gly | Ser | Val | Ser | Ile | Val | Gly | Ala | Val | Ser | |
| | 50 | | | | | 55 | | | | | 60 | | | | | |

| cca | cct | ggt | ggt | gat | ttt | tct | gat | cca | gtc | aca | tct | gct | act | ctg | ggt | 240 |
|---|---|---|---|---|---|---|---|---|---|---|---|---|---|---|---|---|
| Pro | Pro | Gly | Gly | Asp | Phe | Ser | Asp | Pro | Val | Thr | Ser | Ala | Thr | Leu | Gly | |
| 65 | | | | | 70 | | | | | 75 | | | | | 80 | |

| att | gtt | cag | gtg | ttc | tgg | ggc | ttg | gat | aag | aag | cta | gct | cag | cgc | aag | 288 |
|---|---|---|---|---|---|---|---|---|---|---|---|---|---|---|---|---|
| Ile | Val | Gln | Val | Phe | Trp | Gly | Leu | Asp | Lys | Lys | Leu | Ala | Gln | Arg | Lys | |
| | | | | 85 | | | | | 90 | | | | | 95 | | |

| cac | ttc | ccg | tcc | gtc | aac | tgg | ctc | att | agc | tac | agc | aag | tac | atg | cgc | 336 |
|---|---|---|---|---|---|---|---|---|---|---|---|---|---|---|---|---|
| His | Phe | Pro | Ser | Val | Asn | Trp | Leu | Ile | Ser | Tyr | Ser | Lys | Tyr | Met | Arg | |
| | | | 100 | | | | | 105 | | | | | 110 | | | |

| gcc | ctg | gac | gag | tac | tat | gac | aaa | cac | ttc | aca | gag | ttc | gtg | cct | ctg | 384 |
|---|---|---|---|---|---|---|---|---|---|---|---|---|---|---|---|---|
| Ala | Leu | Asp | Glu | Tyr | Tyr | Asp | Lys | His | Phe | Thr | Glu | Phe | Val | Pro | Leu | |
| | | | 115 | | | | | 120 | | | | | 125 | | | |

| agg | acc | aaa | gct | aag | gag | att | ctg | cag | gaa | gag | gag | gat | ctg | gcg | gaa | 432 |
|---|---|---|---|---|---|---|---|---|---|---|---|---|---|---|---|---|
| Arg | Thr | Lys | Ala | Lys | Glu | Ile | Leu | Gln | Glu | Glu | Glu | Asp | Leu | Ala | Glu | |
| | 130 | | | | | 135 | | | | | 140 | | | | | |

| atc | gtg | cag | ctc | gtg | gga | aag | gcg | tct | tta | gca | gag | aca | gat | aaa | atc | 480 |
|---|---|---|---|---|---|---|---|---|---|---|---|---|---|---|---|---|
| Ile | Val | Gln | Leu | Val | Gly | Lys | Ala | Ser | Leu | Ala | Glu | Thr | Asp | Lys | Ile | |
| 145 | | | | | 150 | | | | | 155 | | | | | 160 | |

| acc | ctg | gag | gta | gca | aaa | ctt | atc | aaa | gat | gac | ttc | cta | caa | caa | aat | 528 |
|---|---|---|---|---|---|---|---|---|---|---|---|---|---|---|---|---|
| Thr | Leu | Glu | Val | Ala | Lys | Leu | Ile | Lys | Asp | Asp | Phe | Leu | Gln | Gln | Asn | |
| | | | | 165 | | | | | 170 | | | | | 175 | | |

| ggg | tac | act | cct | tat | gac | agg | ttc | tgt | cca | ttc | tat | aag | acg | gtg | ggg | 576 |
|---|---|---|---|---|---|---|---|---|---|---|---|---|---|---|---|---|
| Gly | Tyr | Thr | Pro | Tyr | Asp | Arg | Phe | Cys | Pro | Phe | Tyr | Lys | Thr | Val | Gly | |
| | | | 180 | | | | | 185 | | | | | 190 | | | |

| atg | ctg | tcc | aac | atg | att | tca | ttc | tat | gat | atg | gcc | cgc | cgg | gct | gtg | 624 |
|---|---|---|---|---|---|---|---|---|---|---|---|---|---|---|---|---|
| Met | Leu | Ser | Asn | Met | Ile | Ser | Phe | Tyr | Asp | Met | Ala | Arg | Arg | Ala | Val | |
| | | | 195 | | | | | 200 | | | | | 205 | | | |

| gag | acc | acc | gcc | cag | agt | gac | aat | aag | atc | aca | tgg | tcc | att | atc | cgt | 672 |
|---|---|---|---|---|---|---|---|---|---|---|---|---|---|---|---|---|
| Glu | Thr | Thr | Ala | Gln | Ser | Asp | Asn | Lys | Ile | Thr | Trp | Ser | Ile | Ile | Arg | |
| | 210 | | | | | 215 | | | | | 220 | | | | | |

| gag | cac | atg | ggg | gag | att | ctc | tat | aaa | ctt | tcc | tcc | atg | aaa | ttc | aag | 720 |
|---|---|---|---|---|---|---|---|---|---|---|---|---|---|---|---|---|
| Glu | His | Met | Gly | Glu | Ile | Leu | Tyr | Lys | Leu | Ser | Ser | Met | Lys | Phe | Lys | |
| 225 | | | | | 230 | | | | | 235 | | | | | 240 | |

| gat | cca | gtg | aag | gat | ggc | gag | gca | aag | atc | aag | gcc | gac | tac | gca | cag | 768 |
|---|---|---|---|---|---|---|---|---|---|---|---|---|---|---|---|---|
| Asp | Pro | Val | Lys | Asp | Gly | Glu | Ala | Lys | Ile | Lys | Ala | Asp | Tyr | Ala | Gln | |
| | | | | 245 | | | | | 250 | | | | | 255 | | |

| ctt | ctt | gaa | gat | atg | cag | aac | gca | ttc | cgt | agc | ctg | gaa | gat | | | 810 |
|---|---|---|---|---|---|---|---|---|---|---|---|---|---|---|---|---|
| Leu | Leu | Glu | Asp | Met | Gln | Asn | Ala | Phe | Arg | Ser | Leu | Glu | Asp | | | |
| | | | 260 | | | | | 265 | | | | | 270 | | | | tagaactgtg acttctctcc tcctcttccg cagctcatat gtgtatattt tcctgaattt    870

-continued

```
ctcatctcca acccttttgct tccatattgt gcagctttga gactagtgcc tcgtgcgttc    930
tcgttcattt tgctgtttct tggtaggtc  ttataaaaca cacattcctg tgctccgctg    990
tctgaaggag ctcctgacct tgtctgaag  tggtgaatgt agtgcatatg atacacagtg    1050
taacatacac attgtaacat atacgttctg taaacttgta tgtaaggtga ctacccctcc    1110
cctcctctcc agtaaactgt aaacaggact actgcatgtg ctctattggg gatggaaggc    1170
cagatctcca taccgtggac aggtacataa ggaaactaga ccacttgcaa cttagtgttt    1230
gttgagtaac cattttgcag gaagtatttc catttaaaaa acaaaagatt aatgttccaa    1290
ttatttgtag cttccccagt atcaatcagg actgtttgtg gcgcacttgg gaactatttt    1350
gttttcctaa cagacgtttg caaggctgaa cgtaatagat aaatcagttc cctctgaaag    1410
tgtgaaagta aaagagagc  taggtggtca gacttaaatt gacatcgtct tgtttaagca    1470
tattttattt cactgagaga tttaatatca aggacttta  tatactcaat tactaggaaa    1530
tcttttttta agtacaattt aaaaatcatt gaaaatgtga tccacatcat agccattttc    1590
cttatattta gtcagatgag ctcagagtgg ggagggtgtg ggttagaata ccacaaggac    1650
acgcagcagt gcctgcaggc agtgtggccg ggggccagag cggcattgtt ttcacgaggt    1710
acgtgtgtgg cgtgtgtgtt tgcttgttga cactctgaaa acagcaagct taccagttcc    1770
aggaaatatt ttgttttctt tcactggctc agaaagctcc tcaaagtacc tggtccctga    1830
agcttcctat ctgttaatag agacgagaga ggttcttaaa tttaactggt gacaaaacaa    1890
aaagaaaaaa aagatcgatt tttgtcttgc tgttttggtg tgtttaaata ataattccat    1950
atttgcataa cgaggctcgc ttctgagagc ttggagatcg tgctccctct tcactctccg    2010
gggtgataat gctggcgcca tgctacctct tcaggagggg aagggggattg aacatggcta    2070
acactctcaa gtacacaagc gtaacgacaa agtatttatt ttaagccttg gtatgttgtt    2130
taaattatta ggtggtgcat ttcttatggt cttttgggta gacatagtat acacttcaga    2190
tgtaatgtgt aaatccttgc tagtgcatgt ctacacgata gactgctatt caagaaggat    2250
attcttccac ataacaattt aaaaactatt aaatcagata tggattatgc aatgacttgt    2310
tgagaggtgg attaacggtg ctgcttaatc agtttgcttc caatatggct tcgtatccag    2370
aagccctgac tagtggagat gagaaagatt caaaacctg  tctgcctaca cctaccagca    2430
acctaggctt gtgatcagaa tgaatgatcc caagaaacta cttgaccaag tgtgttttgt    2490
tgtcctggat ttgagatgtg cgttcttcct ccctctgaga ctgttgatgt atgagtgtga    2550
agaagttaca gaaacaacgc tcagattttc acggtaactt tccctctgcc cacactgtag    2610
agtttcagat tgttcactga tagtgcttct ttcgtaagga tgtgttaaaa tatagcagtc    2670
ttttttaaaag attatgcagt tctctatttta ttgtgctgtg cctggtccta agtgcagccg    2730
gttaaacaag tttcatatgt attttttccag tgttaaatct catacctatg ccctttggaa    2790
agctccatcc tgaacaatga atagaagagg ctatataaat tgcctcctta tccttaagat    2850
ttcactatct ttatgttaag agtaatgtat aattattaaa atctatgaaa ataaaaagt     2910
ggatttaaat taagagatc                                                 2929
```

<210> SEQ ID NO 59
<211> LENGTH: 270
<212> TYPE: PRT
<213> ORGANISM: Rattus sp.

<400> SEQUENCE: 59

```
Ala Asp Ser Thr Ser Arg Trp Ala Glu Ala Leu Arg Glu Ile Ser Gly
 1               5                  10                  15

Arg Leu Ala Glu Met Pro Ala Asp Ser Gly Tyr Pro Ala Tyr Leu Gly
                 20                  25                  30

Ala Arg Leu Ala Ser Phe Tyr Glu Arg Ala Gly Arg Val Lys Cys Leu
             35                  40                  45

Gly Asn Pro Glu Arg Glu Gly Ser Val Ser Ile Val Gly Ala Val Ser
         50                  55                  60

Pro Pro Gly Gly Asp Phe Ser Asp Pro Val Thr Ser Ala Thr Leu Gly
 65                  70                  75                  80

Ile Val Gln Val Phe Trp Gly Leu Asp Lys Lys Leu Ala Gln Arg Lys
                 85                  90                  95

His Phe Pro Ser Val Asn Trp Leu Ile Ser Tyr Ser Lys Tyr Met Arg
                100                 105                 110

Ala Leu Asp Glu Tyr Tyr Asp Lys His Phe Thr Glu Phe Val Pro Leu
            115                 120                 125

Arg Thr Lys Ala Lys Glu Ile Leu Gln Glu Glu Asp Leu Ala Glu
        130                 135                 140

Ile Val Gln Leu Val Gly Lys Ala Ser Leu Ala Glu Thr Asp Lys Ile
145                 150                 155                 160

Thr Leu Glu Val Ala Lys Leu Ile Lys Asp Asp Phe Leu Gln Gln Asn
                165                 170                 175

Gly Tyr Thr Pro Tyr Asp Arg Phe Cys Pro Phe Tyr Lys Thr Val Gly
            180                 185                 190

Met Leu Ser Asn Met Ile Ser Phe Tyr Asp Met Ala Arg Arg Ala Val
        195                 200                 205

Glu Thr Thr Ala Gln Ser Asp Asn Lys Ile Thr Trp Ser Ile Ile Arg
        210                 215                 220

Glu His Met Gly Glu Ile Leu Tyr Lys Leu Ser Ser Met Lys Phe Lys
225                 230                 235                 240

Asp Pro Val Lys Asp Gly Glu Ala Lys Ile Lys Ala Asp Tyr Ala Gln
                245                 250                 255

Leu Leu Glu Asp Met Gln Asn Ala Phe Arg Ser Leu Glu Asp
            260                 265                 270

<210> SEQ ID NO 60
<211> LENGTH: 1489
<212> TYPE: DNA
<213> ORGANISM: Rattus sp.
<220> FEATURE:
<221> NAME/KEY: CDS
<222> LOCATION: (1)..(1053)

<400> SEQUENCE: 60 gca cgg ctc ccg gcc ccg gag cat gcg cga cag cag ccc ctc ctc tcc        48
Ala Arg Leu Pro Ala Pro Glu His Ala Arg Gln Gln Pro Leu Leu Ser
 1               5                  10                  15 ggc cct gag ccc gga tcg tcc gcc cgg gtt cca gtt ccc ggc gtg gcc       96
Gly Pro Glu Pro Gly Ser Ser Ala Arg Val Pro Val Pro Gly Val Ala
                 20                  25                  30 agt agg cgg cag ccg cga ggc ggc aag cca ccc agc ggg gac ggc ctg      144
Ser Arg Arg Gln Pro Arg Gly Gly Lys Pro Pro Ser Gly Asp Gly Leu
             35                  40                  45 gag tcg ggc ccc tct cca cgc ccc ctt ctc cac gcg cgc ggg gag gca      192
Glu Ser Gly Pro Ser Pro Arg Pro Leu Leu His Ala Arg Gly Glu Ala
         50                  55                  60 ggg ctc cac cgc cag tct gga agg gtt cca cat aca gga acg gcc tac      240
```

```
                                                        -continued

Gly Leu His Arg Gln Ser Gly Arg Val Pro His Thr Gly Thr Ala Tyr
 65                  70                  75                  80 ttc gca gat gag ccc acc gag gct cag gct ccg ggc gga ttc tgc gtg        288
Phe Ala Asp Glu Pro Thr Glu Ala Gln Ala Pro Gly Gly Phe Cys Val
                    85                  90                  95 tca ccc tcg ctc ctt ggg gtc cgc tgg ccg gcc tgt gcc acc cgg acg        336
Ser Pro Ser Leu Leu Gly Val Arg Trp Pro Ala Cys Ala Thr Arg Thr
                100                 105                 110 ccc ggc tca ctg cct ctg tct ccc cca tca gcg cag ccc cgg acg cta        384
Pro Gly Ser Leu Pro Leu Ser Pro Pro Ser Ala Gln Pro Arg Thr Leu
            115                 120                 125 tgg ccc acc cct cca gct ggc ccc tcg agt agg atg gta gca cgt aac        432
Trp Pro Thr Pro Pro Ala Gly Pro Ser Ser Arg Met Val Ala Arg Asn
        130                 135                 140 cag gtg gca gcc gac aat gcg atc tcc ccg gca tca gag ccc cga cgg        480
Gln Val Ala Ala Asp Asn Ala Ile Ser Pro Ala Ser Glu Pro Arg Arg
145                 150                 155                 160 cgg cca gag cca tcc tcg tcc tcg tct tcg tcc tcg ccg gcg gcc ccg        528
Arg Pro Glu Pro Ser Ser Ser Ser Ser Ser Ser Pro Ala Ala Pro
                165                 170                 175 gcg cgt ccc cgg ccc tgc ccg gtg gtc ccg gcc ccg gct ccg ggc gac        576
Ala Arg Pro Arg Pro Cys Pro Val Val Pro Ala Pro Ala Pro Gly Asp
                180                 185                 190 act cac ttc cgc acc ttc cgc tcc cac tct gat tac cgg cgc atc acg        624
Thr His Phe Arg Thr Phe Arg Ser His Ser Asp Tyr Arg Arg Ile Thr
            195                 200                 205 cgg acc agc gct ctc ctg gac gcc tgc ggc ttc tac tgg gga ccc ctg        672
Arg Thr Ser Ala Leu Leu Asp Ala Cys Gly Phe Tyr Trp Gly Pro Leu
        210                 215                 220 agc gtg cat ggg gcg cac gaa cgg ctg cgt gcc gag ccc gtg ggc acc        720
Ser Val His Gly Ala His Glu Arg Leu Arg Ala Glu Pro Val Gly Thr
225                 230                 235                 240 ttc ttg gtg cgc gac agt cgc cag cgg aac tgc ttc ttc gcg ctc agc        768
Phe Leu Val Arg Asp Ser Arg Gln Arg Asn Cys Phe Phe Ala Leu Ser
                245                 250                 255 gtg aag atg gct tcg ggc ccc acg agc att cgt gtg cac ttc cag gcc        816
Val Lys Met Ala Ser Gly Pro Thr Ser Ile Arg Val His Phe Gln Ala
                260                 265                 270 ggc cgc ttc cac ctg gac ggc agc cgc gag acc ttc gac tgc ctc ttc        864
Gly Arg Phe His Leu Asp Gly Ser Arg Glu Thr Phe Asp Cys Leu Phe
            275                 280                 285 gag ctg ctg gag cac tac gtg gcg gcg ccg cgc cgc atg ttg ggg gcc        912
Glu Leu Leu Glu His Tyr Val Ala Ala Pro Arg Arg Met Leu Gly Ala
        290                 295                 300 cca ctg cgc cag cgc cgc gtg cgg ccg ctg cag gag ctg tgt cgc cag        960
Pro Leu Arg Gln Arg Arg Val Arg Pro Leu Gln Glu Leu Cys Arg Gln
305                 310                 315                 320 cgc atc gtg gcc gcc gtg ggt cgc gag aac ctg gca cgc atc cct ctt       1008
Arg Ile Val Ala Ala Val Gly Arg Glu Asn Leu Ala Arg Ile Pro Leu
                325                 330                 335 aac ccg gta ctc cgt gac tac ctg agt tcc ttc ccc ttc cag atc           1053
Asn Pro Val Leu Arg Asp Tyr Leu Ser Ser Phe Pro Phe Gln Ile
                340                 345                 350 tgaccggctg ccgccgtgcc cgcagcatta agtgggagcg ccttattatt tcttattatt     1113
aattattatt atttttctgg aaccacgtgg gagccctccc cgcctaggtc ggagggagtg     1173
ggtgtggagg gtgagatgcc tcccacttct ggctggagac cttatcccgc ctctcggggg     1233
gcctcccctc ctggtgctcc ctcccggtcc cctggttgt agcagcttgt gtctggggcc      1293
```

```
aggacctgaa ctccacgcct acctctccat gtttacatgt tcccagtatc tttgcacaaa   1353 ccagggtgg gggagggtct ctggcttcat ttttctgctg tgcagaatat tctatttat    1413 atttttacat ccagtttaga taataaactt tattatgaaa gttttttttt taagaaaaa    1473 aaaaaaaaaa aaaaaa                                                   1489
```

<210> SEQ ID NO 61
<211> LENGTH: 351
<212> TYPE: PRT
<213> ORGANISM: Rattus sp.

<400> SEQUENCE: 61

```
Ala Arg Leu Pro Ala Pro Glu His Ala Arg Gln Gln Pro Leu Leu Ser
 1               5                  10                  15

Gly Pro Glu Pro Gly Ser Ser Ala Arg Val Pro Val Pro Gly Val Ala
            20                  25                  30

Ser Arg Arg Gln Pro Arg Gly Gly Lys Pro Pro Ser Gly Asp Gly Leu
        35                  40                  45

Glu Ser Gly Pro Ser Pro Arg Pro Leu Leu His Ala Arg Gly Glu Ala
 50                  55                  60

Gly Leu His Arg Gln Ser Gly Arg Val Pro His Thr Gly Thr Ala Tyr
 65                  70                  75                  80

Phe Ala Asp Glu Pro Thr Glu Ala Gln Ala Pro Gly Gly Phe Cys Val
                85                  90                  95

Ser Pro Ser Leu Leu Gly Val Arg Trp Pro Ala Cys Ala Thr Arg Thr
            100                 105                 110

Pro Gly Ser Leu Pro Leu Ser Pro Pro Ser Ala Gln Pro Arg Thr Leu
        115                 120                 125

Trp Pro Thr Pro Pro Ala Gly Pro Ser Ser Arg Met Val Ala Arg Asn
130                 135                 140

Gln Val Ala Ala Asp Asn Ala Ile Ser Pro Ala Ser Glu Pro Arg Arg
145                 150                 155                 160

Arg Pro Glu Pro Ser Ser Ser Ser Ser Ser Ser Pro Ala Ala Pro
                165                 170                 175

Ala Arg Pro Arg Pro Cys Pro Val Val Pro Ala Pro Ala Pro Gly Asp
                180                 185                 190

Thr His Phe Arg Thr Phe Arg Ser His Ser Asp Tyr Arg Arg Ile Thr
        195                 200                 205

Arg Thr Ser Ala Leu Leu Asp Ala Cys Gly Phe Tyr Trp Gly Pro Leu
210                 215                 220

Ser Val His Gly Ala His Glu Arg Leu Arg Ala Glu Pro Val Gly Thr
225                 230                 235                 240

Phe Leu Val Arg Asp Ser Arg Gln Arg Asn Cys Phe Phe Ala Leu Ser
                245                 250                 255

Val Lys Met Ala Ser Gly Pro Thr Ser Ile Arg Val His Phe Gln Ala
            260                 265                 270

Gly Arg Phe His Leu Asp Gly Ser Arg Glu Thr Phe Asp Cys Leu Phe
        275                 280                 285

Glu Leu Leu Glu His Tyr Val Ala Ala Pro Arg Arg Met Leu Gly Ala
290                 295                 300

Pro Leu Arg Gln Arg Arg Val Arg Pro Leu Gln Glu Leu Cys Arg Gln
305                 310                 315                 320

Arg Ile Val Ala Ala Val Gly Arg Glu Asn Leu Ala Arg Ile Pro Leu
                325                 330                 335
```

```
                Asn Pro Val Leu Arg Asp Tyr Leu Ser Ser Phe Pro Phe Gln Ile
                            340                 345                 350

<210> SEQ ID NO 62
<211> LENGTH: 1194
<212> TYPE: DNA
<213> ORGANISM: Rattus sp.
<220> FEATURE:
<221> NAME/KEY: CDS
<222> LOCATION: (130)..(765)

<400> SEQUENCE: 62
ggcacggctc ccggccccgg agcatgcgcg acagcagccc cggaaccccc agccgcggcg        60
ccccgcgtcc cgccgccagc gcagccccgg acgctatggc ccaccctcc agctggcccc       120 tcgagtagg atg gta gca cgt aac cag gtg gca gcc gac aat gcg atc tcc      171
           Met Val Ala Arg Asn Gln Val Ala Ala Asp Asn Ala Ile Ser
            1               5                  10 ccg gca tca gag ccc cga cgg cgg cca gag cca tcc tcg tcc tcg tct        219
Pro Ala Ser Glu Pro Arg Arg Arg Pro Glu Pro Ser Ser Ser Ser Ser
 15                  20                  25                  30 tcg tcc tcg ccg gcg gcc ccg gcg cgt ccc cgg ccc tgc ccg gtg gtc        267
Ser Ser Ser Pro Ala Ala Pro Ala Arg Pro Arg Pro Cys Pro Val Val
                 35                  40                  45 ccg gcc ccg gct ccg ggc gac act cac ttc cgc acc ttc cgc tcc cac        315
Pro Ala Pro Ala Pro Gly Asp Thr His Phe Arg Thr Phe Arg Ser His
             50                  55                  60 tct gat tac cgg cgc atc acg cgg acc agc gct ctc ctg gac gcc tgc        363
Ser Asp Tyr Arg Arg Ile Thr Arg Thr Ser Ala Leu Leu Asp Ala Cys
         65                  70                  75 ggc ttc tac tgg gga ccc ctg agc gtg cat ggg gcg cac gaa cgg ctg        411
Gly Phe Tyr Trp Gly Pro Leu Ser Val His Gly Ala His Glu Arg Leu
     80                  85                  90 cgt gcc gag ccc gtg ggc acc ttc ttg gtg cgc gac agt cgc cag cgg        459
Arg Ala Glu Pro Val Gly Thr Phe Leu Val Arg Asp Ser Arg Gln Arg
 95                 100                 105                 110 aac tgc ttc ttc gcg ctc agc gtg aag atg gct tcg ggc ccc acg agc        507
Asn Cys Phe Phe Ala Leu Ser Val Lys Met Ala Ser Gly Pro Thr Ser
                115                 120                 125 att cgt gtg cac ttc cag gcc ggc cgc ttc cac ctg gac ggc agc cgc        555
Ile Arg Val His Phe Gln Ala Gly Arg Phe His Leu Asp Gly Ser Arg
            130                 135                 140 gag acc ttc gac tgc ctc ttc gag ctg ctg gag cac tac gtg gcg gcg        603
Glu Thr Phe Asp Cys Leu Phe Glu Leu Leu Glu His Tyr Val Ala Ala
        145                 150                 155 ccg cgc cgc atg ttg ggg gcc cca ctg cgc cag cgc cgc gtg cgg ccg        651
Pro Arg Arg Met Leu Gly Ala Pro Leu Arg Gln Arg Arg Val Arg Pro
    160                 165                 170 ctg cag gag ctg tgt cgc cag cgc atc gtg gcc gcc gtg ggt cgc gag        699
Leu Gln Glu Leu Cys Arg Gln Arg Ile Val Ala Ala Val Gly Arg Glu
175                 180                 185                 190 aac ctg gca cgc atc cct ctt aac ccg gta ctc cgt gac tac ctg agt        747
Asn Leu Ala Arg Ile Pro Leu Asn Pro Val Leu Arg Asp Tyr Leu Ser
                195                 200                 205 tcc ttc ccc ttc cag atc tgaccggctg ccgccgtgcc cgcagcatta               795
Ser Phe Pro Phe Gln Ile
            210 agtgggagcg ccttattatt tcttattatt aattattatt attttctgg aaccacgtgg       855 gagccctccc cgcctaggtc ggagggagtg ggtgtgaggg gtgagatgcc tcccacttct      915 ggctggagac cttatcccgc ctctcggggg gcctcccctc ctggtgctcc ctcccggtcc      975
```

-continued

| | |
|---|---|
| ccctggttgt agcagcttgt gtctggggcc aggacctgaa ctccacgcct acctctccat | 1035 |
| gtttacatgt tcccagtatc tttgcacaaa ccaggggtgg gggagggtct ctggcttcat | 1095 |
| ttttctgctg tgcagaatat tctattttat atttttacat ccagtttaga taataaactt | 1155 |
| tattatgaaa gttttttttt taaaaaaaaa aaaaaaaa | 1194 |

<210> SEQ ID NO 63
<211> LENGTH: 212
<212> TYPE: PRT
<213> ORGANISM: Rattus sp.

<400> SEQUENCE: 63

```
Met Val Ala Arg Asn Gln Val Ala Ala Asp Asn Ala Ile Ser Pro Ala
 1               5                  10                  15
Ser Glu Pro Arg Arg Pro Glu Pro Ser Ser Ser Ser Ser Ser Ser Ser
                20                  25                  30
Ser Pro Ala Ala Pro Ala Arg Pro Arg Pro Cys Pro Val Val Pro Ala
            35                  40                  45
Pro Ala Pro Gly Asp Thr His Phe Arg Thr Phe Arg Ser His Ser Asp
        50                  55                  60
Tyr Arg Arg Ile Thr Arg Thr Ser Ala Leu Leu Asp Ala Cys Gly Phe
 65                  70                  75                  80
Tyr Trp Gly Pro Leu Ser Val His Gly Ala His Glu Arg Leu Arg Ala
                85                  90                  95
Glu Pro Val Gly Thr Phe Leu Val Arg Asp Ser Arg Gln Arg Asn Cys
            100                 105                 110
Phe Phe Ala Leu Ser Val Lys Met Ala Ser Gly Pro Thr Ser Ile Arg
        115                 120                 125
Val His Phe Gln Ala Gly Arg Phe His Leu Asp Gly Ser Arg Glu Thr
    130                 135                 140
Phe Asp Cys Leu Phe Glu Leu Leu Glu His Tyr Val Ala Ala Pro Arg
145                 150                 155                 160
Arg Met Leu Gly Ala Pro Leu Arg Gln Arg Arg Val Arg Pro Leu Gln
                165                 170                 175
Glu Leu Cys Arg Gln Arg Ile Val Ala Ala Val Gly Arg Glu Asn Leu
            180                 185                 190
Ala Arg Ile Pro Leu Asn Pro Val Leu Arg Asp Tyr Leu Ser Ser Phe
        195                 200                 205
Pro Phe Gln Ile
        210
```

<210> SEQ ID NO 64
<211> LENGTH: 600
<212> TYPE: DNA
<213> ORGANISM: Rattus sp.
<220> FEATURE:
<221> NAME/KEY: CDS
<222> LOCATION: (52)..(336)

<400> SEQUENCE: 64

| | |
|---|---|
| cttccaaaga ctgcagcgcc tcagggccca ggtttcaaca gattcttcaa a atg cca<br>                                                                                                                                                                                                                                                             Met Pro<br>                                                                                                                                                                                                                                                                   1 | 57 |
| tcc caa atg gag cat gcc atg gaa acc atg atg ctt aca ttt cac agg<br>Ser Gln Met Glu His Ala Met Glu Thr Met Met Leu Thr Phe His Arg<br>  5                             10                         15 | 105 |
| ttt gca ggg gaa aaa aac tac ttg aca aag gag gac ctg aga gtg ctc | 153 |

```
                Phe Ala Gly Glu Lys Asn Tyr Leu Thr Lys Glu Asp Leu Arg Val Leu
                 20                  25                  30 atg gaa agg gag ttc cct ggg ttt ttg gaa aat caa aag gac cct ctg       201
Met Glu Arg Glu Phe Pro Gly Phe Leu Glu Asn Gln Lys Asp Pro Leu
 35                  40                  45                  50 gct gtg gac aaa ata atg aaa gac ctg gac cag tgc cga gat gga aaa       249
Ala Val Asp Lys Ile Met Lys Asp Leu Asp Gln Cys Arg Asp Gly Lys
                 55                  60                  65 gtg ggc ttc cag agc ttt cta tca cta gtg gcg ggg ctc atc att gca       297
Val Gly Phe Gln Ser Phe Leu Ser Leu Val Ala Gly Leu Ile Ile Ala
         70                  75                  80 tgc aat gac tat ttt gta gta cac atg aag cag aag aag taggccaact        346
Cys Asn Asp Tyr Phe Val Val His Met Lys Gln Lys Lys
     85                  90                  95 ggagccctgg tacccacacc ttgatgcgtc ctctcccatg gggtcaactg aggaatctgc     406
cccactgctt cctgtgagca gatcaggacc cttaggaaat gtgcaaataa catccaactc     466
caattcgaca agcagagaaa gaaaagttaa tccaatgaca gaggagcttt cgagttttat     526
attgtttgca tccggttgcc ctcaataaag aaagtctttt tttttaagtt ccgaaaaaaa     586
aaaaaaaaaa aaaa                                                      600

<210> SEQ ID NO 65
<211> LENGTH: 95
<212> TYPE: PRT
<213> ORGANISM: Rattus sp.

<400> SEQUENCE: 65

Met Pro Ser Gln Met Glu His Ala Met Glu Thr Met Met Leu Thr Phe
 1               5                  10                  15

His Arg Phe Ala Gly Glu Lys Asn Tyr Leu Thr Lys Glu Asp Leu Arg
             20                  25                  30

Val Leu Met Glu Arg Glu Phe Pro Gly Phe Leu Glu Asn Gln Lys Asp
         35                  40                  45

Pro Leu Ala Val Asp Lys Ile Met Lys Asp Leu Asp Gln Cys Arg Asp
     50                  55                  60

Gly Lys Val Gly Phe Gln Ser Phe Leu Ser Leu Val Ala Gly Leu Ile
 65                  70                  75                  80

Ile Ala Cys Asn Asp Tyr Phe Val Val His Met Lys Gln Lys Lys
                 85                  90                  95

<210> SEQ ID NO 66
<211> LENGTH: 639
<212> TYPE: DNA
<213> ORGANISM: Rattus sp.
<220> FEATURE:
<221> NAME/KEY: CDS
<222> LOCATION: (1)..(636)

<400> SEQUENCE: 66 atg gcg tac gcc tat ctc ttc aag tac atc atc atc ggc gac aca ggt        48
Met Ala Tyr Ala Tyr Leu Phe Lys Tyr Ile Ile Ile Gly Asp Thr Gly
 1               5                  10                  15 gtt ggt aaa tcg tgc tta ttg cta cag ttt aca gac aag agg ttt cag        96
Val Gly Lys Ser Cys Leu Leu Leu Gln Phe Thr Asp Lys Arg Phe Gln
             20                  25                  30 ccg gtg cat gac ctc aca att ggt gta gag ttt ggt gct cga atg ata       144
Pro Val His Asp Leu Thr Ile Gly Val Glu Phe Gly Ala Arg Met Ile
         35                  40                  45 acc att gat ggg aaa cag ata aaa ctc cag atc tgg gat aca gca ggg       192
Thr Ile Asp Gly Lys Gln Ile Lys Leu Gln Ile Trp Asp Thr Ala Gly
```

```
                 Thr Ile Asp Gly Lys Gln Ile Lys Leu Gln Ile Trp Asp Thr Ala Gly
                      50                  55                  60 cag gag tcc ttt cgt tct atc aca agg tca tat tac aga ggt gca gcg                 240
Gln Glu Ser Phe Arg Ser Ile Thr Arg Ser Tyr Tyr Arg Gly Ala Ala
 65                  70                  75                  80 ggg gct tta cta gtg tat gat att aca agg aga gac acg ttc aac cac                 288
Gly Ala Leu Leu Val Tyr Asp Ile Thr Arg Arg Asp Thr Phe Asn His
                 85                  90                  95 ttg aca acc tgg tta gaa gac gcc cgt cag cat tcc aat tcc aac atg                 336
Leu Thr Thr Trp Leu Glu Asp Ala Arg Gln His Ser Asn Ser Asn Met
            100                 105                 110 gtc atc atg ctt att gga aat aaa agt gac tta gaa tct agg aga gaa                 384
Val Ile Met Leu Ile Gly Asn Lys Ser Asp Leu Glu Ser Arg Arg Glu
        115                 120                 125 gtg aaa aag gaa gaa ggt gaa gct ttt gca cga gag cat gga ctt atc                 432
Val Lys Lys Glu Glu Gly Glu Ala Phe Ala Arg Glu His Gly Leu Ile
    130                 135                 140 ttc atg gaa act tct gcc aag act gct tct aat gta gag gag gca ttt                 480
Phe Met Glu Thr Ser Ala Lys Thr Ala Ser Asn Val Glu Glu Ala Phe
145                 150                 155                 160 att aac aca gca aaa gaa att tat gaa aaa atc caa gaa ggg gtc ttt                 528
Ile Asn Thr Ala Lys Glu Ile Tyr Glu Lys Ile Gln Glu Gly Val Phe
                165                 170                 175 gac att aat aat gag gca aac ggc atc aaa att ggc cct cag cat gct                 576
Asp Ile Asn Asn Glu Ala Asn Gly Ile Lys Ile Gly Pro Gln His Ala
            180                 185                 190 gct acc aat gca tct cac gga ggc aac caa gga ggg cag cag gca ggg                 624
Ala Thr Asn Ala Ser His Gly Gly Asn Gln Gly Gly Gln Gln Ala Gly
        195                 200                 205 gga ggc tgc tgc tga                                                             639
Gly Gly Cys Cys
    210

<210> SEQ ID NO 67
<211> LENGTH: 212
<212> TYPE: PRT
<213> ORGANISM: Rattus sp.

<400> SEQUENCE: 67

Met Ala Tyr Ala Tyr Leu Phe Lys Tyr Ile Ile Ile Gly Asp Thr Gly
 1               5                  10                  15

Val Gly Lys Ser Cys Leu Leu Leu Gln Phe Thr Asp Lys Arg Phe Gln
                20                  25                  30

Pro Val His Asp Leu Thr Ile Gly Val Glu Phe Gly Ala Arg Met Ile
            35                  40                  45

Thr Ile Asp Gly Lys Gln Ile Lys Leu Gln Ile Trp Asp Thr Ala Gly
        50                  55                  60

Gln Glu Ser Phe Arg Ser Ile Thr Arg Ser Tyr Tyr Arg Gly Ala Ala
 65                  70                  75                  80

Gly Ala Leu Leu Val Tyr Asp Ile Thr Arg Arg Asp Thr Phe Asn His
                85                  90                  95

Leu Thr Thr Trp Leu Glu Asp Ala Arg Gln His Ser Asn Ser Asn Met
            100                 105                 110

Val Ile Met Leu Ile Gly Asn Lys Ser Asp Leu Glu Ser Arg Arg Glu
        115                 120                 125

Val Lys Lys Glu Glu Gly Glu Ala Phe Ala Arg Glu His Gly Leu Ile
    130                 135                 140

Phe Met Glu Thr Ser Ala Lys Thr Ala Ser Asn Val Glu Glu Ala Phe
```

```
                145                 150                 155                 160
                Ile Asn Thr Ala Lys Glu Ile Tyr Glu Lys Ile Gln Glu Gly Val Phe
                                165                 170                 175

Asp Ile Asn Asn Glu Ala Asn Gly Ile Lys Ile Gly Pro Gln His Ala
                            180                 185                 190

Ala Thr Asn Ala Ser His Gly Gly Asn Gln Gly Gly Gln Gln Ala Gly
                        195                 200                 205

Gly Gly Cys Cys
                    210

<210> SEQ ID NO 68
<211> LENGTH: 816
<212> TYPE: DNA
<213> ORGANISM: Rattus sp.
<220> FEATURE:
<221> NAME/KEY: CDS
<222> LOCATION: (1)..(813)

<400> SEQUENCE: 68 atg gtg ctg ctc aag gaa tat cgg gtc atc ctg cct gtg tct gta gat      48
Met Val Leu Leu Lys Glu Tyr Arg Val Ile Leu Pro Val Ser Val Asp
  1               5                  10                  15 gag tat caa gtg ggg cag ctg tac tct gtg gct gaa gcc agt aaa aat      96
Glu Tyr Gln Val Gly Gln Leu Tyr Ser Val Ala Glu Ala Ser Lys Asn
                 20                  25                  30 gaa act ggt ggt ggg gaa ggt gtg gag gtc ctg gtg aac gag ccc tac     144
Glu Thr Gly Gly Gly Glu Gly Val Glu Val Leu Val Asn Glu Pro Tyr
             35                  40                  45 gag aag gat gat ggc gag aaa ggc cag tac aca cac aag atc tac cac     192
Glu Lys Asp Asp Gly Glu Lys Gly Gln Tyr Thr His Lys Ile Tyr His
         50                  55                  60 tta cag agc aaa gtt ccc acg ttt gtt cga atg ctg gcc cca gaa ggc     240
Leu Gln Ser Lys Val Pro Thr Phe Val Arg Met Leu Ala Pro Glu Gly
 65                  70                  75                  80 gcc ctg aat ata cat gag aaa gcc tgg aat gcc tac cct tac tgc aga     288
Ala Leu Asn Ile His Glu Lys Ala Trp Asn Ala Tyr Pro Tyr Cys Arg
                 85                  90                  95 acc gtt att aca aat gag tac atg aag gaa gac ttt ctc att aaa att     336
Thr Val Ile Thr Asn Glu Tyr Met Lys Glu Asp Phe Leu Ile Lys Ile
                100                 105                 110 gaa acc tgg cac aag cca gac ctt ggc acc cag gag aat gtg cat aaa     384
Glu Thr Trp His Lys Pro Asp Leu Gly Thr Gln Glu Asn Val His Lys
            115                 120                 125 ctg gag cct gag gca tgg aaa cat gtg gaa gct ata tat ata gac atc     432
Leu Glu Pro Glu Ala Trp Lys His Val Glu Ala Ile Tyr Ile Asp Ile
        130                 135                 140 gct gat cga agc caa gta ctt agc aag gat tac aag gca gag gaa gac     480
Ala Asp Arg Ser Gln Val Leu Ser Lys Asp Tyr Lys Ala Glu Glu Asp
145                 150                 155                 160 cca gca aaa ttt aaa tct atc aaa aca gga cga gga cca ttg ggc ccg     528
Pro Ala Lys Phe Lys Ser Ile Lys Thr Gly Arg Gly Pro Leu Gly Pro
                165                 170                 175 aat tgg aag caa gaa ctt gtc aat cag aag gac tgc cca tat atg tgt     576
Asn Trp Lys Gln Glu Leu Val Asn Gln Lys Asp Cys Pro Tyr Met Cys
            180                 185                 190 gca tac aaa ctg gtt act gtc aag ttc aag tgg tgg ggc ttg cag aac     624
Ala Tyr Lys Leu Val Thr Val Lys Phe Lys Trp Trp Gly Leu Gln Asn
        195                 200                 205 aaa gtg gaa aac ttt ata cat aag caa gag aag cgt ctg ttt aca aac     672
Lys Val Glu Asn Phe Ile His Lys Gln Glu Lys Arg Leu Phe Thr Asn
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     |     | 210 |     |     |     |     | 215 |     |     |     |     | 220 |     |     |     |
| ttt | cac | agg | cag | ctg | ttc | tgt | tgg | ctt | gat | aaa | tgg | gtt | gat | ctg | act | 720 |
| Phe | His | Arg | Gln | Leu | Phe | Cys | Trp | Leu | Asp | Lys | Trp | Val | Asp | Leu | Thr |     |
| 225 |     |     |     |     | 230 |     |     |     |     | 235 |     |     |     |     | 240 |     |
| atg | gat | gac | att | cgg | agg | atg | gaa | gaa | gag | acg | aag | aga | cag | ctg | gat | 768 |
| Met | Asp | Asp | Ile | Arg | Arg | Met | Glu | Glu | Glu | Thr | Lys | Arg | Gln | Leu | Asp |     |
|     |     |     |     | 245 |     |     |     |     | 250 |     |     |     |     | 255 |     |     |
| gag | atg | aga | caa | aag | gac | ccc | gtg | aaa | gga | atg | aca | gca | gat | gac | tag | 816 |
| Glu | Met | Arg | Gln | Lys | Asp | Pro | Val | Lys | Gly | Met | Thr | Ala | Asp | Asp |     |     |
|     | 260 |     |     |     |     | 265 |     |     |     |     | 270 |     |     |     |     |     |

<210> SEQ ID NO 69
<211> LENGTH: 2263
<212> TYPE: DNA
<213> ORGANISM: Simian sp.

<400> SEQUENCE: 69

| | | | | | |
|---|---|---|---|---|---|
| cgctctcctc | ctcccctttc | tctagcagta | gccttcttaa | tgtagtttaa | tggctttaca | 60 |
| aagaaagcca | ggcagaggag | cacttctcag | tggctgtggt | cggaccatga | cctagctgac | 120 |
| catgaacttg | gaagggcttg | aaatgatagc | agttctgatc | gtcattgtgc | tttttgttaa | 180 |
| attattggaa | cagtttgggc | tgattgaagc | aggtttagaa | gacagcgtgg | aagatgaact | 240 |
| ggagatggcc | actgtcaggc | atcggcctga | ggcccttgag | cttctggaag | cccagagcaa | 300 |
| atttaccaag | aaagagcttc | agatccttta | cagaggattt | aagaacgaat | gccccagtgg | 360 |
| tgttgttaat | gaagaaacct | tcaaagagat | ttactcgcag | ttctttccac | agggagactc | 420 |
| tacaacatat | gcacattttc | tgttcaatgc | gtttgatacg | gaccacaatg | gagctgtgag | 480 |
| tttcgaggat | tcatcaaag | gtctttccat | tttgctccgg | gggacagtac | aagaaaaact | 540 |
| caattgggca | tttaatctgt | atgatataaa | taaagatggc | tacatcacta | agaggaaat | 600 |
| gcttgatata | atgaaagcaa | tatacgacat | gatgggtaaa | tgtacatatc | ctgtcctcaa | 660 |
| agaagatgca | cccagacaac | acgtcgaaac | atttttcag | aaaatggaca | aaataaaga | 720 |
| tggggttgtt | accatagatg | agttcattga | aagctgccaa | aaagatgaaa | acataatgcg | 780 |
| ctccatgcag | ctcttgaaa | atgtgattta | acttgtcaac | tagatcctga | atccaacaga | 840 |
| caaatgtgaa | ctattctacc | acccttaaag | tcggagctac | cacttttagc | atagattgct | 900 |
| cagcttgaca | ctgaagcata | ttatgcaaac | aagctttgtt | ttaatataaa | gcaatcccca | 960 |
| aaagatttga | gtttctcagt | tataaatttg | catcctttcc | ataatgccac | tgagttcatg | 1020 |
| ggatgttcta | actcatttca | tactctgtga | atattcaaaa | gtaatagaat | ctggcatata | 1080 |
| gttttattga | ttccttagcc | atgggattat | tgaggctttc | acatatcagt | gattttaaaa | 1140 |
| taccagtgtt | ttttgctact | catttgtatg | tattcagtcc | taggattttg | aatggttttc | 1200 |
| taatatactg | acatctgcat | ttaatttcca | gaaattaaat | taattttcat | gtctgaatgc | 1260 |
| tgtaattcca | tttatatact | ttaagtaaac | aaataagatt | actacaatta | aacacatagt | 1320 |
| tccagtttct | atggccttca | cttcccacct | tctattagaa | attaattta | tctggtattt | 1380 |
| ttaaacattt | aaaaatttat | catcagatat | cagcatatgc | ctaattatgc | ctaatgaaac | 1440 |
| ttaataagca | tttaattttc | catcatacat | tatagtcaag | gcctatatac | tatatataat | 1500 |
| tttggatttg | tttaatctta | caggctgttt | tccattgtat | catcaagtgg | aagttcaaga | 1560 |
| cggcatcaaa | caaacaagg | atgtttacag | acatatgcaa | agggtcagga | tatctatcct | 1620 |
| ccagtatatg | ttaatgctta | ataacaagta | atcctaacag | cattaaaggc | caaatctgtc | 1680 |
| ctctttcccc | tgacttcctt | acagcatgtt | tatattacaa | gccattcagg | gacaaagaaa | 1740 |

-continued

```
ccttgactac cccactgtct actaggaaca aacaaacagc aagcaaaatt cactttgaaa      1800
gcaccagtgg ttccattaca ttgacaacta ctaccaagat tcagtagaaa ataagtgctc      1860
aacaactaat ccagattaca atatgattta gtgcatcata aaattccaac aattcagatt      1920
atttttaatc acctcagcca caactgtaaa gttgccacat tactaaagac acacacatcg      1980
tccctgtttt gtagaaatat cacaaagacc aagaggctac agaaggagga aatttgcaac      2040
tgtctttgca acaataaatc aggtatctat tctggtgtag agataggatg ttgaaagctg      2100
ccctgctatc accagtgtag aaattaagag tagtacaata catgtacact gaaatttgcc      2160
atcgcgtgtt tgtgtaaact caatgtgcac attttgtatt tcaaaagaa aaaataaaag       2220 caaaataaaa tgtttataac tctaaaaaaa aaaaaaaaa aaa                         2263
```

<210> SEQ ID NO 70
<211> LENGTH: 229
<212> TYPE: PRT
<213> ORGANISM: Simian sp.

<400> SEQUENCE: 70

```
Met Asn Leu Glu Gly Leu Glu Met Ile Ala Val Leu Ile Val Ile Val
  1               5                  10                  15

Leu Phe Val Lys Leu Leu Glu Gln Phe Gly Leu Ile Glu Ala Gly Leu
                 20                  25                  30

Glu Asp Ser Val Glu Asp Glu Leu Glu Met Ala Thr Val Arg His Arg
             35                  40                  45

Pro Glu Ala Leu Glu Leu Leu Glu Ala Gln Ser Lys Phe Thr Lys Lys
         50                  55                  60

Glu Leu Gln Ile Leu Tyr Arg Gly Phe Lys Asn Glu Cys Pro Ser Gly
 65                  70                  75                  80

Val Val Asn Glu Glu Thr Phe Lys Glu Ile Tyr Ser Gln Phe Phe Pro
                 85                  90                  95

Gln Gly Asp Ser Thr Thr Tyr Ala His Phe Leu Phe Asn Ala Phe Asp
            100                 105                 110

Thr Asp His Asn Gly Ala Val Ser Phe Glu Asp Phe Ile Lys Gly Leu
        115                 120                 125

Ser Ile Leu Leu Arg Gly Thr Val Gln Glu Lys Leu Asn Trp Ala Phe
    130                 135                 140

Asn Leu Tyr Asp Ile Asn Lys Asp Gly Tyr Ile Thr Lys Glu Glu Met
145                 150                 155                 160

Leu Asp Ile Met Lys Ala Ile Tyr Asp Met Met Gly Lys Cys Thr Tyr
                165                 170                 175

Pro Val Leu Lys Glu Asp Ala Pro Arg Gln His Val Glu Thr Phe Phe
            180                 185                 190

Gln Lys Met Asp Lys Asn Lys Asp Gly Val Val Thr Ile Asp Glu Phe
        195                 200                 205

Ile Glu Ser Cys Gln Lys Asp Glu Asn Ile Met Arg Ser Met Gln Leu
    210                 215                 220

Phe Glu Asn Val Ile
225
```

<210> SEQ ID NO 71
<211> LENGTH: 2259
<212> TYPE: DNA
<213> ORGANISM: Simian sp.

<400> SEQUENCE: 71

-continued

```
gtcgacagac gcccctggcc ggtggactcc tgagtcttac tcctgcaccc tgcgtcccca      60
gacatgaatg tgaggagagt ggaaagcatt tcggctcagc tggaggaggc cagctccaca     120
ggcggttttcc tgtatgctca aacagcacc aagcgcagca ttaaagagcg gctcatgaag     180
ctcttgccct gctcagctgc caaaacatcg tctcctgcta ttcaaaacag cgtggaagat     240
gaactggaga tggccactgt caggcatcgg cctgaggccc ttgagcttct ggaagcccag     300
agcaaattta ccaagaaaga gcttcagatc ctttacagag gatttaagaa cgaatgcccc     360
agtggtgttg ttaatgaaga aaccttcaaa gagatttact cgcagttctt tccacaggga     420
gactctacaa catatgcaca ttttctgttc aatgcgtttg atacggacca caatggagct     480
gtgagtttcg aggatttcat caaaggtctt tccatttttgc tccgggggac agtacaagaa     540
aaactcaatt gggcatttaa tctgtatgat ataaataaag atggctacat cactaaagag     600
gaaatgcttg atataatgaa agcaatatac gacatgatgg gtaaatgtac atatcctgtc     660
ctcaaagaag atgcacccag acaacacgtc gaaacatttt ttcagaaaat ggacaaaaat     720
aaagatgggg ttgttaccat agatgagttc attgaaagct gccaaaaaga tgaaaacata     780
atgcgctcca tgcagctctt tgaaaatgtg atttaacttg tcaactagat cctgaatcca     840
acagacaaat gtgaactatt ctaccaccct taaagtcgga gctaccactt ttagcataga     900
ttgctcagct tgacactgaa gcatattatg caaacaagct ttgttttaat ataaagcaat     960
ccccaaaaga tttgagtttc tcagttataa atttgcatcc tttccataat gccactgagt    1020
tcatgggatg ttctgactca tttcatactc tgtgaatatt caaaagtaat agaatctggc    1080
atatagtttt attgattcct tagccatggg attattgagg ctttcacata tcagtgattt    1140
taaaatacca gtgttttttg ctactcattt gtatgtattc agtcctagga ttttgaatgg    1200
ttttctaata tactgacatc tgcatttaat ttccagaaat taaattaatt ttcatgtctg    1260
aatgctgtaa ttccatttat atactttaag taaacaaata agattactac aattaaacac    1320
atagttccag tttctatggc cttcacttcc caccttctat tagaaattaa ttttatctgg    1380
tatttttaaa catttaaaaa tttatcatca gatatcagca tatgcctaat tatgcctaat    1440
gaaacttaat aagcatttaa ttttccatca tacattatag tcaaggccta tatactatat    1500
ataattttgg atttgtttaa tcttacaggc tgttttccat tgtatcatca agtggaagtt    1560
caagacggca tcaaacaaaa caaggatgtt tacagacata tgcaaagggt caggatatct    1620
atcctccagt atatgttaat gcttaataac aagtaatcct aacagcatta aaggccaaat    1680
ctgtcctctt tcccctgact tccttacagc atgtttatat tacaagccat tcagggacaa    1740
agaaaccttg actaccccac tgtctactag gaacaaacaa acagcaagca aaattcactt    1800
tgaaagcacc agtggttcca ttacattgac aactactacc aagattcagt agaaaataag    1860
tgctcaacaa ctaatccaga ttacaatatg atttagtgca tcataaaatt ccaacaattc    1920
agattatttt taatcacctc agccacaact gtaaagttgc cacattacta agacacaca     1980
catcgtccct gttttgtaga aatatcacaa agaccaagag gctacagaag gaggaaattt    2040
gcaactgtct ttgcaacaat aaatcaggta tctattctgg tgtagagata ggatgttgaa    2100
agctgccctg ctatcaccag tgtagaaatt aagagtagta caatacatgt acactgaaat    2160
ttgccatcgc gtgtttgtgt aaactcaatg tgcacatttt gtatttcaaa agaaaaaat     2220
aaaagcaaaa taaaatgtta aaaaaaaaa aaaaaaaa                              2259
```

<210> SEQ ID NO 72

-continued

```
<211> LENGTH: 250
<212> TYPE: PRT
<213> ORGANISM: Simian sp.

<400> SEQUENCE: 72

Met Asn Val Arg Arg Val Glu Ser Ile Ser Ala Gln Leu Glu Glu Ala
 1               5                  10                  15

Ser Ser Thr Gly Gly Phe Leu Tyr Ala Gln Asn Ser Thr Lys Arg Ser
            20                  25                  30

Ile Lys Glu Arg Leu Met Lys Leu Leu Pro Cys Ser Ala Ala Lys Thr
            35                  40                  45

Ser Ser Pro Ala Ile Gln Asn Ser Val Glu Asp Glu Leu Glu Met Ala
        50                  55                  60

Thr Val Arg His Arg Pro Glu Ala Leu Glu Leu Leu Glu Ala Gln Ser
65                  70                  75                  80

Lys Phe Thr Lys Lys Glu Leu Gln Ile Leu Tyr Arg Gly Phe Lys Asn
                85                  90                  95

Glu Cys Pro Ser Gly Val Val Asn Glu Glu Thr Phe Lys Glu Ile Tyr
            100                 105                 110

Ser Gln Phe Phe Pro Gln Gly Asp Ser Thr Thr Tyr Ala His Phe Leu
        115                 120                 125

Phe Asn Ala Phe Asp Thr Asp His Asn Gly Ala Val Ser Phe Glu Asp
130                 135                 140

Phe Ile Lys Gly Leu Ser Ile Leu Leu Arg Gly Thr Val Gln Glu Lys
145                 150                 155                 160

Leu Asn Trp Ala Phe Asn Leu Tyr Asp Ile Asn Lys Asp Gly Tyr Ile
                165                 170                 175

Thr Lys Glu Glu Met Leu Asp Ile Met Lys Ala Ile Tyr Asp Met Met
            180                 185                 190

Gly Lys Cys Thr Tyr Pro Val Leu Lys Glu Asp Ala Pro Arg Gln His
        195                 200                 205

Val Glu Thr Phe Phe Gln Lys Met Asp Lys Asn Lys Asp Gly Val Val
    210                 215                 220

Thr Ile Asp Glu Phe Ile Glu Ser Cys Gln Lys Asp Glu Asn Ile Met
225                 230                 235                 240

Arg Ser Met Gln Leu Phe Glu Asn Val Ile
                245                 250

<210> SEQ ID NO 73
<211> LENGTH: 10
<212> TYPE: PRT
<213> ORGANISM: Simian sp.

<400> SEQUENCE: 73

Ser Asn Ala Lys Ala Val Glu Thr Asp Val
 1               5                  10
```